(12) United States Patent
Forsell

(10) Patent No.: US 12,295,870 B2
(45) Date of Patent: May 13, 2025

(54) TREATMENT OF GERD

(71) Applicant: Peter Forsell, Sachseln (CH)

(72) Inventor: Peter Forsell, Sachseln (CH)

( * ) Notice: Subject to any disclaimer, the term of this patent is extended or adjusted under 35 U.S.C. 154(b) by 927 days.

(21) Appl. No.: 17/460,361

(22) Filed: Aug. 30, 2021

(65) Prior Publication Data
US 2023/0067764 A1 Mar. 2, 2023

(51) Int. Cl.
*A61F 5/00* (2006.01)
*A61B 17/00* (2006.01)
*A61B 17/12* (2006.01)
*A61N 1/05* (2006.01)
*A61N 1/36* (2006.01)

(52) U.S. Cl.
CPC ...... *A61F 5/0059* (2013.01); *A61B 17/12009* (2013.01); *A61N 1/0509* (2013.01); *A61N 1/36007* (2013.01); *A61B 2017/00827* (2013.01)

(58) Field of Classification Search
CPC ............ A61F 5/0059; A61B 17/12009; A61B 2017/00827; A61N 1/0509; A61N 1/36007; A61N 1/0517; A61N 1/36171; A61N 1/36175; A61N 1/36178; A61N 1/37211; A61N 1/3787; G16H 20/30; G16H 40/40; G16H 40/63
See application file for complete search history.

(56) References Cited

U.S. PATENT DOCUMENTS

2010/0312356 A1\* 12/2010 Forsell ............... A61B 17/0469
623/23.65

\* cited by examiner

*Primary Examiner* — Mark W. Bockelman

(57) ABSTRACT

The present disclosure relates to treatment of reflux disease of a human patient. More particularly, a device is disclosed, which is configured to be implanted in the body of the human to restrict movement of the cardia of the patient's stomach towards the diaphragm opening into the patient's thorax, and/or to prevent stomach contents from passing from the stomach into the esophagus.

26 Claims, 28 Drawing Sheets

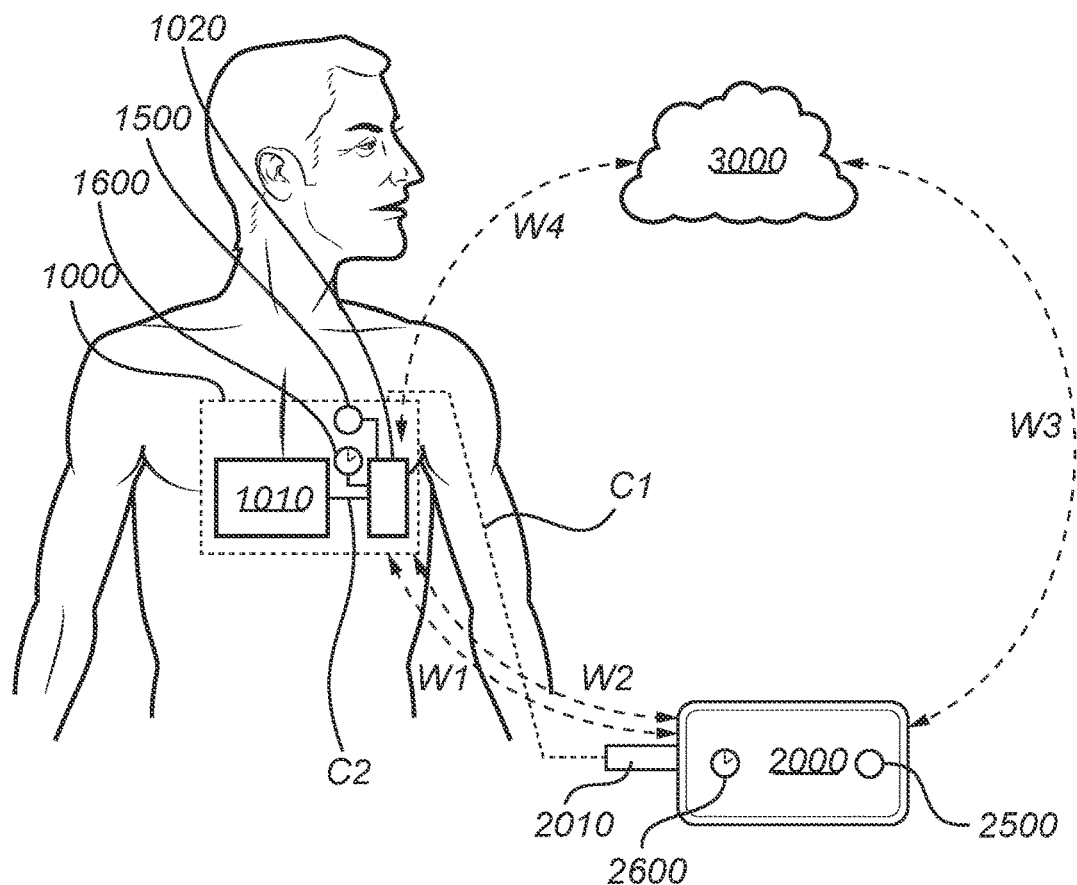
Fig. 46A
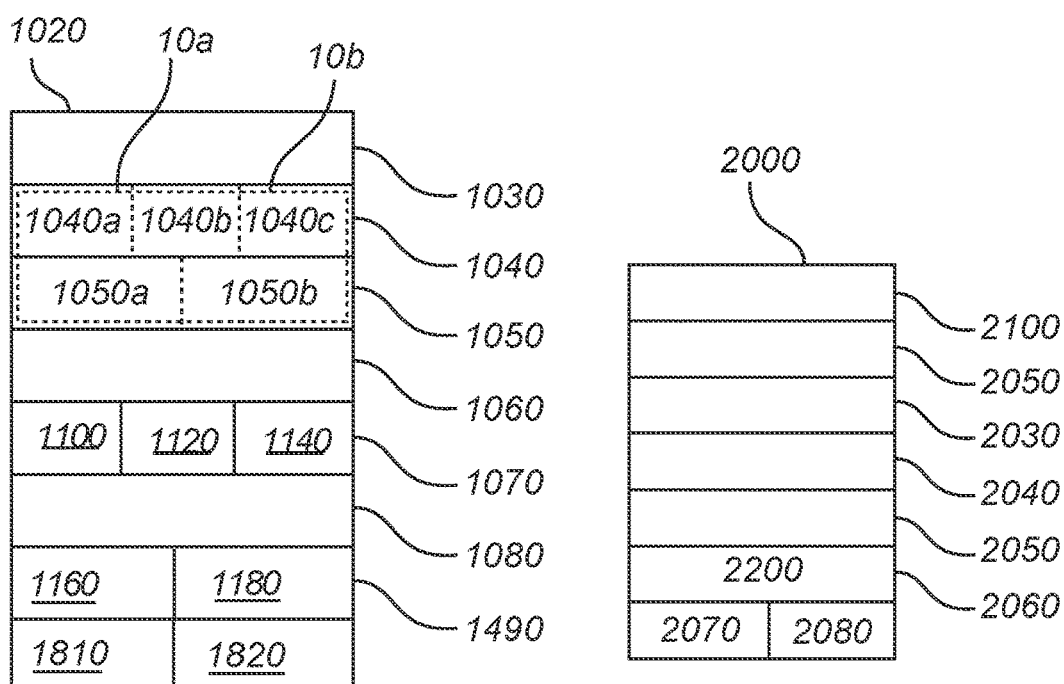
Fig. 46B
Fig. 46C

TREATMENT OF GERD

TECHNICAL FIELD

The present inventive concept generally relates to medial implants. More specifically the inventive concept relates to medical implants for treating gastroesophageal reflux disease (GERD).

BACKGROUND

Gastroesophageal reflux disease (GERD), or reflux disease, is a condition resulting in mucosal damage in the esophagus caused by recurring occurrence of acid reflux in the esophagus. GERD can be treated in a number of different ways, including both medical and surgical treatments. An example of a surgical treatment is Nissen fundoplication surgery, in which the upper curve of the stomach (the fundus) is wrapped around the lower esophageal sphincter (LES) to strengthen the sphincter, prevent acid reflux, and repair a hiatal hernia. This method however risks causing a constriction of the food passageway, making it more difficult for the patient to swallow.

Another example is the Anglechik prosthesis, in which a device formed like a horseshoe is placed around the esophagus above the cardia. The intended effect is to prevent the cardia from slipping up into the thorax cavity. However, this device is associated with a number of complications, including migrating through and damaging the esophagus. Further, the body tends to react to a medical implant, partly because the implant is a foreign object, and partly because the implant interacts mechanically with tissue of the body. Exposing tissue to long-term engagement with, or pressure from, an implant may deprive the cells of oxygen and nutrients, which may lead to deterioration of the tissue, atrophy and eventually necrosis.

It would therefore be advantageous to provide more efficient and/or less damaging techniques for treating GERD.

SUMMARY

It is an object of the present inventive concept to overcome, or at least alleviate, at least some of the drawbacks associated with the above-mentioned treatments of GERD. Further and/or alternative objectives may be understood from the following.

According to an aspect, an apparatus for treating reflux disease of a human patient is provided, comprising an implantable movement restriction device and an electrode arrangement. The implantable movement restriction device has a shape and size that allows it to be arranged to rest against a fundus wall portion of the patient's stomach and to be at least partly invaginated by the fundus wall portion, such that the movement restriction device is implanted at a position between the patient's diaphragm and a lower portion of the fundus wall, and such that movement of the cardia of the patient's stomach towards the diaphragm is restricted to hinder the cardia from sliding through the diaphragm opening into the patient's thorax. The electrode arrangement is configured to be arranged between the movement restriction device and the fundus wall portion and to engage and electrically stimulate muscle tissue of the fundus wall portion to exercise the muscle tissue to improve the conditions for long term implantation of the movement restriction device.

According to an aspect, an apparatus for treating reflux disease of a human patient is provided, comprising an at least partly ring-shaped implantable movement restriction device and an electrode arrangement. The implantable movement restriction device comprises a first portion configured to be at least partly invaginated by a first wall portion of the patient's stomach and arranged such that at least a part of the first portion is arranged above the cardiac notch of the patient's stomach, and such that movement of the cardia towards the diaphragm is restricted to prevent the cardia from sliding through the diaphragm opening into the patient's thorax. The electrode arrangement is configured to be arranged between the movement restriction device and the first wall portion and to electrically stimulate muscle tissue of the first wall portion to exercise the muscle tissue to improve the conditions for long term implantation of the movement restriction device.

According to an aspect, an apparatus for treating reflux disease of a human patient is provided, comprising an elongated core and a tubular cover. The elongated core has a length allowing the core to at least partly encircle the esophagus of the patient, wherein the length is variable to allow the core to be arranged in a constricting state for hindering fluid from passing from the stomach into the esophagus and in an expanded state for allowing food to pass into the stomach in response to the patient swallowing. The tubular cover is configured to encloses at least a part of the core and comprises a plurality of portions adapted to bend relative to each other to allow the core to change between the constricting state and the expanded state, when the cover is at least partly covered by fibrotic tissue, without being substantially hindered or impeded by the presence of said fibrotic tissue.

According to an aspect, an apparatus for treating reflux disease of a human patient is provided, comprising an elongated core having a length allowing the core to at least partly encircle the esophagus of the patient, wherein the length is variable to allow the core to be arranged in a constricting state for hindering fluid from passing from the stomach into the esophagus and in an expanded state for allowing food to pass into the stomach in response to the patient swallowing. The apparatus further comprises an electrode arrangement comprising an electrode element supported by the core and configured to be arranged between the apparatus and the esophagus and to electrically stimulate muscle tissue of the esophagus.

According to an aspect, an apparatus for treating reflux disease of a human patient, is provided comprising a tubular device having a length allowing the tubular device to at least partly encircle the esophagus of the patient, wherein the length is variable to allow the tubular cover to be arranged in a constricting state for hindering fluid from passing from the stomach into the esophagus and in an expanded state for allowing food to pass into the stomach in response to the patient swallowing. The outer surface of the tubular device may comprise a plurality of portions adapted to bend relative to each other to allow the tubular device to change between the constricting state and the expanded state, when the outer surface is at least partly covered by fibrotic tissue, without being substantially hindered or impeded by the presence of said fibrotic tissue.

According to an aspect, an apparatus for treating reflux disease of a human patient is provided, comprising an elongated core having a length allowing the core to at least partly encircle the esophagus of the patient. The length may be variable to allow the core to be arranged in a constricting state for hindering fluid from passing from the stomach into the esophagus and in an expanded state for allowing food to pass into the stomach in response to the patient swallowing. Further, the elongated core has a size allowing at least a portion of the elongated core to protrude above the cardiac sphincter of the patient, when implanted, such that movement of the cardia towards the diaphragm is restricted to hinder the cardia from sliding through the diaphragm opening into the patient's thorax.

According to an aspect, an apparatus for treating reflux disease of a human patient is provided, which is adapted to at least partly encircle the esophagus (20) of the patient. The apparatus comprises a first implantable portion and a second implantable portion, wherein the first implantable portion has a shape and size allowing it to be arranged to rest against a fundus wall portion of the patient's stomach and to be at least partly invaginated by the fundus wall portion, such that the first implantable portion is implanted at a position between the patient's diaphragm and a lower portion of the fundus wall, and such that movement of the cardia of the patient's stomach towards the diaphragm is restricted to hinder the cardia from sliding through the diaphragm opening into the patient's thorax. The second implantable portion is elongated to at least partly encircle the esophagus and has a variable length for allowing the apparatus be arranged in a constricting state for hindering fluid from passing from the stomach into the esophagus and in an expanded state for allowing food to pass into the stomach in response to the patient swallowing.

According to an aspect, an apparatus for treating reflux disease of a human patient is provided, which is adapted to at least partly encircle the esophagus of the patient. The apparatus comprises a movement restriction device, an elongated support device and an electrode arrangement. The movement restriction device has a shape and size allowing it to be arranged to rest against a fundus wall portion of the patient's stomach and to be at least partly invaginated by the fundus wall portion, such that the first implantable portion is implanted at a position between the patient's diaphragm and a lower portion of the fundus wall, and such that movement of the cardia of the patient's stomach towards the diaphragm is restricted to hinder the cardia from sliding through the diaphragm opening into the patient's thorax. The elongated support device is connected to the movement restriction device and configured to at least partly encircle the esophagus. The electrode arrangement comprises an electrode element supported by the support device and configured to electrically stimulate muscle tissue of the esophagus. Further, the support device comprises a rigidity that allows the position of the electrode element relative to the esophagus to be determined mainly by the position and orientation of the movement restriction device.

According to an aspect, a method for treating reflux disease of a human patient is provided. The method involves implanting a movement restriction device such that the movement restriction device is arranged to restrict movement of the cardia of the patient's stomach towards the diaphragm to hinder the cardia from sliding through the diaphragm opening into the patient's thorax. The method comprises placing the movement restriction device such that a lower portion of the movement restriction device rests against the serosa at the angle of His, and such that an upper portion of the movement restriction device defines a gap between the movement restriction device and the patient's esophagus, when the lower portion rests against the angle of His. The method further comprises arranging a portion of the fundus of the stomach in the gap and attaching the fundus to the patient's esophagus to at least partly enclose the movement restriction device by the portion of the fundus.

According to an aspect, an apparatus for treating reflux disease of a human patient is provided, comprising an implantable movement restriction device and an elongated attacher configured to be attached to the movement restriction device and to be at least partly invaginated by a wall portion of the patient's stomach. The attacher comprises a shape and size allowing it to be invaginated by the wall portion to hinder rotation of the movement restriction device. The attacher is further configured to be invaginated by the wall portion such that the movement restriction device is arranged at a position between the patient's diaphragm and the wall portion, distant from the patient's esophagus, to restrict movement of the cardia of the patient's stomach towards the diaphragm to hinder the cardia from sliding through the diaphragm opening into the patient's thorax.

According to an aspect, a method of treating reflux disease in a human patient is provided, involving implanting an apparatus comprising a movement restriction device and an elongated support device, such that the support device at least partly encircles the esophagus of the patient and such that the movement restriction device is at arranged on the fundus side of the esophagus to restrict the movement of the cardia in relation to the diaphragm to hinder the cardia to from sliding through the diaphragm opening into the patient's thorax. The method comprises the steps of introducing the apparatus into the abdominal cavity, placing the apparatus such that the movement restriction device rests against the outside of the stomach's fundus, wrapping a portion of the fundus around at least a part of the movement restriction device, affixing the fundus to the esophagus such that the movement restriction device is arranged at a position between the diaphragm and the cardiac sphincter, and such that a part of the fundus is arranged between the movement restriction device and the esophagus and arranging the support device to at least partly encircle the esophagus. The movement restriction device and the second portion form a ring-shaped body extending through the pouch to at least partly encircle the esophagus.

According to an aspect, a method for affixing a fundus portion of the stomach of a human patient to the patient's esophagus is provided, wherein the fundus portion extends from the angle of His and in a direction away from the esophagus. The method comprises folding the fundus portion towards the esophagus such that the fundus portion rests against the esophagus, from the angle of His and upwards along the esophagus, and affixing the fundus portion to the esophagus by means of fasteners arranged along a first line and a second line. The first line and the second line extend along the esophagus and are arranged such that a distance between the first line and the second line increases with an increasing distance from the angle of His.

According to an aspect, an apparatus for treating reflux disease in a human patient according to any of the above aspects is provided. The apparatus comprises an electrode arrangement for electrically stimulating the patient's muscle tissue to exercise the muscle tissue to improve the conditions for long term implantation of the apparatus, as outlined above. The apparatus further comprises an implantable energy source configured to provide the electrode arrangement with electrical power, a controller operably connected to the electrode arrangement for controlling the electrical stimulation of the muscle tissue.

According to an aspect, an apparatus for treating reflux disease of a human patient according to any one of the above aspects is provided. The apparatus comprises an electrode arrangement, an implantable energy source configured to provide the apparatus with electrical power, an external energy source configured be arranged outside of the patient's body and configured to provide energy to the implantable energy source, and an implantable charger configured to be electrically connected to the implantable energy source and enable charging of the implantable energy source by the external energy source.

According to an embodiment, an apparatus for treating reflux disease of a human patient according to any one of the above aspects is provided. The apparatus when comprises an electrode arrangement, and a controller configured to be operably connected to the electrode arrangement for controlling the electrical stimulation of the muscle tissue. The controller comprises an implantable communicator for transmitting and/or receiving a signal to/from the outside of the patient's body.

According to an embodiment of the above aspects, the electrode arrangement may be arranged on an outer surface of the movement restriction device.

According to some embodiments of the above aspects, the electrode arrangement may comprise a plurality of electrode elements, wherein each of the electrode elements is configured to engage and electrically stimulate the muscle tissue. The electrode arrangement may further comprise a coiled wire for increasing a contact surface between the electrode arrangement and the muscle tissue and for allowing the electrode arrangement to follow contraction and relaxation of the muscle tissue.

According to some embodiments of the above aspects, the electrode arrangement may comprise a bare electrode portion configured to form a metal-tissue interface with the muscle tissue so as to allow faradaic charge transfer to the be predominant charge transfer mechanism over the interface. Alternatively, or additionally the electrode arrangement may comprise an electrode portion that is at least partly covered by a dielectric material configured to form a dielectric-tissue interface with the muscle tissue so as to allowing a faradaic portion of the charge transfer mechanism over the interface to be reduced.

According to some embodiments, the electrode arrangement may be configured to be arranged to electrically stimulate the cardiac sphincter to cause the cardiac sphincter to contract. The electrode arrangement may comprise at least two electrode elements configured to be arranged on opposing sides of the cardiac sphincter. Further, the apparatus may comprise a holder configured to support the at least two electrode elements at the opposing sides of the cardiac sphincter.

Exemplary embodiments of a movement restriction device according to at least some of the above aspects will now be discussed.

According to an embodiment, a volume of the movement restriction device may be non-adjustable after implantation. According to another embodiment, the volume of the movement restriction device may be adjustable after implantation. The volume may be adjustable invasively or non-invasively. In an example, the movement restriction device comprises an injection port for allowing a fluid to be injected or extracted from the inside of the movement restriction device so as to vary the volume of the movement restriction device after implantation.

According to an embodiment, the movement restriction device may comprise a biocompatible outer surface configured to rest against the fundus wall portion.

According to an embodiment, the movement restriction device may be substantially spherical or egg-shaped. In an example, the movement restriction device may have a portion configured to be arranged to point away from the esophagus when implanted. In a further example, a lower portion of the movement restriction device may be wider that an upper portion.

According to an embodiment, the movement restriction device may be configured to be invaginated when placed on the outside of the fundus wall portion. In another embodiment, the movement restriction device may be configured to be invaginated when placed on the inside of the fundus wall portion.

According to an embodiment, the movement restriction device may be configured to be introduced in the patient's body by means of a gastroscope or an intraluminal instrument. The movement restriction device may for example be configured to change its shape to allow it to pass through a trocar during insertion into the patient's body.

According to an embodiment, the movement restriction device may be formed of at least two distinct and separable pieces configured to be assembled into the movement restriction device after insertion in the patient's body.

According to an embodiment, a minimum width of the movement restriction device, as measured from side to side, may be 20 mm or larger, such as 30 mm or larger, such as 40 mm or larger, such as 50 mm or larger.

According to some embodiments, the movement restriction device may comprise a first and a second portion, wherein the first and second portions are configured to be arranged on opposite sides of the cardia. In an example, the movement restriction device may be configured to be arranged such that a gap is formed between the second portion of the movement restriction device and the esophagus. In an example, the second portion of the movement restriction device may be configured to be at least partly invaginated by a second wall portion of the stomach.

According to an embodiment, the movement restriction device may be configured to be arranged such that a portion of the first wall portion is arranged between the first portion of the movement restriction device and the esophagus.

According to an embodiment, the movement restriction device may be configured to be at least partly invaginated by the first wall portion along at least half of the toroidal length of the movement restriction device.

According to an embodiment, the movement restriction device may be configured to be invaginated when placed on the outside of the stomach wall.

According to an embodiment, the movement restriction device may comprise two end portions configured to be coupled to each other to form a closed ring. The end portions may be configured to be releasably attached to each other.

According to an embodiment, a poloidal circumference of the movement restriction device may be larger for the first portion and for the second portion. In an example, a minimum width of the first portion of the movement restriction device, as measured from side to side, is 20 mm or larger, such as 30 mm or larger, such as 40 mm or larger, such as 50 mm or larger. Alternatively, the width may be defined as a height measured along a normal to the plane in which the circumference extends.

According to an embodiment, the movement restriction device may have a shape conforming to a torus.

According to an embodiment, the movement restriction device may have C-shaped cross section.

According to an embodiment, an upper portion of the movement restriction device may comprise a recess defined in the outer surface of the movement restriction device.

According to an embodiment, a lower portion of the movement restriction device may comprise a curved outer surface, which may be arranged to face the esophagus. The curved outer surface may comprise a radius of curvature corresponding to or exceeding the radius of curvature of the esophagus.

According to an embodiment, an elongated support, protruding from the movement restriction device, may be at least partly invaginated in the fundus before the fundus is attached to the esophagus. The support may be oriented along the esophagus.

Exemplary embodiments of a core and a cover according to at least some of the above aspects will now be discussed.

According to some embodiments, the core may be configured to allow a transition from the constricting state into the expanded state caused by the food passing through esophagus. The core may be configured to exert an encircling pressure on the esophagus in the constricting state.

According to an embodiment, the apparatus may further comprise an attractor for resiliently attracting adjacent portions of the core to one another to generate the encircling pressure. The attractor may comprise an elastic element, and/or at least two mutually attracting magnets. Further, the apparatus may comprise a link connecting a first and a second one of said at least two magnets to each other. The link may be configured to extend into at least one of said magnets in response to said magnets moving towards each other.

According to some embodiments, the core may comprise two end portions configured to be coupled to each other to form a closed ring around the esophagus. The end portions may be configured to be releasably attached to each other and may comprise a respective interlockable attacher.

According to an embodiment, the core may comprise a plurality of core elements configured to be arranged in an annular array around the esophagus. The core may further comprise a plurality of links, wherein each link may extend between a respective pair of core elements arranged adjacent to each other. The links may be configured to allow the respective core elements to move towards and away from each other, and may be configured to extend into at least one of the core elements of the respective pair of core elements as the core elements move towards each other.

According to an embodiment, the cover may comprise an array of tubular segments.

According to some embodiments, the cover may comprise a biocompatible outer surface for long-term implantation. The cover may for example be configured to rest against an outer surface of the esophagus and may further comprise a surface for promoting tissue growth. The cover may for example be formed of a polymer material, such as silicone. In further examples, the cover may be formed of or comprise a carbon-based material, such as carbon fiber material.

According to some embodiments, the cover may be formed of a material having a thickness of 0.1-10 mm, such as 1-5 mm. The cover may comprise at least one predefined fold along which the cover is allowed to fold in response to the core varying its length. The cover may in some examples comprise lowered and elevated portions allowing the cover to vary its length while maintaining its surface area. Thus, the cover may be configured to be compressible and expandable in its length direction, wherein the length is varied mainly due to the folding of the cover rather than elastic properties of the material. Thus, the cover may be considered to be formed of an inelastic material. In some examples, a length of the cover enclosing the at least a part of the core may exceed a length of the at least a part of the core when the at least a part of the core is arranged in the constricting state.

Exemplary embodiments of the attacher, which comprises a shape and size that allows it to be invaginated by the wall portion to hinder rotation of the movement restriction device as set out above in connection with some of the aspects, will now be described in the following.

According to some embodiments, a first end portion of the attacher may be configured to be invaginated by the wall portion and a second end portion to be attached to the movement restriction device. The first portion and the second portion may extend in different directions relative to each other, wherein the first portion may be configured to be invaginated by the wall portion to hinder rotation of the movement restriction device around a first axis, and wherein the second portion may be configured to be invaginated by the wall portion to hinder rotation of the movement restriction device around a second axis, different from the first axis. The first and second portions of the attacher may be curved to follow a curvature of the wall portion. The first portion and the second portion may be arranged at an angle to each other, the angle being in the interval of 60-120 degrees, such as 90 degrees.

According to some embodiments, the attacher may be configured to be releasably attached to the movement restriction device. The attacher may be configured to allow a position of the movement restriction device to be adjusted after invagination of the attachment means. In some examples, the apparatus may be configured to allow a distance between the movement restriction device and the attacher to be varied to allow the position of the movement restriction device relative to the diaphragm to be adjusted. Further, the apparatus may be configured to allow an orientation of the movement restriction device relative to the attachments means to be varied to allow the position of the movement restriction device relative to the diaphragm to the adjusted.

In an embodiment, the attacher may comprise a third portion, configured to be arranged to protrude from the wall portion when implanted, and to define a distance between the wall portion and the movement restriction device. The third portion may comprise a curvature allowing the third portion to be arranged to point away from the esophagus when implanted.

According to an embodiment, the movement restriction device and the attacher may be integrally formed into a single piece.

According to an embodiment, each of the movement restriction device and the attachments means may comprise a biocompatible outer surface. The attacher may comprises an outer surface configured to promote tissue growth. In some examples, the attacher may be formed of a metal. In further examples, the movement restriction device may be formed of a polymer.

According to an embodiment, an outer surface of the movement restriction device may comprise a material for hindering growth of fibrotic tissue.

Exemplary embodiments of the method of treating reflux disease in a human patient by implanting an apparatus comprising a movement restriction device and an elongated support device, as set out in some of the above aspects, will now be discussed in the following.

According to an embodiment, the apparatus may be placed such that the movement restriction device rests against the outside of the fundus at a position between the cardiac sphincter and the portion of the fundus that is to be affixed to the esophagus.

According to an embodiment, the apparatus may be placed such that the portion of the fundus that is affixed to the esophagus is arranged between the cardiac sphincter and the movement restriction device.

According to an embodiment, the pouch may be formed to be open in a least two positions to form a tunnel through which the apparatus extends.

According to an embodiment, the portion of the fundus may be affixed to the patient's diaphragm.

According to an embodiment, affixing the portion of the fundus to the esophagus may include suturing or stapling.

According to an embodiment, the support device may comprise a first and a second end portion between which the esophagus can be introduced. The first and second end portions can be coupled to each other so as to fixate the support device to the esophagus in an encircling manner.

According to an embodiment, the method may further comprise inserting a needle or a tube-like instrument into the patient's abdomen, using the needle or tube-like instrument to fill the abdomen with a gas, placing at least two laparoscopic trocars in the abdomen, inserting a camera through one of the laparoscopic trocars into the abdomen, inserting at least one dissecting tool through one the laparoscopic trocars, dissecting a portion of the stomach, and at least partly closing the pouch by means of sutures, such as barbed sutures, or staples.

In the following, exemplary embodiments of the method for affixing a fundus portion of the stomach of a human patient to the patient's esophagus according to the above aspect will now be described.

According to an embodiment, the abdominal part of the esophagus and the fundus can be divided by a plane into a ventral and a dorsal side. The method may comprise providing the first line on the dorsal side of the plane and the second line on the ventral side of the plane. The first line may begin less than 1 cm above the angle of His and the second line began less than 3 cm above the angle of His. The second line may in some examples begin at a distance less than 2 cm from the first line.

According to an embodiment, a separating angle between the first line and the second line may be in the range of 90-150 degrees.

According to some embodiments, the method may comprise providing an additional fastener between the first line and the second line, at the top of the fundus portion.

In some examples, the fasteners may comprise staples. In some examples, the fasteners may comprise sutures, such as for example barbed sutures. The first line of fasteners may for example comprise a first continuous suture, and the second line of fasteners a second continuous suture.

According to some embodiments, the method may further comprises placing a movement restriction device on the fundus, forming a pouch in the fundus, arranging the movement restriction device at least partly in the pouch, and invaginating the movement restriction device by the fundus by at least partly closing the pouch by fasteners. The movement restriction device may be arranged at a position between the diaphragm and the cardiac sphincter to hinder the cardia from sliding through the diaphragm opening into the patient's thorax. The movement restriction device may be invaginated after affixing the fundus portion to the esophagus. Further, the pouch may be formed to be open in a least two positions to form a tunnel through which the movement restriction device may extend. In an example, the fundus may be affixed to the diaphragm.

According to some embodiments an energy source may be provided. The energy source may be configured to be implanted in the body of the patient. The energy source may be configured to provide energy consuming components of the implant with electrical power. Examples of energy consuming components include controllers, sensors, electrodes, and the like, as outlined above in connection with the previous embodiments and examples. Thus, in some embodiments the energy source may be configured to provide the electrode arrangement, or electrode, as outlined above with electrical power.

The implantable energy source may be configured to be arranged inside, or integrated with, the implanted device, such as the movement restriction device, support device, attachment means, core, or cover according to any of the embodiments and examples described above. In some examples the energy source, or a part of the energy source, may be configured to be implanted outside the apparatus or implanted device, such as for example subcutaneously.

The energy source may comprise a primary cell, or galvanic cell, designed to be discarded after use, and not recharged like a secondary cell. Alternatively, or additionally the energy source may comprise a secondary cell, or rechargeable battery, designed to be recharged repeatedly.

According to some embodiments, the implantable energy source may be configured to be charged by an external energy source, i.e., an energy source arranged outside the patient's body. This may for example be achieved by means of an implantable charger, which may be configured to be electrically connected to the implantable energy source and to enable charging of the implantable energy source by the external energy source. Thus, the charger may be configured to transmit the electrical power from the outside of the patient's body to the implanted energy source. The transmission may for example be performed wirelessly from the external source, and the charger may in some examples comprise an electromagnetic coil for facilitating the transfer.

According to some embodiments, the charger may be configured to control the charging of the implantable energy source by controlling a receipt of electrical power from the external energy source at the implantable charger, and/or by controlling a transmission of electrical power from the external energy source to the implantable charger.

According to some embodiments, the charging of the implantable energy source may be controlled based on a functional status of the implanted energy source. This may for example be realized by controlling the electrical power delivered or emitted by an external energy source, or by controlling the electrical power received by a charger as outlined above. Further, the charging may in some examples be controlled by controlling the electrical power delivered by the charger to the implantable energy source, either by controlling the power output from the charger or by controlling the power received or absorbed by the implantable energy source. Thus, it will be appreciated that the charging of the implantable energy source may be controlled by varying or controlling the electrical power, supplied by the external energy source, at any point along the way to the implantable energy source. As exemplified above, the electrical power that is supplied to the implantable energy source may hence be controlled at the external energy source, at the charger or at the implantable energy source itself.

The functional status of the implanted energy source may for example include a charge level or a temperature. The temperature may for example be related to the energy source, the muscle tissue, or a part of the implant such as the electrode arrangement. Thus, the charging may be reduced or even stopped in case the charge level (or accumulated energy) reaches an upper limit, or in case the temperature exceeds a predetermined interval.

According to some embodiments, there may be provided a controller (or processor or control circuitry) for controlling various parts or functions of the implanted device or apparatus according to any of the embodiments described above. The controller may for example be configured to include the functional status of the implanted energy source in a signal that is transmitted to the outside of the body.

The controller may be configured to be operable connected to the electrode arrangement for controlling the electrical stimulation of the muscle tissue. The stimulation may for example be controlled such that the muscle tissue is stimulated by a series of electrical pulses. The electrical pulses may be characterized by their voltage and/or current. In some examples, a pulse of a first polarity may be followed by a pulse of a second, reversed polarity. The first polarity may for example be a positive current and the second polarity a negative current relative a current flow direction. Alternatively, or additionally the first polarity may be characterized by a positive voltage relative to a reference such as ground, and the second polarity by a negative voltage.

The controller may be configured to generate a pulsed electrical stimulation signal comprising a pulse frequency of 0.01-150 Hz. The pulse duration may be 0.01-100 ms, and the pulse amplitude in the interval 1-15 mA. Specific examples of electrical stimulation signals may be characterized by a pulse frequency of 0.15-0.25 Hz, a pulse duration of 20-30 ms and a pulse amplitude of 3-10 mA.

The controller may further be configured to generate a pulsed electrical stimulation signal having a varying composition, including different periods including build-up periods in which the amplitude is gradually increasing, stimulation periods in which the stimulation is ongoing, and pause periods wherein the stimulation is paused. Thus, in an example, the electrical stimulation signal may comprise a build-up period of 0.01-2 s, a stimulation period of 1-60 s, and a stimulation pause of 0.01-60 s. During the build-up period and the stimulation period the signal may comprises a pulse frequency of 1-50 Hz and a pulse duration of 0.1-10 ms. These periods may be varied and combined depending on the desired stimulation of the muscle tissue and may further be varied based on a response which fort example may be monitored by means of a sensor connected to the controller. The sensor may for example be configured to measure a motoric response in the muscle tissue, which may be measured as a mechanical movement or an electrical response.

According to some embodiments, there may be provided an implantable sensor for sensing action potentials generated by pacemaker cells of the muscle tissue. The sensor may be communicatively coupled to the controller, which may be configured to control the electrical stimulation based at least partly on the sensed action potentials. This may be particularly advantageous when stimulating smooth muscle tissue, which may exhibit period contractions that are paced by the pacemaker cells. The present embodiments thus allow for the electrical stimulation signal to be tailored to amplify the sensed action potentials.

Remote Controlling

According to some embodiments, the controller may comprise an external controller configured to be arranged outside the patient's body, and an internal controller, or implantable controller, configured to be arranged inside the patient's body. The wireless remote control may comprise an external signal transmitter configured to communicate with the internal controller. The internal controller may thus be configured to receive a signal transmitted by the external signal transmitter and to control an operation of the apparatus or medical implant based on the signal. The signal may in some examples be selected from the group consisting of: a sound signal, an ultrasound signal, an electromagnetic signal, and infrared signal, a visible light signal, an ultra violet light signal, a laser signal, a microwave signal, a radio wave signal, an X-ray radiation signal and a gamma radiation signal.

The various apparatuses and methods according to the above aspects can be combined with any of the features, examples and effects described in the present application.

BRIEF DESCRIPTION OF THE DRAWINGS

The above, as well as additional object, features and advantages of the present inventive concept will be better understood through the following illustrative and non-limiting detailed description, with reference to the appended drawings.

FIGS. 12-18B are schematic views of further examples of apparatuses for treating reflux disease.

FIG. 19A shows the apparatus in an expanded state and FIG. 19B shows the apparatus in a constricting state.

FIGS. 20A-21 are schematic views of various examples of apparatuses for treating reflux disease.

FIGS. 22-23C are schematic views of various examples of methods for treating reflux disease and/or implanting an apparatus for treating reflux disease.

FIGS. 29-38B are schematic views of various examples of apparatuses for treating reflux disease.

FIGS. 46A-C, 47 and 48 illustrate communication systems according to some embodiments.

DETAILED DESCRIPTION

Figure 1:
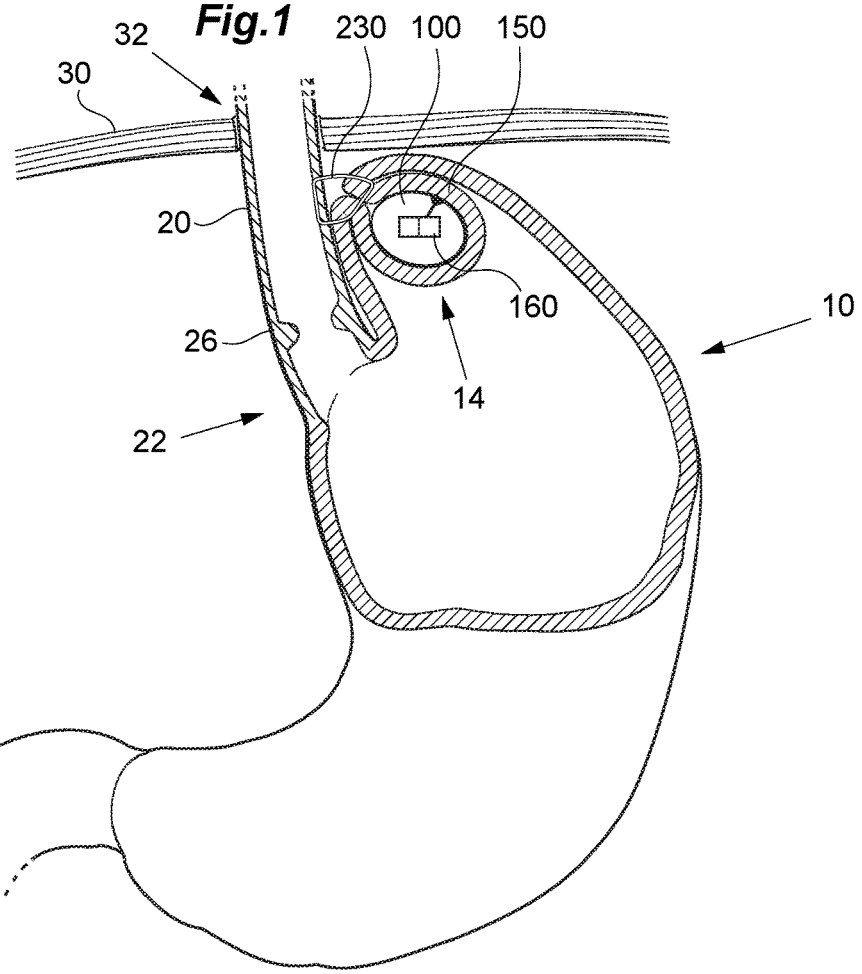
FIGS. 1-11 are schematic views of various examples of apparatuses for treating reflux disease, wherein the apparatuses are implanted in the body of the patient.

In the following a detailed description of embodiments of the invention will be given with reference to the accompanying drawings. It will be appreciated that the drawings are for illustration only and are not in any way restricting the scope of the invention. Thus, any references to directions, such as "up" or "down", are only referring to the directions shown in the figures. It should be noted that the features having the same reference numerals have the same function, a feature in one embodiment could thus be exchanged for a feature from another embodiment having the same reference numeral unless clearly contradictory. The descriptions of the features having the same reference numerals should thus be seen as complementing each other in describing the fundamental idea of the feature and thereby showing the features versatility.

FIG. 1 is a schematic illustration of an apparatus 100 according to some embodiments of the present disclosure. The apparatus 100 may be used for treatment of a human patient suffering from gastroesophageal reflux disease (GERD), also referred to as reflux disease. As illustrated in the present figure, the apparatus 100 may comprise a movement restriction device 110 configured to be implanted in the stomach 10 for hindering the cardia 22 from sliding through the diaphragm opening 32, and an electrode arrangement 150 for stimulating and exercising muscle tissue of the stomach 10 to improve the conditions for long-term implantation.

The movement restriction device 110 may be arranged to rest against a fundus wall portion 14 of the stomach 10. In the present example, the movement restriction device 110 is arranged to rest against the outside of the stomach wall. However, the movement restriction device 110 may in alternative examples and implementations be arranged to rest against the inside of the stomach wall.

The movement restriction device 110 may have a shape and size that allows it to be fully or at least partly invaginated by the fundus wall portion 14. This may be achieved by forming a pouch or recess in the fundus wall portion 14 and at least partly closing the opening of the pouch or recess so as to hinder the movement restriction device 110 to be removed from the fundus wall portion 14. The invagination by the fundus wall portion 14 allows for the movement restriction device 110 to be implanted at a position between the patient's diaphragm 30 and a lower portion of the fundus wall 12, such that movement of the cardia 22 towards the diaphragm 30 is restricted. By restricting this movement, the cardia 22 may be hindered from sliding up towards, and possibly through, the diaphragm opening 32 into the patient's thorax, and the supporting pressure against the cardiac sphincter 26 exerted from the abdomen can therefore be maintained.

As illustrated in the example in FIG. 1, the movement restriction device 110 may be coupled, of affixed to the esophagus 20 at a position above the cardiac sphincter 26. The affixation of the movement restriction device 110 may preferably be of an indirect nature, achieved by affixing a part of the fundus 14 to the esophagus 20 such that the invagination can act as a mechanical stop against the diaphragm 30 when the esophagus is moving upwards through the diaphragm opening 32. Further, in order to protect the tissue of the esophagus 20 from being damaged by the movement restriction device 110, the movement restriction device 110 may be implanted such that a part of the fundus is arranged between the movement restriction device 110 and the outside of the esophagus 20.

The shape and size of the movement restriction device 110 is an important factor for allowing the invagination to act as a mechanical stop against the diaphragm 30. Preferably, the movement restriction device 110 may have a size and shape that allows for the invagination to be sufficiently large to hinder the fundus wall portion 14 to slide through the diaphragm opening 32 together with the cardia. Further, the movement restriction device 100 may have a size and shape that allows it to be invaginated by the fundus 12 of the stomach without causing an unjustified reduction of the total volume of the stomach cavity. In addition to this, the movement restriction device 100 may at the same time be sufficiently small to allow it to generate a mechanical stop against the diaphragm muscle while leaving the food passageway substantially intact and unaffected. Thus, the movement restriction device 100 disclosed herein advantageously allows for the symptoms of reflux disease to be addressed while reducing the risk for compressing the food passageway.

To facilitate invagination and reduce the risk for damaging the tissue of the fundus wall portion 14 the movement restriction device 110 may have a substantially smooth outer surface. Any corners, edges, joints, or seams may be rounded so as not to damage or irritate the tissue against which the movement restriction device 110 may rest when implanted. In some examples the movement restriction device 110 may have a rounded shape, for example conforming to a sphere, a spheroid, or an egg.

The minimum width of the movement restriction device 110, as measured from side to side, may in some examples be 30 mm or larger, such as 40 mm or larger. Additionally, or alternatively a minimum outer circumference of the movement restriction device 110 may be 150 mm or less, such as 130 mm or less, such as 110 mm or less. In further examples, the minimum outer circumference may be 90 mm or less, such as 70 mm or less, such as 50 mm or less, and such that 30 mm or less. It will however be appreciated that the dimensions of the movement restriction device may vary according to the anatomy of the actual individual into which the movement restriction device 110 is to be implanted. The size and shape of the movement restriction device 110 may be adapted to the individual patient to allow for the invagination to act as a mechanical stop as outlined above and thereby have an effect on reflux disease.

The movement restriction device 110 may be formed of a biocompatible material that is suitable for long-term implantation in the human body. Alternatively, or additionally, the outer surface of the movement restriction device 110 may be provided with a layer or coating of such a material. Examples of biocompatible materials include titanium or a medical grade metal alloy, such as medical grade stainless steel. In an alternative, movement restriction device 110 may be made from of comprise a ceramic material such as zirconium carbide, or a stiff medical grade polymer material such as Ultra-high-molecular-weight polyethylene (UHMWPE) or Polytetrafluoroethylene (PTFE) or a thermoplastic polyester such as polylactide (PLA). Movement restriction device 110 could also comprise at least one composite material, such as any combination of metallic/ceramic and polymer materials or a polymer material reinforced with organic or inorganic fibers, such as carbon or mineral fibers. Further, the movement restriction device may comprise an enclosure made from one of or a combination of: a carbon based material (such as graphite, silicon carbide, or a carbon fiber material), a boron material, a polymer material (such as silicone, Peek®, polyurethane, UHWPE or PTFE), a metallic material (such as titanium, stainless steel, tantalum, platinum, niobium or aluminum), a ceramic material (such as zirconium dioxide, aluminum oxide or tungsten carbide) or glass.

Further, the movement restriction device 110 may according to some examples be configured to be introduced into the patient's body by means of a gastroscope or an intraluminal instrument, thereby allowing the apparatus 100 to be implanted by means of natural orifice transluminal endoscopic surgery (NOTES). Hence, the movement restriction device 110 may have a shape and size allowing it to be introduced and pass through a tubular instrument. In some examples, the movement restriction device 110 may be configured to change its shape, preferably resiliently, to temporarily assume a smallest width that allows for the movement restriction device 110 to pass through such an instrument.

The apparatus 100 may further comprise an electrode arrangement 150 configured to be arranged between the movement restriction device 110 and the stomach wall portion 14 when the apparatus 100 is implanted. The electrode arrangement 150 may be configured to electrically stimulate muscle tissue of the stomach wall portion 14 so as to exercise the muscle tissue and thereby improve the conditions for long term implantation of the movement restriction device 110. The electrode arrangement 14 may comprise at least one electrode element 152, which may be configured to abut the tissue against which the movement restriction device 110 is arranged to rest when implanted and to transmit electrical impulses to the muscle tissue. It is appreciated that the electrode element 152 may be arranged in direct contact with the muscle tissue, or in indirect contact via intermediate tissue such as for example connective tissue or fibrous tissue. Thus, the electrode arrangement 150 may be configured to rest against, abut or engage the tissue at least partly surrounding the implanted movement restriction device 100. The interaction between the electrode arrangement 150 and the muscle tissue will be described in greater detail in connection with FIGS. 38-41.

The electrode element 152 may be attached directly to an outer surface of the movement restriction device 110, as shown in FIG. 1. In some examples, however, the electrode element 152 may be arranged on a support, such as a flexible patch, which may be configured to be attached to the medical implant. In further examples the electrode arrangement 150 may be provided as a separate item, physically distinct from the movement restriction device 110.

The apparatus 100 may further comprise an implantable energy source 160, which may be configured to supply the electrode arrangement 150 with electrical power for the electrical stimulation of the muscle tissue. The energy source 160 may be integrated in the in the movement restriction device 110 as shown in the present figure, wherein the energy source 160 is placed inside the movement restriction device 110 and electrically connected to the electrode element 152 arranged between the outer surface of the movement restriction device 110 and the fundus wall portion 12. The energy source 160 may in some examples be arranged outside the movement restriction device 110 as well, forming as a separate structural entity that can be implanted in the abdomen or elsewhere, such as subcutaneously.

According to some examples the energy source 160 may comprise a primary cell, i.e., a battery designed to not be recharged. In further examples, the energy source 160 may comprise a secondary cell designed to be recharged, preferably by means of an external energy source located outside the patient's body. Various examples of charging of the energy source 160 and powering of the electrode arrangement 150 is described in connection with FIGS. 42-44, together with examples of how to control and operate the electrode arrangement 150.

Figure 2:
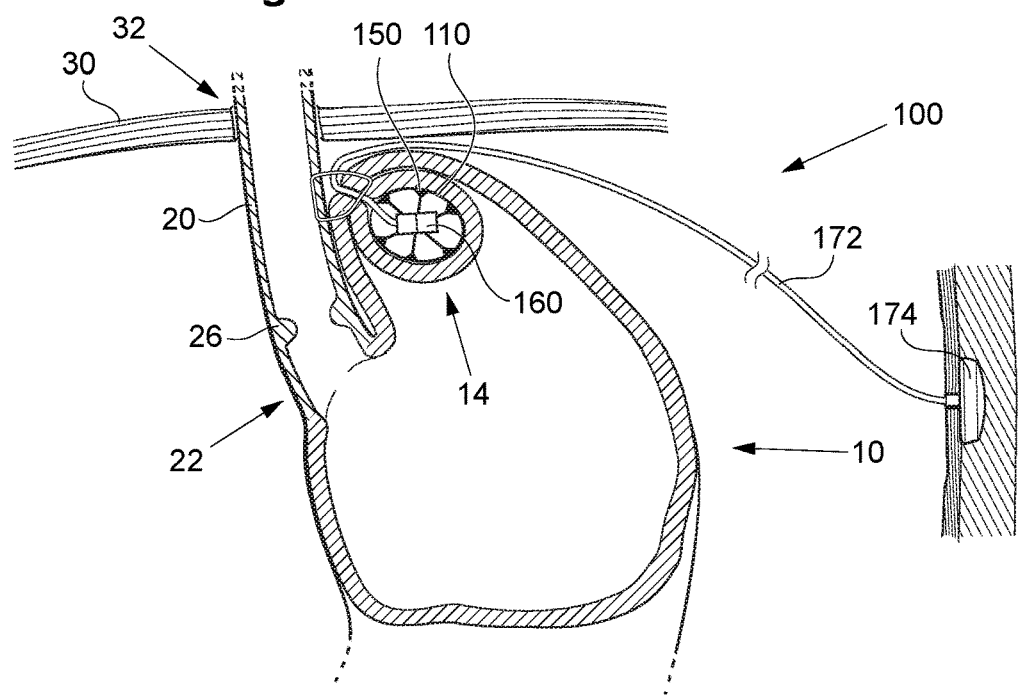

FIG. 2 is a schematic illustration of an apparatus 100 according to some embodiments, which may be similarly configured as the embodiments discussed with reference to FIG. 1. Hence, the apparatus 100 is shown when implanted in a patient to treat reflux disease, and may comprise a movement restriction device 110 and an electrode arrangement 150 for generating an electric signal causing the muscle cells of the fundus wall portion 14 to contract and relax repeatedly. This action, or exercising of the cells by means of the electrode arrangement as shown in FIGS. 1 and 2 has been found to have a positive impact in terms of preventing deterioration and damage of the tissue and help increasing tolerance of the tissue for pressure and mechanical forces generated by the medical implant.

The present example differs from the one of FIG. 1 in that the movement restriction device is coupled to a user interface allowing the patient or persons, such as medical staff, to interact with the apparatus 100. More specifically, the user interface may allow for communication with the implant and/or control of the operation of the implant. It may also comprise means for supplying power to the implant. The user interface may for example comprise a peripheral device 174, such as a regulator or a push-button, that is connected to the movement restriction device 110 via a communication channel 172 such as a wiring or electrical lead. The peripheral device 174 may for example be implanted subcutaneously so as to facilitate access from outside the body. A user, such as the patient himself or a medical staff may interact with the peripheral device 174 to regulate or control the electrical stimulation of the muscle tissue. The peripheral device 174 may for example be used to initiate or end the stimulation, or to adjust the electrical signal used for the stimulation, as described in connection with FIGS. 38-41. The regulation and control of the electrical stimulation may be provided by a controller (not shown), which may be arranged within the movement restriction device 110, integrated in the peripheral device 174, or implanted elsewhere in the body or arranged external to the body. In case of the controller being arranged outside the body, control signals may be sent to the implanted apparatus via the peripheral device 174. Such a controller may for example comprise an energy source, an electric switch, or an injection port for varying a volume of the movement restriction device, depending on actual circumstances and application of the implant.

The electrode arrangement 150 may comprise a plurality of electrode elements 152 distributed over the outer surface of the movement restriction device 110 so as to allow for the tissue abutting the movement restriction device to be electrically stimulated and exercised. Each of the electrode elements 152 may comprise a contact pad, or contact surface, configured to form a junction with the surrounding tissue and which is electrically connected to a circuitry inside the movement restriction device 110. The circuitry may be configured to generate an electrical signal, for example comprising a pattern of electrical pulses, that is transmitted to the muscle tissue via the electrode elements 152.

Figure 3:
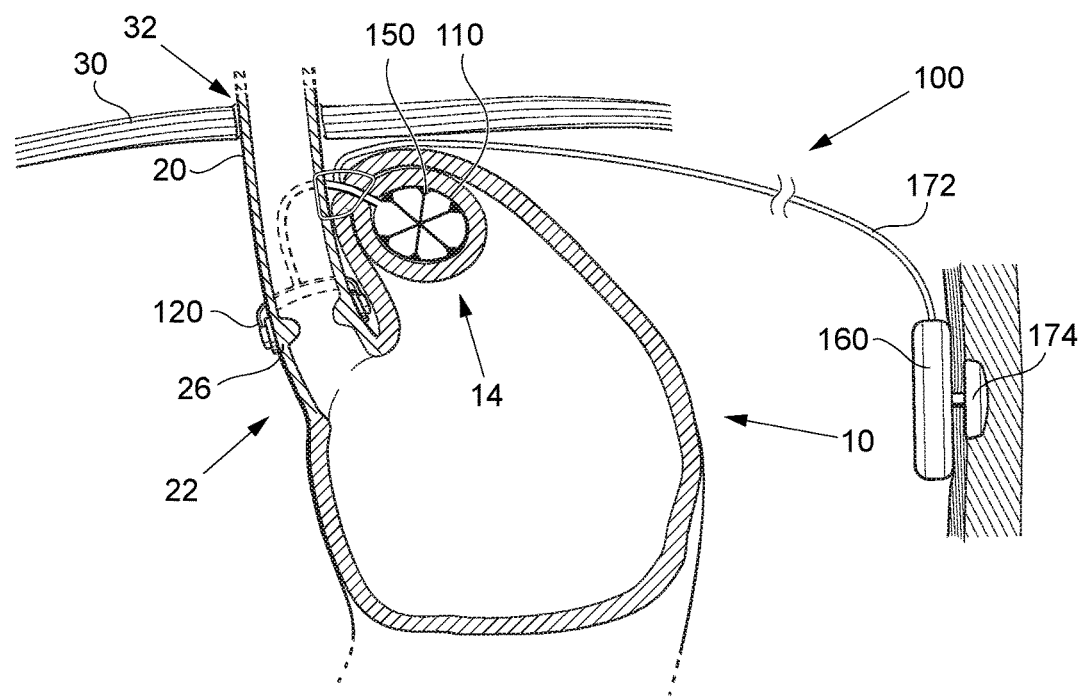

FIG. 3 illustrates an apparatus 100 for treating reflux disease of a human patient, when implanted in the patient. The apparatus 100 may be similarly configured as the apparatuses disclosed in connection with FIGS. 1-3, with the difference of an elongated support device 120 which may be configured to at least partly encircle the esophagus 20. Hence, the apparatus 100 of FIG. 3 may comprise a movement restriction device 110 configured to be implanted to hinder the cardia from sliding through the diaphragm opening as discussed above, and an elongated support device 120 that may be connected to the movement restriction device 110 in a manner that allows the elongated support device 120 to be held in place around the esophagus 20 by the movement restriction device 110. The elongated support device 120 may comprise a mechanical stability, or rigidity that allows for its position relative to the esophagus 20 to be determined mainly by the position and orientation of the movement restriction device 110. Thus, the elongated support device 120 may be implanted and kept in position without having to be secured to the tissue of the esophagus 20.

The elongated support device 120 may be formed as a bracket or brace having a shape that allows it to follow at least a part of the outside of the esophagus 20. In some examples, the elongated support device 120 may have a shape conforming to a "C". The elongated support device 120 may be formed of the same material as the movement restriction device 110, or by a different material. Examples of materials include metals and polymers. Further, the elongated support device 120 may comprise a surface layer or coating configured to hinder or reduce growth of fibrotic tissue.

The elongated support device 120 may be integrally formed with the movement restriction device 110, such that the movement restriction device 110 and the elongated support device 120 form a single piece. The elongated support device 120 may hence be referred to as a protrusion of the movement restriction device 110, having a length and orientation relative to the body of the movement restriction device 110 that allows for the protrusion to be arranged at least partly around the esophagus 20. In alternative examples the elongated support device 120 and the movement restriction device 110 may be formed as separate pieces that can be joined or attached to each other when implanted.

Similar to the movement restriction device 110, the elongated support device 120 may be formed of a biocompatible material that is suitable for long-term implantation in the human body. Alternatively, or additionally, the outer surface of the elongated support device 120 may be provided with a layer or coating of such a material. Examples of biocompatible materials include titanium or a medical grade metal alloy, such as medical grade stainless steel. In an alternative, support device 120 may be made from of comprise a ceramic material such as zirconium carbide, or a stiff medical grade polymer material such as Ultra-high-molecular-weight polyethylene (UHMWPE) or Polytetrafluoroethylene (PTFE) or a thermoplastic polyester such as polylactide (PLA). The support device 120 could also comprise at least one composite material, such as any combination of metallic/ceramic and polymer materials or a polymer material reinforced with organic or inorganic fibers, such as carbon or mineral fibers. Further, the support device 120 may comprise an enclosure made from one of or a combination of: a carbon based material (such as graphite, silicon carbide, or a carbon fiber material), a boron material, a polymer material (such as silicone, Peek®, polyurethane, UHWPE or PTFE), a metallic material (such as titanium, stainless steel, tantalum, platinum, niobium or aluminum), a ceramic material (such as zirconium dioxide, aluminum oxide or tungsten carbide) or glass.

The apparatus 100 may further comprise an electrode arrangement 150 comprising an electrode element 154 that is supported by the elongated support device 120, or holder 120 and configured to electrically stimulate muscle tissue of the esophagus 20. The electrode element 154 may hence be arranged between the holder 120 and the outside of the esophagus 20 and configured to transmit an electrical stimulation signal to the tissue of the esophagus 20.

The electrical stimulation of the tissue may be similar as the stimulation described above for the movement restriction device 110, i.e., for exercising the muscle tissue to improve the conditions for long term implantation. However, in additional or alternative examples the electrical stimulation may be configured to cause the cardiac sphincter 26 to contract. In the present example in FIG. 3 the apparatus 100 may be provided with an electrode arrangement 150 for electrical stimulation of the muscle tissue close to the implanted movement restriction device 110 and for electrical stimulation of the cardiac sphincter muscle 26. However, it is appreciated that the electrode arrangement 150 may comprise an electrode element 154 for the stimulation of the cardiac sphincter 26 only. In other words, the electrode arrangement 150 at the movement restriction device 110 may be optional.

The electrode arrangement 150 may comprise at least two electrode elements 154 that are supported by the elongated support device 120 at two different positions of the cardia 22, preferably at opposing sides, so as to allow for the cardiac sphincter 26 to be electrically stimulated. The electrode arrangement 150 may be controlled to alternate between at least two modes, i.e., an operation mode in which the cardiac sphincter 26 is stimulated with electrical energy and a resting mode, in which the cardiac sphincter 26 is not stimulated to allow the muscle tissue to recover.

The apparatus 100 may further comprise a user interface, comprising a peripheral device 174 and a communication channel 172 which may be similarly configured to the example described above in connection with FIG. 2. The user interface may allow for the patient, or medical staff, to choose when the electrode arrangement 150 should be in the operation mode and when it should be in the resting mode. For example, for some patients is may be sufficient to keep the stimulation temporarily "on" when the patient experiences reflux symptoms, such as at night the patient is lying down, whereas other patients may need the cardiac sphincter 26 to be stimulated continuously, with the exception of when eating.

The user interface may further allow for the power of the electrical signal to be adjusted over time. For example, the power used for the stimulation may be increased to compensate for an increased resistance at the junction between the electrode element 154 and the tissue caused by formation of fibrotic tissue.

As indicated in the present figure, the apparatus 100 may comprise an energy source 160 for supplying the electrode arrangement 150 with electrical power. The energy source 160 may be implantable, for example at a location outside the movement restriction device 110, such as subcutaneously as illustrated in FIG. 3. The communication channel 172 may hence be configured to convey the electrical power, i.e., the electrical signal, from the energy source 160 to electrode arrangement 150. The communication channel 172 may for example comprise an electrical conductor for electrically connecting the electrode arrangement 150 of the elongated support device 120 (and, optionally, the movement restriction device 110) with the energy source 160.

It will be appreciated that the movement restriction device 110 may be implanted in the fundus wall portion 14 is a number of different ways, and that FIGS. 1-3 are merely illustrative examples. In FIGS. 1-3 the movement restriction device 110 is invaginated in the fundus wall portion 14 from outside the stomach. A plurality of stomach-to-stomach sutures or staples may be applied to maintain the invagination intact and the movement restriction device 110 in the desired position relative to the cardia 22 and the diaphragm 30 of a standing patient. This allows for a growth of fibrotic tissue for keeping the invagination intact over time.

Figure 4:
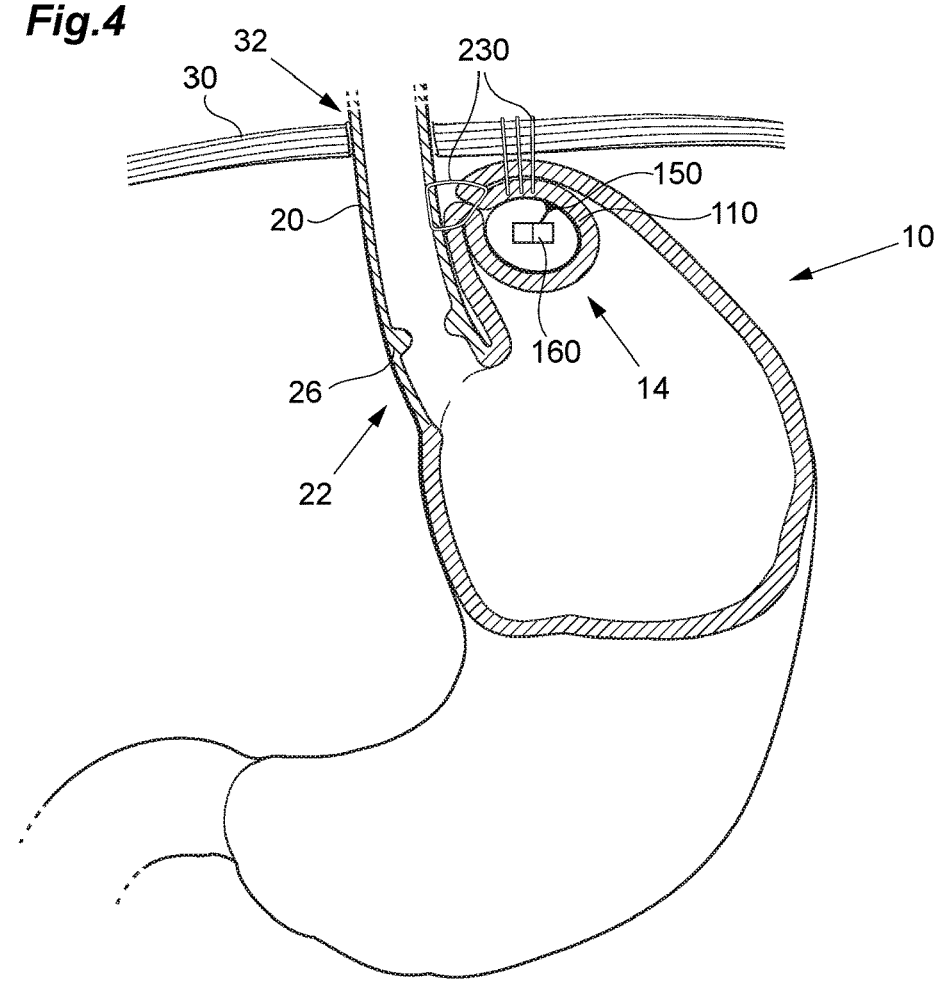

Additionally, or alternatively, an affixation may be provided between the fundus wall portion 14 and the diaphragm 30, and/or the fundus wall portion 14 and the esophagus 20 as illustrated in FIG. 4. The movement restriction device 110 depicted in FIG. 4 may be similarly configured as the embodiments discussed in connection with FIGS. 1-3, and FIG. 4 hence discloses a movement restriction device 110 implanted in in the fundus 12 and arranged at a position above the cardia 22 so as to provide a mechanical stop reducing the symptoms of reflux disease. The movement restriction device 110 may also comprise an electrode arrangement 150 for electrically stimulating and exercising the muscle tissue affected by the implanted device 110, as described above.

However, in the example shown in FIG. 4, the movement restriction device 110 is invaginated from the inside of the stomach 10, instead of from the outside of the stomach 10. The movement restriction device 110 is hence adapted to rest against a portion of the inside wall of the fundus wall portion 14 in a position between the diaphragm 30 and at least a portion of the lower part of the invaginated stomach fundus wall 12. After invagination, a number of stomach-to-stomach sutures or staples may be applied from the inside of the stomach 10 to keep the invagination intact and to allow growth of tissue to keep the invagination over time. Additional affixations may be provided between the outside of the fundus wall portion 14 and the esophagus 20 and/or the diaphragm muscle 30 to hold the movement restriction device 110 in the desired position.

Figure 5:
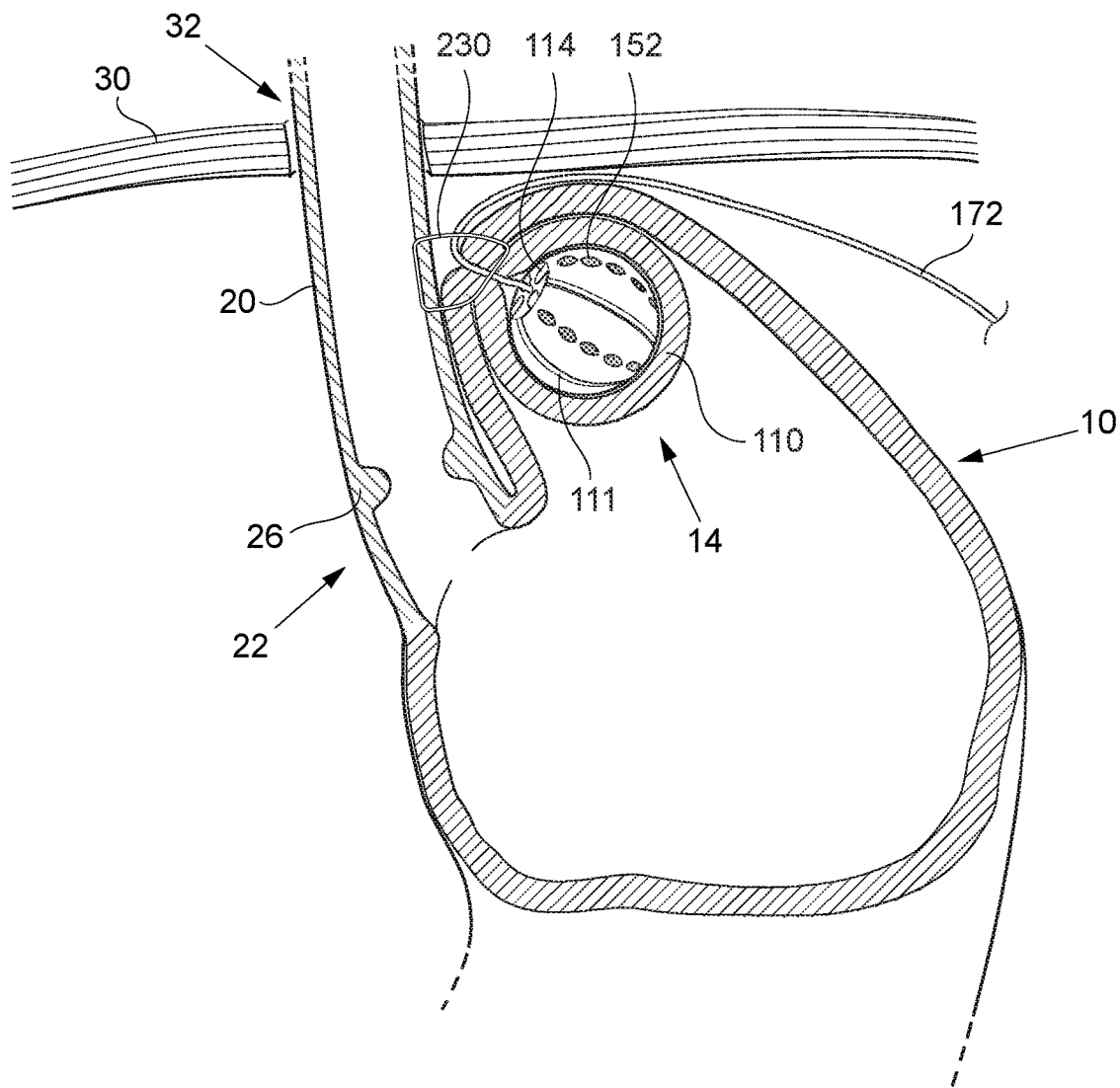

The movement restriction device 110 disclosed in FIGS. 1-4 may have several different configurations and may not necessarily be limited to the schematic versions outlined therein. Other configurations and designs are conceivable within the inventive concept, as defined by the appended claims. An example of such a variant is illustrated in FIG. 5, showing a movement restriction device 110 similar to the ones in FIGS. 1-4 but formed of a plurality of segments 111 that are configured to be attached to be assembled into a complete movement restriction device 110. The segments 111 may for example be secured to each other by means of mutually engaging structures 114 such as protruding slits and receiving grooves, snap-fit connectors, or the like. In the present example, the movement restriction device 110 may be formed of five segments 111: four outer parts 112 and an inner, core part 113 around which the outer parts 112 may be arranged to form a rounded and substantially smooth body suitable for invagination. The segments 111 may be configured to be securely attached to each other, or to be loosely fitted and kept in their right position when invaginated by the surrounding fundus wall 12. In some examples, the segments 111 may be secured to each other by means of a wire. The wire may be biodegradable and eventually dissolved. The segments 111 may be configured to be introduced in the body of the patient separately, one by one, and assembled into the movement restriction device 110 in connection with being implanted.

As shown in the present figure, a plurality of electrode elements 152 may be arranged on an outer surface of the segments 111, i.e., the surface of the outer parts 112 that is to be arranged to rest against the fundus wall portion 14 when the assembled movement restriction device 110 is implanted. The segments 111 may be electrically connected to each other to allow for an electrical stimulation signal to be transmitted to the electrode elements 152 on the outer surface of the movement restriction device 110.

The movement restriction device 110 according to any of the above-mentioned examples may have a volume that is adjustable or non-adjustable after implantation. In case of a non-adjustable volume, the movement restriction device 110 may be formed of a body (or several segments) being solid, i.e., which is not hollow and/or comprises substantially the same material throughout. This may allow for the shape to be varied, for example during insertion into the body, such as through a tubular instrument, while the volume may be substantially the same. In case the movement restriction device 110 is adjustable in terms of volume, the device may be formed of a body (or several segments) comprising one or several cavities or voids capable of accumulating an releasing a fluid for causing a corresponding expansion and reduction of the movement restriction device 110. The fluid may for example be a gas or a liquid, such as a gel, which may be introduced and extracted from the movement restriction device 110 prior to implantation, during the implantation procedure, or after it has been implanted.

Figure 6:
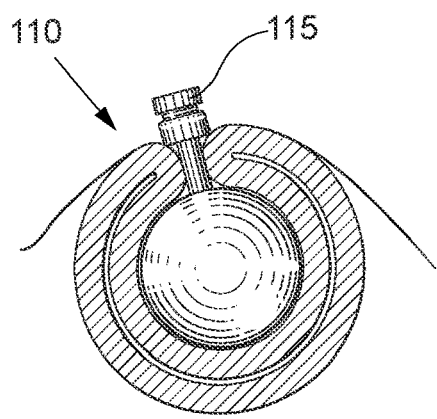
Figure 6:
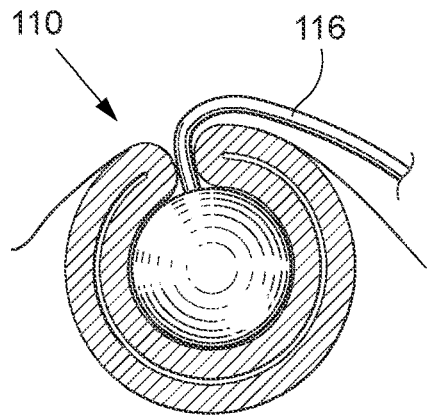

FIGS. 6a and 6b illustrate an example of a movement restriction device 110, similar to the ones discussed with reference to FIGS. 1-5, comprising a fluid communication port 115, or injection port, that can be used to add or remove a fluid to/from the inside of the movement restriction device 110 to thereby vary its volume. It may be desired to adjust the volume of the movement restriction device 110 post-operatively in order to fine tune or adjust the movement restriction device's 110 capability of acting as a mechanical stop against the diaphragm. It may for example be determined after the implantation, in a subsequent evaluation of the results of the operation, that an implant of another size would have been more optimal for the specific patient. This may be solved by adjusting the volume of the implant posit-operatively.

As shown in the present figures, the port 115 may be positioned such that it is accessible from outside the invagination, i.e., such that the port 115 can be accessed by an instrument or connection without having to penetrate the fundus wall portion 14. In FIG. 6a the port protrudes to the outside of the invagination, passing between sutures or staples used for at least partly closing the pouch in which the movement restriction device 110 is arranged. The port 115 may thus be available for connection to a tube or a syringe from the abdominal region of the patient. In FIG. 6b the port 115 is positioned inside the invagination and accessed by a tube 116 that is connected to the port 115 and extends into the abdominal region of the patient.

The volume of the movement restriction device 110 may according to some examples be adjustable non-invasively after implantation. A non-invasive adjustment may be allowed by means of the tube 116, that may be connected to the port 115 and led to the outside of the patient's body or to an implanted volume regulator, such as a pump or a reservoir, for non-invasive regulation of the volume of the movement restriction device 110. According to other examples, the volume of the movement restriction device 110 may be adjustable invasively, e.g. by means of an instrument that is inserted into the patient's body and connected directly to the port 115 or the tube 116 for adding or removing fluid from the movement restriction device 110. Alternatively, or additionally, an instrument such as a syringe may be inserted directly into the inside of the movement restriction device 110, penetrating and passing through the surrounding fundus wall portion 14 on the way to the movement restriction device 110.

It will be appreciated that the adjustable and non-adjustable characteristics of the volume of the movement restriction device 110 generally refer to a permanent state of the movement restriction device 110. In other words, an adjustment of the volume may, in the above context, result in a new volume that is substantially constant over time until the amount of fluid in the movement restriction device 110 is varied again. This may be contrasted with temporary changes of the volume, which for example may be caused by a temporary or resilient compression of the material forming the movement restriction device 110. Such a temporary change in volume may for example occur during introduction of the movement restriction device 110 into the body, e.g. via a tubular instrument. In other words, the movement restriction device 110 according to the examples outlined above with reference FIGS. 1-6 may be flexible or elastic, allowing the device 110 to at least temporarily assume different shapes and, in some examples, volumes, in response to being exposed to external mechanical forces.

An apparatus for treating reflux disease, as outlined above, will now be described with reference to FIGS. 7-13. The figures schematically illustrate an apparatus 100 comprising an at least partly ring-shaped implantable movement restriction device comprising a first portion 110 configured to be at least partly invaginated by a first wall portion of the patient's stomach 10 and arranged such that at least a part of the first portion of the apparatus 100 is arranged above the cardia 22 of the patient's stomach 10, and such that movement of the cardia towards the diaphragm is restricted to prevent the cardia 22 from sliding through the diaphragm opening 32 into the patient's thorax. The configuration and function of the first portion 110 of the apparatus 100 may hence be similar to the movement restriction devices 110 previously described with reference to FIGS. 1-6. Further, the apparatus 100 may comprise an electrode arrangement 150 which may be similar to the electrode arrangement 150 described in connection with the examples of FIGS. 1-6, and may hence be configured to be arranged between the first portion 110 of the apparatus 100 and the first wall portion 14 to electrically stimulate muscle tissue of the first wall portion 14 to exercise the muscle tissue and thereby improve the conditions for long term implantation of the apparatus 100.

The apparatus 100 may further comprise a second portion 120, which may be configured to be arranged on an opposite side of the cardia 22, as seen from the first portion 110. The first portion 110 and the second portion 120 may together form the at least partly ring-shaped movement restriction device 110, 120, which as indicated in the present figures may be configured to be arranged to at least partly encircle the esophagus 20 of the patient. The first portion 110 may for example be configured to be arranged on the fundus side of the esophagus 20, whereas the second portion 120 may be configured to be arranged on the side of the esophagus 20, i.e., the side opposing the fundus 12. The movement restriction device 110 may in some examples be formed of a substantially smooth, ring-shaped body configured to encircle the esophagus 20. The movement restriction device 110 may for example have a shape conforming to a torus, with the first portion 110 forming the part arranged at the fundus side of the esophagus and the second portion 120 forming the part arranged at the opposite side of the esophagus 20.

Figure 7:
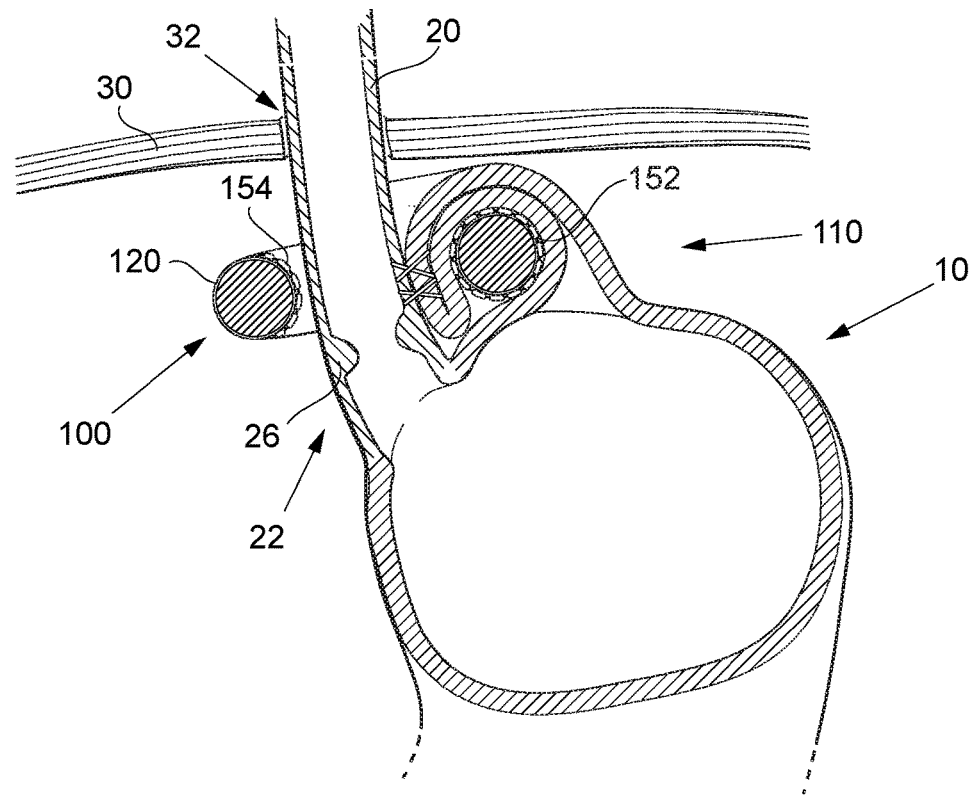
Figure 8:
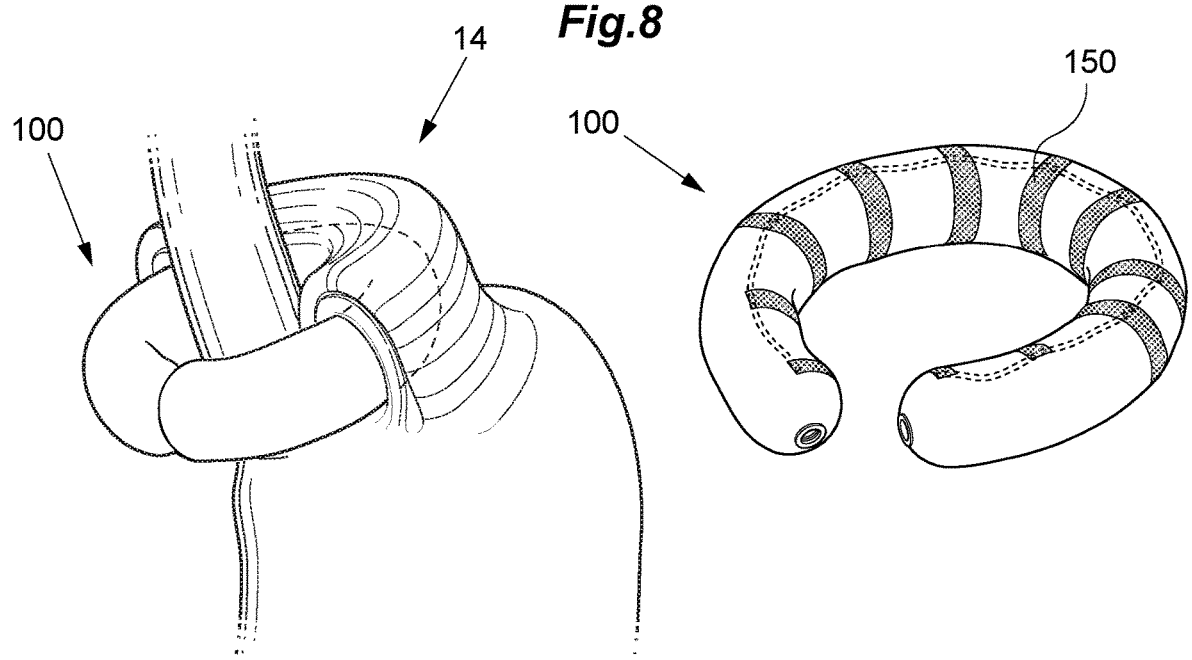
Figure 9:
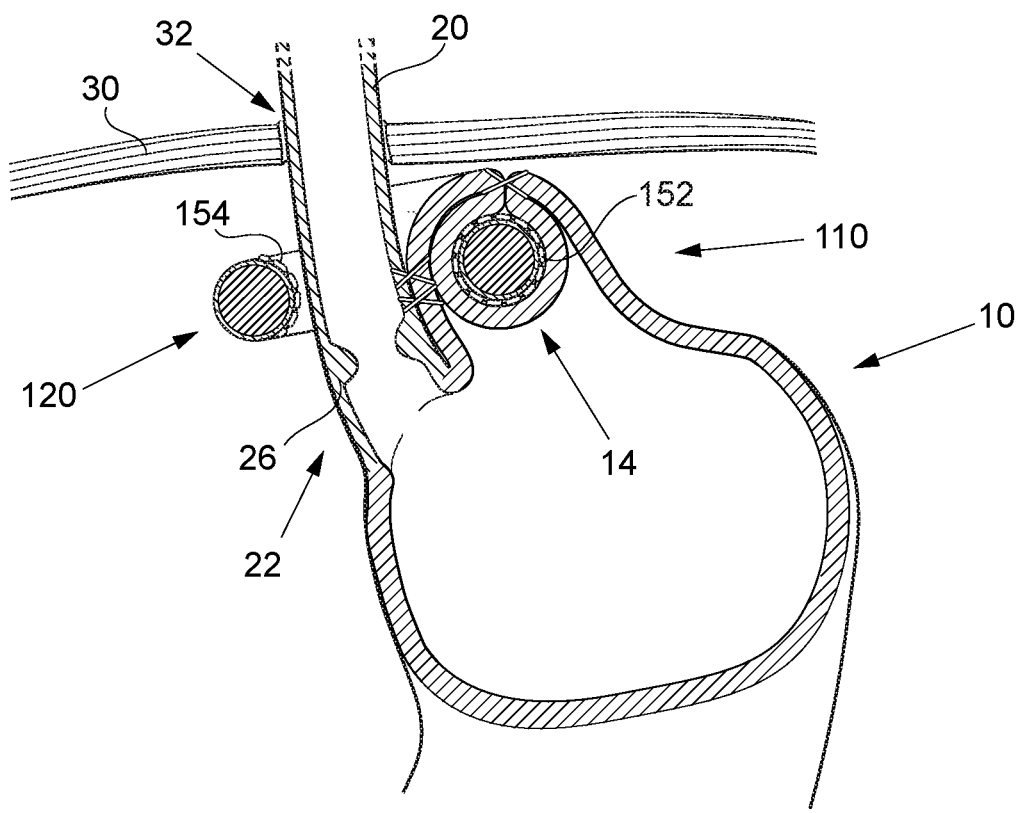

The ring-shaped body of the movement restriction device 110 may comprise an opening, or be possible to open, so as to allow the body to be arranged around the esophagus. After the movement restriction device 110 has been placed around the esophagus 20, the movement restriction device 110 may be affixed in a desired position, preferably at least partly above the cardia 22, by for example invaginating at least one of the first portion 110 and the second portion 120 by the outer wall of the stomach 10, or by wrapping a part of the stomach wall around at least a part of the ring-shaped body. Preferably, the movement restriction device 110 is implanted such that a part of the stomach wall is arranged between the movement restriction device 110 and the outside of the esophagus 20 to as to protect the tissue of the esophagus from being damaged by the movement restriction device 110, 120 abutting the tissue of the esophagus 20. As illustrated in the examples of FIGS. 7-9 a part of the fundus 12 may be arranged between the first portion 110 and the esophagus 20 and at the same time provide an affixation of the device to the stomach 10. Further, the movement restriction device may be provided with a shape and size allowing for a gap to be defined and maintained between the second portion 120 and the side of the esophagus opposite to the fundus side. Due to the affixation of the first portion 110 to the fundus 12, the separating gap between the second portion 120 and the tissue of the esophagus 20 may be maintained after implantation.

Figure 10:
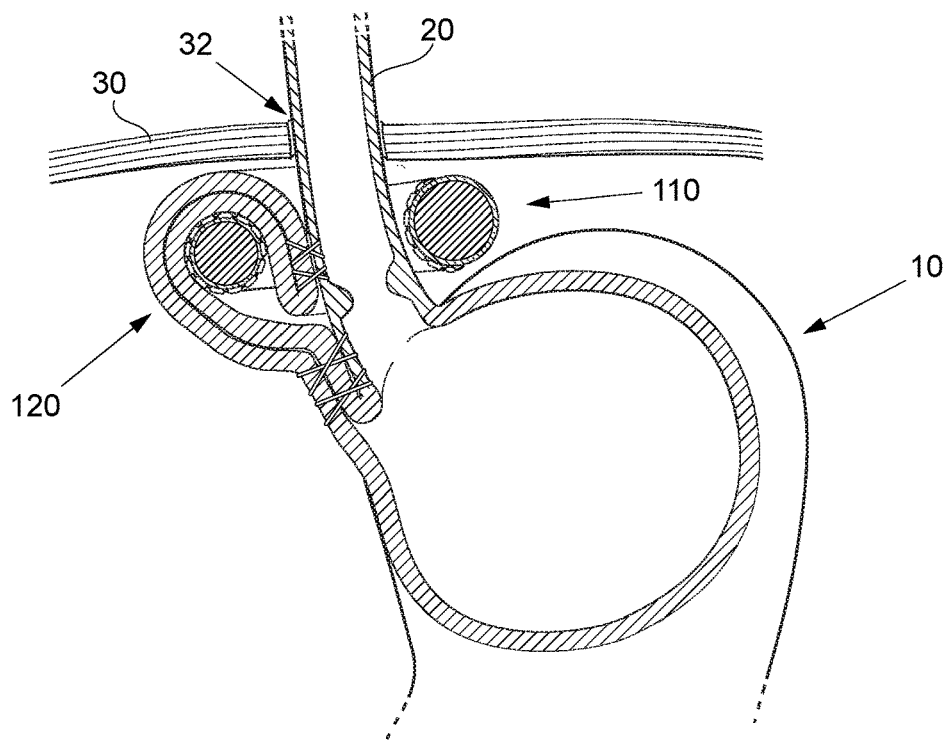

FIG. 10 shows an alternative example, in which the second portion 120 of the movement restriction device 110, 120 is arranged with a part of the stomach wall between the second portion 120 and the esophagus 20, on the side of the esophagus 20 opposing the fundus 12. On the fundus side, however, the first portion 110 may be arranged to define a distance or gap to the esophagus 20, similar to what is described FIGS. 7-9.

Figure 11:
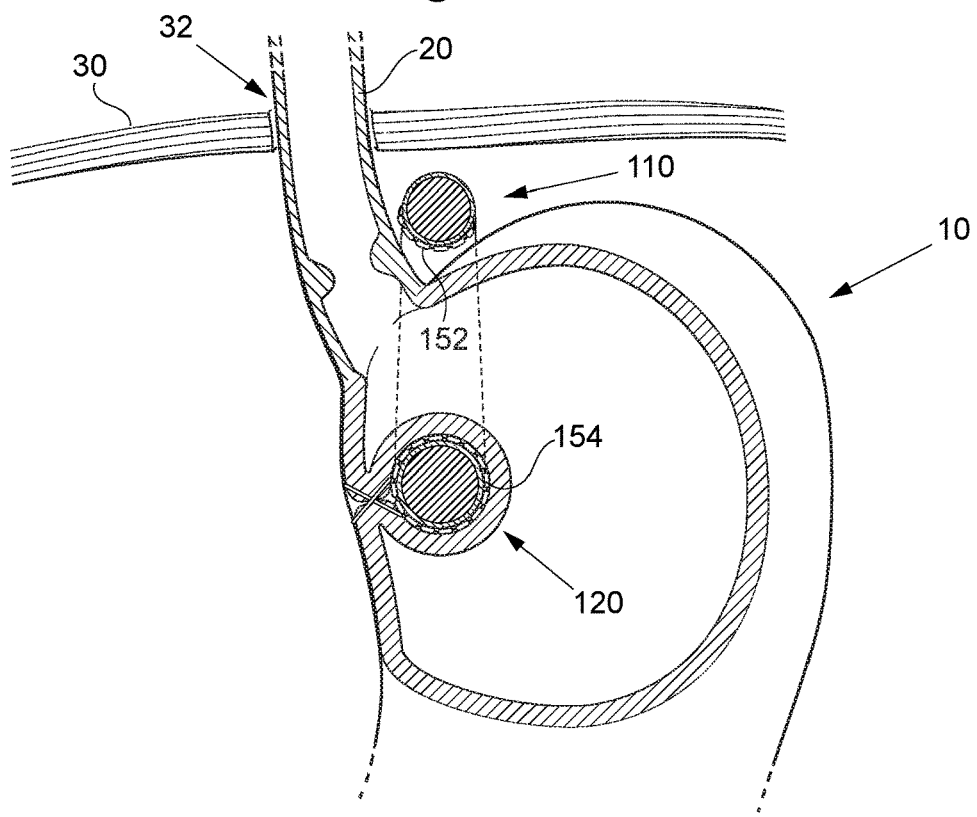

FIG. 11 shows a further example, wherein the first portion 110 may be placed at the angle of His and the second portion 120 invaginated by a pouch protruding into the stomach wall on the opposite side of the esophagus 20. The pouch may be arranged further down, compared to the example in FIG. 10. As a result, the first portion 110 and the second portion 120 may in FIG. 10 be implanted at substantially the same height relative to the cardia, whereas in FIG. 11 only the first portion 110 is implanted at least partly above the cardia 12.

Figure 12:
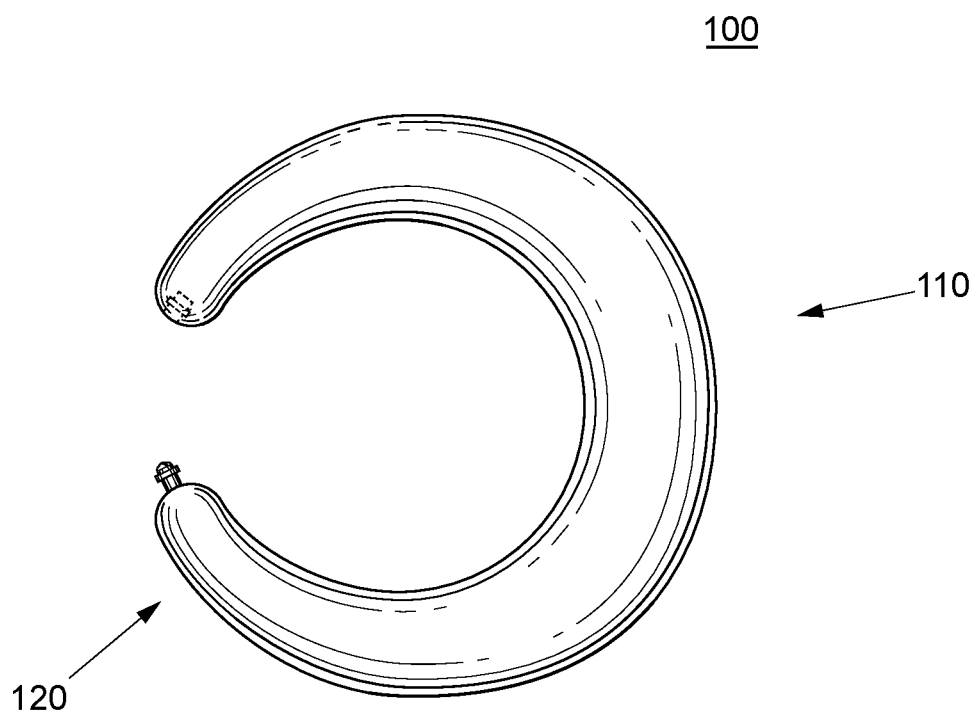
Figure 13:
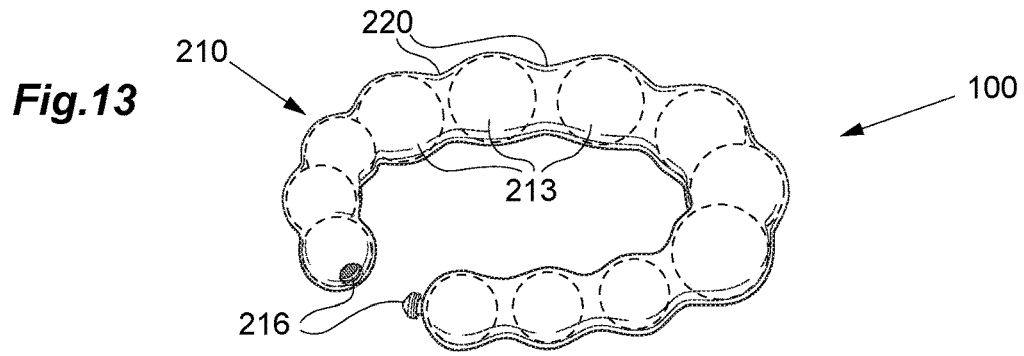

FIGS. 12 and 13 show various examples of at least partly ring-shaped movement restriction devices 110, 120, wherein the first portion 110 and the second portion 120 may be integrally formed into a single piece as shown in FIG. 12, or be formed of a plurality of core elements 213 arranged in a cover 220 as shown in FIG. 13. The movement restriction devices 110, 120 may for example conform to a torus, which may be closed or at least partly closed when implanted. Similar to the apparatuses illustrated in FIG. 7-11, the apparatus may be implanted in a position wherein it at least partly encircles the esophagus 20 and may function as a movement restriction device. The apparatuses may further comprise an electrode arrangement 150.

The electrode arrangement 150 of the examples shown in FIGS. 7-13 may comprise one or several electrode elements 152, 154, which may be arranged between at least one of the first portion 110 and the second portion 120 and the tissue against which the respective portion 110, 120 rests and operate according to principles similar to the ones discussed with reference to FIGS. 1-6. Thus, the electrode arrangement 150 may be configured to electrically stimulate and exercise muscle tissue of the fundus wall 12 or the esophagus 20 to improve conditions for long term implantation, and in some examples to electrically stimulate the cardiac sphincter muscle 26 so as to cause the sphincter to contract. In the latter case, the second portion 120 may be configured to act as an elongated support device for the electrode elements 154 for the cardiac sphincter stimulation, similar to the examples disclosed in connection with the previous figures.

The apparatus 100 may be configured to be at least partly invaginated, or covered, by the stomach wall along at least half of the toroidal length (i.e., the length as seen in the direction of the circumference encircling the esophagus). An example is illustrated in FIG. 8, wherein a toroidally shaped apparatus is at least partly covered by the fundus 14 along at least half the toroidal length. A similar arrangement is illustrated in FIGS. 7, 9, 10 and 11, wherein at least 25%, such as for example 50%, of the circumferential length of the apparatus may be at least partly invaginated or covered by stomach wall tissue.

As shown in the perspective views of FIGS. 8, 12 and 13 the apparatus 100 may be substantially ring-shaped and may comprises two end portions configured to be coupled to each other to form a closed ring. The end portions are configured to be releasably attached to each other, for example by means of a locking mechanism 216 or a fastener 216.

In case of the apparatus being at least partly ring-shaped, or conforming to a torus, the size of the apparatus may be characterized by its poloidal circumference and its toroidal circumference. The poloidal direction may be understood as a direction following a small circular ring around the surface, while the toroidal direction follows a large circular ring around the torus or ring, encircling the central void in which the esophagus may be arranged. In some examples, the poloidal circumference of the apparatus may be larger for the first portion 110 than for the second portion 120, as shown in FIGS. 12 and 13. Preferably, the first portion 110, forming the movement restriction device 110, may have a larger poloidal circumference so as to provide a mechanical stop hindering movement of the cardia towards and/or through the opening in the diaphragm.

In some examples, the first portion 110 may have a minimal width or cross section, as measured orthogonal to the toroidal direction, being 30 mm or larger, such as 40 mm or larger.

In some examples, a minimum poloidal circumference of the first portion 110 of the movement restriction device may be 150 mm or less, such as 130 mm or less, such as 110 mm or less, such as 90 mm or less, such as 70 mm or less, such as 50 mm or less, such as 30 mm or less.

In some examples, a maximum width of a cross section taken across a length direction (i.e. across toroidal direction) of the first portion 110, or movement restriction device 110, may be larger than a maximum width of a cross section taken across a length direction of the second portion 120, or support device 120.

The apparatus 100 may be affixed to the stomach wall in several different ways, all of which may include to at least partly wrap the stomach wall 10 around at least a portion of the apparatus 100 and affixing the stomach wall 10 to itself and/or to the esophagus 20. Some non-limiting examples of placing and affixing the apparatus 100 at the stomach wall 10 will now be discussed with reference to the ring-shaped movement restriction device 110, 120 disclosed in FIGS. 7-13.

In FIG. 7, the movement restriction device has been placed around the esophagus 20, such that the first portion 110 is arranged at the fundus side and the second portion 120 at the opposing side of the esophagus. A part of the fundus wall 12 has then been wrapped around the first portion 110 of the movement restriction device, from the outside of the device and into the center hole of the ring-shaped body, such that the part of the fundus wall 12 is arranged between the inner periphery of the ring-shaped body and the esophagus 20. The part of the fundus wall 12 that is wrapped around the first portion 110 may be considered as a "flap" formed of the fundus wall, which may be formed outside the ring-shape and pushed into the hole defined by the ring-shape and affixed to the esophagus 20.

FIG. 8 shows a perspective view of an apparatus 100 which may be similar to the one in FIG. 7, illustrating the affixation of the first portion 110 of the movement restriction device 110, 120 to the fundus 12. The part of the fundus that is wrapped around the first portion 110 and affixed to the esophagus may form a tunnel through which the ring-shaped body may extend on its way around the esophagus.

FIG. 9 shows an another example, in which the fundus portion closest to the angle of His has been folded to rest against the esophagus, from the angle of His and upwards along the esophagus, and affixed to the esophagus with one or several lines of fasteners, such as staples or sutures, extending along the esophagus. The first portion 110 of the movement restriction device may then be invaginated by another portion of the fundus, arranged further away from the angle of His, such that the movement restriction device is kept in place by the affixation to the esophagus and encircling the esophagus such that the second portion 120 is arranged on the opposite side of the esophagus 20.

Put differently, the method according to FIGS. 7 and 8 may result in the first portion 110 being arranged between the esophagus 20 and the portion of the fundus that is affixed to the esophagus 20, whereas the method according to FIG. 9 may result in the portion of the fundus 12 that is affixed to the esophagus 20 being arranged between the esophagus 20 and the first portion 110 of the movement restriction device. In the former example a part of the fundus may be pushed into the hole of the ring-shaped body from below, whereas in the latter example a part of the fundus may be pushed into the hole from above.

FIG. 10 shows a similar method as in FIG. 7, with the difference that it is the stomach wall on the side opposite to the fundus, i.e., the non-fundus side of the stomach wall, that is wrapped around the second portion 120 and introduced into the hole defined by the ring-shaped body and affixed to the esophagus. The portion of the stomach wall 10 closest to the esophagus 20 may further be folded to rest against the esophagus 20 and affixed to the esophagus 20 similar to the example of FIG. 9 so as to allow the second portion 120 of the movement restriction device to be arranged higher up, and preferably above the cardiac sphincter 26. The portion of the stomach wall closest to the esophagus 20 may be attached to the esophagus 20 before the stomach wall is wrapped around the second portion 120 and introduced into the hole defined by the ring-shaped body.

An apparatus for treating reflux disease of a human patient according to some examples will now be described with reference to FIGS. 14-21. FIGS. 14-21 illustrate an apparatus 100 comprising an elongated core 210 having a length that allows the core 210 to be arranged to at least partly encircle the esophagus 20 of an adult human the patient. The length is variable to allow the core 210 to be arranged in a constricting state for hindering fluid from passing from the stomach 10 into the esophagus 20, and in an expanded state for allowing food to pass into the stomach 10 in response to the patient swallowing. The apparatus may hence by used for treating reflux disease by assisting contraction of the cardiac sphincter 26 and hindering stomach contents to rise up into the esophagus 20. The transition from the constricting state into the expanded state may be caused by the food passing through esophagus 20, wherein the core 210 may be configured to exert an encircling pressure on the esophagus 20 in at least the constricting state. The encircling pressure may for example be generated by an attractor 212 configured to resiliently attracting adjacent portions 213 of the core to one another. Further, the apparatus 100 may according to some example comprise an electrode arrangement 150 comprising an electrode element 154 configured to be arranged between the apparatus 100 and the esophagus 20 and to electrically stimulate muscle tissue of the esophagus 20. The electrical stimulation may for example employed to stimulate the muscle tissue of the outer wall of the esophagus 20 so as to exercise the muscle tissue to improve the conditions for long term implantation of the apparatus 100, and/or to stimulate the cardiac sphincter 26 of the patient to cause the cardiac sphincter 26 to contract.

Figure 14:
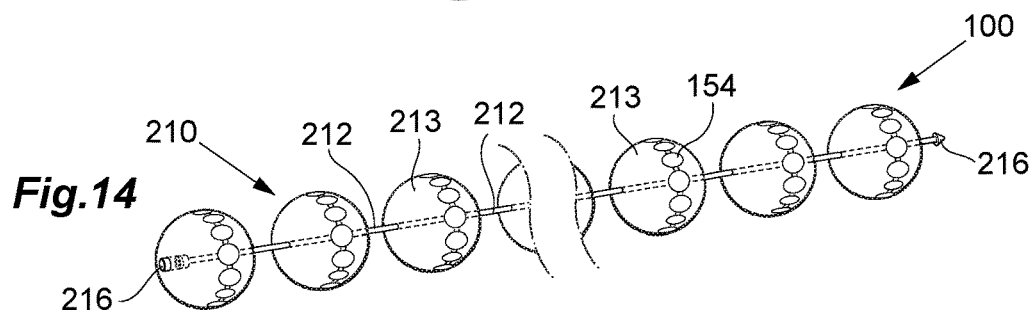

FIG. 14 shows a core 210 comprising an array of adjacent portions 213, wherein neighboring portions 213 of the array are interconnected by an attractor 212. The portions 213 of the array may for example be ball-shaped, having a substantially smooth outer surface suitable for resting against the tissue of the outer wall of the esophagus 20. The portions 213 may for example be formed of a metal or a polymer and may preferably comprise a biocompatible outer surface suitable for long-term implantation in the body. The attractors 212, connecting neighboring portions 213 to each other, may comprise an elastic element, such as an elastic band or string, allowing for the portions 213 to be resiliently pushed away from each other when entering the expanded state (e.g. in response to the patient swallowing a bolus of food), and pulling the neighboring portions 213 towards each other again to assume the constricting state for hinder stomach contents for pass into the esophagus 20. The core 210 may comprise a plurality of attractors 212, wherein each of the attractors 212 may have a first end connected to a first one of the portions 213 and a second end to a second one of the portions 213. Thus, each attractor 212 may be arranged to extend from a first one of a pair of neighboring portions 213 to the other one of the pair of neighboring portions 213. Alternatively, a single attractor 212 may be arranged to interconnect more than two portions 213 of the core 210. As indicated in FIG. 14, the attractor 212 may be formed of a string or band extending through each of the portions 213 of the core 210.

The core 210 may further comprise an attacher 216, or locking means, arranged at the end portions of the array of neighboring portions 213. The attacher 216 may for example comprise a first part, arranged at a first end portion, which can be inserted in, or attached to, a second part arranged at the other end portion of the core 210. Examples of attachers 216 include interlocking components, snap fasteners, and a screw assembles.

Alternatively, or additionally, resiliency of the core 210, which allows it to assume the expanded state and the constricting state and to exert an encircling pressure on the esophagus 20, may be achieved at least part by means of attractive forces between permanent magnets. In this case, the portions of the array may comprise permanent magnets 213, which may be arranged such that there is a mutual attraction between neighboring magnets 213 of the array. The magnets 213 may be attached to each other by a connector or link, such as a band or string 212 as outlined above, which may or may not be elastic so as to further contribute to the resiliency of the core and its ability to exert an encircling pressure on the esophagus 20. The magnets 213 may in some examples be referred to as attractors.

Figure 15:
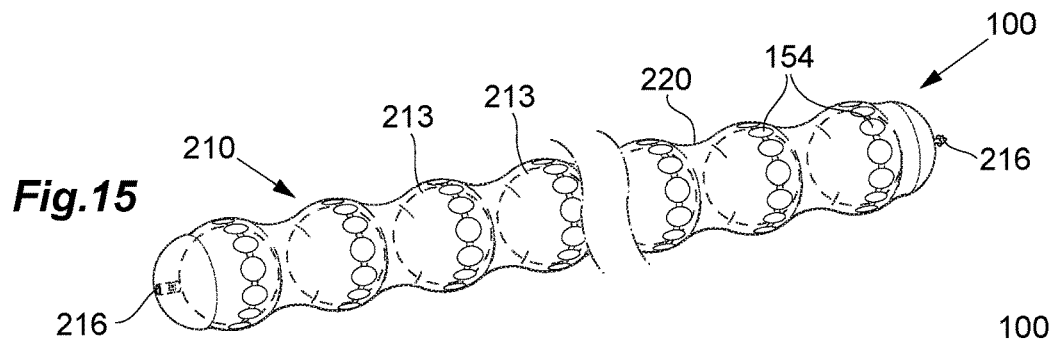

FIG. 15 shows an example wherein the core 210 comprises a plurality of magnetic portions 213, or permanent magnets 213 arranged in an array extending along the length direction of the elongated core 210. The example in FIG. 15 may thus be similarly configured as the apparatus 100 shown in FIG. 14, with the difference that the present apparatus 100 comprises a tubular cover 220 enclosing at least a part of the core 210. The cover 220 may comprise a plurality of portions 222 adapted to bend relative to each other to allow the core 210 to change between the constricting state and the expanded state, when the cover 220 is at least partly covered by fibrotic tissue, without being substantially hindered or impeded by the presence of the fibrotic tissue.

The implantation of a foreign body into the human body tends to cause an inflammatory response. The response generally persists until the foreign body has been encapsulated in a relatively dense layer of fibrotic connective tissue, which protects the human body from the foreign body. The process may start with the implant immediately and spontaneously acquiring a layer of host proteins. The blood protein-modified surface enables cells to attach to the surface, enabling monocytes and macrophages to interact on the surface of the implant. The macrophages secrete proteins that modulate fibrosis and in turn develop the fibrosis capsule around the foreign body, i.e., the implant. In practice, a fibrosis capsule may be formed of a dense layer of excess fibrous connective tissue. The inelastic properties of the fibrotic capsule may lead to hardening, tightness, deformity, and distortion of the implant, which in severe cases may result in revision surgery. On a medical device implanted in the abdomen, in the region of the stomach, the fibrotic capsule has been observed to typically grow a thickness of about 0.5-2 mm.

The presence of such a capsule of fibrotic tissue risks to hinder movement of the elongated core 210 of the apparatus 100 as described in connection with the examples of FIGS. 14-21. In particular, the presence of a relatively thick and inelastic layer of fibrotic tissue may hinder the core's 210 ability to change between the expanded state and the constricting state. To address this issue, the elongated core 210 may be arranged in, or at least partly covered by, the cover 220, which allows the core 210 to change its length without being substantially hindered by fibrotic tissue surrounding the cover 220. This is allowed by the cover 220 being capable of changing its length without stretching the material of which the cover 220 is formed. While the fibrotic tissue may be inelastic and thereby withstanding stretching, it may be easier to bend or fold. Thus, the cover 220 can be considered to make use of the fact that the fibrotic tissue may be more flexible than elastic in its nature, which allows for the apparatus to change its length (or circumference, as it is arranged around the esophagus 20) by folding or bending a plurality of portions of the core relative to each other. Put differently, the cover 220 may be configured to maintain a substantially constant surface as the core changes between the expanded state and the constricting state, thereby allowing for the length of the elongated core 210 to vary without stretching the surrounding fibrotic tissue to a corresponding degree. The cover 220 may thus have a length that exceeds a length of the core 210 when the core 210 is arranged in the constricting state.

FIG. 15 shows an example of a cover 220 which is tubular and arranged to accommodate an array of permanent magnets 213. The permanent magnets 213 may be attached to each other, for example by means of an attractor 212 as discussed above in connection with FIG. 14, or be freely arranged in the cover 220, without any interconnections. In some examples, the permanent magnets 213 may be affixed to the cover 220, such that each permanent magnet 213 may be maintained at a predetermined position relative to the cover 220. When going from the expanded state to the constricting state, neighboring magnets 213 may be pulled towards each other such that the distance between the magnets 213 in the array is reduced. The cover 220 may follow this movement by allowing the portions of the cover 220 arranged between the magnets 213 to fold or bend relative the portions of the cover 220 arranged at the respective magnets 213, such that the cover 220 is configured to be compressible and expandable in its length direction.

The cover 220 may comprises a biocompatible outer surface suitable for long-term implantation in the human body, and preferably for long-term implantation in a position where it rests against an outer surface of the esophagus 20. In some examples, the cover comprises a surface promoting tissue growth. The cover 220 may for example be formed of or at least comprise a polymer material (such as silicone, Peek®, polyurethane, UHWPE or PTFE). Further, the cover may have a wall thickness of 0.1-5 mm. In some examples the cover 220 may be provided with a coating, such as Parylene, polytetrafluoroethylene (PTFE), or polyurethane, or a combination of such coatings, for improving the resistance to wear.

Further, the cover may comprise an electrode arrangement 150, similar to the one discussed above in connection with the examples of FIG. 14. The electrode arrangement 150 may hence comprise at least one electrode element 154 configured to be arranged between the cover 220 and the esophagus 20 for electrically stimulating muscle tissue of the esophagus 20. The electrode element 154 may for example be configured to stimulate muscle tissue at the outer surface of the esophagus so as to improve the conditions for long-term implantation, and/or the cardiac sphincter 26 so as to cause it to contract.

Figure 16:
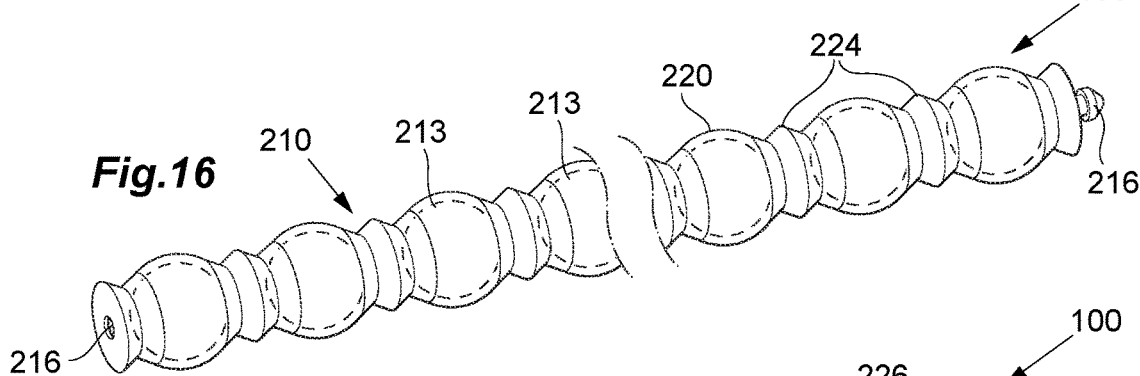

FIG. 16 shows an example of an apparatus 100 that may be similarly configured as the apparatuses discussed in connection with FIGS. 14 and 15. However, as indicated in the present figure, the cover 220 may comprise at least one predefined fold 224 along which the cover is allowed to fold in response to the core 210 varying its length. In some examples, the cover 220 may comprise a bellows-shaped structure of a plurality of lowered portions 225 and elevated portions 226 that allow the cover 220 to vary its length while maintaining its surface area substantially constant. A distance between two elevated portions 226 may be long enough to prevent growth of fibrotic tissue directly connecting to adjacent elevated portions 226. Thus, fibrotic tissue may grow on the surfaces of the lowered portions 225 and the elevated portions 226, but due to the distance between adjacent elevated portion 226 fibrotic tissue may be hindered from growing directly from one elevated portion 226 to another elevated portion 226 without first passing over the intermediate lowered portion 225. The cover 220 may hence comprise a ridges and grooves, or elevated 226 and lowered 225 portions dimensioned such that the connective tissue follows the surface of the elevated 226 and lowered 225 portions and leaves a separating gap between neighboring elevated portions 226, or ridges. In case the fibrotic tissue has a thickness of about 0.5-1.5 mm, as an example, the distance between adjacent elevated portions 226 may be greater than twice the maximum thickness of the fibrotic tissue, i.e., greater than about 3 mm.

Figure 17:
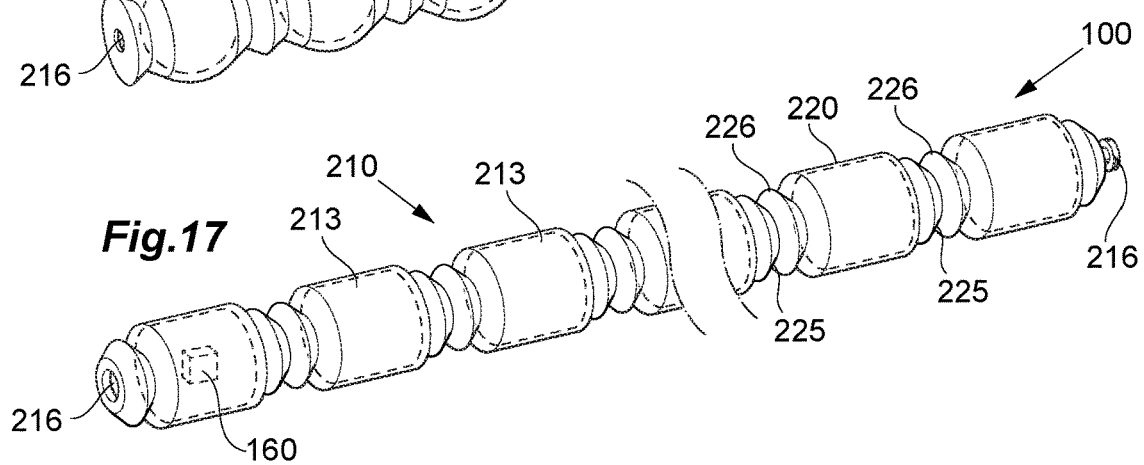
Figure 18:
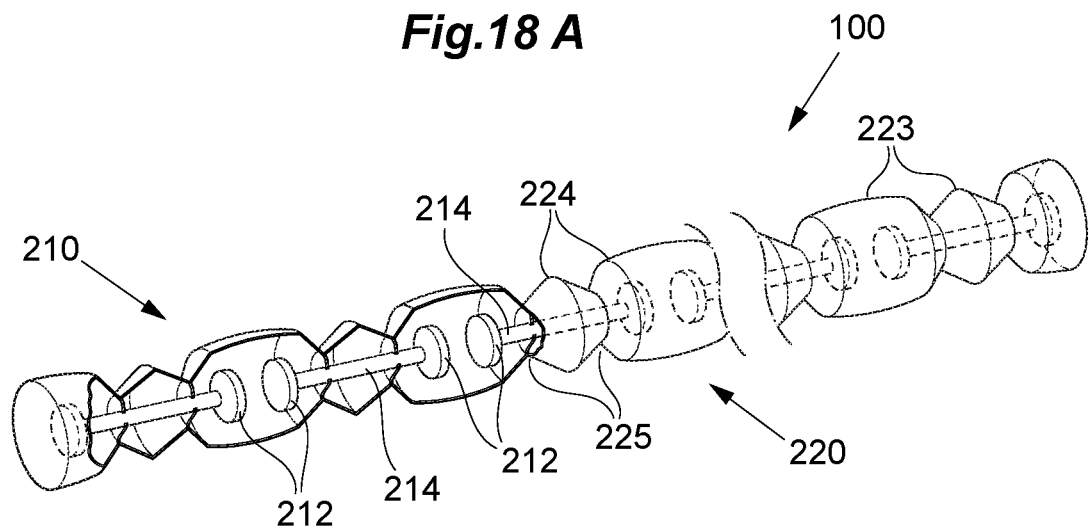
Figure 18:
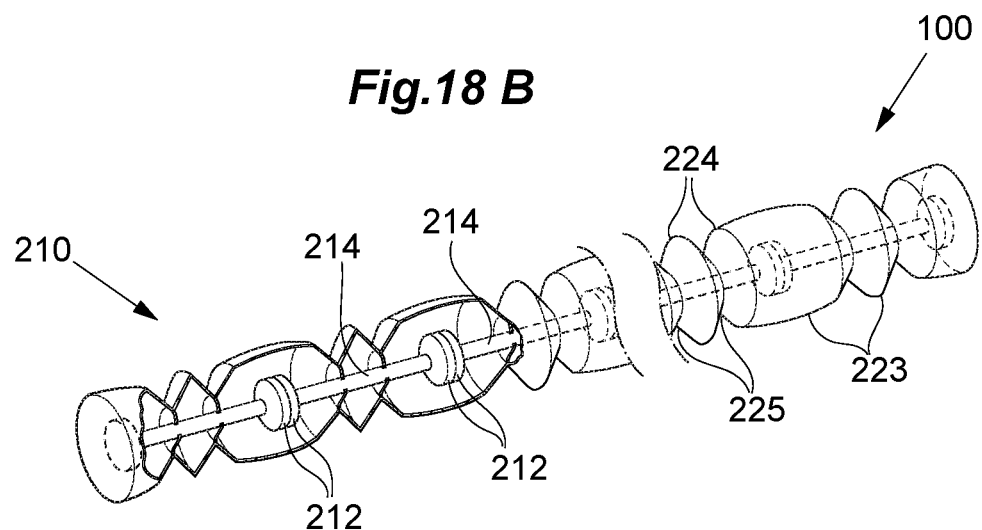
Figure 19:
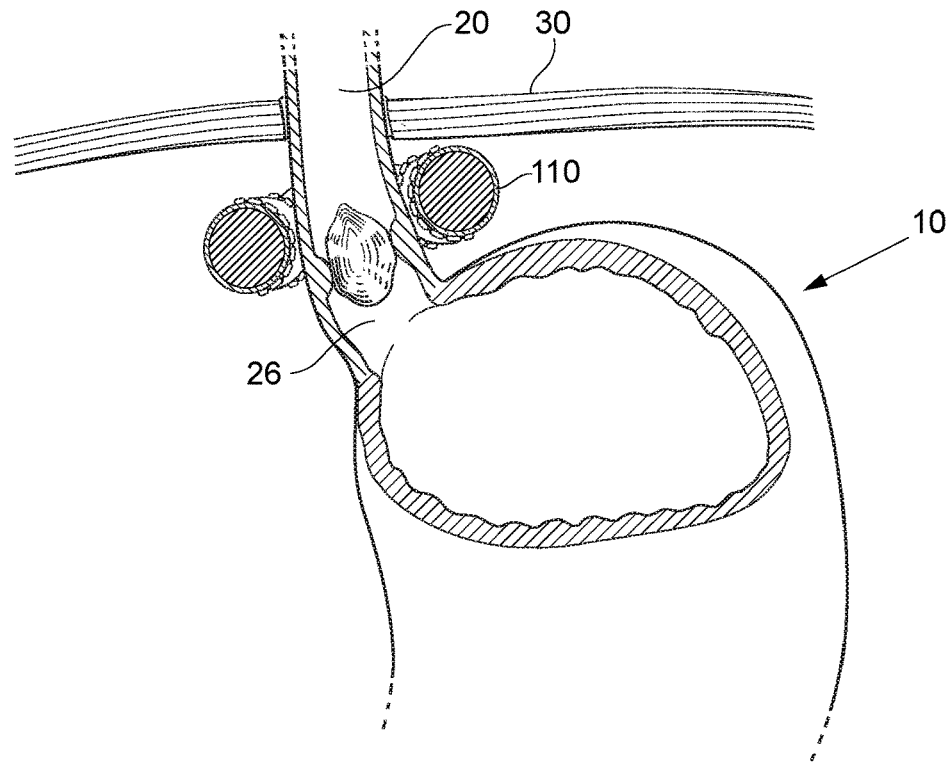
FIGS. 19A and 19B are schematic views of an example of an apparatus for treating reflux disease, wherein the apparatus is implanted in the body of the patient.
Figure 19:
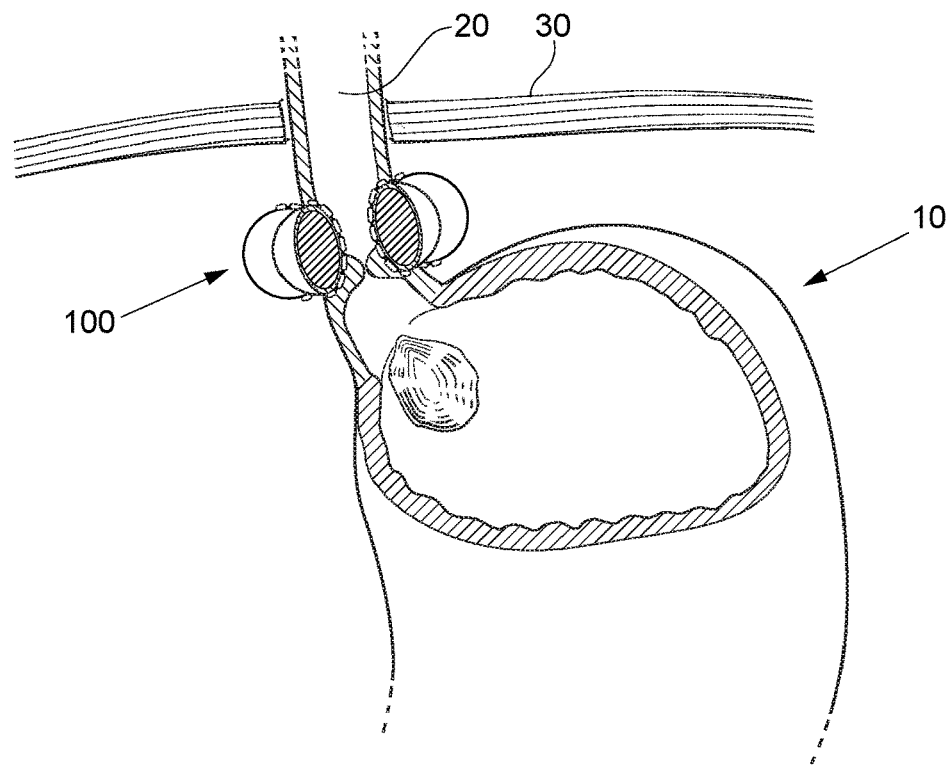
Figure 20:
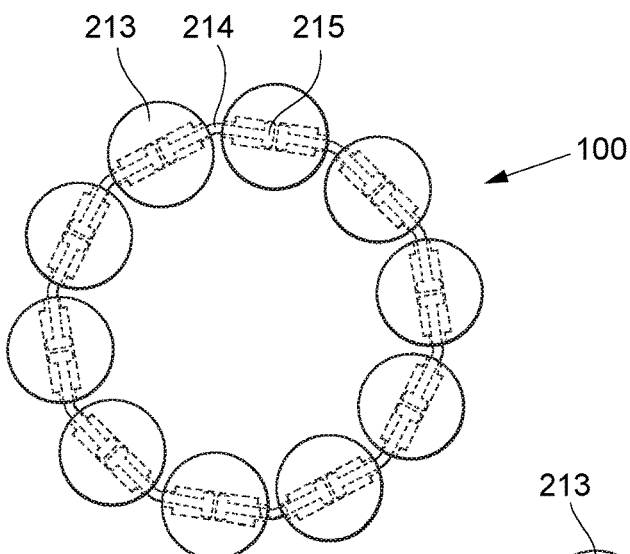
Figure 20:
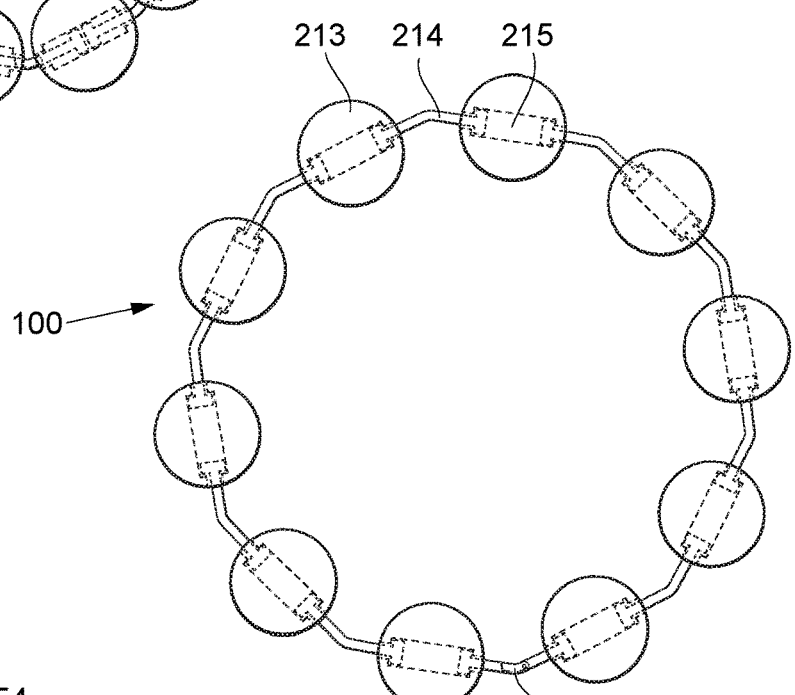

FIG. 17 shows an apparatus 100 which may be similarly configured to the examples of FIGS. 14-16. However, FIG. 17 further discloses an implantable energy source 160 for supplying the electrode arrangement 150 with electrical power for the electrical stimulation of the muscle tissue. The energy source 160 may be integrated in the in the elongated core 210, such as in one or several of the portions 213, as shown in the present figure. However, the energy source 160 may in some examples be arranged outside the apparatus 100 as well, forming as a separate structural entity that can be implanted in the abdomen or elsewhere, such as subcutaneously. The energy source 160 may comprise a primary cell, i.e., a battery designed to not be recharged. In further examples, the energy source 160 may comprise a secondary cell designed to be recharged, preferably by means of an external energy source located outside the patient's body. Various examples of charging of the energy source 160 and powering of the electrode arrangement 150 is described in connection with FIGS. 42-44, together with examples of how to control and operate the electrode arrangement 150.

FIGS. 18a and 18b show an apparatus 100 which may be similarly configured as the examples shown in FIGS. 14-17. The apparatus 100 may comprise an elongated core 210 having a variable length which allows the apparatus to be arranged to at least partially encircle the esophagus 20 in a constricting state for hindering stomach contents from passing into the esophagus 20, and an expanded state for allowing a food bolus to pass into the stomach 10 in response to the patient swallowing. The encircling pressure exerted on the esophagus 20 may be generated by a plurality of attractors 212, which in the present example may comprise permanent magnets arranged in mutually attracting pairs. In FIGS. 18a and 18b the elongated core 210 is formed of an array of links 214, such as rods or levers, extending along the length direction of the elongated core 210 and having a permanent magnet 213 attached to its respective end portion. By arranging the magnets 213 of the end portions of the links 214 such that magnets 213 of neighboring links attract each other, the attracting forces between the magnets 213 can be utilized to cause the elongated core to transition from an expanded state shown in FIG. 18a to a constricting state shown in FIG. 18b. In the constricting state indicated in FIG. 18b, adjacent magnets 213 are arranged closer to each other than in the expanded state in FIG. 18a. If allowed to move freely, adjacent magnets 213 may abut each other. When the patient swallows food or liquids, the passing matter may cause the esophagus 20 to expand radially. This expansion may generate an expanding force acting on the apparatus 100, which may eventually overcome the attracting forces between the magnets 213 and thereby cause the core 210 to expand its circumference and assume the expanded state. Once the food or liquid has passed the apparatus 100, the attracting (or constricting) forces within the apparatus 100 may once again overcome the expanding forces of the esophagus 20, and the core 210 may hence reduce its circumference and the apparatus 100 return to the constricting state.

The apparatus 100 may further comprise a cover 220 enclosing at least a part of the elongated core 210. The cover 220 may be similar to the cover 220 discussed in connection with FIGS. 15-17 and may be configured to hinder fibrotic tissue from growing directly on the elongated core 210. Further, the cover 220 may be configured to provide mechanical support to the elements of the elongated core 210, such as the links 214 provided with the magnets 213. The cover 220 may be tubular, comprising a wall at least partially surrounding or encasing the elongated core 210 and having an at least partly hollow interior capable of accommodating the elements of the core 210. According to the example of the present figure, the cover 220 may comprise an array of tubular segments 222 distributed along the length of the elongated core 210. In the present example, a segment 222 may be configured to accommodate at least two mutually attracting magnets 213, wherein a first one of the magnets 213 may be attached to an end portion of a first link 214 and a second of the magnets 213 may be attached to an end portion of a second, neighboring link 214 of the elongated core 213. The variation of the length of the core 210, as the apparatus 100 transitions between the expanded state and the constricting state, may thus be achieved by said magnets moving towards and away from each other in the length direction of the core 210 and within the segment 222 in which they are accommodated.

The cover 220 may be configured to follow/allow the variation of length of the core 210 by means of a first portion and a second portion of the cover 220 bending relative to each other so as to compensate for the varying length without stretching the material of the cover 220. The first portion and the second portions may be separated by a fold 224 as indicated in the figure and may further be considered as a lowered portion 225 and an elevated portion 226, respectively. Put differently, the segment 222 of the cover 220 may be configured to act as a bellows compressing and expanding in response to the elongated core 210 contracting and expanding. The cover 220 may comprise one or several further segment 223 arranged between neighboring segments 222 comprising the magnets 213 as outlined above and accommodating a portion of the link 214 interconnecting the magnets 213.

The dimensions and configuration of the cover 220 may be adapted to allow fibrotic tissue to at least partly encapsule the outside of the cover 220, preferably in a layer following the outer contour of the segments such that the different portions of the cover 220 may bend and fold relative to each other while bending, rather that stretching, the fibrotic tissue.

The cover 220 may further comprise an electrode arrangement 150, similar to the cover 220 disclosed in FIGS. 15 and 16, for electrically stimulating muscle tissue of the esophagus 20. Preferably, the electrical stimulation may be adjusted to compensate for the presence of fibrotic tissue, which may prevent the electrode element from directly abutting or engaging the muscle tissue. Thus, the presence of fibrotic tissue in the interface or junction between the electrical element and the muscle tissue may be compensated for by adjusting the electrical stimulation signal accordingly, as will be discussed in more detail in connection with FIGS. 38-41.

FIGS. 19a and 19b illustrate an apparatus 100 according to any of the examples shown in FIGS. 14-18 when implanted around the esophagus 20 of a human patient. Preferably, the apparatus 100 may be placed at the same height as the cardiac sphincter 26 so as to help the sphincter to contract. The apparatus 100 may be affixed to the esophagus 20 so as to maintain its desired position, for example by means of sutures of staples. The affixation by means of attachers such as staples or sutures may be of a temporary nature, and the apparatus 100 may be more permanently affixed by fibrotic tissue eventually encapsulating the apparatus 100. In further examples, the apparatus 100 may be arranged at the junction between the esophagus 20 and the stomach 10.

The apparatus 100 may be configured to exert an encircling pressure on the esophagus 26 so as to constrict the esophagus 26 and thereby reduce the risk for stomach content from entering the esophagus 26. The resilient forces within the apparatus 100, causing the elongated core 210 to contract, may be generated by an elastic means, such as an elastic band or a spring, or by magnetic attraction as outlined above, and may be balanced so as to allow food and liquids to pass through the esophagus 20 in response to the patient swallowing, and to allow stomach contents to pass through the esophagus 20 in response to the patient belching or vomiting.

The apparatus 100 may further comprise an electrode arrangement 150 as outlined above, for electrically stimulating and constricting the cardiac sphincter 26 and/or exercising the muscle tissue of the esophagus 20 so as to improve the conditions for long-term implantation.

FIGS. 20a and 20b show an apparatus 100 according to an example, which may be similarly configured as the apparatuses 100 discussed above with reference to FIGS. 14-19. The apparatus 100 comprises an elongated core 210 comprising an array of adjacent portions, or core elements 213, which can be moved towards each other and away from each other in the array so as to vary the length of the elongated core 210. Further, the end portions 216 of the core 210 may attached to each other so as to form an annular or ring-shaped array, having a variable circumference and being possible to arrange to at least partly encircle the esophagus 20 of the patient. At least two of the core elements 213, or bodies 213, in the array may be provided with a respective permanent magnet adapted to attract each other and thereby generate a contracting force within the core 210.

The core 210 may further comprise a plurality of links 214 connecting the bodies 213 of the array to each other. The links 214 may be relatively rigid so as to provide mechanical support and guide the bodies 213 of the array in their movement towards and away from each other. Thus, the links 214 may be configured to maintain substantially the same shape during the operation of the apparatus, i.e., as the elongated core 210 changes between the expanded state and the constricting state. The links 214 may be configured to extend into at least one of the bodies 213 it interconnects in response to the bodies 213 moving towards each other. As indicated in the present figures, the body 213 may comprise a channel or passage 215 extending into the interior of the body 213. The channel 215 may be configured to allow an end portion of the link 214 to slide back and forth along the channel 215 in response to the core 210 varying its length. The end portion of the link 214 may further comprise a stop or abutment hindering the link 214 from leaving the channel 215 and thereby disconnect the bodies 213 of the array from each other.

FIG. 20a show the elongated core 210 in the constricting state. In the particular example illustrated in the figure, the elongated core 210 has assumed a minimum length (or circumference) defined by the bodies 213 of the array abutting each other. It will however be appreciated that the constricting state may be assumed also without the bodies 213 of the array touching each other. It may suffice if the bodies 213 of the array are arranged closer to each other than in the expanded state.

The constricting state may be maintained by the attractive forces between adjacent bodies 213 in the array. The forces may be overcome by expanding forces from within the esophagus 20, pushing the bodies 213 of the array apart so that the elongated core 210 assumed the expanded state instead. The expanding forces may for example be caused by the patient swallowing food, belching, or vomiting. Preferably, the attractive forces are strong enough to hinder or at least reduce passage of stomach contents into the esophagus in other cases than when the patient belches or vomits.

FIG. 20b shows the apparatus 100 in FIG. 20a in the expanded state, and in the particular example in a maximally expanded state defined by the stop 217 at the ends of the links 214.

Similar to the previous examples of the apparatus 100, an electrode arrangement 150 may be provided between the bodies 213 of the array and the surrounding tissue when implanted. The electrode arrangement 150 may for example comprise one or several electrode elements 154 arranged on the outer surface of one of several of the bodies 213 of the array. Similar to the examples discussed with reference to FIGS. 1-19, the electrode element(s) 154 may be configured to operate as a cathode during the stimulation, using the tissue of the human body as the anode. Alternatively, or additionally, a first one of the electrode elements 154 may be configured to operate as a cathode and a second one of the electrode elements 154 as an anode, allowing an electric signal to pass between the electrode elements 154, using the tissue of the human body as an electrical conductor. In some examples, the electrode arrangement 150 may be configured to provide at least two electrode elements 154 on opposing sides of the cardiac sphincter 26 so as to facilitate contraction of the sphincter 26.

Figure 21:
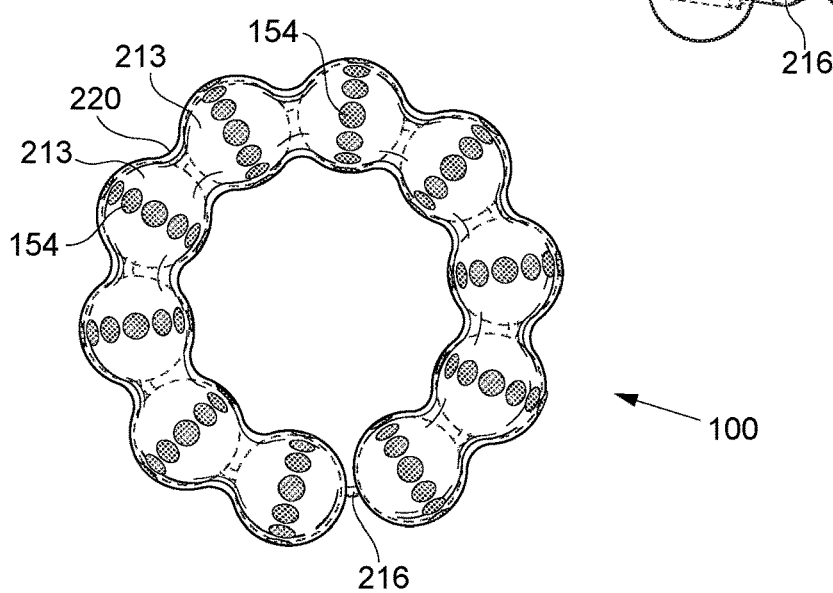

The apparatus 100 in FIGS. 20a and 20b may further comprise a cover 220, which may be similarly configured as the examples described in connection with e.g. FIGS. 15-19. An example of such an apparatus 100 is shown in FIG. 21, in which the elongated core 210 of FIGS. 20a and 20b is at least partly enclosed in a cover 220 allowing the core 210 to change between the constricting state and the expanded state without being substantially hindered or impeded by the presence of fibrotic tissue on the outer surface of the cover 220. Similar to the previous examples, an electrode arrangement 150 may be arranged between the cover 220 and the tissue against which the cover 220 rests when implanted. The electrode arrangement 150 may for example be arranged on the outer surface of the cover 220.

Figure 22:
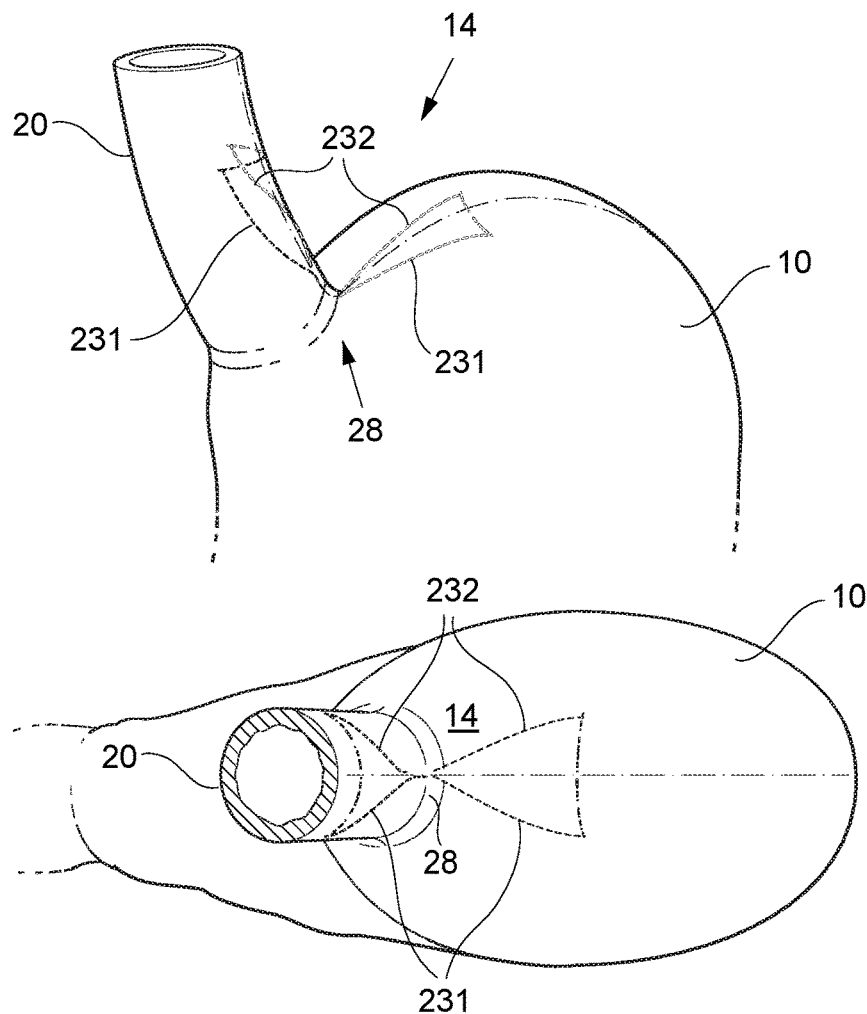

A method for implanting the apparatus 100 according in the body of a patient will now be discussed with reference to the examples illustrated in FIGS. 22a, 22b and 23. The present method may be used for affixing the apparatus 100 in the desired position by invaginating or wrapping at least a part of the device in the fundus 12 of the stomach 10, may hence be considered as an alternative to the placement shown in the for example FIGS. 19a and 19b, wherein the apparatus 100 instead is arranged to encircle the esophagus without being invaginated or wrapped in a portion of the fundus 12. Preferably, the following method may be used when implanting a movement restriction device for reinforcing the fundus 12 to interact with the diaphragm and hindering movement of the cardia 22 up into the thorax.

Preferably, the apparatus 100 may be placed relatively high-up, above the upper edge of the lower esophageal sphincter (LES) so as to improve the effect on the reflux disease symptoms and allow the angle of His to assume its original, anatomically correct position and the LES to remain the abdomen. The present method can be divided into two separate parts: a first part in which a part of the stomach wall 14 is attached to the esophagus 20 so as to provide a "platform" positioning the apparatus 100 at the desired high, and a second part in which the apparatus 100 is placed in a pouch formed in the outside of the fundus, or wrapped in a portion of the fundus wall.

Figure 23:
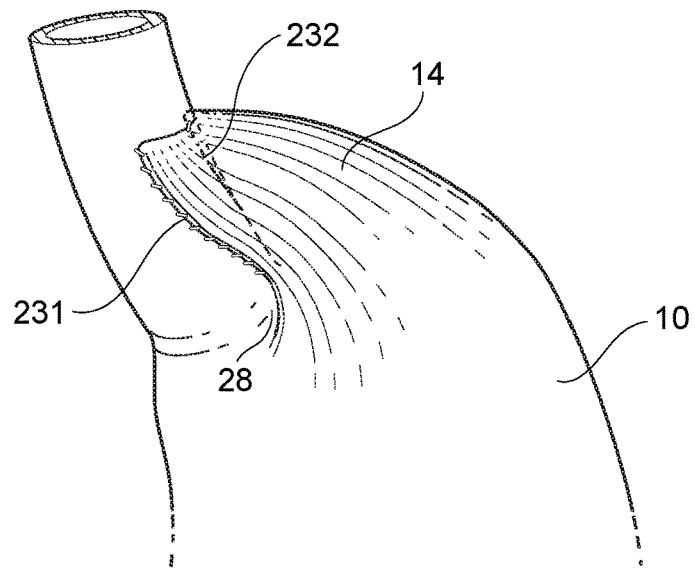
Figure 23:
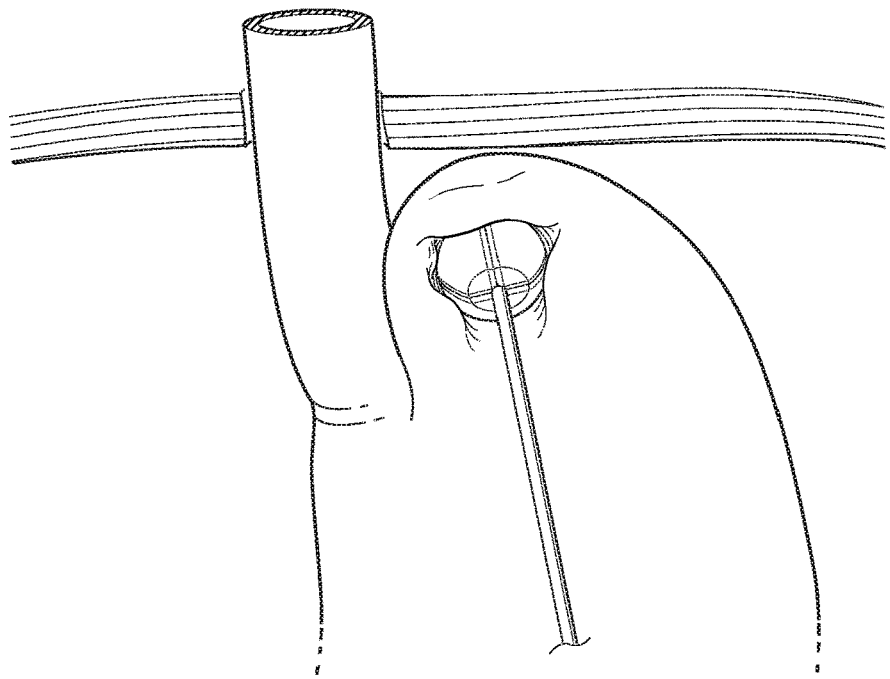
Figure 23:
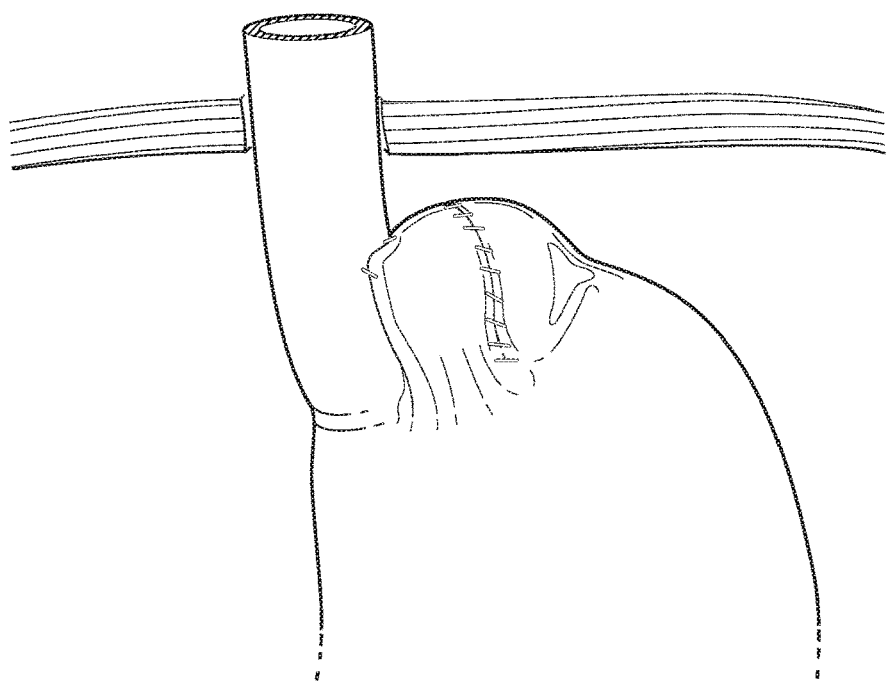

The first part of the method is illustrated in FIGS. 22a, 22b and 23, wherein a fundus portion 14, extending from the angle of His 28 and in a direction away from the esophagus, is affixed to the esophagus 20 after the esophagus 20 has been dissected in mediastinum. According to the method, the fundus portion 14 may be folded towards the esophagus 20 such that the fundus portion 14 rests against the esophagus 20, from the angle of His 28 and upwards along the esophagus 20. The fundus portion 14 may then be affixed to the esophagus 20 by means of fasteners 230 arranged along a first line 231 and a second line 232. The first line 231 and the second line 232 may extend along the esophagus 20 and may be arranged such that a distance between the first line 231 and the second line 232 increases with an increasing distance from the angle of His 28. The positions of the first line 231 and the second line 232 are indicated by the dashed lines in FIGS. 22a and 22b, before the fundus portion 14 has been folded against and affixed to the esophagus 20. The fasteners 230 may for example comprise staples or sutures and may preferably be of a non-resorbable type). In case of the fasteners 230 comprising sutures, the first line 231 and the second line 232 may comprise a respective continuous suture.

The abdominal part of the esophagus 20 and the fundus 12 may be divided by a plane into a ventral and a dorsal side. In this case, the first line 231 may be considered to be arranged on the dorsal side of the plane, whereas the second line 232 may be arranged on the ventral side of the plane. The first line 231 and the second line 232 may in some example be placed at an angle of 45-75 degrees relative to the plane, such as for example 60 degrees. Put differently, a separating angle between the first line 231 and the second line 232 may be in the range of 90-150 degrees, such as for example 120 degrees. In some examples, the maximum separation between the two lines 231, 232, at the top of the lines 231, 232, may be about 2-3 cm, such as about 2.5 cm. The orientation of the lines of fasteners can be considered to describe a "V" or "Y", with the lines being separated at the top and gradually tapering towards each other towards the angle of His 28. Optionally, an additional fastener, such as a staple or suture, may be provided at the top of the "V" or "Y" shapes. Alternatively, a third line of sutures 233 may be provided between the first and second lines 231, 232.

In some examples, the method may comprise beginning the first line 231 less than 1 cm, such as about 0.5 cm, above the angle of His and beginning the second line 232 less than 3 cm, such as about 2 cm above the angle of His. Preferably, the second line 232 may be started less than 2 cm, such as about 1 cm, more ventral than the first line 231.

FIG. 23a shows the stomach 10 in FIGS. 22a and 22b after the fundus wall portion 14 has been affixed to the esophagus 20 according to the method outlined above. The method may now be followed by the implantation of the apparatus 100, such as for example the movement restriction device as shown in FIGS. 1-11. The apparatus 100 may be placed relatively high-up on the outside of the stomach fundus wall 12 and invaginated or covered by stomach tissue. This may be achieved by forming a pouch or recess 240 in the fundus 12, placing at least a part of the apparatus 100 in the pouch or recess 240, and at least partly closing the pouch or recess by fasteners 242 as illustrated in FIGS. 23b and 23c. Preferably, the apparatus 100 is placed such that the top of the apparatus 100 is positioned at a distance from the LES that exceeds the total height of the apparatus 100 so as to reduce the risk of the LES sliding through the diaphragm opening 32. Alternatively, the top of the apparatus may be arranged further down, such at a distance from the LES exceeding half of the total height of the apparatus 100. Arranging the apparatus even further down may lead to an increased risk for the LES sliding into the thorax and thereby a malfunction of apparatus 100.

Preferably, the apparatus 100 is placed relatively close to the esophagus 20, such that the distance between the apparatus 100 and the esophagus 20 primarily is determined by the thickness of the doubled stomach wall 14 placed between the apparatus 100 and the esophagus 20. This distance may for example be less than 2 cm, such as less than 1.5 cm, depending on the thickness of the stomach wall 14.

A few examples of apparatuses for treating reflux disease of a human patient will now be described with reference to FIGS. 24-27. The apparatuses 100 may be configured to operate by combining a restriction of movement of the cardia towards the diaphragm, as discussed in connection with for example FIGS. 1-11, with electrical stimulation for contracting the cardiac sphincter 26, as disclosed in connection with for example FIGS. 3 and 14-20, and/or an encircling pressure on the esophagus 20, as discussed with reference to the examples of FIGS. 14-20, for hindering stomach contents from rising through the esophagus 20. Hence, the apparatuses 100 of FIGS. 24-27 may be configured to at least partly encircle the esophagus 20, and may comprise a first implantable portion 110 (also referred to as a movement restriction device) having a shape and size allowing it to be arranged to rest against a fundus wall portion 14 of the patient's stomach 10 and to be at least partly invaginated or covered by the fundus wall portion 14, such that the first implantable portion 110 is implanted at a position between the patient's diaphragm 30 and a lower portion of the fundus wall 14, and such that movement of the cardia 22 of the patient's stomach 10 towards the diaphragm 30 is restricted to hinder the cardia 22 from sliding through the diaphragm opening 32 into the patient's thorax. The apparatus may further comprise a second implantable portion 120 (also referred to as an elongated support device), which may be configured to at least partly encircle the esophagus 20. In some examples, the second implantable portion 120 may have a variable length for allowing the apparatus 100 to be arranged in a constricting state for hindering fluid from passing from the stomach 10 and upwards through the esophagus 20, and in an expanded state for allowing food to pass into the stomach 10 in response to the patient swallowing. In some examples, the second implantable portion 120 is formed as an elongated support device 120 connected to the first implantable portion 110 (or movement restriction device) and configured to support an electrode arrangement 150 such that it is positioned at the esophagus 20. The support device 120 may comprise a rigidity that allows the position of the electrode arrangement 150 relative to the esophagus 20 to be determined mainly by the position and orientation of the movement restriction device 110.

Figure 24:
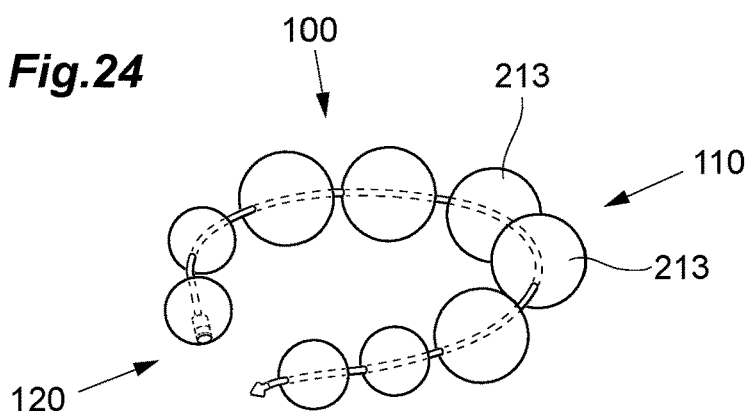
FIGS. 24-27 are schematic views of various examples of apparatuses for at least partly encircling the esophagus to treat reflux disease.

More specifically, FIG. 24 shows an apparatus 100 comprising a plurality of core elements 213 arranged in an array and connected to each other by means of a plurality of links 214. At least one of the core elements 213 may be larger than the other core elements 213 of the array, and may be configured to form the first implantable portion 110 to be affixed to the fundus 14, for example by invagination or by at least partly covering the at least one larger core element 213 by stomach tissue. The at least one larger core element 213 may thus form a movement restriction device as discussed above in connection with FIGS. 1-6. The smaller ones of the core elements 213 may form the second implantable portion 120 and may be arranged to encircle at least a part of the esophagus 20. The second implantable portion 120 may have a variable length so as to allow the apparatus 100 to change between the expanded state and the constricting state as outlined above in the previous examples. A maximum width of a cross section taken across a length direction of the first implantable portion 110 may preferably be larger than a maximum width of a cross section taken across a length direction of the second implantable portion 120.

The first implantable portion 110 may be configured to have a substantially fixed size and shape during operation of the apparatus, whereas the second implantable portion 120 may be configured to vary its length, and hence the constriction of the esophagus 20, in response to the patient swallowing and, preferably, belching or vomiting. The second portion 120 may thus be arrangeable in an expanded state in which a food bolus may pass through the cardiac sphincter 26, and in a constricting state in which the second portion 120 exerts an encircling pressure on the esophagus 20 so as to help the cardiac sphincter 26 to close or at least constrict the passageway of the esophagus 20.

An electrode arrangement 150, similarly configured as the electrode arrangement 150 discussed above in connection with for example FIGS. 1 and 14, may be arranged between the first portion 110 and the fundus wall portion 14, and/or between the second portion 120 and the esophagus 20. The electrode arrangement 150 may comprise one or several electrode elements 152, 154 for electrically stimulating and thereby exercising muscle tissue affected by the implanted apparatus 100, and/or for electrically stimulating and thereby contracting the cardiac sphincter 26.

The combined apparatus 100 shown in FIG. 24 advantageously employs several different mechanisms for addressing reflux symptoms. Firstly, the first portion 110, acting as a mechanical stop against the diaphragm muscle 30, makes use of the technique to hinder the cardia 22 from sliding through the diaphragm opening 32 into the thorax. Secondly, the second portion 120, acting as a constricting device, utilizes the technique to assist the cardiac sphincter 26 in its closing movement so as to further improve the closing or constrictive function of the sphincter 26. Thirdly, the electrode arrangement 150 may be employed to electrically stimulate the cardiac sphincter muscle 26 so as to further stimulate constricting.

Figure 25:
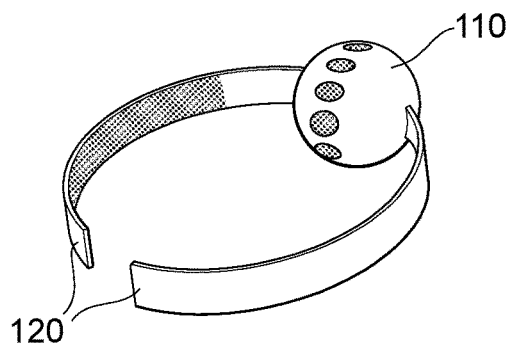

FIG. 25 shows an apparatus 100, which may be similarly configured as the embodiment discussed above with reference to FIG. 24. However, the present apparatus 100 may differ in that the second portion comprises an elongated support device 120 similar to the one disclosed in for example FIG. 3. Thus, while the first portion 110 may be invaginated or at least partly covered by the fundus tissue and arranged to act as a movement restriction device, the second portion 120 may, instead of the array of core elements shown in FIG. 24, comprise an elongated support device 120 that is attached to the first portion 110 and configured to at least partly encircle the esophagus 20. Preferably, the support device 110 is configured to support the electrode element 154 at a position where it can electrically stimulate muscle tissue of the esophagus 20. In some examples the support device 120 may be formed as a band 120 configured to be arranged around at least a part of the esophagus 20, and wherein a first and a second end portion of the band is coupled to the first implantable portion 110. Alternatively, or additionally, the support device 120 may comprise a rigidity that allows the position of the electrode element relative to the esophagus to be determined mainly by the position and orientation of the movement restriction device. This allows for the elongated support device 120, and thus the electrode element 154, to be arranged and maintained in a desired position at the esophagus 20 without being affixed, such as sutures or staples, directly to the tissue of the esophagus 20. Instead, the location and orientation of the first portion 110, which may be affixed to the fundus 14, may be adjusted until the electrode element 154 is arranged at the desired position.

Figure 26:
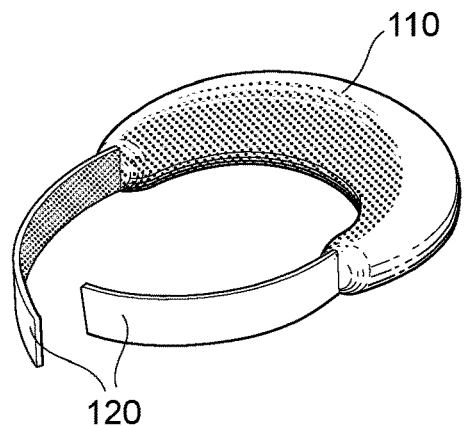

FIG. 26 shows an apparatus 100 which may be similarly configured as the embodiment of FIG. 25. The present apparatus 100 may however differ in that the first portion 110, which may be configured to function as a movement restriction device 110, may be formed as a segment of a ring-shape, such as a segment of a torus as indicated in the embodiments of for example FIGS. 7-11. The function and configuration may be similar to the ones of the embodiment of FIG. 26, allowing for the electrode element 154 to be positioned at the esophagus 20 without having to be affixed directly to the esophagus 20 by means of for example sutures or staples. The first portion 110 may have a curvature that conforms to a curvature of the esophagus 20, allowing for an inner curvature of the segment to be arranged to phase an outer surface of the esophagus 20, on the fundus side of the esophagus 20. The first portion 110 may for example be configured to be arranged to rest directly against the esophagus 20, such as at the angle of His 28, or be affixed to the fundus 12 in a way that allows for fundus tissue to be positioned between the first portion 110 and the esophagus 20. The at least partly ring-shaped first portion 110 may advantageously improve the stability of the apparatus 100 when implanted, allowing for the first portion 110 to be more securely affixed to the fundus 12 with a reduced risk for rotations to occur over time.

Figure 27:
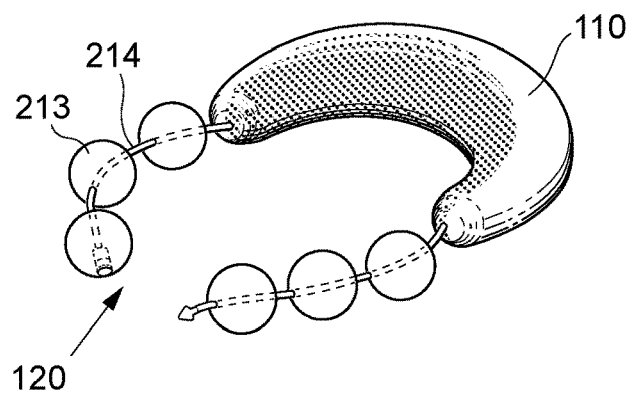

FIG. 27 shows an apparatus 100 which may be similarly configured as the embodiment of FIG. 26. The present apparatus 100 may however differ in that the second portion 120 may comprise a plurality of core elements 213 arranged in an array and connected to each other by means of a plurality of links 214, similar to what is described in connection with the embodiment of FIG. 24. The core elements 213 of the second implantable portion 120 may hence be arranged to encircle at least a part of the esophagus 20, and the second implantable portion 120 may have a variable length so as to allow the apparatus 100 to change between the expanded state and the constricting state as outlined above in the previous examples. The first portion 110, or the restriction device 110, may be similar to the corresponding portion of the embodiment of FIG. 26.

The apparatus 100 according to the embodiments described above in connection to FIGS. 1-13 and 24-27 may be implanted in the body and affixed by the fundus in several different ways. As previously described, the implantation method may involve placing the first portion 110 (or movement restriction device 110) in a pouch formed in the inside or outside wall of the fundus 12, or at least partly covering the first portion 110 by fundus tissue, and affixing the first portion 110 by stomach-to-stomach sutures, before the fundus 12 is affixed to the esophagus 20 and/or diaphragm 30 so as to arrange the apparatus 100 in a predetermined or desired position in the body. Further exemplary methods will now be described with reference to FIG. 28.

The apparatus 100 according to any of the embodiments described above in connection to FIGS. 1-13 and 24-27 may be affixed to the fundus such that the first portion 110, also referred to as a movement restriction device 110, is at arranged on the fundus side of the esophagus to restrict the movement of the stomach notch in relation to the diaphragm to hinder the cardia to from sliding through the diaphragm opening into the patient's thorax. This may be achieved by a method which may be referred to as "tunneling", i.e., at least partly wrapping or covering a part of the apparatus 100 in fundus tissue forming a pouch or cavity that is open in two ends so that the apparatus can extend through the pouch or cavity. Thus, the method may comprise placing the apparatus 100 such that the movement restriction device 110 rests against the outside of the stomach's fundus 12, wrapping a portion of the fundus 12 around at least a part of the movement restriction device 110, and affixing the fundus 12 to the esophagus 20 such that the movement restriction device 110 is arranged at a position between the diaphragm 30 and the cardiac sphincter 26, and such that a part of the fundus 12 is arranged between the movement restriction device 110 and the esophagus 20.

Figure 28:
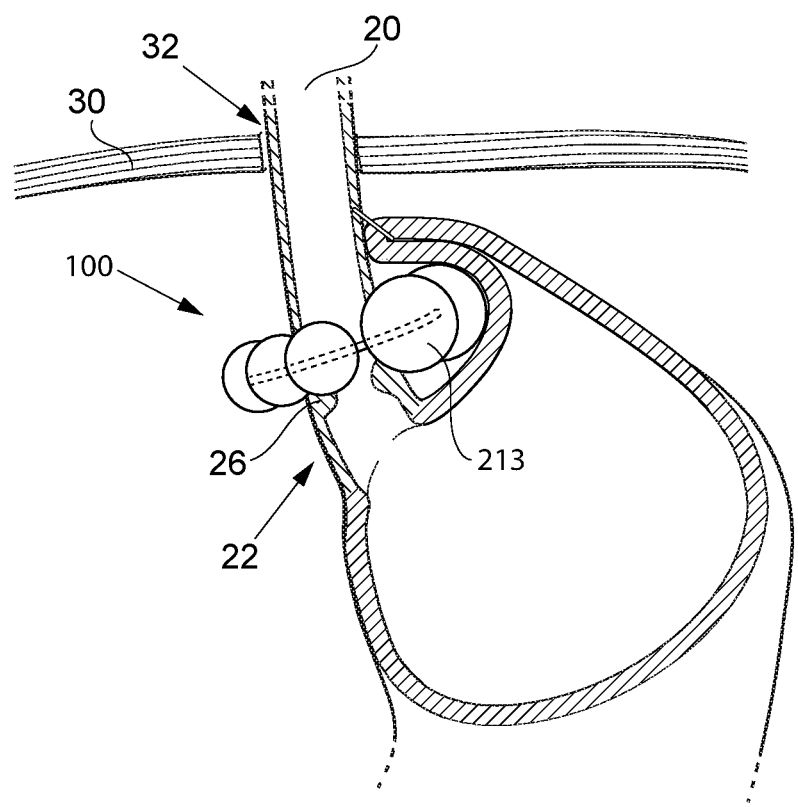
FIG. 28 schematically illustrates how an apparatus for treating reflux disease can be implanted in the patient.

FIG. 28 shows an apparatus 100, wherein the first portion 110 has been placed to rest at the outside of the fundus 12 at a position between the esophagus 20 and a portion of the fundus 12 that is wrapped over at least a part of the first portion 110 and introduced between the first portion 110 and the esophagus 20. In the present example, the apparatus 100 is ring-shaped so as to at least partly encircle the esophagus 20. The ring-shaped body formed by the first and second portions 110, 120 may thus define an inner hole, through which the esophagus 20 may extend and into which a portion of the fundus 12 may be introduced and affixed to the esophagus 20. The resulting structure, by which the apparatus 100 is affixed in the body of the patient, may thus be understood as a "tunnel" having a first opening a second opening through which the apparatus 100 may extend.

Alternatively, or additionally the apparatus 100 may be implanted by first affixing a portion of the fundus 12 arranged between the first portion 110 of the apparatus 100 and the esophagus 20 to the outside of the esophagus 20, in a similar manner as discussed above in connection with FIGS. 22 and 23. A portion of the fundus extending from the angle of His may thus be folded upwards, along the esophagus 20 and affixed to the esophagus 20, for example by means of fixators extending along a first and a second line arranged such that a distance between the lines increases with an increasing distance from the angle of His. The first portion 110 of the apparatus 100 may then be invaginated, or at least partly covered by, a portion of the fundus which is not affixed to the esophagus 20. The resulting structure may thus be understood as a "tunnel". The apparatus 100 may be affixed and secured in a position relative the esophagus 20 by means of stomach-to-esophagus fixators (such as sutures or staples) shown in FIG. 28, or invaginated and secured by means of stomach-to-stomach fixators. Additional fixators may in some examples be provided to also affix the fundus 12 to the diaphragm 30 (not shown in FIG. 28).

While the exemplary apparatus 100 shown in FIG. 28 is a ring-shaped apparatus formed of a first portion 110 and a second portion 120, it will be appreciated that other configurations of the apparatus 100 is possible as well. The apparatus may for example comprise only a first portion 110, i.e., not have a second portion 120, thereby being a movement restriction device 110 similar to the one disclosed in for example FIGS. 1-6. Alternatively, the apparatus may be formed as an encircling torus as indicated in FIGS. 7-13, or comprise a core and, optionally, a cover as illustrated in FIGS. 14-21. In further examples, the apparatus 100 may be similarly configured as the examples illustrated with reference to any of FIGS. 24-27.

Generally, the apparatus 100 may be implanted in the body of the patient by means of laparoscopic surgery. In an example, the method may comprise the steps of inserting a needle or a tube-like instrument into the patient's abdomen and using the needle or tube-like instrument to fill the abdomen with a gas. Then, at least two laparoscopic trocars may be placed in the abdomen, and a camera be inserted through one of the laparoscopic trocars into the abdomen. At least one dissecting tool may be inserted through one the laparoscopic trocars and be used for dissecting an area around esophagus in mediastinum. The apparatus may be introduced into the abdominal cavity, for example via one of the trocars, and placed as illustrated above. The fundus may be affixed to itself (forming the invagination) and/or to the esophagus using sutures or staples such that the apparatus 100 is secured in a desired position relative to the cardia 22 the diaphragm 30.

The apparatus 100 according to the embodiments described above in connection to FIGS. 1-13 and 24-27 may be placed at, or in the vicinity of, the junction between the esophagus 20 and the stomach 10. The position of the apparatus 100 may be secured by wrapping or folding a portion of the fundus 12 over the apparatus 100 and affixing the fundus portion to the esophagus 20, as indicated in FIGS. 29-31 and 33. The position where the esophagus 20 meets the stomach 10 may be referred to as the angle of His 28, or cardiac notch. With this placement, the apparatus 100 may be supported by the junction, abutting a portion of the outside wall of the fundus 12 extending from the angle of His and, preferably, also a lower portion of the outside wall of the esophagus 20. The outermost layer of the stomach wall may generally be formed of a serous membrane, also referred to as serosa, which is a smooth tissue membrane wall protecting the stomach wall. Due to the protective nature of the serosa, it may be desirable to place the apparatus 100 to rest against the serosa when implanted. The serosa has been observed to cover also a part of the outside wall of the esophagus 20, close to the stomach 10, and it may therefore be advisable to allow the apparatus 100 to rest also against a lower part of the esophagus 20, covered by serosa, while avoiding placing the apparatus 100 against other parts of the esophagus 20 which are not covered by serosa. This may be achieved either by folding the fundus 12 such that fundus tissue is arranged between the apparatus 100 and the esophagus 20, as shown in for example FIGS. 1-3, 7-10 and 28. Alternatively, or additionally, this may be achieved by means of an apparatus 100, such as a movement restriction device 110 similar to the previous embodiments of FIGS. 1-3, 7-10 and 28, having a shape that allows for the device 100 to be placed such that an upper portion points or tapers away from the esophagus 20. Referring to FIGS. 29-33, the disclosed examples of movement restriction devices 110 may have a side phasing the esophagus 20, wherein a curvature of that side allows the movement restriction device 110 to be arranged such that a gap is defined between the movement restriction device 110 and the esophagus 20 along at least a portion of the esophagus 20. As indicated in the examples of the present figures, the gap may increase with an increasing distance from the junction between the esophagus 20 and the stomach 10. Put differently, the apparatus 100 may comprise an outer shape that allows it to be positioned to rest against a lower portion of the esophagus 20, comprising serosa, and to fall away, or point away, from the esophagus 20 as seen in an upward direction along the esophagus 20, towards regions of the esophagus 20 that generally are not covered by serosa. Preferably, the movement restriction device 110 has a rounded, substantially smooth outer surface so as to make it suitable for implantation.

These characteristics of the shape allows for the movement restriction device 110 to be placed to rest against, and supported by, the lowest portion of the esophagus 20 and extend upwards, towards the diaphragm 30, while avoiding contacting or abutting portions of the esophagus 20 which are arranged further up and generally not covered by a protecting layer of serosa. Preferably, the movement restriction device 110, when arranged in such a position, may comprise an upper portion having an extension that is large enough to allow the movement restriction device 110 to function as a mechanical stop against the diaphragm 30, hindering the cardia 22 from sliding upwards through the diaphragm opening 32 and thereby reducing the risk for reflux symptoms. Preferably, the movement restriction device 110 may be configured to abut the serosa of the part of the esophagus 20 extending below the cardiac sphincter 26, and leave a gap to the outer surface of part of the esophagus 20 above the cardiac sphincter 26. By allowing an upper portion of the movement restriction device 110 to extend above the cardiac sphincter 26 and towards the diaphragm 30, the top portion of the movement restriction device 110 may be positioned sufficiently high to hinder the cardiac sphincter 26 from sliding through the diaphragm opening into the patient's thorax.

Figure 30:
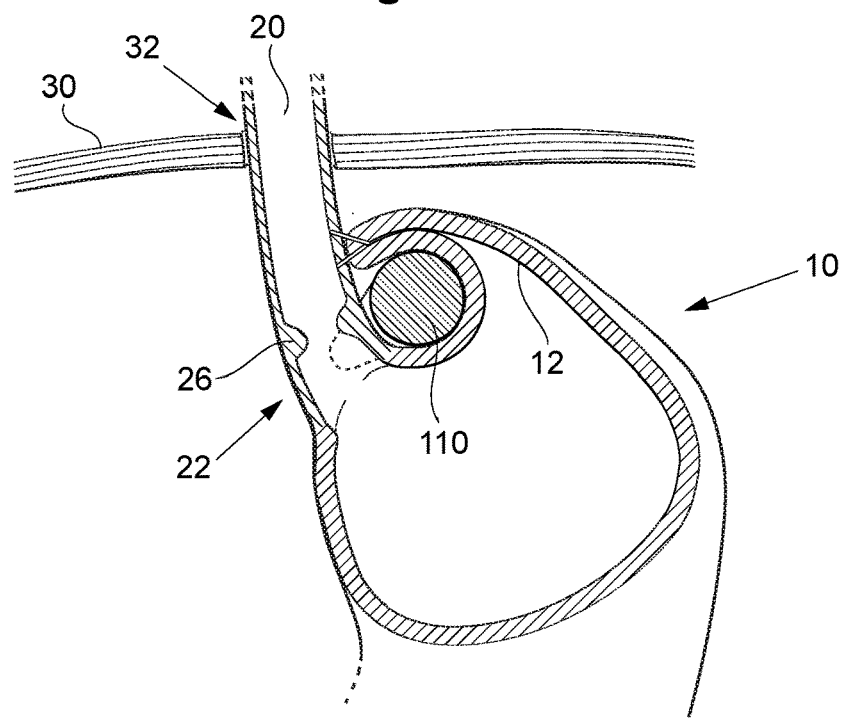

FIG. 30 shows a movement restriction device 110 having a lower portion with a curvature that allows for the movement restriction device 110 to at least partly follow the circumferential curvature of the esophagus 20. Thus, the movement restriction device 110 may be configured to be arranged at the junction between the esophagus 20 and the stomach 10, and such that it at least partly encircles the lower portion of the esophagus 20, which generally is covered with serosa. The movement restriction device 110 may thus be provided with C-shaped cross section along the surface adapted to be arranged to follow the circumference of the esophagus 20. Similar to what is described above, the movement restriction device 110 may point slightly away from the esophagus 20 further up along the esophagus 20, to define a separating gap between the outer surface of the esophagus 20 (which generally does not comprise any serosa further away from the angle of His) and the outer surface of the movement restriction device 110. The movement restriction device 110 may hence comprise at least two different curvatures—a first one along the circumferential curvature of the esophagus 20, and a second one allowing the upper portion of the movement restriction device 110 to fall away from the esophagus 20. The first curvature, adapted to phase the circumferential curvature of the esophagus, may comprise a radius of curvature that corresponds to or exceeds the radius of curvature of the esophagus 20.

Figure 29:
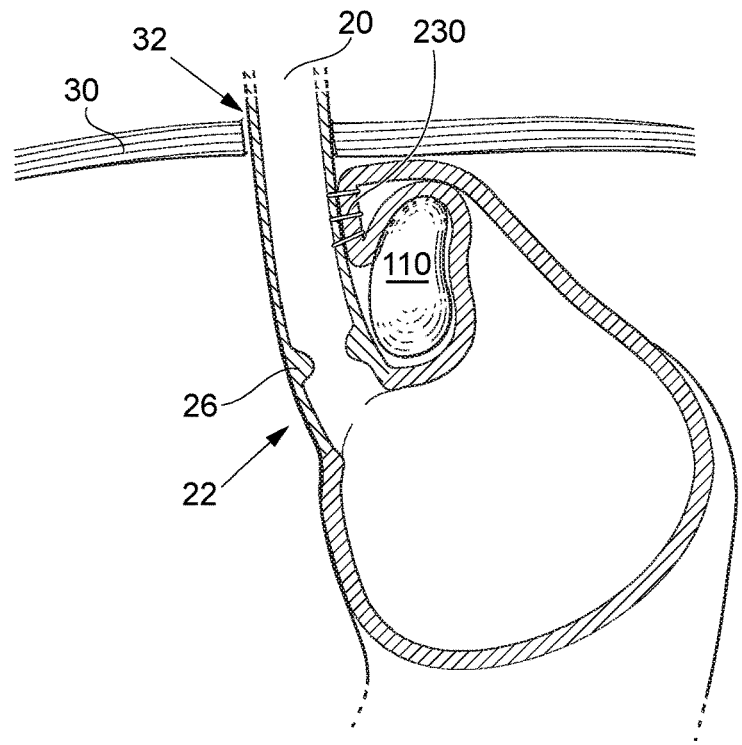

FIGS. 31A-F illustrate various examples of movement restriction devices 110, which may be similarly configured as the ones discussed with reference to the embodiments shown in FIGS. 29 and 30. It should be noted that the illustrations are schematic and not necessarily to scale. The actual shape and size of the movement restriction device 110 may vary depending on the physiology of the individual patient and may advantageously be adapted accordingly. A few characteristics may however be common to all examples illustrated in FIGS. 31A-F. The movement restriction device 110 may have a size and outer curvature that allows it to be arranged to rest against, and supported by, the lowest portion of the esophagus 20 and/or the portion of the fundus 12 arranged close to the esophagus 20, and extend upwards, towards the diaphragm 30, while avoiding contacting or abutting portions of the esophagus 20 which are arranged further up and generally not covered by a protecting layer of serosa.

FIG. 31A illustrates an example wherein the lower portion of the movement restriction device 110 is wider than the upper portion, such that the lower portion can rest against the angle of His while the upper portion may be arranged in a position defining a gap between the movement restriction device 110 and the esophagus, similar to what is described with reference to FIG. 29.

FIG. 31B illustrates a movement restriction device 110 having a curvature that can be arranged to follow the circumference of the esophagus 20 at the angle of His, and thereby at least partly encircle the esophagus 20, and a further curvature allowing the movement restriction device 20 to taper off from the esophagus, as seen along a length direction of the esophagus. The embodiment may be similarly configured as the one described with reference to FIG. 30.

Figure 31:
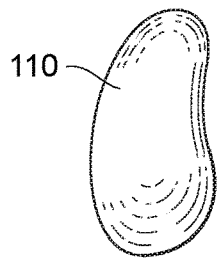
Figure 31:
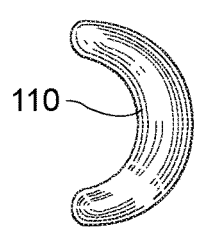
Figure 31:
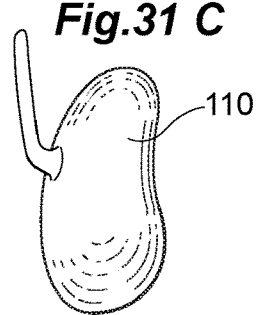
Figure 31:
Figure 31:
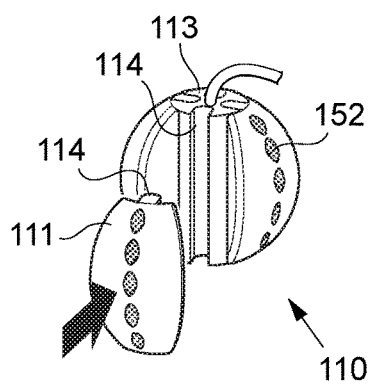
Figure 31:
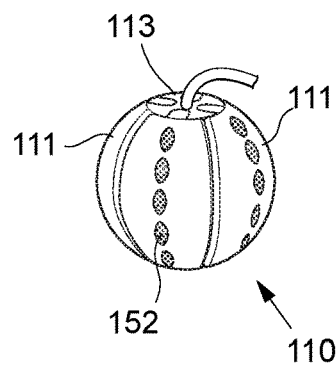
Figure 32:
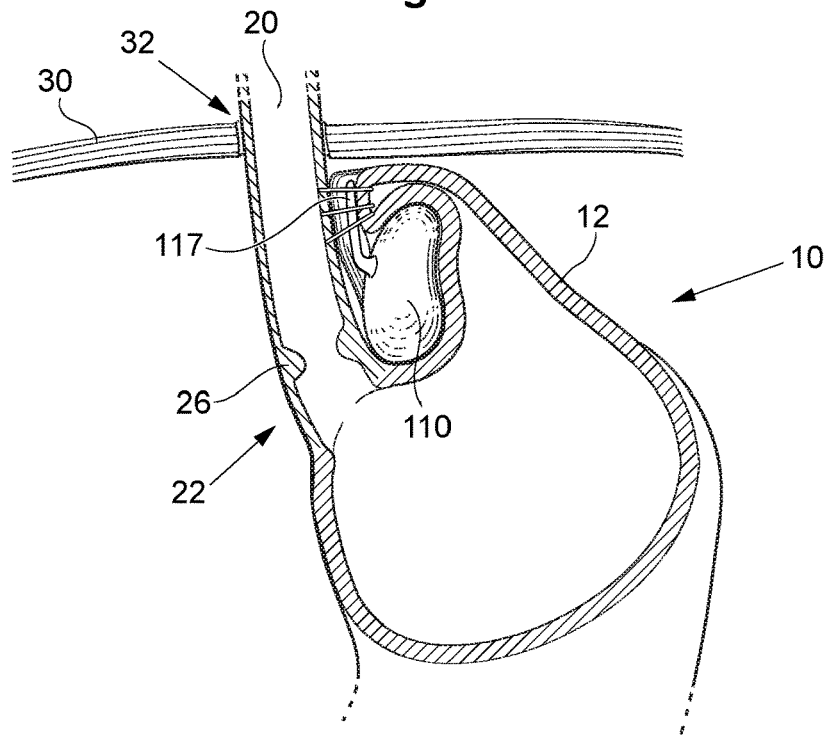

FIG. 31C shows the movement restriction device 110 in FIG. 31A with an elongated support 117 as shown in FIG. 32. The elongated support 117 may be attached to any of the examples of the movement restriction devices 110 discussed in the context of the present application for further improving the attachment of the movement restriction device 110 to the stomach 10 and reducing the risk for the movement restriction device 110 moving or changing is location and/or orientation relative to the esophagus 20. The support 117 may be configured to be affixed to the esophagus or fundus as discussed below with reference to FIG. 32.

FIG. 31D shows a further example of the movement restriction device 110, being substantially ball-shaped or spherical. For some patients it may be possible to arrange such a movement restriction device 110 at the angle of His and such that the upper part of the movement restriction device 110 do not abut the part of the esophagus 20 not covered by serosa. This depends on the anatomy and physiology of the actual patient, and further on the size and curvature of the movement restriction device 110. In some, non-limiting example the movement restriction device may have a shape conforming to a sphere having a diameter of 3 cm or more, such as 4 cm or more, such as 5 cm or more.

FIGS. 31E and F illustrate a movement restriction device 110 which may have a similar shaped and size as the embodiment shown in FIG. 31D, with the difference that the movement restriction device 110 may be formed of a plurality of segments 111 similar to the embodiment shown in FIG. 5. The embodiments of FIGS. 29-31 may further be combined with an electrode arrangement 150 for electrically stimulate and exercise the muscle tissue of the tissue against which the movement restriction device 110 rests when implanted, as discussed above in connection with for example FIGS. 1-5.

FIG. 32 shows an apparatus 100 which may be similarly configured as the embodiments discussed in connection with FIGS. 29-31, with the difference that the present example comprises an elongated support 117, or fastener, protruding from the movement restriction device 110. The elongated support 117, which may be shaped as a lever, may be configured to be oriented to extend along the esophagus 20 and affixed to the fundus 12 so as to provide additional mechanical support of the movement restriction device 110. The support 117 may be invaginated, or at least partly covered, by the fundus 12 tissue that may be wrapped around the movement restriction device 110 and affixed to the esophagus at least partly above the movement restriction device 110. The support 117 may protrude from the movement restriction device 110 with an angle that allows for the movement restriction device 110 to be arranged (and preferably secured over time) at a position reducing or avoiding direct contact between the movement restriction device 110 and regions of the esophagus 20 not comprising any serosa. The support 117 may be folded into, or at least partly invaginated by the fundus tissue in such a way that fundus tissue is arranged between the support 117 and the tissue of the esophagus 20.

Figure 33:
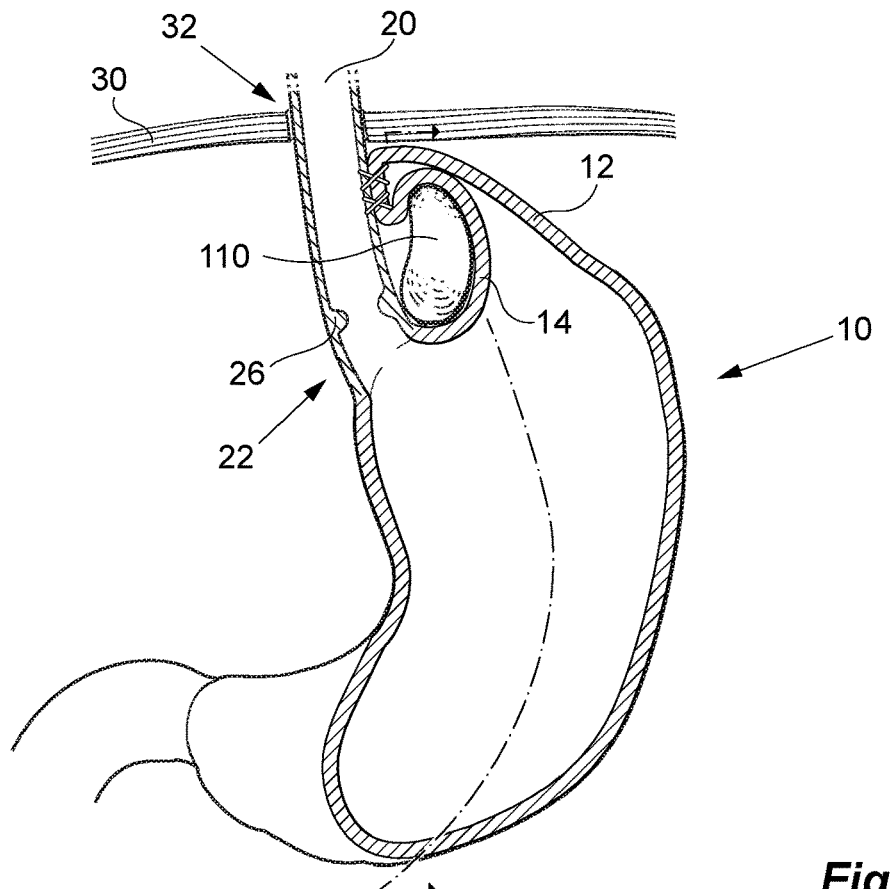
Figure 34:
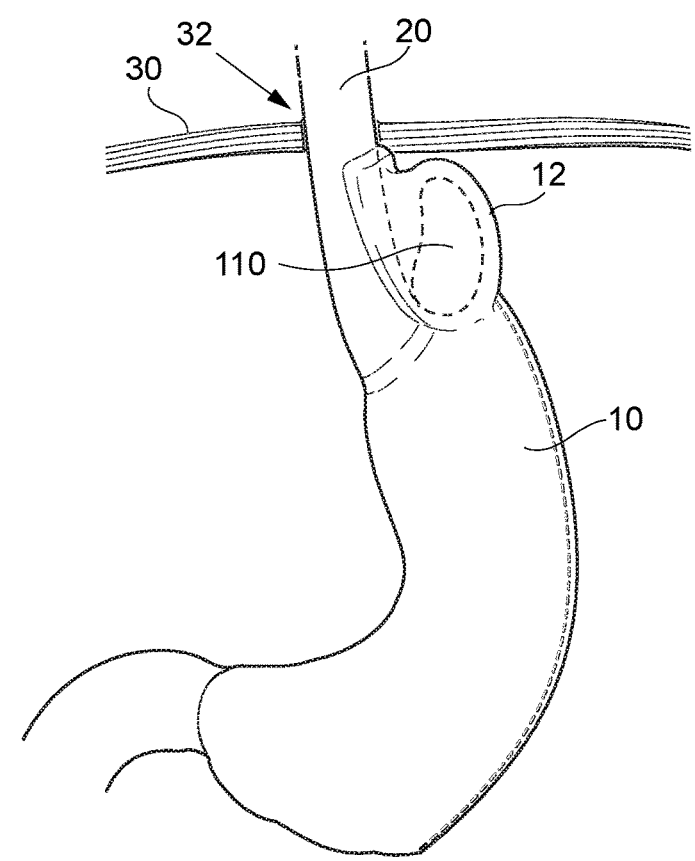

FIGS. 33 and 34 illustrate an example wherein the apparatus 100 according to the embodiments of FIGS. 29-32 is used in combination with a bariatric procedure, such as for example sleeve gastrectomy. Sleeve gastrectomy, or gastric sleeve, is a surgical weight-loss procedure in the stomach is reduced in size by surgical (often laparoscopic) removal of a relatively large portion of the stomach along the greater curvature. In FIG. 34a the dashed line delimits the part that is to be removed, with the result shown in FIG. 34b. According to the present example, the implantation of the movement restriction device 100 and the sleeve gastrectomy may be performed during the same procedure, wherein the movement restriction device 100 may be positioned to rest against the angle of His and secured in this position by a portion of the fundus being affixed to the esophagus at a position above the movement restriction device 110 before the stomach is reduced along the greater curvature. It is advisable to implant the movement restriction device 110 before the sleeve gastrectomy is performed, so as to ensure that there is a sufficiently large portion of the fundus 12 available for the fixation of the movement restriction device 110. FIG. 34b shows the result, wherein the movement restriction device 110 may be encapsulated by the fundus 12 that is affixed to the esophagus 20 to form an enclosure accommodating the movement restriction device 110. The encapsulated movement restriction device 110 may thus form a mechanical stop hindering the cardia from sliding up through the diaphragm opening 32, while the overall volume of the stomach cavity has been reduced by the sleeve gastrectomy.

In case the stomach wall, such as the fundus, is not sufficiently large for allowing an apparatus according any of the embodiments of FIGS. 1-13 and 24-34, and in particular the movement restriction device 110 as discussed in connection with any of the previous embodiments, to be at least partly invaginated or covered by the stomach wall so that the apparatus may function as a movement restriction device of the cardia, an alternative apparatus shown in FIGS. 35-37 may be employed. The present apparatus may comprise an implantable movement restriction device 110 and an elongated attacher 117 configured to be attached to the movement restriction device and to be at least partly invaginated by a wall portion of the patient's stomach 10. As indicated in the present figures, the attacher 117 may comprise a shape and size allowing it to be invaginated by the wall portion to hinder rotation of the movement restriction device 110 when implanted. The attacher 117 may be configured to be invaginated by the outside of the wall portion such that the movement restriction device 110 is arranged at a position between the patient's diaphragm 30 and the wall portion of the stomach 10, distant from the patient's esophagus 20, to restrict movement of the cardia 22 of the patient's stomach towards the diaphragm 30 to hinder the cardia from sliding through the diaphragm opening 32 into the patient's thorax. The attacher 117 may also be referred to as a fixator, attaching means, support, and the like.

Thus, a first end portion of the attacher 117 may be configured to be affixed to the wall portion of the stomach 10 and a second end portion to be attached to the movement restriction device 110. The first end portion of the attacher 117 may be at least partly invaginated or covered by tissue of the stomach wall, which hence may be achieved using a relatively small portion of the outer wall of the stomach 10 compared to invaginating the entire movement restriction device 110 as discussed above in connection with the previous embodiments. The present embodiment hence allows for the movement restriction device 110 to be positioned so as to function as a mechanical stop of movement towards the diaphragm 30 also in cases when there is a relatively limited amount of stomach wall available. This may for example be the case after a gastric sleeve operation.

The attacher 117 may be releasably attached to the movement restriction device 110 to allow the surgeon to insert the attacher 117 and the movement restriction device 110 as separate items. Once inserted in the body of the patient, the movement restriction device 110 and the attacher 117 may be assembled into a single unit and then affixed to the outside of the stomach 110. The attacher 117 and the movement restriction device 110 may for example be secured to each other by means of interlocking attachment means, such as a snap fitting or a form fitting. The attacher 117 may also be attached to the movement restriction device 110 by means of a fastener means such as a threading, allowing the movement restriction device 110 to be screwed onto the attacher 117. In alterative examples, however, the movement restriction device 110 and the attacher 117 may integrally formed into a single piece.

Figure 35:
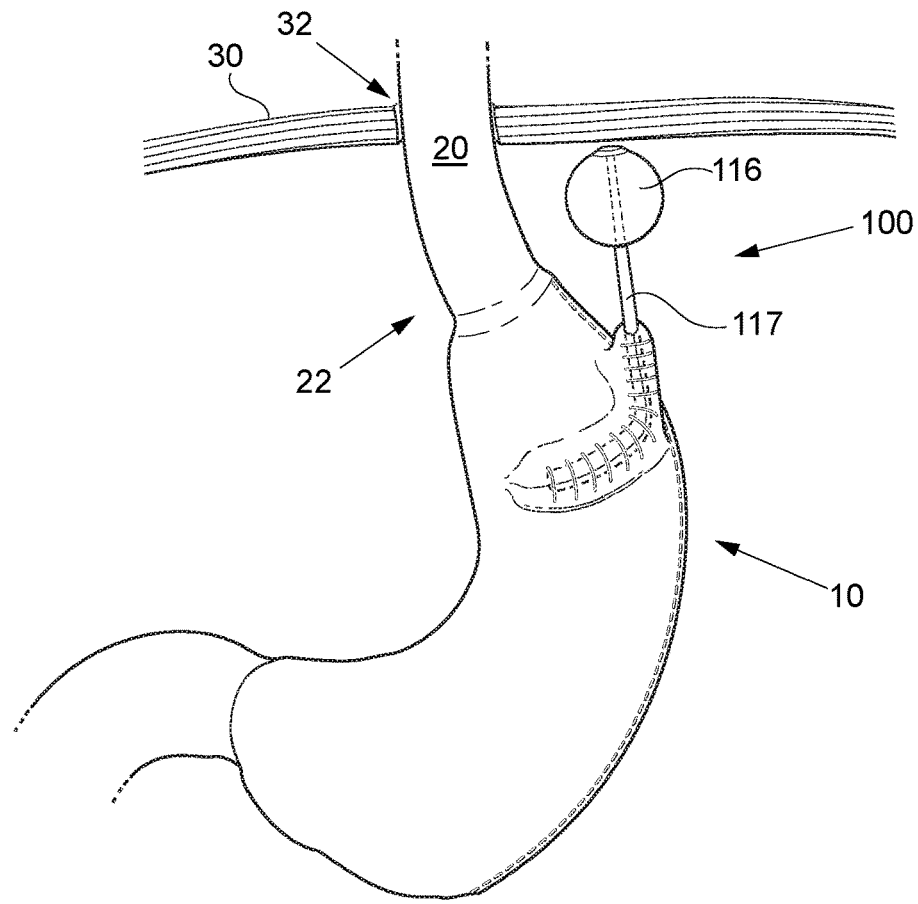
Figure 36:
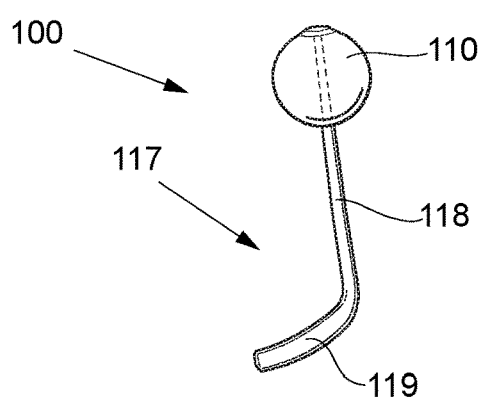

FIGS. 35 and 36 show an attacher 117 comprising a first portion 118 and a second portion 119 extending in different directions relative to each other, wherein the first portion 118 is configured to be invaginated by the wall portion to hinder rotation of the movement restriction device 110 around a first axis, and wherein the second portion 119 is configured to be invaginated by the wall portion to hinder rotation of the movement restriction device 110 around a second axis, different from the first axis. The first and second portions 118, 119 of the attacher 119 may further be curved to follow a curvature of the stomach. In some examples, the first portion 118 and the second portion 119 may be arranged at an angle to each other, wherein the angle for example may be in the interval of 60-120 degrees, such as about 90 degrees, so as to allow for the movement restriction device 110 to be mechanically supported by the stomach wall and movement of the restriction device 110 hindered in at least two different planes relative to the stomach portion. The attacher 117 may further comprise a third portion, being an extension of the second portion 119, which may be configured to be arranged to protrude from the wall portion when implanted to define a distance between the wall portion and the movement restriction device 110. In some examples, the third portion may comprises a curvature, which preferably may be adjustable, allowing the third portion to be arranged to point away from the esophagus 20 when implanted so as to reduce the risk for the movement restriction device 110 interfering with and constricting the esophagus 20.

The attacher 117 may be affixed to the stomach 10 in a procedure wherein the attacher 117 is placed onto the outer surface of the stomach 10, in a recess or fold which may be at least partly closed by means of stomach-to-stomach sutures or staples. Thus, the attached 117 may be at least partly covered and mechanically supported by tissue of the stomach wall. Eventually, the suture closing the recess or fold along the attacher 117 may be covered or encapsulated by fibrous tissue, further improving the affixation, and allowing for long-term implantation of the apparatus 100. Preferably, the attacher 117 is formed or, or at least comprises an outer surface of a biocompatible material suitable for long-term implantation in the body. Examples of biocompatible materials include titanium or a medical grade metal alloy, such as medical grade stainless steel. Further examples include ceramic materials such as zirconium carbide, or a stiff medical grade polymer material such as Ultra-high-molecular-weight polyethylene (UHMWPE) or Polytetrafluoroethylene (PTFE) or a thermoplastic polyester such as polylactide (PLA). Further, the attacher 117 could comprise at least one composite material, such as any combination of metallic/ceramic and polymer materials or a polymer material reinforced with organic or inorganic fibers, such as carbon or mineral fibers.

The attacher 117 may also comprise an electrode arrangement 150 for electrical stimulation and exercise of the muscle tissue against which the attacher 117 rests when implanted. The electrode arrangement 150 may be configured and operate as any of the previous electrode arrangements 150 described with reference to FIGS. 1-34.

Figure 37:
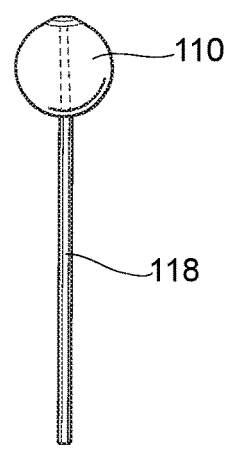
Figure 38:
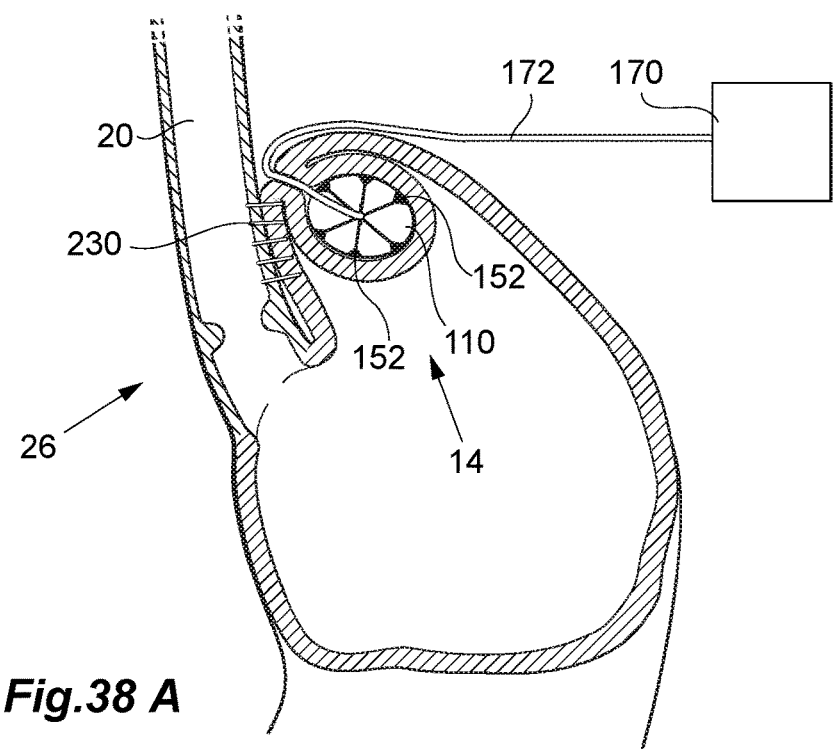
Figure 38:
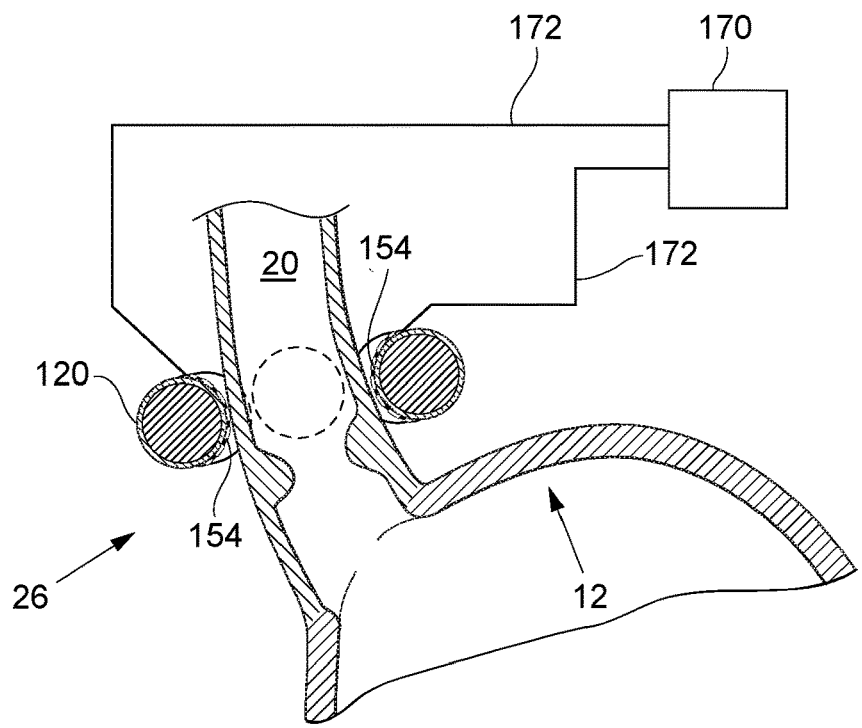

As illustrated in FIGS. 35-37, the movement restriction device 110 may have a rounded shape, for example conforming to a sphere, so as to reduce the risk for causing potential damage to surrounding tissue. The movement restriction device 117 may be formed of a polymer, or at least comprise an outer surface of such a material. The outer surface may further be provided with a material for hindering growth of fibrotic tissue. The outer surface may for example comprise a permanent or degradable polymer, containing an active pharmaceutical agent, coated on the movement restriction device 117. The coating may preferably allow for a gradual release of an antifibrotic drug. The eluted drug may thus be deposited at the contact point between the movement restriction device 110 and the tissue against which it abuts, such as the diaphragm 30, thereby providing targeted drug therapy. Examples of polymers include a blend of polyethylene-co-vinyl acetate (PEVA) and polybutyl methacrylate (PBMA) and poly(styrene-b-isobutylene-b-styrene), respectively. Further examples may include phosphorylcholine and poly(vinylidene fluoride-co-hexafluoropropylene) polymeric coatings, respectively.

Further, the movement restriction device 110 may comprise an electrode arrangement 150 for electrical stimulation and exercise of the muscle tissue against which the movement restriction device 110 rests when implanted. The electrode arrangement 150 may be configured and operate as any of the previous electrode arrangements 150 described with reference to FIGS. 1-34

The movement restriction device 110 may have a shape and size that allows it to function as a mechanical stop abutting against the diaphragm 30, being sufficiently large to hinder the movement restriction device 110 from passing through the diaphragm 30 and sufficiently small so as to not push against the esophagus 20 and cause constriction of the food passageway. In some examples, a minimum width of the movement restriction device 110, as measured from side to side, may be 30 mm or larger, such as 40 mm or larger.

When implanted, the movement restriction device 110 may be supported by the attacher 117, which is affixed to the stomach 10, such that the movement restriction device 110 functions as a mechanical stop against the diaphragm 30 and thereby hinders the cardia 22 from sliding upwards towards the diaphragm opening 32. Preferably, the movement restriction device 110 may be arranged relatively close to the diaphragm opening 32, such as less than 2 cm away from the part of the esophagus 20 passing through diaphragm opening 32, without constricting the food passageway defined by the esophagus 20.

The position of the movement restriction device 110 relative to the diaphragm 30 and/or cardia may be adjusted after affixation of the attacher 117 to the stomach 10. The adjustment may for example be achieved by the attacher 117 being adjustable in terms of length and/or angle, wherein the attacher 117 for example may be extendible/retractable along the length directions, and/or bendable. This allows for the attacher to be affixed to a region on the outside of the stomach 10 which is suitable or even optimal for affixing the attacher 117, and for the movement restriction device 110 to be correctly aligned/positioned afterwards, without having to rearrange the affixation of the attacher 117 to the stomach 10.

In the following a detailed description of a method and system for electrically stimulating the muscle tissue against the apparatuses according to any of the embodiments discussed with reference to FIGS. 1-37 may rest when implanted. The electrical stimulation may be performed for exercising the muscle tissue and thereby improve the conditions for long term implantation. The electrical electrode arrangement described and the electrical electrodes comprised in the arrangement may be implemented in any of the embodiments of the apparatus described herein for the purpose of exercising the muscle tissue which is in contact with the apparatus, or mechanically affected by the apparatus.

The body tends to react to a medical implant, partly because the implant is a foreign object, and partly because the implant interacts mechanically with tissue of the body. Exposing tissue to long-term engagement with, or pressure from, an implant may deprive the cells of oxygen and nutrients, which may lead to deterioration of the tissue, atrophy and eventually necrosis. The interaction between the implant and the tissue may also result in fibrosis, in which the implant becomes at least partially encapsulated in fibrous tissue. It is therefore desirable to stimulate or exercise the cells to stimulate blood flow and increase tolerance of the tissue for pressure from the implanted apparatus.

Muscle tissue is generally formed of muscle cells that are joined together in tissue that can be either striated or smooth, depending on the presence or absence, respectively, of organized, regularly repeated arrangements of myofibrillar contractile proteins called myofilaments. Striated muscle tissue is further classified as either skeletal or cardiac muscle tissue. Skeletal muscle tissue is typically subject to conscious control and anchored by tendons to bone. Cardiac muscle tissue is typically found in the heart and not subject to voluntary control. A third type of muscle tissue is the so-called smooth muscle tissue, which is typically neither striated in structure nor under voluntary control. Smooth muscle tissue can be found within the walls of organs and in for example the wall of the stomach 10 and the esophagus 20.

The contraction of the muscle tissue may be activated both through the interaction of the nervous system as well as by hormones. The different muscle tissue types may vary in their response to neurotransmitters and endocrine substances depending on muscle type and the exact location of the muscle.

A nerve is an enclosed bundle of nerve fibers called axons, which are extensions of individual nerve cells or neurons. The axons are electrically excitable, due to maintenance of voltage gradients across their membranes, and provide a common pathway for the electrochemical nerve impulses called action potentials. An action potential is an all-or-nothing electrochemical pulse generated by the axon if the voltage across the membrane changes by a large enough amount over a short interval. The action potentials travel from one neuron to another by crossing a synapse, where the message is converted from electrical to chemical and then back to electrical.

The distal terminations of an axon are called axon terminals and comprise synaptic vesicles storing neurotransmitters. The axonal terminals are specialized to release the neurotransmitters into an interface or junction between the axon and the muscle cell. The released neurotransmitter binds to a receptor on the cell membrane of the muscle cell for a short period of time before it is dissociated and hydrolyzed by an enzyme located in the synapse. This enzyme quickly reduces the stimulus to the muscle, which allows the degree and timing of muscular contraction to be regulated delicately.

The action potential in a normal skeletal muscle cell is similar to the action potential in neurons and is typically about −90 mV. Upon activation, the intrinsic sodium/potassium channel of the cell membrane is opened, causing sodium to rush in and potassium to trickle out. As a result, the cell membrane reverses polarity and its voltage quickly jumps from the resting membrane potential of −90 mV to as high as +75 mV as sodium enters. The muscle action potential lasts roughly 2-4 ms, the absolute refractory period is roughly 1-3 ms, and the conduction velocity along the muscle is roughly 5 m/s. This change in polarity causes in turn the muscle cell to contract.

The contractile activity of smooth muscle cells is typically influenced by multiple inputs such as spontaneous electrical activity, neural and hormonal inputs, local changes in chemical composition, and stretch. This in contrast to the contractile activity of skeletal and cardiac muscle cells, which may rely on a single neural input. Some types of smooth muscle cells are able to generate their own action potentials spontaneously, which usually occur following a pacemaker potential or a slow wave potential. However, the rate and strength of the contractions can be modulated by external input from the autonomic nervous system. Autonomic neurons may comprise a series of axon-like swellings, called varicosities, forming motor units through the smooth muscle tissue. The varicosities comprise vesicles with neurotransmitters for transmitting the signal to the muscle cell.

The muscle cells described above, i.e., the cardiac, skeletal, and smooth muscle cells are known to react to external stimuli, such as electrical stimuli applied by electrodes. A distinction can be made between stimulation transmitted by a nerve and direct electrical stimulation of the muscle tissue. In case of stimulation via a nerve, an electrical signal may be provided to the nerve at a location distant from the actual muscle tissue, or at the muscle tissue, depending on the accessibility and extension of the nerve in the body. In case of direct stimulation of the muscle tissue, the electrical signal may be provided to the muscle cells by an electrode arranged in direct or close contact with the cells. However, other tissue such as fibrous tissue and nerves may of course be present at the interface between the electrode and the muscle tissue, which may result in the other tissue being subject to the electrical stimulation as well.

In the context of the present application, the electrical stimulation discussed in connection with the various aspects and embodiments may be provided to the tissue in direct or indirect contact with the implantable apparatus, such as for example the movement restriction device. Preferably, the electrical stimulation is provided by one or several electrode elements arranged at the interface or contact surface between the apparatus and the tissue. Thus, the electrical stimulation may, in terms of the present disclosure, be considered as a direct stimulation of the tissue. Particularly when contrasted to stimulation transmitted over a distance by a nerve, which may be referred to as an indirect stimulation or nerve stimulation.

Hence, an electrode arrangement comprising one or several electrode elements may be arranged in, partly in, on, or in close vicinity of the tissue that is to be exercised by means of an electrical signal, similar to what is described above in connection with the embodiments of FIGS. 1-37. Preferably, the electrode may be arranged to transmit the electrical signal to the portions of the tissue that is affected, or risks to be affected, by mechanical forces exerted by the medical implant. Thus, the electrode element may be considered to be arranged between the implanted apparatus and the tissue against which the apparatus is arranged to rest when implanted.

During operation of the implantable apparatus, or the electrode arrangement, the electric signal may cause the muscle cells to contract and relax repeatedly. This action of the cells may be referred to as exercise and may have a positive impact in terms of preventing deterioration and damage of the tissue. Further, the exercise may help increasing tolerance of the tissue for pressure and mechanical forces generated by the apparatus The interaction between the implanted electrode element and the tissue against which it rests is to a large extent determined by the properties at the junction between the tissue and the electrode element. The active electrically conducting surface of the electrode element (in the following referred to as "metal", even though other materials is equally conceivable) can either be uncoated resulting in a metal-tissue interface, or insulated with some type of dielectric material. The uncoated metal surface of the electrode element may also be referred to as a bare electrode. The interface between the electrode element and the tissue may influence the behavior of the electrode element since the electrical interaction with the tissue is transmitted via this interface. In the biological medium surrounding the electrode element, such as the actual tissue and any electrolyte that may be present in the junction, the current is carried by charged ions, while in the material of the electrode element the current is carried by electrons. Thus, in order for a continuous current to flow, there needs to be some type of mechanism to transfer charge between these two carriers.

In some examples, the electrode element may be a bare electrode wherein the metal may be exposed to the surrounding biological medium when implanted in, or at the muscle tissue that is to be stimulated. In this case there may be a charge transfer at a metal-electrolyte interface between the electrode element and the tissue. Due to the natural strive for thermodynamic equilibrium between the metal and the electrolyte, a voltage may be established across the interface which in turn may cause an attraction and ordering of ions from the electrolyte. This layer of charged ions at the metal surface may be referred to as a "double layer" and may physically account for some of the electrode capacitance.

Hence, both capacitive faradaic processes may take place at the electrode element. In a faradaic process, a transfer of charged particles across the metal-electrolyte interface may be considered as the predominant current transfer mechanism. Thus, in a faradaic process, after applying a constant current, the electrode charge, voltage, and composition tend to go to constant values. Instead, in a capacitive (non-faradaic) process charge is progressively stored at the metal surface and the current transfer is generally limited to the amount which can be passed by charging the interface.

In some examples, the electrode element may comprise a bare electrode portion, i.e., an electrode having an uncoated surface portion facing the tissue such that a conductor-tissue interface is provided between the electrode element and the tissue when the electrode element is implanted. This allows for the electric signal to be transmitted to the tissue by means of a predominantly faradaic charge transfer process. A bare electrode may be advantageous from a power consumption perspective since a faradaic process tends to be more efficient than a capacitive charge transfer process. Hence, a bare electrode may be used to increase the current transferred to the tissue for a given power consumption.

In some examples, the electrode element may comprise a portion that is at least partly covered by a dielectric material so as to form a dielectric-tissue interface with the muscle tissue when the electrode is implanted. This type of electrode element allows for a predominantly capacitive, or non-faradaic, transfer of the electric signal to the muscle tissue. This may be advantageous over the predominantly faradaic process associated with bare electrodes since faradaic charge transfer may be associated with several problems. Example of problems associated with faradaic charge transfer include undesirable chemical reactions such as metal oxidation, electrolysis of water, oxidation of saline, and oxidation of organics. Electrolysis of water may be damaging since it produces gases. Oxidation of saline can produce many different compounds, some of which are toxic. Oxidation of the metal may release metal ions and salts into the tissue which may be dangerous. Finally, oxidation of organics in a situation with an electrode element directly stimulating tissue may generate chemical products that are toxic.

These problems may be alleviated if the charge transfer by faradaic mechanisms is reduced, which may be achieved by using an electrode at least partly covered by a dielectric material. Preferably, the dielectric material is chosen to have as high capacitance as possible, restricting the currents flowing through the interface to a predominantly capacitive nature.

Several types of electrode elements can be combined with the present disclosure. The electrode element can for example be a plate electrode, comprising a plate-shaped active part forming the interface with the tissue. In other examples, the electrode may be a wire electrode, formed of a conducting wire that can be brought in electrical contact with the tissue. Further examples may include needle- or pin-shaped electrodes, having a point at the end which can be attached to or inserted in the muscle tissue. The electrodes may for example be encased in epoxy for electrical isolation and protection and comprise gold wires or contact pads for contacting the muscle tissue. Some of these examples of electrodes, methods of stimulating using electrodes, and how the electrode arrangements can be arranged in connection with implantable apparatuses such as described in connection with the embodiments of FIGS. 1-37 will be discussed below with reference to FIGS. 38-45.

FIGS. 38a and 38b show embodiments of the apparatus 100, which may be similarly configured as the embodiments discussed with reference to any of the preceding FIGS. 1-37. Thus, FIG. 38a illustrates an apparatus 100 having a movement restriction device 110 configured to be affixed by the fundus 12 so as to hinder the cardia 22 from sliding upwards through the diaphragm opening, whereas FIG. 38b illustrates an apparatus 100 comprising a portion, such as an elongated core or support device 120, configured to at least partly encircle the esophagus 20. The encircling portion 120 may be configured to assist the cardiac sphincter in it closing of the esophagus, for example by applying an encircling pressure and/or by electrically stimulate the sphincter muscle so as to cause it to contract. The embodiments are illustrated in cross-sectional views when implanted and invaginated by the fundus 12 (movement restriction device in FIG. 38a) or placed around the esophagus (constricting/stimulating device in FIG. 38b).

The apparatus 100 in FIGS. 38a and 38b further comprises an electrode arrangement comprising a plurality of electrode elements 152, 154 for electrically stimulating the tissue of the fundus 12 and/or esophagus 20 for exercising the muscle tissue to improve the conditions for long term implantation of the apparatus 100, as discussed above. In the embodiment of FIG. 38a the electrode arrangement is arranged on an outer surface of the movement restriction device 110 and thus placed in abutment and in electrical contact with the tissue of the stomach fundus 12, to which the movement restriction device 110 may be affixed by means of invagination or at least partly covering the movement restriction device 110 by fundus wall tissue. In the embodiment of FIG. 38b, the electrode arrangement is arranged on an outer surface of a core element 213 and thus placed in abutment and in electrical contact with the tissue of the esophagus 20, around which the apparatus 100 may be arranged. As illustrated in FIG. 38b, the electrode arrangement may comprise at least two electrode elements 154 which may be placed on opposing sides of the esophagus 20 so as to cause the cardiac sphincter 26 to contract.

Each of the electrode elements 152, 154 of the electrode arrangement may be connected to a controller, such as a stimulation controller 170 by means of electrical conduits 172. The controller 170 may be configured to be operably connected to the electrode arrangement for controlling the electrical stimulation of the tissue. In the embodiment shown in FIG. 38a, the controller 170 may be configured to control the electrical stimulation such that the muscle tissue of the fundus 12 is stimulated by a series of electrical pulses. In the embodiment shown in FIG. 38a, the pulses may comprise a pulse of a first polarity followed by a pulse of a second, reversed polarity, and the pulsed electrical stimulation signal generated may comprise a pulse frequency of 0.01-150 Hz. In the embodiment shown in FIG. 38a, the electrical stimulation signal may comprise a pulse duration of 0.01-100 ms and a pulse amplitude of 1-15 mA. More specifically, in the embodiment of FIG. 38a, the electrical stimulation signal may comprise a pulse frequency of 0.15-0.25 Hz, a pulse duration of 20-30 ms and a pulse amplitude of 3-10 mA. Further, in the embodiment of FIG. 38a, the electrical stimulation signal may comprise a build-up period of 0.01-2 s in which the amplitude is gradually increasing, a stimulation period of 1-60 s, and a stimulation pause of 0.01-60 s, wherein the electrical signal comprises a pulse frequency of 1-50 Hz and a pulse duration of 0.1-10 ms.

The controller 170 of FIG. 38a may be integrated in an implantable controller, and the stimulation controller may be configured to receive input from a wireless remote control, directly or via a receiver of the implantable controller, for controlling the stimulation or for programming a stimulation routine for exercising the muscle tissue to improve the conditions for long term implantation of the implantable movement restriction device 110. The programming of a stimulation routine could for example be the programming of the frequency of the stimulation, or the current and/or voltage of the stimulation.

FIG. 38b shows an embodiment of the implantable apparatus 110 wherein the electrode elements 154 are connected to a stimulation controller 170 similarly configured as the one discussed with reference to FIG. 38a. The controller 170 may hence be configured to be operably connected to the electrode arrangement for controlling the electrical stimulation of the tissue of the esophagus 20. The stimulation of the tissue could for example be performed with electrical pulses, such as described with reference to FIG. 38a, or may in the alternative be controlled as a continuous low-energy current providing a continuous stimulation of the cardiac sphincter 26.

In the embodiments shown in FIGS. 38a and 38b, and preferably the movement restriction device 110, the implantable apparatus 110 may further comprise an implantable sensor 180 configured to sense actions potentials generated by pacemaker cells of the tissue of the stomach wall. The implantable sensor 180 may also be connected to the controller 170 by means of a sensor lead 173. The controller 170 may be configured to control the electrical simulation based at least partly on the sensed action potentials and may be configured to generate electrical pulses amplifying the sensed action potentials. The implantable sensor 180 may be implemented in any of the embodiments of implantable apparatuses 100 for treating reflux disease as disclosed in the present application.

As described above in connection with the embodiments illustrated in FIGS. 1-38, the apparatus may be implanted in the body so as to interact with different parts of the stomach and/or the esophagus. A first portion 110 of the apparatus may for example be affixed to the fundus 12 so as to function as a movement restriction device, and whereas a second portion 120 of the apparatus 100 may be arranged to at least partly encircle the esophagus in order to assist in preventing stomach content to rise through the esophagus 20.

Figure 39:
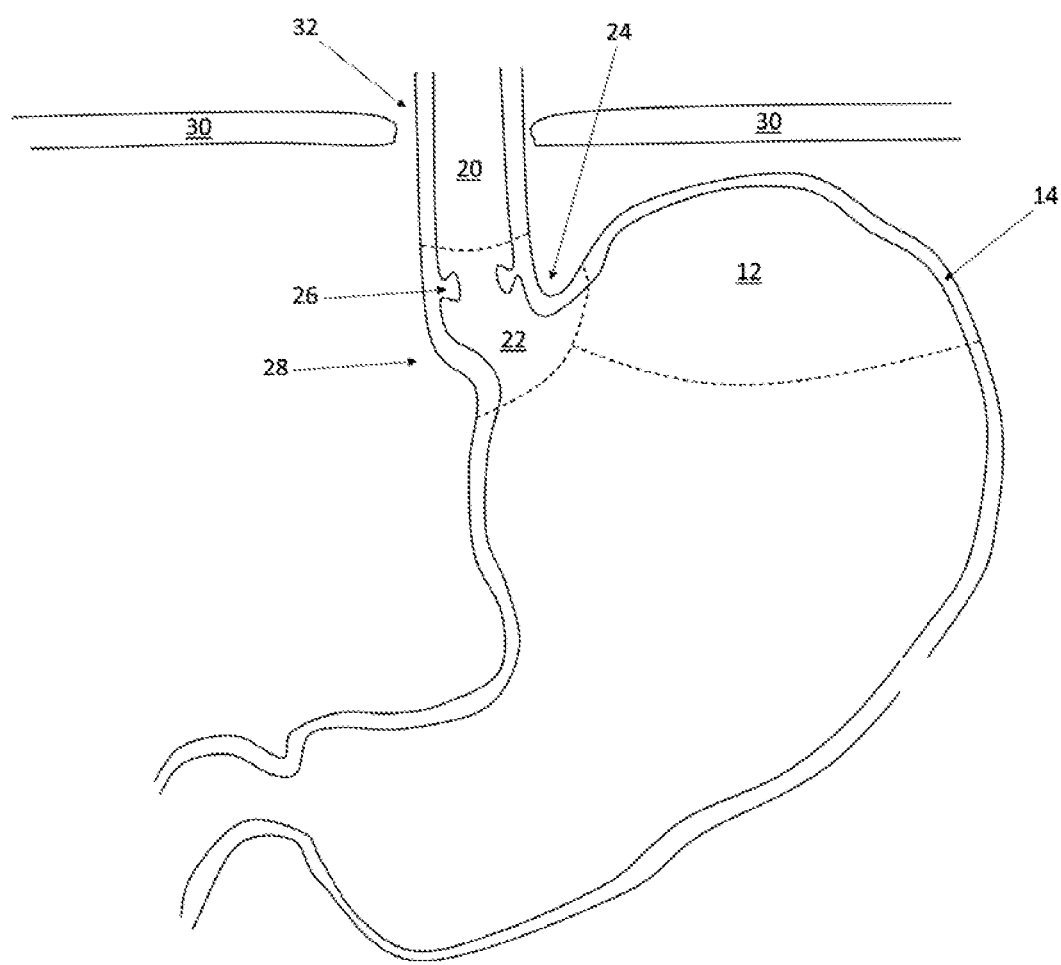
FIG. 39 is a schematic cross section illustrating the anatomy of the stomach of a human patient.

FIG. 39 is a schematic cross section illustrating the general structure of a stomach of a healthy adult. The stomach is located in the patient's abdomen, below the diaphragm 30. Entering occurs through the esophagus 20, which may be an approximately 25 cm long fibromuscular tube passing from the thorax into the abdomen through an opening 32 in the diaphragm 30. The lower part of the esophagus 20 thus be referred to as the abdominal portion of the esophagus 20. The esophagus 20 may connect to the stomach via a shorter segment, typically less than 1 cm, called the cardia 22. The cardia 22 may hence be considered to form the junction or interface between the esophagus 20 and the stomach 10 and may be formed both of a portion of the esophagus 20 and a portion of the stomach. The cardia 22 may join the greater curvature of the stomach (to the right in the figure) in a cardiac notch 24, which creates an acute angle between the esophagus 20 and an upper stomach wall portion. The cardiac notch 24 may also be referred to as the angle of His. Typically, the angle may be around 75 degrees in a healthy adult. FIG. 39 further illustrates the cardiac sphincter 26, which may be located in the wall of the cardia 22. Functionally, the sphincter opens to allow food to pass into the stomach and then quickly closes to prevent stomach contents from flowing back into the esophagus 20. The fundus 12 is formed in the upper curved part of the stomach and may be located above the cardiac notch 24. It normally does not store food, but gas produced during digestion. The volume of an empty stomach of a healthy adult human may be around 50 ml, and the fundus 12 generally makes up a relatively small part of that volume. The outermost layer of the stomach wall is called serosa 14. The thickness off the serosa layer 14 may be around 1-2 mm, compared to the total stomach wall thicknesses which ranges from 3 to 4 mm. The serosa may extend also to the cardia 22 and may cover a lower portion of the esophagus 20. The serosa has been observed to cover the lower portion of the esophagus 20 extending to the cardiac sphincter 26, above which there may be no serosa layer on the outside of the esophagus.

FIG. 40a is an example of a bipolar electrode arrangement 150, comprising a first and a second electrode element 152, 154 which may be similarly configured as the electrode elements discussed with reference to any of the previous embodiments. In the following figures, the first and second electrode elements will be distinguished by reference numerals E1 and E2, respectively. The first and second electrode elements E1, E2 may be connected to different electrical potentials. Thus, the first electrode element E1 can be operated as an anode and the second electrode element E2 can be operated as a cathode. In alternative embodiments, however, both electrode elements E1, E2 may be operated as cathodes, while using the tissue of the body as anode. The electrode elements E1, E2 may be attached directly to an outer surface of the implantable device, such as disclosed with reference to FIGS. 38a and 38b. In some examples the electrode elements E1, E2 may be arranged on a support, such as a flexible patch, which may be configured to be attached to the implantable constriction device. The electrode arrangement 150 can be arranged between the implantable constriction device and the tissue (such as disclosed with reference to FIGS. 38a and 38b) and may in some examples be provided as a separate, physically distinct item and in other examples be integrated in the apparatus 100. The electrode arrangement 150 may comprise one or several contact pads for increasing the contact surface between the electrode and the tissue when implanted. During operation, the electrical signal may be delivered to the muscle tissue by means of the first and second electrode elements E1, E2 so as to stimulate contraction of the muscle cells.

FIG. 40b is another example of an electrode arrangement 150, which in the present example may be a unipolar electrode element 152, 154. The electrode element E1 may for example be operated as a cathode when implanted. The electrode element 152 may be formed of a flat, coiled wire for increasing the contact surface between the electrode element 152 and the tissue. Further, the coiled configuration allows for a certain mechanical flexibility of the electrode element 152 such that it can follow the muscle tissue during contraction and relaxation.

Figure 40:
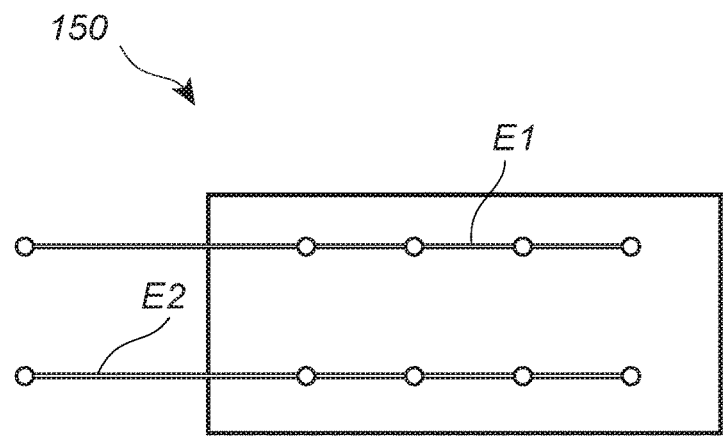
FIGS. 40A-D show various examples of electrode arrangements for electrically stimulating muscle tissue of the patient.
Figure 40:
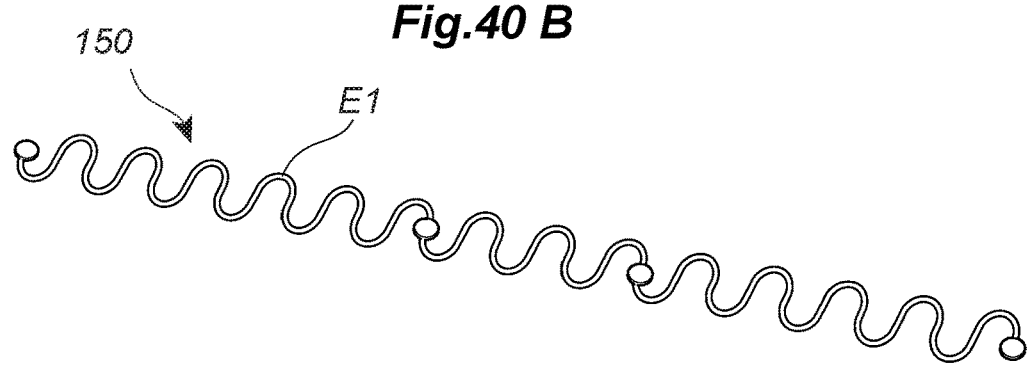
Figure 40C:
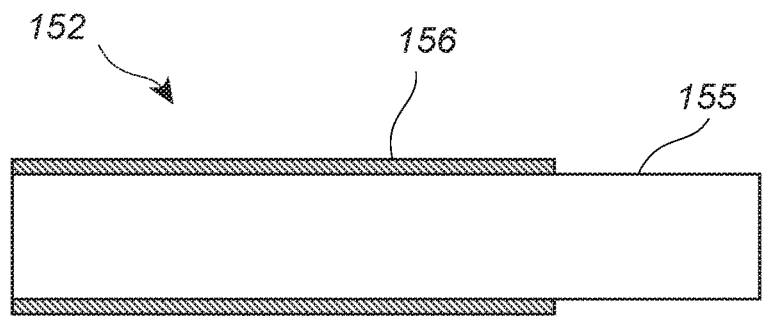
Figure 40:
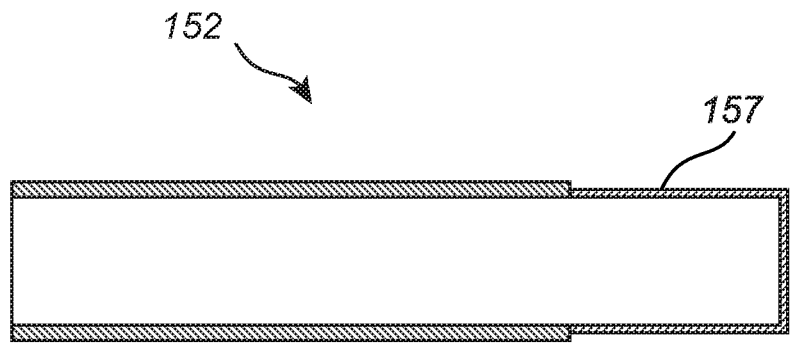

FIG. 40c illustrates the end portion of a needle- or pin-shaped electrode arrangement 150, wherein the active portion of the electrode element 152 is provided as a bare electrode surface 155 at the end of the electrode element 152, protruding from an insulation 156 covering the rest of the electrode element 152. Thus, when implanted at or in the muscle tissue, the active, bare electrode surface 155 of the electrode element 152 may form a metal-tissue interface with the muscle tissue, wherein the interface may surround the end portion of the electrode element 152 so as to provide a relatively large contact surface. The present example is advantageous in that it can be inserted into the tissue, thereby allowing for a selective stimulation at a certain depth of the tissue.

FIG. 40d shows a similar electrode element 152 as the one in FIG. 40c, with the difference that the present electrode element 152 comprises an active portion that is covered by a dielectric material 157 so as to protect the electrode material from deterioration and to facilitate capacitive current transfer. The dielectric material 157 may for example be electrochemically deposited tantalum oxide, which allows the electrical charge to pass through the interface but reduces the risk for electrode corrosion, gas formation and metabolite reactions.

It will be appreciated that both faradaic and capacitive mechanisms may be present at the same time, irrespectively of the type of electrode used. Thus, capacitive charge transfer may be present also for a bare electrode forming a metal-tissue interface, and faradaic charge transfer may be present also for a coated electrode forming a dielectric-tissue interface. It has been found that the faradaic portion of the current delivered to the muscle tissue can be reduced or even eliminated by reducing the duration of the pulses of the electric signal. Reducing the pulse duration has turned out to be an efficient way of increasing the portion of the signal which can be passed through the interface as a capacitive current, rather than by a faradaic current. As a result, shorter pulses may produce less electrode and tissue damage.

The capacitive portion of the current may further be increased, relative to the faradaic portion, by reducing the amplitude of the current pulses of the electrical signal. Reducing the amplitude may reduce or suppress the chemical reactions at the interface between the electrode and the tissue, thereby reducing potential damage that may be caused by compounds and ions generated by such reactions.

In one example, the electrical stimulation may be controlled in such a manner that a positive pulse of the electrical signal is followed by a negative pulse (or, put differently, a pulse of a first polarity being followed by a pulse of a second, reversed polarity), preferably of the same amplitude and/or duration. Advantageously, the subsequent negative (or reversed) pulse may be used to reverse or at least moderate chemical reactions or changes taking place in the interface in response to the first, positive pulse. By generating a reversed pulse, the risk of deterioration of the electrode and/or the tissue at the interface between the electrode and the muscle tissue may be reduced.

Figure 41:
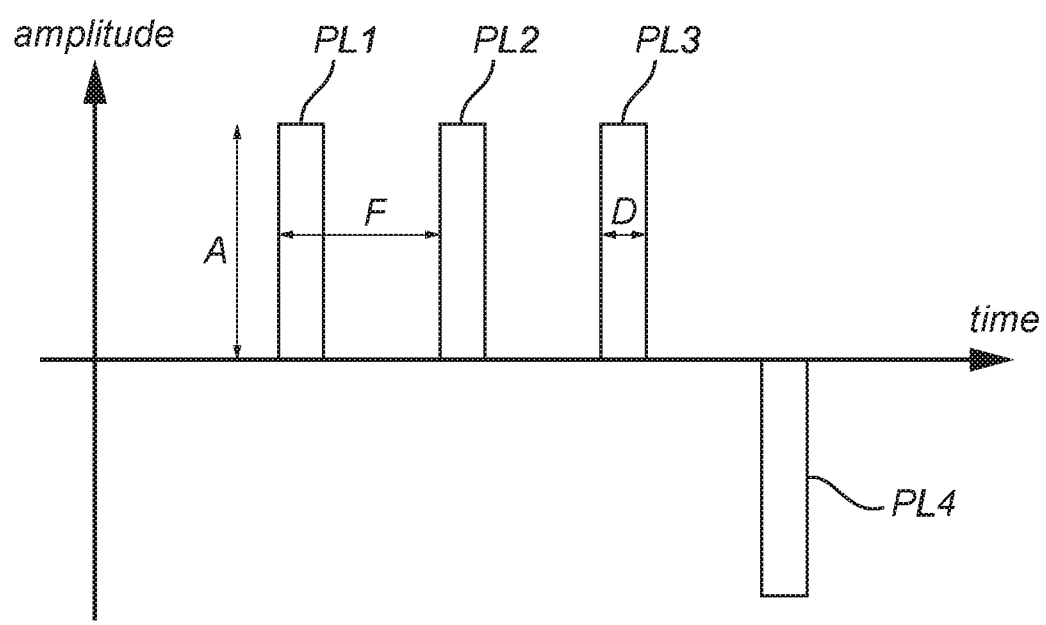
FIGS. 41-42 illustrate a pulsed signal for electrically stimulating muscle tissue.

FIG. 41 shows an example of a pulsed electrical signal to be applied to an electrode for electrically stimulating muscle tissue via an electrode-tissue interface as discussed above. The electrical signal may be generated by a stimulation controller arranged outside the body or implanted in the body (as described with reference to FIGS. 38a and 38b). The stimulation controller 170 may be operatively connected to the electrode element 152, 154 by means of a lead 172, and the electrical signal shown in the present figure may either reflect the signal as generated at the stimulation controller 170, or the signal as delivered to the electrode element 152, 154 at the electrode-tissue interface. The characteristics of the electrical signal may be selected and varied determined on the electrical and properties at the electrode-tissue interface and on the actual response of the tissue. The electrical stimulation delivered to the muscle cells may depend on several factors, such as the configuration and placement of the electrode element 152, 154 at the tissue, the presence of fibrous material at the interface, the composition of the electrolyte in the interface, accumulation of non-conducting material on the electrode surfaces, etcetera. It is therefore suggested that the characteristics of the electric signal, as shown in the present figure, be selected, and varied based on an observed or estimated response from the stimulated tissue.

In the present example, the electrical signal is a pulsed signal comprising square waves PL1, PL2, PL3, PL4. However, other shapes of the pulses may be employed as well. The pulse signal may be periodic, as shown, or may be intermittent (i.e., multiple series of pulses separated by periods of no pulses). The pulses may have an amplitude A, which may be measured in volts, ampere, or the like. Each of the pulses of the signal may have a pulse width D. Likewise, if the signal is periodic, the pulse signal may have a period F that corresponds to a frequency of the signal. Further, the pulses may be either positive or negative in relation to a reference.

The pulse frequency may for example lie within the range of 0.01-150 hertz. More specifically, the pulse frequency may lie within at least one of the ranges of 0.1-1 Hz, 1-10 Hz, 10-50 Hz and 50-150 Hz. It has been observed that relatively low pulse frequencies may be employed to imitate or enhance the slow wave potential associated with pacemaker cells of the smooth muscle tissue. Thus, it may be advantageous to use relatively low pulse frequencies, such as 0.01-0.1 Hz or frequencies below 1 Hz or a few Hz for such applications.

The pulse duration may for example lie within the range of 0.01-100 milliseconds, such as 0.1-20 milliseconds (ms), and preferably such as 1-5 ms. The natural muscle action potential has in some studies been observed to last about 2-4 ms, so it may be advantageous to use a pulse duration imitating that range.

The amplitude may for example lie within the range of 1-15 milliamperes (mA), such as 0.5-5 mA in which range a particularly good muscle contraction response has been observed in some studies.

In a preferred, specific example the electrical stimulation may hence be performed using a pulsed signal having a pulse frequency of 10 Hz, a pulse duration of 3 ms and an amplitude of 3 mA.

Figure 42:
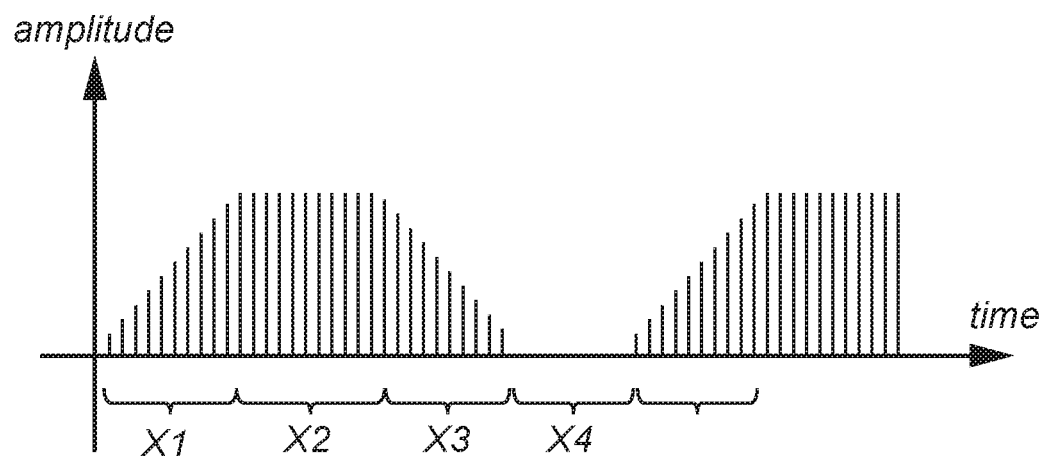

FIG. 42 shows an example of a pulsed signal, comprising build-up period X1, in which the amplitude is gradually increasing, a stimulation period X2 during which the muscle tissue is exposed to a contracting stimulation signal, a ramp down period X3 in which the amplitude is gradually decreasing, and a stimulation pause X4 before a new build-up period is initiated. The build-up period may for example be 0.01-2 seconds, the stimulation period 1-60 seconds, the ramp-down period 0.01-2 seconds, and the stimulation pause 0.01-60 seconds. The pulse frequency may for example be 1-50 Hz, the pulse duration 0.1-10 milliseconds and the amplitude during the stimulation period be 1-15 milliampere. The stimulation of skeletal muscle tissue may for example be performed using a frequency of 50 Hz and pulses having a duration of 100 µs. The current amplitude may be 1, 2.5, 7.5 or 10 mA. In particular, a desired muscle contraction response has been experimentally observed within a range of 0.5 to 5.0 mA. In the present example, a coiled electrode may be used as a cathode. Another example design is a multi-stranded wire arranged in a helical design. They can be imbricated in the muscular wall of the fundus (or esophagus) and can be stimulated in any desired pattern. The stimulus parameters may for example be biphasic pulses, 10 to 40 Hz, lasting 0.1 to 5 ms, with a current density of 3 to 5 mA/cm2.

Figure 43:
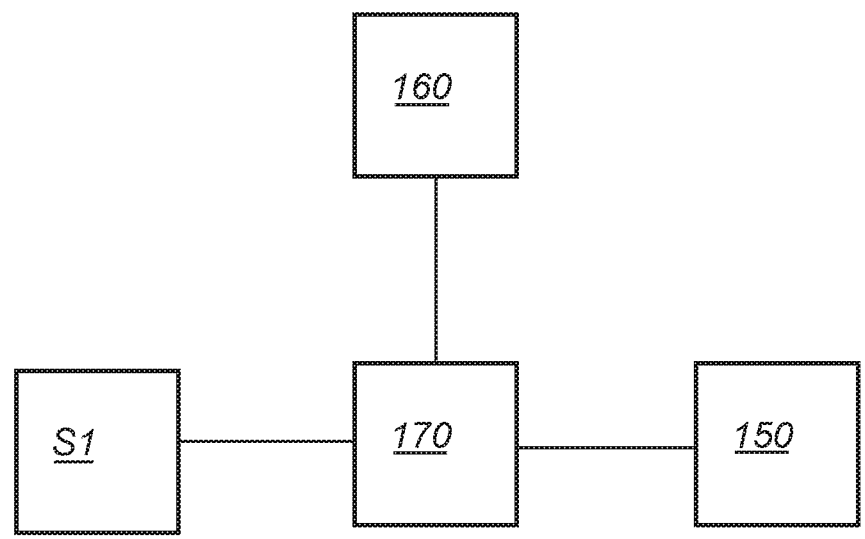
FIGS. 43-45 are schematic illustrations of systems for treating reflux disease.

FIG. 43 is a schematic outline of a system for electrically stimulating or exercising muscle cells to increase tolerance of the tissue for pressure from the apparatus 100. The system may be used in combination with the implantable apparatus 100 and may in some examples be comprised in such an apparatus 100. The system may comprise an electrode arrangement 150 which may be similarly configured as the electrodes arrangements/electrode elements discussed above in connection with the previous examples, an energy source 160 for providing the electrical energy required for generating the electrical signal, and a stimulation controller 170 controlling the generation of the electrical signal.

The electrode arrangement 150, which may comprise one or several electrode elements 152, 154, such as a bare electrode or an electrode at least partly covered by a dielectric material 157 shown in FIG. 39d, may be configured to be implanted in the muscle tissue to be stimulated, or to engage the muscle, so as to form an electrode-tissue interface through which the stimulating signal may be transferred. Alternatively, or additionally, the electrode element 152, 154 may be arranged in close vicinity to the muscle tissue such that an electrical coupling between the electrode element and the muscle tissue may be established. This may for example be the case when other tissue, such as connective tissue, is present between the implanted device and the muscle tissue.

The electrode may be electrically connected to the energy source 160, for example by means of a wiring or a lead 172, such that the electrical signal may be transferred to the electrode-tissue interface. In some examples, the electrode 152, 154 may be integrated with or attached to the apparatus, such as the movement restriction device 110, so that the electrode 152, 154 when implanted in the patient is arranged at the interface between the apparatus 100 and the muscle tissue. The electrode 152, 154 can thereby be used for exercising the muscle tissue that is mechanically affected by the implant.

The energy source 160 may for example be of a non-rechargeable type, such as a primary cell, or of a rechargeable type, such as a secondary cell. The energy source 160 may be rechargeable by energy transmitted from outside the body, from an external energy source, or be replaced by surgery. Further, the electrode arrangement 150 may be operably connected to a stimulation controller 170, which may comprise an electrical pulse generator, for generating the electrical pulse. The stimulation controller 170 may be integrated with the energy source 160 or provided as a separate, physically distinct unit which may be configured to be implanted in the body or operate from the outside of the body. In case of the latter, is may be advantageous to allow the external control unit to communicate wirelessly with the stimulation controller 150.

The system may according to some examples comprise a sensor S1 that is configured to sense a physical parameter of the body and/or the apparatus 100. The sensor S1 may for example be employed to sense or detect a bodily response to the electrical stimulation, such as for example a contraction of the stimulated muscle tissue. In an example, the sensor S1 may be configured to sense action potentials that are being sent to the muscle tissue. The action potentials may for example be generated by pacemaker cells of the muscle tissue, which may be registered by the sensor S1 and transmitted to the stimulation controller 170. The stimulation controller 170 may use the received signal when controlling the energy source 160, such that the generated electrical signal amplifies the sensed action potentials.

The energy source 160 may preferably be an implantable energy source 160 configured to be placed on the inside of the patient's body. Preferably, the implantable energy source 160 may comprise a secondary cell, which can be charged from the outside of the body so as to reduce the need for surgical battery replacement procedures. As indicated in the present figure, the implantable energy source 160 may be configured to be supplied with electrical energy from an external energy source 165 arranged outside the body. In such an example, the system may further comprise an implantable charger 190 configured to be electrically connected to the implantable energy source 160 and to enable charging of the implantable energy source 160 by the external energy source 165. The implantable charger 190 may for example be configured to be electrically connected to the implantable energy source 160 by means of a wiring or a lead 172, such that the electrical energy may be transferred from the implantable charger 190 to the implantable energy source 160. The implantable charger 190 may further be coupled to the external energy source 165 by a wireless coupling or by a wired coupling, using a wiring or lead 172 which may be similar to the one between the charger 190 and the implantable energy source 160. In case of the latter, the wiring or lead 172 may terminate in a terminal which may be access via the skin of the patient, either as a contact port surfacing the skin or being arranged under the skin. Electrical energy may then be transmitted to the charger 190 by connecting the external energy source 165 to the port, for example by incising the skin to expose the port and making it possible for the external energy source 165 to be plugged in.

Alternatively, the implantable charger 190 may be configured to receive energy from the external energy source 165 wirelessly, such as for example inductively. In this case, the charger 190 may comprise an electromagnetic coil configured to receive the electrical power wirelessly from the external energy source 165. The charger 190 may for example be arranged subcutaneously so as to facilitate inductive transfer of the energy via the skin of the patient.

The charging of the implantable energy source 160 may be controlled according to several different schemes. In an example, the charging of the implantable energy source 160 may be controlled by controlling the receipt of electrical power, from the external energy source, at the implantable charger 190. Put differently, the charger 190 may be configured to vary or control its capability of receiving electrical energy from the external energy source 165. Hence, the amount of electrical power delivered to the implantable energy source 160 may be regulated at the implantable charger 190 rather than at the external energy source 165, which hence may be allowed to transmit a substantially constant power. By varying the receipt at the charger 190, rather than the transmission at the external power source 165, the charging of the implantable energy source 160 may be performed without sending control signals to the external energy source 165. Instead, the intelligence required for regulating and controlling the charging of the implanted energy source 160 may be accommodated within the body of the patient, without the need of communication with the outside of the body.

In an alternative embodiment, the charging of the implantable energy source 160 may be controlled by controlling the transmission of electrical power at the external energy source 165. Thus, the charger 190 (or any other component of the apparatus/system arranged in the body) may send transmission instructions, for example via a control signal, to the external energy source 165 which may regulate its transmitting power accordingly.

The charging of the implantable energy source 160 may be controlled by the controller 170, which hence may be configured to issue control instructions to the implantable charger 190 and/or the external energy source 165, as discussed above. In some examples, the controller 170 may be configured to indicate a functional status of the implantable energy source 160, such as for example charge level, charging capacity, voltage and/or temperature of the implantable energy source 160. The functional status may for example be used for controlling the charging of the implantable energy source 160 as described above, and for indicating the status of the implantable energy source 160 to the patient or another, external entity such as medical staff. The functional status may for example be transmitted to the outside of the body, where it can be interpreted and used for diagnosis of the status/condition of the implanted apparatus. Further, the functional status may be transmitted to the outside of the body to provide a warning signal, for example indicating low battery or overheating. The transmission of a signal to/from the controller 170 is described in further detail in connection with the following FIGS. 44-48.

The functional status may for example be based on a signal from a sensor, such as a temperature sensor configured to sense a temperature of the implanted energy source 160, or a current or voltage meter configured to measure an electrical condition of the implanted energy source 160. The sensor output may be transmitted to the controller 170, for example by means of a wiring or electrical conductor 172, where it can be processed and acted upon in the form of an issued signal comprising control instructions for the charger 190/external energy source 165 and/or functional status information.

The functional status may in some examples be transmitted via a carrier signal to the outside of the body by means of a transmitter, which for example may be arranged subcutaneously. In some example the transmitter may be integrated in the charger 190.

Figure 44:
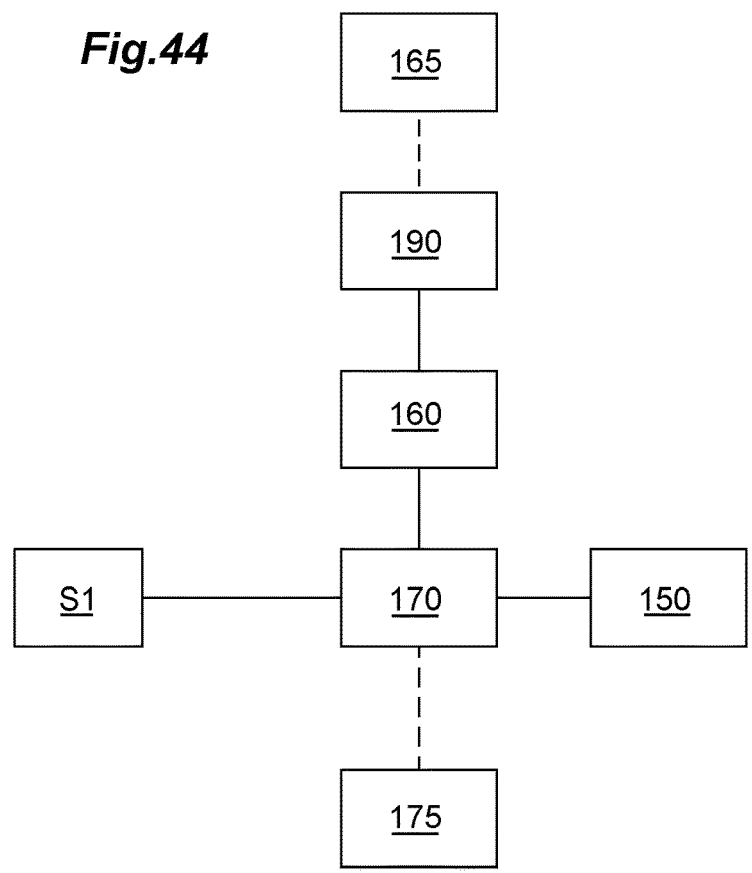

FIG. 44 shows a similar embodiment as the system described above with reference to FIG. 43. However, as indicated in the present figure, the system may further comprise an external signal transmitter 175, such as a wireless remote 175, which may be configured to be operably connected to the controller 170. The external signal transmitter 175 may be arranged to allow for the patient or another external entity, such as a service technician or medical staff, to interact with the controller 170. The external signal transmitter 175 may for example be used to control, or adjust, the operation of the implanted controller 170 in order to affect or adjust the electrical stimulation signal delivered to the tissue by the electrode arrangement 150. The external control of the controller 170 may for example serve the purpose of increasing or reducing an amplitude or frequency of the electrical stimulation signal, or for activating/deactivating the electrical stimulation. In an example, the external signal transmitter 175 may be used for increasing the electrical stimulation of the cardiac sphincter in response to experienced reflux symptoms. In this way, the patient may be allowed to increase the contraction of the cardiac sphincter so as to further hinder stomach contents from rising in the esophagus.

The signal, by which the external signal transmitter 175 is communicating with the implanted controller 170, may be selected from the group consisting of: a sound signal, an ultrasound signal, an electromagnetic signal, and infrared signal, a visible light signal, an ultra violet light signal, a laser signal, a microwave signal, a radio wave signal, an X-ray radiation signal and a gamma radiation signal.

While illustrated as separate components/entities in the figure, it is appreciated that the implanted, or internal, controller 170 may be integrated in the implantable charger 190 and/or in the implantable energy source 160. Further, the external signal transmitter 175 may be integrated in the wireless remote.

Figure 45:
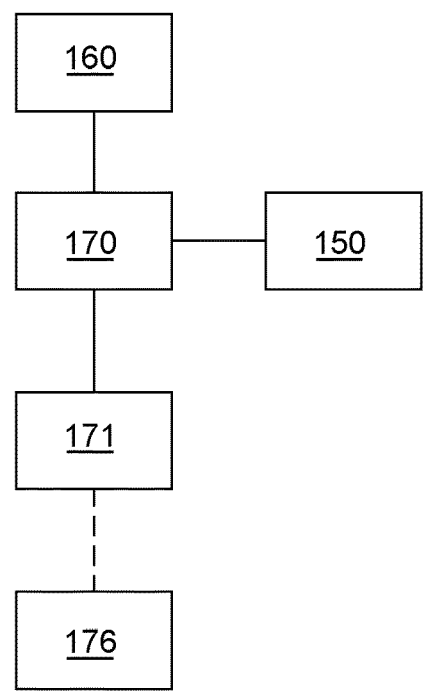

FIG. 45 is a schematic diagram of a system, or an apparatus, which may be similarly configured as the system described with reference to FIGS. 43 and 44. Hence, a system is disclosed, comprising an electrode arrangement 150 for exercising muscle tissue affected by an implanted apparatus according to any of the embodiments discussed above in connection with FIGS. 1-37, and a controller 170 configured to be operably connected to the electrode arrangement 150 for controlling the electrical stimulation of the muscle tissue. The controller 170 may be coupled to an implantable energy source 160 for providing the electrode arrangement with electrical power according to a stimulation signal or pattern generated by the controller 170.

FIG. 45 further illustrates an implantable communicator 171, which may be configured to transmitting a signal between the controller 170 and the outside of the patient's body, similar to what is described above in connection with FIG. 44. The communicator 171 may be comprised in the control unit 170 or provided as a separate unit. The communicator 171 may hence be used for transmitting the signal comprising the functional status of the implantable energy source 160, and for communicating with an external controller 176 used for controlling or adjusting the operation of the implantable controller 170. The external controller 176 may for example be comprised in a remote controller 175 as shown in FIG. 44.

The implantable controller 170, which also may be referred to as an internal controller or a stimulation controller 170, may be understood as any implantable unit capable of controlling the electrical stimulation of the tissue. A controller could include an electrical signal generator, a modulator or other electrical circuitry capable of delivering the electrical stimulation signal to the electrode arrangement. Further, the controller may be capable of processing control signals and generate the electrical stimulation signal in response thereto, and further to generate control signals for the control of other components of the system or apparatus, such as for example the implanted energy source 160 and/or the implantable charger 190. A control signal may thus be understood as any signal capable of carrying information and/or electric power such that a component of the system/apparatus can be directly or indirectly controlled.

The controller may comprise a processing unit, such as a CPU, for handling the control of the electrode arrangement 150 and other components of the system. The processing unit could be a single central processing unit or could comprise two or more processing units. The processing unit could comprise a general-purpose microprocessor and/or an instruction set processor and/or related chips sets and/or special purpose microprocessors such as ASICs (Application Specific Integrated Circuit). The processing unit may also comprise memory for storing instruction and/or data. The controller 170 could be adapted to keep track of different stimulation patterns and periods used for the stimulation of the muscle tissue, and in some examples also the action potentials sensed by the sensor S1. The controller 170 may further comprise a communicator, or communication unit 171 as outlined above, which may be configured for receiving and/or transmitting wireless or wired signals to/from outside the body. The communication unit 171 can enable programming the controller 170 form outside of body of the patient such that the operation of the electrode arrangement 150 can be programmed to function optimally.

The controller 170, as well as other implanted components such as the energy source 160, the charger 190, and the first or second portion 110, 120 of the apparatus 100, may be enclosed by an enclosure so as to protect the components from bodily fluids. The enclosures may be an enclosure made from one of or a combination of: a carbon based material (such as graphite, silicon carbide, or a carbon fiber material), a boron material, a polymer material (such as silicone, Peek®, polyurethane, UHWPE or PTFE), a metallic material (such as titanium, stainless steel, tantalum, platinum, niobium or aluminum), a ceramic material (such as zirconium dioxide, aluminum oxide or tungsten carbide) or glass. In any instance the enclosure should be made from a material with low permeability, such that migration of fluid through the walls of the enclosure is hindered.

As is readily understood by a person skilled in the art the system disclosed in connection with FIGS. 43-45 may be integrated in any of the embodiments discussed with reference to FIGS. 1-38, thus forming part of the disclosed embodiments, and/or be used in connection with such apparatuses in order to address symptoms of a patient suffering from reflux disease.

The function and features of a controller for controlling the apparatuses according to any of the above aspects and embodiments will now described with reference to FIGS. 46A-C, 47 and 48. The features of the controller described with reference to FIGS. 46-48 may be implemented and combined with any of the embodiments of implantable medical devices disclosed herein. The features may for example be implemented in the controllers shown and/or described with reference to FIGS. 1, 38A-B, 40, and 43-45. Any controller may reference to FIGS. 46A-C. The controller disclosed in this description, and any combination of features thereof, may comprise an internal computing unit, also called a processor or controller, for controlling a function of the implant, such as the electrical stimulation of muscle tissue and/or charging of the internal energy source, and it may comprise a communication unit and implement methods for communication, including verification, authentication and encryption of data, as described in the following.

In the following, the term "medical implant" should be understood as referring to any of the apparatuses, or part of the apparatuses, according to the above aspects. Thus, the medical implant may refer to the implantable movement restriction device, the electrode arrangement, the elongated core, the tubular cover, the implantable first and second portions, and/or the elongated support device.

The controller may comprise a collection of communication related sub-units such as a wired transceiver, a wireless transceiver, energy storage, an energy receiver, a computing unit, a memory, or a feedback unit. The sub-units of the controller may cooperate with each other or operate independently with different purposes. The sub-units of the controller may inherit the prefix "internal". This is to distinguish these sub-units from the sub-units of the external devices as similar sub-units may be present for both the implanted controller and the external devices. The sub-units of the external devices may similarly inherit the prefix "external".

A wireless transceiver may comprise both a wireless transmitter and a wireless receiver. The wireless transceiver may also comprise a first wireless transceiver and a second wireless transceiver. In this case, the wireless transceiver may be part of a first communication system (using the first wireless transceiver) and a second communication system (using the second wireless transceiver).

In some embodiments, two communication systems may be implemented using a single wireless transceiver in e.g. the medical implant and a single wireless transceiver in e.g. an external device (i.e. one antenna at the medical implant and one antenna at the external device), but where for example the network protocol used for data transmission from the external device to the medical implant is different from the network protocol used for data transmission from the medical implant to the external device, thus achieving two separate communication systems.

Alternatively, the wireless transceiver may be referred to as either a wireless transmitter or a wireless receiver as not all embodiments of secure wireless communication discussed herein require two-way communication capability of the wireless transceiver. The wireless transceiver may transmit or receive wireless communication via wireless connections. The wireless transceiver may connect to both the medical implant and to external devices, i.e. devices not implanted in the patient.

The wireless connections may be based on radio frequency identification (RFID), near field charge (NFC), Bluetooth, Bluetooth low energy (BLE), or wireless local area network (WLAN). The wireless connections may further be based on mobile telecommunication regimes such as 1G, 2G, 3G, 4G, or 5G. The wireless connections may further be based on modulation techniques such as amplitude modulation (AM), frequency modulation (FM), phase modulation (PM), or quadrature amplitude modulation (QAM). The wireless connection may further feature technologies such as time-division multiple access (TDMA), frequency-division multiple access (FDMA), or code-division multiple access (CDMA). The wireless connection may also be based on infra-red (IR) communication. The wireless connection may feature radio frequencies in the high frequency band (HF), very-high frequency band (VHF), and the ultra-high frequency band (UHF) as well as essentially any other applicable band for electromagnetic wave communication. The wireless connection may also be based on ultrasound communication to name at least one example that does not rely on electromagnetic waves.

A wired transceiver may comprise both a wired transmitter and a wired receiver. The wording wired transceiver aims to distinguish between it and the wireless transceiver. It may generally be considered a conductive transceiver. The wired transceiver may transmit or receive conductive communication via conductive connections. Conductive connections may alternatively be referred to as electrical connections or as wired connections. The wording wired however, does not imply there needs to be a physical wire for conducting the communication. The body tissue of the patient may be considered as the wire. Conductive connection may use the body of the patient as a conductor. Conductive connections may still use ohmic conductors such as metals to at least some extent, and more specifically at the interface between the wired transceiver and the chosen conductor.

Communication, conductive or wireless may be understood as digital or analogue. In analogue communication, the message signal is in analogue form i.e., a continuous time signal. In digital communication, usually digital data i.e., discrete time signals containing information is transmitted.

The controller may comprise a sensation generator. A sensation generator is a device or unit that generates a sensation. The generated sensation may be configured to be experienceable by the patient such that the patient may take actions to authenticate a device, connection, or communication. The sensation generator may be configured to generate a single sensation or a plurality of sensation components. The sensation or sensation components may comprise a vibration (e.g. a fixed frequency mechanical vibration), a sound (e.g. a superposition of fixed frequency mechanical vibrations), a photonic signal (e.g. a non-visible light pulse such as an infra-red pulse), a light signal (e.g. a visual light pulse), an electric signal (e.g. an electrical current pulse) or a heat signal (e.g. a thermal pulse). The sensation generator may be implanted, configured to be worn in contact with the skin of the patient or capable of creating sensation without being in physical contact with the patient, such as a beeping alarm.

The sensations generated by the sensation generator may be configured to be experienceable by a sensory function or a sense of the patient from the list of tactile, pressure, pain, heat, cold, taste, smell, sight, and hearing. Sensations may be generated of varying power or force as to adapt to sensory variations in the patient. Power or force may be increased gradually until the patient is able to experience the sensation. Variations in power or force may be controlled via feedback. Sensation strength or force may be configured to stay within safety margins. The sensation generator may be connected to the medical implant. The sensation generator may be comprised within the medical implant or be a separate unit.

A motor, e.g. of the active device or unit of the medical implant, for controlling a physical function in the body of the patient may provide a secondary function as a sensation generator, generating a vibration or sound. Generation of vibrations or sounds of the motor may be achieved by operating the motor at specific frequencies. When functioning as to generate a sensation the motor may operate outside of its normal ranges for frequency controlling a physical function in the body. The power or force of the motor when operating to generate a sensation may also vary from its normal ranges for controlling a physical function in the body.

An external device is a device which is external to the patient in which the medical implant is implanted in. The external device may be also be enumerated (first, second, third, etc.) to separate different external devices from each other. Two or more external devices may be connected by means of a wired or wireless communication as described above, for example through IP (internet protocol), or a local area network (LAN). The wired or wireless communication may take place using a standard network protocol such as any suitable IP protocol (IPv4, IPv6) or Wireless Local Area Network (IEEE 802.11), Bluetooth, NFC, RFID etc. The wired or wireless communication may take place using a proprietary network protocol. Any external device may also be in communication with the medical implant using wired or wireless communication according to the above. Communication with implanted devices may be thus accomplished with a wired connection or with wireless radiofrequency (RF) telemetry. Other methods of wireless communication may be used to communicate with implants, including optical and ultrasound. Alternatively, the concept of intrabody communication may be used for wireless communication, which uses the conductive properties of the body to transmit signals, i.e. conductive (capacitive or galvanic) communication with the medical implant. Means for conductive communication between an external device and an implant may also be called "electrical connection" between an external device and an implant. The conductive communication may be achieved by placing a conductive member of the external device in contact with the skin of the patient. By doing this, the external device and/or the implant may assure that it is in direct electrical connection with the other device. The concept relies on using the inherent conductive or electrical properties of a human body. Signals may preferably be configured to affect the body or body functions minimally. For conductive communication this may mean using low currents. A current may flow from an external device to an implant or vice versa. Also, for conductive communication, each device may have a transceiver portion for transmitting or receiving the current. These may comprise amplifiers for amplifying at least the received current. The current may contain or carry a signal which may carry e.g. an authentication input, implant operation instructions, or information pertaining to the operation of the implant.

Alternatively, conductive communication may be referred to as electrical or ohmic or resistive communication.

The conductive member may be an integrated part of the external device (e.g. in the surface of a smartwatch that is intended to be in contact with the wrist of the person wearing it), or it may be a separate device which can be connected to the external device using a conductive interface such as the charging port or the headphone port of a smartphone.

A conductive member may be considered any device or structure set up for data communication with the implant via electric conductive body tissue. The data communication to the implant may be achieved by e.g. current pulses transmitted from the conductive member through the body of the patient to be received by a receiver at the implant. Any suitable coding scheme known in the art may be employed. The conductive member may comprise an energy source such as a battery or receive energy from e.g. a connected external device.

The term conductive interface is representing any suitable interface configured for data exchange between the conductive member and the external device. The conductive member may in an alternative configuration receive and transmit data to the external device through a radio interface, NFC, and the like.

An external device may act as a relay for communication between an implant and a remote device, such as e.g. second, third, or other external devices. Generally, the methods of relaying communication via an external device may be preferable for a large number of reasons. The transmission capabilities of the implant may be reduced, reducing its technical complexity, physical dimensions, and medical effects on the patient in which the implant is implanted. Communication may also be more efficient as direct communication, i.e. without a relaying device, with an implant from a remote device may require higher energy transmissions to account for different mediums and different rates of attenuation for different communication means. Remote communication with lower transmission energy may also increase the security of the communication as the spatial area or volume where the communication may be at all noticeable may be made smaller. Utilizing such a relay system further enables the use of different communication means for communication with the implant and communication with remote devices that are more optimized for their respective mediums.

An external device may be any device having processing power or a processor to perform the methods and functions needed to provide safe operation of the implant and provide the patient or other stakeholders (caregiver, spouse, employer etc.) with information and feedback from the implant. Feedback parameters could include battery status, energy level at the controller, the electrical characteristics of the stimulation signal, number of stimulation cycles the electrode arrangement has delivered, properties, version number etc. relating to functionality of the apparatus. The external device may for example be a handset such as a smartphone, smartwatch, tablet etc. handled by the patient or other stakeholders. The external device may be a server or personal computer handled by the patient or other stakeholders. The external device may be cloud based or a virtual machine. In the drawings, the external device handled by the patient is often shown as a smart watch, or a device adapted to be worn by the patient at the wrist of the patient. This is merely by way of example and any other type of external device, depending on the context, is equally applicable.

Several external devices may exist such as a second external device, a third external device, or another external device. The above listed external devices may e.g. be available to and controllable by a patient, in which an implant is implanted, a caregiver of the patient, a healthcare professional of the patient, a trusted relative of the patient, an employer or professional superior of the patient, a supplier or producer of the implant or its related features. By controlling the external devices may provide options for e.g. controlling or safeguarding a function of the implant, monitoring the function of the implant, monitoring parameters of the patient, updating or amending software of the implant etc.

An external device under control by a supplier or producer of the implant may be connected to a database comprising data pertaining to control program updates and/or instructions. Such database may be regularly updated to provide new or improved functionality of the implant, or to mitigate for previously undetected flaws of the implant. When an update of a control program of an implant is scheduled, the updated control program may be transmitted from the database in a push mode and optionally routed via one or more further external devices before received by the implanted controller. In another embodiment, the update is received from the database by request from e.g. an external device under control by the patient having the implant implanted in his/her body, a pull mode.

The external device may require authentication to be operated in communication with other external devices or the implant. Passwords, multi-factor authentication, biometric identification (fingerprint, iris scanner, facial recognition, etc.) or any other way of authentication may be employed.

The external device may have a user interface (UI) for receiving input and displaying information/feedback from/to a user. The UI may be a graphical UI (GUI), a voice command interface, speaker, vibrators, lamps, etc.

The communication between external devices, or between an external device and the implant may be encrypted. Any suitable type of encryption may be employed such as symmetric or asymmetric encryption. The encryption may be a single key encryption or a multi-key encryption. In multi-key encryption, several keys are required to decrypt encrypted data. The several keys may be called first key, second key, third key, etc. or first part of a key, second part of the key, third part of the key, etc. The several keys are then combined in any suitable way (depending on the encryption method and use case) to derive a combined key which may be used for decryption. In some cases, deriving a combined key is intended to mean that each key is used one by one to decrypt data, and that the decrypted data is achieved when using the final key.

In other cases, the combination of the several key result in one "master key" which will decrypt the data. In other words, it is a form of secret sharing, where a secret is divided into parts, giving each participant (external device(s), internal device) its own unique part. To reconstruct the original message (decrypt), a minimum number of parts (keys) is required. In a threshold scheme this number is less than the total number of parts (e.g. the key at the implant and the key from one of the two external device are needed to decrypt the data). In other embodiments, all keys are needed to reconstruct the original secret, to achieve the combined key which may decrypt the data.

In should be noted that it is not necessary that the generator of a key for decryption is the unit that in the end sends the key to another unit to be used at that unit. In some cases, the generator of a key is merely a facilitator of encryption/decryption, and the working in behalf of another device/user.

A verification unit may comprise any suitable means for verifying or authenticating the use (i.e. user authentication)

of a unit comprising or connected to the verification unit, e.g. the external device. For example, a verification unit may comprise or be connected to an interface (UI, GUI) for receiving authentication input from a user. The verification unit may comprise a communication interface for receiving authentication data from a device (separate from the external device) connected to the device comprising the verification unit. Authentication input/data may comprise a code, a key, biometric data based on any suitable techniques such as fingerprint, a palm vein structure, image recognition, face recognition, iris recognition, a retinal scan, a hand geometry, and genome comparison, etc. The verification/authentication may be provided using third party applications, installed at or in connection with the verification unit.

The verification unit may be used as one part of a two-part authentication procedure. The other part may e.g. comprise conductive communication authentication, sensation authentication, or parameter authentication.

The verification unit may comprise a card reader for reading a smart card. A smart card is a secure microcontroller that is typically used for generating, storing, and operating on cryptographic keys. Smart card authentication provides users with smart card devices for the purpose of authentication. Users connect their smart card to the verification unit. Software on the verification unit interacts with the keys material and other secrets stored on the smart card to authenticate the user. In order for the smart card to operate, a user may need to unlock it with a user-PIN. Smart cards are considered a very strong form of authentication because cryptographic keys and other secrets stored on the card are very well protected both physically and logically and are therefore hard to steal.

The verification unit may comprise a personal e-ID that is comparable to, for example, passport and driving license. The e-ID system comprises is a security software installed at the verification unit, and a e-ID which is downloaded from a web site of a trusted provided or provided via a smart card from the trusted provider.

The verification unit may comprise software for SMS-based two-factor authentication. Any other two-factor authentication systems may be used. Two-factor authentication requires two things to get authorized: something you know (your password, code, etc.) and something you have (an additional security code from your mobile device (e.g. a SMS, or a e-ID) or a physical token such as a smart card).

Other types of verification/user authentication may be employed. For example, a verification unit which communicate with an external device using visible light instead of wired communication or wireless communication using radio. A light source of the verification unit may transmit (e.g. by flashing in different patterns) secret keys or similar to the external device which uses the received data to verify the user, decrypt data or by any other means perform authentication. Light is easier to block and hide from an eavesdropping adversary than radio waves, which thus provides an advantage in this context. In similar embodiments, electromagnetic radiation is used instead of visible light for transmitting verification data to the external device.

Parameters relating to functionality of the implant may comprise for example a status indicator of the implant such as battery level, version of control program, properties of the implant, status of a motor of the implant, etc.

Data comprising operating instructions sent to the implant may comprise a new or updated control program, parameters relating to specific configurations of the implant, etc. Such data may for example comprise instructions how to operate the electrode arrangement for simulating and exercising the muscle tissue in a multi functionality implant, instructions to collect patient data at the implant, instructions to transmit feedback from the implant to an external device, etc.

The expressions "confirming the electrical connection between an implant and an external device" or "authenticating a connection between an implant and an external device", or similar expressions, are intended to encompass methods and processes for ensuring or be reasonably sure that the connection has not been compromised. Due to weaknesses in the wireless communication protocols, it is a simple task for a device to "listen" to the data and grab sensitive information, e.g. personal data regarding the patient sent from the implant, or even to try to compromise (hack) the implant by sending malicious commands or data to the implant. Encryption may not always be enough as a security measure (encryption schemes may be predictable), and other means of confirming or authenticating the external device being connected to the implant may be needed.

The expression "network protocol" is intended to encompass communication protocols used in computer networks. A communication protocol is a system of rules that allow two or more entities of a communications system to transmit information via any kind of variation of a physical quantity. The protocol defines the rules, syntax, semantics and synchronization of communication and possible error recovery methods. Protocols may be implemented by hardware, software, or a combination of both. Communication protocols have to be agreed upon by the parties involved. In this field, the term "standard" and "proprietary" is well defined. A communication protocol may be developed into a protocol standard by getting the approval of a standards organization. To get the approval the paper draft needs to enter and successfully complete the standardization process. When this is done, the network protocol can be referred to a "standard network protocol" or a "standard communication protocol". Standard protocols are agreed and accepted by whole industry. Standard protocols are not vendor specific. Standard protocols are often, as mentioned above, developed by collaborative effort of experts from different organizations.

Proprietary network protocols, on the other hand, are usually developed by a single company for the devices (or Operating System) which they manufacture. A proprietary network protocol is a communications protocol owned by a single organization or individual. Specifications for proprietary protocols may or may not be published, and implementations are not freely distributed. Consequently, any device may not communicate with another device using a proprietary network protocol, without having the license to use the proprietary network protocol, and knowledge of the specifications for proprietary protocol. Ownership by a single organization thus gives the owner the ability to place restrictions on the use of the protocol and to change the protocol unilaterally.

A control program is intended to define any software used for controlling the implant. Such software may comprise an operating system of the implant, of parts of an operating system or an application running on the implant such as software controlling a specific functionality of the implant (e.g. the active unit of the implant, feedback functionality of the implant, a transceiver of the implant, encoding/decoding functionality of the implant, etc.). The control program may thus control the medical function of the implant, for example the electrical stimulation of the muscle tissue, etc. Alternatively, or additionally, the control program may control internal hardware functionality of the implant such as energy usage, transceiver functionality, etc.

The controller may alternatively be called an internal control unit and may include any software or hardware for controlling the implant or the communication unit. The internal control unit may comprise an internal communication unit and a storage unit and a processor for running any control program or software. The term "internal control unit" may be used to encompass any part of the implant not being the active unit or body engaging unit.

The systems and methods disclosed hereinabove may be implemented as software, firmware, hardware, or a combination thereof. In a hardware implementation, the division of tasks between functional units referred to in the above description does not necessarily correspond to the division into physical units; to the contrary, one physical component may have multiple functionalities, and one task may be carried out by several physical components in cooperation. Certain components or all components may be implemented as software executed by a digital signal processor or microprocessor or be implemented as hardware or as an application-specific integrated circuit. Such software may be distributed on computer readable media, which may comprise computer storage media (or non-transitory media) and communication media (or transitory media). As is well known to a person skilled in the art, the term computer storage media includes both volatile and non-volatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information, and which can be accessed by a computer. Further, it is well known to the skilled person that communication media typically embodies computer readable instructions, data structures, program modules or other data in a modulated data signal such as a carrier wave or other transport mechanism and includes any information delivery media.

An embodiment of the system will now be described with reference to FIGS. 46A-C. FIG. 46A shows a patient with an implant 100. The implant 100 is in FIG. 46A placed in the abdominal area of the patient but could equally be placed in other parts of the body. The implant 100 comprises an active unit (further described in other sections of the description) 1010 which is directly or indirectly connected to the body of the patient for performing a function in relation to the body of the patient. The active unit may for example be the electrode arrangement for electrically stimulating the muscle tissue, and/or a controller as outlined above. The active unit is connected to a communication unit 1020 via an electrical connection C2 or a wireless connection W1. The communication unit 1020 (further described with reference to FIG. 46B) is configured to communicate with an external device 2000 (further described with reference to FIG. 46c). The communication unit 1020 can communicate wirelessly with the external device 2000 through a wireless connection W1, and/or through an electrical connection C1. As described above, the communication unit may be comprised in a controller.

Referring now to FIG. 46B, the communication unit 1020 will be described in more detail. The communication unit 1020 comprises an internal computing unit 1060 configured to control the function performed by the implant 1000. The computing unit 1060 comprises an internal memory 1070 configured to store programs thereon. The internal memory 1070 comprises a first control program 1100 which can control the function of the implant. The first control program 1100 may be seen as a program with minimum functionality to be run at the implant only during updating of the second control program 1120. When the implant is running with the first control program 1100, the implant may be seen as running in safe mode, with reduced functionality. For example, the first control program 1100 may result in that no sensor data is stored in the implant while being run, or that no feedback is transmitted from the implant while the first control program 1100 is running. By having a low complexity first control program, memory at the implant is saved, and the risk of failure of the implant during updating of the second control program 1120 is reduced.

The second control program 1120 is the program controlling the implant in normal circumstances, providing the implant with full functionality and features.

The memory 1070 can further comprise a second, updatable, control program 1120. The term updatable is to be interpreted as the program being configured to receive incremental or iterative updates to its code or be replaced by a new version of the code. Updates may provide new and/or improved functionality to the implant as well as fixing previous deficiencies in the code. The computing unit 1060 can receive updates to the second control program 1120 via the communication unit 1020. The updates can be received wirelessly W1 or via the electrical connection C1. As shown in FIG. 46B, the internal memory 1070 of the implant 100 can possibly store a third program 1140. The third program 1140 can control the function of the implant 100 and the computing unit 1060 may update the second program 1120 to the third program 1140, i.e. the second program may be updated by the first program The third program 1140 can, for example, be utilized when rebooting an original state of the second program 1120. The third program 1140 may thus be seen as providing a factory reset of the implant 100, e.g. restore it back to factory settings. The third program 1140 may thus be included in the implant 100 in a secure part of the memory 1070 to be used for resetting the software (second control program 1120) found in the implant 100 to original manufacturer settings.

The implant may comprise a reset function 1160, which in some examples is comprised in the controller, connected to or part of the internal computing unit 1060 or transmitted to said internal computing unit 1060. The reset function 1160 is configured to make the internal computing unit 1060 switch from running the second control program 1120 to the first control program 1100. The reset function 1160 could be configured to make the internal computing unit 1060 delete the second control program 1120 from the memory 1070. The reset function 1160 can be operated by palpating or pushing/put pressure on the skin of the patient. This could be performed by having a button on the implant which can be operated by pushing/put pressure on the skin of the patient. Alternatively, the reset function 1160 can be invoked via a timer or a reset module. Temperature sensors and/or pressure sensors can be utilized for sensing the palpating. The reset function 1160 could also be operated by penetrating the skin of the patient. It is further plausible that the reset function 1160 can be operated by magnetic means. This could be performed by utilizing a magnetic sensor and applying a magnetic force from outside the body. The reset function 1160 could be configured such that it only responds to magnetic forces applied for a duration of time exceeding a limit, such as 2 seconds. The time limit could equally plausible be 5 or 10 seconds, or longer. In these cases, the implant could comprise a timer. The reset function 1160 may thus include or be connected to a sensor for sensing such magnetic force.

In addition to or as an alternative to the reset function described above, the implant may comprise an internal processor 1060 or an internal computing unit 1060 (comprising an internal processor) having the second control program 1120 for controlling a function of the implant, and a first reset function 1180. The first reset function 1180 may be configured to restart or reset said second control program 1120 in response to: i. a timer of the first reset function 1180 has not been reset, or ii. a malfunction in the first control program.

The first reset function 1180 may, for example, comprise a computer operating properly, COP, function connected to the internal computing unit 1060. The COP function may be configured to restart or reset the first or the second control program 1120 using a second reset function. The COP function comprises a timer, and the first or the second control program is configured to periodically reset the timer.

The COP function 1180 may further comprise a third reset function connected to the internal computing unit and to the second reset function. The third reset function may in an example be configured to trigger a corrective function for correcting the first 1100 or second control program 1120, and the second reset function is configured to restart the first 1100 or second control program 1120 some time after the corrective function has been triggered. The corrective function may be a soft reset or a hard reset.

The second or third reset function may, for example, configured to invoke a hardware reset by triggering a hardware reset by activating an internal or external pulse generator which is configured to create a reset pulse. Alternatively, the second or third reset function may be implemented by software.

The communication unit 1020 may further comprise an internal wireless transceiver 1080. The transceiver 1080 communicates wirelessly with the external device 2000 through the wireless connection W1. The transceiver may further communicate with an external device 2000, 3000 via wireless connection W2 or W4. The transceiver may both transmit and receive data via either of the connections C1, W1, W2 and W4. Optionally, the external devices 2000 and 3000, when present, may communicate with each other, for example via a wireless connection W3.

The communication unit 1020 can further be electrically connected C1 to the external device 2000 and communicate by using the patient's body as a conductor. The communication unit may thus comprise a wired transceiver 1030 or an internal transceiver 1030 for the electrical connection C1.

The confirmation/authentication of the electrical connection can be performed as described herein in the section for confirmation and/or authentication. In these cases, the implant and/or external device(s) comprises the necessary features and functionality (described in the respective sections of this document) for performing such confirmation/authentication. By authenticating according to these aspects, security of the authentication may be increased as it may require a malicious third party to know or gain access to either the transient physiological parameter of the patient or detect randomized sensations generated at or within the patient.

In FIGS. 46A-C the patient is a human, but other mammals are equally plausible. It is also plausible that the communication is performed by inductive means. It is also plausible that the communication is direct.

The communication unit 1020 of the implant 100 according to FIG. 46B further comprises a feedback unit 1490. The feedback unit 1490 provides feedback related to the switching from the second control program 1120 to the first control program 1100. The feedback could for example represent the information on when the update of the software, i.e. the second control program 1120, has started, and when the update has finished. This feedback can be visually communicated to the patient, via for example a display on the external device 2000. This display could be located on a watch, or a phone, or any other external device 2000 coupled to the communication unit 1020. Preferably, the feedback unit 1490 provides this feedback signal wirelessly W1 to the external device 2000. Potentially, the words "Update started", or "Update finished", could be displayed to the patient, or similar terms with the same meaning. Another option could be to display different colors, where green for example could mean that the update has finished, and red or yellow that the update is ongoing. Obviously, any color is equally plausible, and the user could choose these depending on personal preference. Another possibility would be to flash a light on the external device 2000. In this case the external device 2000 comprises the light emitting device(s) needed. Such light could for example be a LED. Different colors could, again, represent the status of the program update. One way of representing that the update is ongoing and not yet finished could be to flash the light, i.e. turning the light on and off. Once the light stops flashing, the patient would be aware of that the update is finished. The feedback could also be audible, and provided by the implant 100 directly, or by the external device 2000. In such cases, the implant 100 and external device 2000 comprises means for providing audio. The feedback could also be tactile, for example in the form of a vibration that the user can sense. In such case, either the implant 100 or external device comprises means for providing a tactile sensation, such as a vibration and/or a vibrator.

As seen in FIG. 46B, the communication unit 1020 can further comprise a first power supply 10*a*. The first power supply 10*a* runs the first control program 1100. The communication unit 1020 further comprises a second power supply 10*b* which runs the second control program 1120. This may further increase security during update, since the first control program has its own separate energy supply. The first power supply 10*a* can comprise a first energy storage 1040*a* and/or a first energy receiver 1050*a*. The second power supply 10*b* can comprise a second energy storage 1040*b* and/or a second energy receiver 1050*b*. The energy can be received wirelessly by inductive or conductive means. An external energy source can for example transfer an amount of wireless energy to the energy receiver 1050*a*, 1050*b* inside the patient's body by utilizing an external coil which induces a voltage in an internal coil (not shown in figures). It is plausible that the first energy receiver 1050*a* receives energy via a RFID pulse. The feedback unit 1490 can the provide feedback pertaining to the amount of energy received via the RFID pulse. The amount of RFID pulse energy that is being received can be adjusted based on the feedback, such that the pulse frequency is successively raised until a satisfying level is reached.

The external device is represented in FIG. 46C. The external device 2000 can be placed anywhere on the patient's body, preferably on a convenient and comfortable place. The external device 2000 could be a wristband, and/or have the shape of a watch. It is also plausible that the external device is a mobile phone or other device not attached directly to the patient. The external device as shown in FIG. 46C comprises a wired transceiver 2030, and an energy storage 2040. It also comprises a wireless transceiver 2080 and an energy transmitter 2050. It further comprises a computing unit 2060 and a memory 2070. The feedback unit 2100 in the external device 2000 is configured to provide feedback related to the computing unit 2060. The feedback provided by the feedback unit 2100 could be visual. The external device 2000 could have a display showing such visual feedback to the patient. It is equally plausible that the feedback is audible, and that the external device 2000 comprises means for providing audio. The feedback given by the feedback unit 2100 could also be tactile, such as vibrating. The feedback could also be provided in the form of a wireless signal W1, W2, W3, W4.

The second, third or fourth communication methods W2, W3, W4 may be a wireless form of communication. The second, third or fourth communication method W2, W3, W4 may preferably be a form of electromagnetic or radio-based communication. The second, third and fourth communication method W2, W3, W4 may be based on telecommunication methods. The second, third or fourth communication method W2, W3, W4 may comprise or be related to the items of the following list: Wireless Local Area Network (WLAN), Bluetooth, Bluetooth 5, BLE, GSM or 2G (2nd generation cellular technology), 3G, 4G or 5G.

The external device 2000 may be adapted to be in electrical connection C1 with the implant 100, using the body as a conductor. The electrical connection C1 is in this case used for conductive communication between the external device 2000 and the implant 100.

In one embodiment, the communication between communication unit 1020 of the implant 100 and the external device 2000 over either of the communication methods W2, W3, W4, C1, 3000 may be encrypted and/or decrypted with public and/or private keys, now described with reference to FIGS. 46A-C. For example, the communication unit or the implant may comprise a private key and a corresponding public key, and the external device may comprise a private and a corresponding public key.

The communication unit and the external device may exchange public keys and the communication may thus be performed using public key encryption. The person skilled in the art may utilize any known method for exchanging the keys.

The communication unit may encrypt data to be sent to the external device using a public key corresponding to the external device. The encrypted data may be transmitted over a wired, wireless, or electrical communication channel C1, W1, W2, W3 to the external device. The external device may receive the encrypted data and decode it using the private key comprised in the external device, the private key corresponding to the public key with which the data has been encrypted. The external device may transmit encrypted data to the communication unit of the implant. The external device may encrypt the data to be sent using a public key corresponding to the private key of the implant. The external device may transmit the encrypted data over a wired, wireless, or electrical connection C1, W1, W2, W3, W4, directly or indirectly, to the communication unit of the implant. The communication unit may receive the data and decode it using the private key comprised in the implant or in the communication unit.

In an alternative to the public key encryption, described with reference to FIGS. 46A-C, the data to be sent between an implant 100 and an external device 2000, 3000 or between an external device 2000, 3000 and the implant 100 may be signed. In a method for sending data from the implant 100 to the external device 2000, 3000, the data to be sent from the implant 100 may be signed using the private key of the implant 100 or the communication unit 1020. The data may be transmitted over a communication channel or connection C1, W1, W2, W3, W4. The external device 2000, 3000 may receive the message and verify the authenticity of the data using the public key corresponding to the private key of the implant 100 or the communication unit 1020. In this way, the external device 2000, 3000 may determine that the sender of the data was sent from the implant 100 or the communication unit 1020 and not from another device or source.

A method for communication between an external device 2000 and an implant 100 using a combined key is now described with reference to FIGS. 46A-C. A first step of the method comprises receiving, at the implant, by a wireless transmission W1, W2, W3, W4 or otherwise, a first key from an external device 2000, 3000. The method further comprises receiving, at the implant, by a wireless transmission W1, W2, W3, a second key. The second key may be generated by a second external device, separate from the external device 2000, 3000 or by another external device being a generator of the second key on behalf of the second external device 2000, 3000. The second key may be received at the implant from anyone of, the external device 2000, the second external device 3000, and the generator of the second key. The second external device may be controlled by a caretaker, or any other stakeholder. Said another external device may be controlled by a manufacturer of the implant, or medical staff, caretaker, etc.

In case the implant 100 is receiving the second key from the external device 2000, this means that the second key is routed through the external device from the second external device 3000 or from another external device (generator). The routing may be performed as described herein under the tenth aspect. In these cases, the implant and/or external device(s) comprises the necessary features and functionality (described in the respective sections of this document) for performing such routing. Using the external device 2000 as a relay, with or without verification from the patient, may provide an extra layer of security as the external device 2000 may not need to store or otherwise handle decrypted information. As such, the external device 2000 may be lost without losing decrypted information.

The implant comprises a computing unit 1060 configured for deriving a combined key by combining the first key and the second key with a third key held by the implant 100, for example in memory 1070 of the implant. The third key could for example be a license number of the implant or a chip number of the implant. The combined key may be used for decrypting, by the computing unit 1060, encrypted data transmitted by a wireless transmission W1 from the external device 2000 to the implant 100. Optionally, the decrypted data may be used for altering, by the computing unit 1060 an operation of the implant. The altering an operation of the implant may comprise controlling or switching an active unit 1010 of the implant. In some embodiments, the method further comprises at least one of the steps of, based on the decrypted data, updating a control program running in the implant 100, and operating the implant 100 using operation instructions in the decrypted data.

Methods for encrypted communication between an external device 2000 and an implant 100 are provided. These methods comprise:

receiving, at the external device 100 by a wireless receiver 2080, a first key, the first key being generated by a second external device 3000, separate from the external device 2000 or by another external device being a generator of the second key on behalf of the second external device 2000, the first key being received from anyone of the second external device 2000 and the generator of the second key, receiving, at the external device 2000 by the wireless receiver 2080, a second key from the implant 100, deriving a combined key, by a computing unit 2060 of the external device 2000, by combining the first key and the second key with a third key held by the external device 2000 (e.g. in memory 2070), transmitting encrypted data from the implant to the external device and receiving the encrypted data at the external device by the wireless receiver 208, and decrypting, by the computing unit 2060, the encrypted data, in the external device 2000, using the combined key.

As described above, further keys may be necessary to decrypt the data. Consequently, the wireless transceiver 2080 is configured for:

receiving a fourth key from a third external device, wherein the computing unit 2060 is configured for:

deriving a combined key by combining the first, second and fourth key with the third key held by the external device, and decrypting the encrypted data using the combined key.

These embodiments further increase the security in the communication. The computing unit 2060 may be configured to confirm the communication between the implant and the external device, wherein the confirmation comprises:

measuring a parameter of the patient, by the external device, receiving a measured parameter of the patient, from the implant, comparing the parameter measured by the implant to the parameter measured by the external device, performing confirmation of the connection based on the comparison, and as a result of the confirmation, decrypting the encrypted data, in the external device, using the combined key.

The keys described in this section may in some embodiments be generated based on data sensed by sensors described herein under the twelfth or thirteenth aspect, e.g. using the sensed data as seed for the generated keys. A seed is an initial value that is fed into a pseudo random number generator to start the process of random number generation. The seed may thus be made hard to predict without access or knowledge of the physiological parameters of the patient which it is based on, providing an extra level of security to the generated keys.

Further, increased security for communication between an external device(s) and an implant is provided.

A method of communication between an external device 2000 and an implant 100 is now described with reference to FIGS. 46A-C, when the implant 100 is implanted in a patient and the external device 2000 is positioned external to the body of the patient. The external device 2000 is adapted to be in electrical connection C1 with the implant 100, using the body as a conductor. The electrical connection C1 is used for conductive communication between the external device 2000 and the implant 100. The implant 100 comprises a communication unit 1020. Both the implant 100 and the external device 2000 comprises a wireless transceiver 1080, 2080 for wireless communication C1 between the implant 100 and the external device 2000. The wireless transceiver 1080 (included in the communication unit 1020) may in some embodiments comprise sub-transceivers for receiving data from the external device 2000 and other external devices, e.g. using different frequency bands, modulation schemes etc.

In a first step of the method, the electrical connection C1 between the implant 100 and the external device 2000 is confirmed and thus authenticated. The confirmation and authentication of the electrical connection may be performed as described herein under the fifth, thirteenth and fifteenth aspect. In these cases, the implant and/or external device(s) comprises the necessary features and functionality (described in the respective sections of this document) for performing such authentication. By authenticating according to these aspects, security of the authentication may be increased as it may require a malicious third party to know or gain access to either the transient physiological parameter of the patient or detect randomized sensations generated at or within the patient.

The implant may comprise a first transceiver 1030 configured to be in electrical connection C1 with the external device, using the body as a conductor. The implant may comprise a first external transmitter 2030 configured to be in electrical connection C1 with the implant, using the body as a conductor, and the wireless transmitter 2080 configured to transmit wireless communication W1 to the implant 100. The first transmitter 2030 of the external device may be wired or wireless. The first transmitter 2030 and the wireless transmitter 2080 may be the same or separate transmitters. The first transceiver 1030 of the implant 100 may be wired or wireless. The first transceiver 1030 and the wireless transceiver 1020 may be the same or separate transceivers. The implant 100 may comprise a computing unit 1060 configured to confirm the electrical connection between the external device 2000 and the internal transceiver 1030 and accept wireless communication W1 (of the data) from the external device 2000 on the basis of the confirmation.

Data is transmitted from the external device 2000 to the implant 100 wirelessly, e.g. using the respective wireless transceiver 1080, 2080 of the implant 100 and the external device 2000. Data may alternatively be transmitted through the electrical connection C1. As a result of the confirmation, the received data may be used for instructing the implant. For example, a control program 1100 running in the implant 100 may be updated, the implant 100 may be operated using operation instructions in the received data. This may be handled by the computing unit 1060.

The method may comprise transmitting data from the external device 2000 to the implant 100 wirelessly comprises transmitting encrypted data wirelessly. To decrypt the encrypted data (for example using the computing unit 106), several methods may be used.

In one embodiment, a key is transmitted using the confirmed conductive communication channel C1 (i.e. the electrical connection) from the external device 2000 to the implant 100. The key is received at the implant (by the first internal transceiver 1030). The key is then used for decrypting the encrypted data.

In some embodiments the key is enough to decrypt the encrypted data. In other embodiments, further keys are necessary to decrypt the data. In one embodiment, a key is transmitted using the confirmed conductive communication channel C1 (i.e. the electrical connection) from the external device 2000 to the implant 100. The key is received at the implant 100 (by the first internal transceiver 1030). A second key is transmitted (by the wireless transceiver 2080) from the external device 2000 using the wireless communication W1 and received at the implant 100 by the wireless transceiver 1080. The computing unit 1060 is then deriving a combined key from the key and second key and uses this for decrypting the encrypted data.

In yet other embodiments, a key is transmitted using the confirmed conductive communication channel C1 (i.e. the electrical connection) from the external device 2000 to the implant 100. The key is received at the implant (by the first internal transceiver 1030). A third key is transmitted from a second external device 3000, separate from the external device 2000, to the implant wirelessly W2. The third key may be received by a second wireless receiver (part of the wireless transceiver 1080) of the implant 100 configured for receiving wireless communication W2 from second external device 3000.

The first and third key may be used to derive a combined key by the computing unit 1060, which then decrypts the encrypted data. The decrypted data is then used for instructing the implant 100 as described above.

The second external device 3000 may be controlled by for example a caregiver, to further increase security and validity of data sent and decrypted by the implant 100.

It should be noted that in some embodiments, the external device is further configured to receive W2 secondary wireless communication from the second external device 3000, and transmit data received from the secondary wireless communication W2 to the implant. This routing of data may be achieved using the wireless transceivers 1080, 2080 (i.e. the wireless connection W1, or by using a further wireless connection W4 between the implant 100 and the external device 2000. In these cases, the implant and/or external device(s) comprises the necessary features and functionality for performing such routing. Consequently, in some embodiments, the third key is generated by the second external device 3000 and transmitted W2 to the external device 2000 which routes the third key to the implant 100 to be used for decryption of the encrypted data. In other words, the step of transmitting a third key from a second external device, separate from the external device, to the implant wirelessly, comprises routing the third key through the external device. Using the external device 2000 as a relay, with or without verification from the patient, may provide an extra layer of security as the external device 2000 may not need to store or otherwise handle decrypted information. As such, the external device 2000 may be lost without losing decrypted information.

In yet other embodiments, a key is transmitted using the confirmed conductive communication channel C1 (i.e. the electrical connection) from the external device 2000 to the implant 100. The key is received at the implant (by the first internal transceiver 1030). A second key is transmitted from the external device 2000 to the implant 100 wirelessly W1, received at the at the implant. A third key is transmitted from the second external device, separate from the external device, to the implant 100 wirelessly W4. Encrypted data transmitted from the external device 2000 to the implant 100 is then decrypted using a derived combined key from the key, the second key and the third key.

The external device may be a wearable external device.

The external device 2000 may be a handset. The second external device 3000 may be a handset. The second external device 3000 may be a server. The second external device 3000 may be cloud based.

In some embodiments, the electrical connection C1 between the external device 2000 and the implant 100 is achieved by placing a conductive member 2010, configured to be in connection with the external device 2000, in electrical connection with a skin of the patient for conductive communication C1 with the implant. In these cases, the implant and/or external device(s) comprises the necessary features and functionality (described in the respective sections of this document) for performing such conductive communication. The communication may thus be provided with an extra layer of security in addition to the encryption by being electrically confined to the conducting path e.g. external device 2000, conductive member 2010, conductive connection C1, implant 100, meaning the communication will be excessively difficult to be intercepted by a third party not in physical contact with, or at least proximal to, the patient.

The keys described in this section may in some embodiments be generated based on data sensed by sensors described herein, e.g. using the sensed data as seed for the generated keys. A seed is an initial value that is fed into a pseudo random number generator to start the process of random number generation. The seed may thus be made hard to predict without access or knowledge of the physiological parameters of the patient which it is based on, providing an extra level of security to the generated keys.

Increased security for communication between an external device(s) and an implant is provided, now described with reference to FIGS. 46A-C.

In these embodiments, a method for communication between an external device 2000 and an implant 100 is provided. The implant 100 is implanted in a patient and the external device 2000 is positioned external to the body of the patient. The implant and the external device each comprise a wireless transceiver 1080, 2080 for wireless communication W1 between the implant 100 and the external device 2000. The wireless transceiver 1080 (included in a communication unit 1020 of the implant) may in some embodiments comprise sub-transceivers for receiving data from the external device 2000 and other external devices 3000, e.g. using different frequency bands, modulation schemes etc.

A first step of the method comprises receiving, at the implant, by a wireless transmission W1 or otherwise, a first key from an external device 3000. The method further comprises receiving, at the implant, by a wireless transmission W1, W2, W3, a second key. The second key may be generated by a second external device, separate from the external device or by another external device being a generator of the second key on behalf of the second external device 3000. The second key may be received at the implant from anyone of, the external device 2000, the second external device 3000, and a generator of the second key. The second external device may be controlled by a caretaker, or any other stakeholder. Said another external device may be controlled by a manufacturer of the implant, or medical staff, caretaker, etc.

In case the implant is receiving the second key from the external device 2000, this means that the second key is routed through the external device from the second external device 3000 or from the another external device (generator). In these cases, the implant and/or external device(s) comprises the necessary features and functionality (described in the respective sections of this document) for performing such routing. Using the external device 2000 as a relay, with or without verification from the patient, may provide an extra layer of security as the external device 2000 may not need to store or otherwise handle decrypted information. As such, the external device 2000 may be lost without losing decrypted information.

The implant comprises a computing unit 1060 configured for deriving a combined key by combining the first key and the second key with a third key held by the implant 100, for example in memory 1070 of the implant. The combined key may be used for decrypting, by the computing unit 1060, encrypted data transmitted by a wireless transmission W1 from the external device 2000 to the implant 100. Optionally, the decrypted data may be used for altering, by the computing unit 1060 an operation of the implant. The altering an operation of the implant may comprise controlling or switching an active unit 1010 of the implant. In some embodiments, the method further comprises at least one of the steps of, based on the decrypted data, updating a control program running in the implant, and operating the implant 100 using operation instructions in the decrypted data.

In some embodiments, further keys are necessary to derive a combined key for decrypting the encrypted data received at the implant 100. In these embodiments, the first and second key are received as described above. Further, the method comprises receiving, at the implant, a fourth key from a third external device, the third external device being separate from the external device, deriving a combined key by combining the first, second and fourth key with the third key held by the implant 100, and decrypting the encrypted data, in the implant 100, using the combined key. Optionally, the decrypted data may be used for altering, by the computing unit 1060, an operation of the implant as described above. In some embodiments, the fourth key is routed through the external device from the third external device.

In some embodiments, further security measures are needed before using the decrypted data for altering, by the computing unit 1060, an operation of the implant. For example, an electrical connection C1 between the implant and the external device, using the body as a conductor, may be used for further verification of validity of the decrypted data. The electrical connection C1 may be achieved by placing a conductive member 2010, configured to be in connection with the external device, in electrical connection with a skin of the patient for conductive communication C1 with the implant. The communication may thus be provided with an extra layer of security in addition to the encryption by being electrically confined to the conducting path e.g. external device 2000, conductive member 2010, conductive connection C1, implant 100, meaning the communication will be excessively difficult to be intercepted by a third party not in physical contact with, or at least proximal to, the patient.

Accordingly, in some embodiments, the method comprising confirming the electrical connection between the implant and the external device, and as a result of the confirmation, altering an operation of the implant based on the decrypted data. The confirmation and authentication of the electrical connection may be performed as described herein under the general features section. In these cases, the implant and/or external device(s) comprises the necessary features and functionality (described in the respective sections of this document) for performing such authentication. By authenticating according to these aspects, security of the authentication may be increased as it may require a malicious third party to know or gain access to either the transient physiological parameter of the patient or detect randomized sensations generated at or within the patient.

In some embodiments, the confirmation of the electrical connection comprises: measuring a parameter of the patient, by the implant, measuring the parameter of the patient, by the external device, comparing the parameter measured by the implant to the parameter measured by the external device, and authenticating the connection based on the comparison. As mentioned above, as a result of the confirmation, an operation of the implant may be altered based on the decrypted data.

Further methods for encrypted communication between an external device 2000 and an implant 100 are provided. These methods comprise:

receiving, at the external device 100 by a wireless receiver 2080, a first key, the first key being generated by a second external device 3000, separate from the external device 2000 or by another external device being a generator of the second key on behalf of the second external device 2000, the first key being received from anyone of the second external device 2000 and the generator of the second key, receiving, at the external device 2000 by the wireless receiver 2080, a second key from the implant 100, deriving a combined key, by a computing unit 2060 of the external device 2000, by combining the first key and the second key with a third key held by the external device 2000 (e.g. in memory 2070), transmitting encrypted data from the implant to the external device and receiving the encrypted data at the external device by the wireless receiver 2080, and decrypting, by the computing unit 2060, the encrypted data, in the external device 2000, using the combined key.

As described above, further keys may be necessary to decrypt the data. Consequently, the wireless transceiver 2080 is configured for:

receiving a fourth key from a third external device, wherein the computing unit 2060 is configured for:

deriving a combined key by combining the first, second and fourth key with the third key held by the external device, and decrypting the encrypted data using the combined key.

In some embodiments, the communication between the implant 100 and the external device 2000 needs to be confirmed (authenticated) before decrypting the data. In these cases, the implant and/or external device(s) comprises the necessary features and functionality (described in the respective sections of this document) for performing such authentication.

These embodiments further increase the security in the communication. In these embodiments the computing unit 2060 is configured to confirm the communication between the implant and the external device, wherein the confirmation comprises:

measuring a parameter of the patient, by the external device, receiving a measured parameter of the patient, from the implant, comparing the parameter measured by the implant to the parameter measured by the external device, performing confirmation of the connection based on the comparison, and as a result of the confirmation, decrypting the encrypted data, in the external device, using the combined key.

One or more of the first, second and third key may comprise a biometric key.

The keys described in this section may in some embodiments be generated based on data sensed by sensors, e.g. using the sensed data as seed for the generated keys. A seed is an initial value that is fed into a pseudo random number generator to start the process of random number generation. The seed may thus be made hard to predict without access or knowledge of the physiological parameters of the patient which it is based on, providing an extra level of security to the generated keys.

Further, increased security for communication between an external device(s) and an implant is provided, described with reference to FIGS. 46A-C. The system for communication between an external device 2000 and an implant 100 implanted in a patient. The system comprises a conductive member 2010 configured to be in connection (electrical/conductive or wireless or otherwise) with the external device, the conductive member 2010 being configured to be placed in electrical connection with a skin of the patient for conductive communication C1 with the implant 100. By using a conductive member 2010 as defined herein, an increased security for communication between the external device and the implant may be achieved. For example, when a sensitive update of a control program of the implant 100 is to be made, or if sensitive data regarding physical parameters of the patient is to be sent to the externa device 2000 (or otherwise), the conductive member 2010 may ensure that the patient is aware of such communication and actively participate in validating that the communication may take place. The conductive member may, by being placed in connection with the skin of the patient, open the conductive communication channel C1 between the external device and the implant to be used for data transmission.

Electrical or conductive communication, such as this or as described under the other embodiments, may be very hard to detect remotely, or at least relatively so, in relation to wireless communications such as radio transmissions. Direct electrical communication may further safeguard the connection between the implant and the external device from electromagnetic jamming i.e. high-power transmissions other a broad range of radio frequencies aimed at drowning other communications within the frequency range. Electrical or conductive communication will be excessively difficult to be intercepted by a third party not in physical contact with, or at least proximal to, the patient, providing an extra level of security to the communication.

In some embodiments, the conductive member comprises a conductive interface for connecting the conductive member to the external device.

In some embodiments, the conductive member 2010 is a device which is plugged into the external device 2000, and easily visible and identifiable for simplified usage by the patient. In other embodiments, the conductive member 2010 is to a higher degree integrated with the external device 2000, for example in the form of a case of the external device 2000, the case comprising a capacitive area configured to be in electrical connection with a skin of the patient. In one example, the case is a mobile phone case (smartphone case) for a mobile phone, but the case may in other embodiments be a case for a personal computer, or a body worn camera or any other suitable type of external device as described herein. The case may for example be connected to the phone using a wire from the case and connected to the headphone port or charging port of the mobile phone.

The conductive communication C1 may be used both for communication between the implant 100 and the external device 2000 in any or both directions. Consequently, according to some embodiments, the external device 2000 is configured to transmit a conductive communication (conductive data) to the implant 100 via the conductive member 2010.

According to some embodiments, the implant 100 is configured to transmit a conductive communication to the external device 2000. These embodiments start by placing the conductive member 2010, configured to be in connection with the external device, in electrical connection with a skin of the patient for conductive communication C1 with the implant. The conductive communication between the external device 2000 and the implant 100 may follow an electrically/conductively confined path comprising e.g. the external device 200, conductive member 2010, conductive connection C1, implant 100.

For the embodiments when the external device 2000 transmits data to the implant, the communication may comprise transmitting a conductive communication to the implant 100 by the external device 2000.

The transmitted data may comprise instructions for operating the implant. Consequently, some embodiments comprise operating the implant 100 using operation instructions, by an internal computing unit 1060 of the implant 100, wherein the conductive communication C1 comprises instructions for operating the implant. The operation instruction may for example involve adjusting or setting up (e.g. properties or functionality of) an active unit 1010 of the implant.

The transmitted data may comprise instructions for updating a control program 1100 stored in memory 1070 of the implant 100. Consequently, some embodiments comprise updating the control program 1100 running in the implant, by the internal computing unit 1060 of the implant, wherein the conductive communication comprises instructions for updating the control program.

For the embodiments when the implant 100 transmits data to the external device 2000, the communication may comprise transmitting conductive communication C1 to the external device 2000 by the implant 100. The conductive communication may comprise feedback parameters (battery status, properties, version number etc.) relating to functionality of the implant. In other embodiments, the conductive communication C1 comprises data pertaining to least one physiological parameter of the patient, such as blood pressure etc. The physiological parameter(s) may be stored in memory 1070 of the implant 100 or sensed in prior (in real time or with delay) to transmitting the conductive communication C1. Consequently, in some embodiments, the implant comprises a sensor 1500 for sensing at least one physiological parameter of the patient, wherein the conductive communication comprises said at least one physiological parameter of the patient.

To further increase security of the communication between the implant 100 and the external device 2000, different types of authentication, verification and/or encryption may be employed. In some embodiments, the external device 2000 comprises a verification unit 2200. The verification unit may be any type of unit suitable for verification of a user, i.e. configured to receive authentication input from a user, for authenticating the conductive communication between the implant and the external device. In some embodiments, the verification unit and the external device comprises means for collecting authentication input from the user (which may or may not be the patient). Such means may comprise a fingerprint reader, a retina scanner, a camera, a GUI for inputting a code, a microphone, device configured to draw blood, etc. The authentication input may thus comprise a code or any be based on a biometric technique selected from the list of: a fingerprint, a palm vein structure, image recognition, face recognition, iris recognition, a retinal scan, a hand geometry, and genome comparison. The means for collecting the authentication input may alternatively be part of the conductive member which comprise any of the above examples of functionality, such as a fingerprint reader or other type of biometric reader.

In some embodiments, the security may thus be increased by receiving an authentication input from a user by a verification unit 2200 of the external device and authenticating the conductive communication between the implant and the external device using the authentication input. Upon a positive authentication, the conductive communication channel C1 may be employed for comprising transmitting a conductive communication to the implant 100 by external device 2000 and/or transmitting a conductive communication to the external device 2000 by the implant 100. In other embodiments, a positive authentication is needed prior to operating the implant based on received conductive communication, and/or updating a control program running in the implant as described above.

FIGS. 46A-C show an implant 100 implanted in a patient and an external device 2000. The figures further show the implant 100 being connected to a sensation generator 1810.

The sensation generator 1810 may be configured to generate a sensation. The sensation generator 1810 may be contained within the implant 100 or be a separate unit. The sensation generator 1810 may be implanted. The sensation generator 1810 may also be located so that it is not implanted as such but still is in connection with a patient so that only the patient may experience sensations generated. The implant 100 is configured for storing authentication data, related to the sensation generated by the sensation generator 1810.

The implant 100 is further configured for receiving input authentication data from the external device 2000. Authentication data related to the sensation generated may by stored by a memory 1070 of the implant 100. The authentication data may include information about the generated sensation such that it may be analyzed, e.g. compared, to input authentication data to authenticate the connection, communication, or device. Input authentication data relates to information generated by a patient input to the external device 2000. The input authentication data may be the actual patient input or an encoded version of the patient input, encoded by the external device 2000. Authentication data and input authentication data may comprise a number of sensations or sensation components.

The authentication data may comprise a timestamp. The input authentication data may comprise a timestamp of the input from the patient. The timestamps may be a time of the event such as the generation of a sensation by the sensation generator 1810 or the creation of input authentication data by the patient. The timestamps may be encoded. The timestamps may feature arbitrary time units, i.e. not the actual time. Timestamps may be provided by an internal clock 1600 of the implant 100 and an external clock 2600 of the external device. The clocks 1600, 2600 may be synchronized with each other. The clocks 1600, 2600 may be synchronized by using a conductive connection C1 or a wireless connection W1 for communicating synchronization data from the external device 2000, and its respective clock 2600, to the implant 100, and its respective clock 1600, and vice versa. Synchronization of the clocks 1600, 2600 may be performed continuously and may not be reliant on secure communication.

Authentication of the connection may comprise calculating a time difference between the timestamp of the sensation and the timestamp of the input from the patient, and upon determining that the time difference is less than a threshold, authenticating the connection. An example of a threshold may be 1 s. The analysis may also comprise a low threshold as to filter away input from the patient that is faster than normal human response times. The low threshold may e.g. be 50 ms.

Authentication data may comprise a number of times that the sensation is generated by the sensation generator, and wherein the input authentication data comprises an input from the patient relating to a number of times the patient detected the sensation. Authenticating the connection may then comprise: upon determining that the number of times that the authentication data and the input authentication data are equal, authenticating the connection.

A method of authenticating the connection between an implant 100 implanted in a patient, and an external device 2000 according includes the following steps.

Generating, by a sensation generator 1810, a sensation detectable by a sense of the patient. The sensation may comprise a plurality of sensation components. The sensation or sensation components may comprise a vibration (e.g. a fixed frequency mechanical vibration), a sound (e.g. a superposition of fixed frequency mechanical vibrations), a photonic signal (e.g. a non-visible light pulse such as an infra-red pulse), a light signal (e.g. a visual light pulse), an electric signal (e.g. an electrical current pulse) or a heat signal (e.g. a thermal pulse). The sensation generator may be implanted, configured to be worn in contact with the skin of the patient or capable of creating sensation without being in physical contact with the patient, such as a beeping alarm.

Sensations may be configured to be consistently felt by a sense of the patient while not risking harm to or affecting internal biological processes of the patient.

The sensation generator 1810, may be contained within the implant 100 or be a separate entity connected to the implant 100. The sensation may be generated by a motor of the implant 100 for controlling a physical function in the body of the patient, wherein the motor being the sensation generator 1810. The sensation may be a vibration, or a sound created by running the motor. The sensation generator 1810 may be located close to a skin of the patient and thus also the sensory receptors of the skin. Thereby the strength of some signal types may be reduced.

Storing, by the implant 100, authentication data, related to the generated sensation.

Providing, by the patient input to the external device, resulting in input authentication data. Providing the input may e.g. comprise an engaging an electrical switch, using a biometric input sensor or entry into digital interface running on the external device 2000 to name just a few examples.

Transmitting the input authentication data from the external device to the implant 100. If step was performed, the analysis may be performed by the implant 100.

Transmitting the authentication data from the implant 100 to the external device 2000. If the step was performed, the analysis may be performed by the external device 2000. The wireless connection W1 or the conductive connection C1 may be used to transmit the authentication data or the input authentication data.

Authenticating the connection based on an analysis of the input authentication data and the authentication data e.g. by comparing a number of sensations generated and experienced or comparing timestamps of the authentication data and the input authentication data. If step was performed, the analysis may be performed by the implant 100.

Communicating further data between the implant and the external device following positive authentication. The wireless connection W1 or the conductive connection C1 may be used to communicate the further data. The further data may comprise data for updating a control program 1100 running in the implant 100 or operation instructions for operating the implant 100. The further data may also comprise data sensed by a sensor 1500 connected to the implant 100.

If the analysis was performed by the implant 100, the external device 200 may continuously request or receive, information of an authentication status of the connection between the implant 100 and the external device 200, and upon determining, at the external device 200, that the connection is authenticated, transmitting further data from the external device 200 to the implant 100.

If the analysis was performed by the external device 200, the implant 100 may continuously request or receive, information of an authentication status of the connection between the implant 100 and the external device 2000, and upon determining, at the implant 100, that the connection is authenticated, transmitting further data from the implant 100 to the external device 2000.

A main advantage of authenticating a connection according to this method is that only the patient may be able to experience the sensation. Thus, only the patient may be able to authenticate the connection by providing authentication input corresponding to the sensation generation.

The sensation generator 1810, sensation, sensation components, authentication data, input authentication data, and further data may be further described herein. In these cases, the implant and/or external device(s) comprises the necessary features and functionality (described in the respective sections of this document). Further information and definitions can be found in this document in conjunction with the other aspects.

The method may further comprise transmitting further data between the implant and the external device, wherein the further data is used or acted upon, only after authentication of the connection is performed.

The analysis or step of analyzing may be understood as a comparison or a step of comparing.

In one method, increased security for communication between an external device(s) and an implant is provided. FIGS. 46A-C show an implant 100, a communication unit 1020 and an external device 2000 which may form a system.

The implant 100 comprises a transceiver 1080, 1030 configured to establish a connection with an external device 2000, i.e. with a corresponding transceiver 2080, 2030. The connection may be an electrical connection C1 using the transceivers 1030, 2030, or a wireless connection W1 using the transceivers 1080, 2080. The implant further comprising a computing unit 1060 configured to verify the authenticity of instructions received at the transceiver 1080, 1030 from the external device 2000. In this aspect, the concept of using previously transmitted instructions for verifying a currently transmitted instructions are employed. Consequently, the transmitting node (in this case the external device) need to be aware of previously instructions transmitted to the implant, which reduces the risk of a malicious device instructing the implant without having the authority to do so.

In an embodiment, the computing unit 1060 is configured to verify the authenticity of instructions received at the transceiver 1080, 1030 by extracting a previously transmitted set of instructions from a first combined set of instructions received by the transceiver. The external device 2000 may thus comprise an external device comprising a computing unit 2060 configured for: combining a first set of instructions with a previously transmitted set of instructions, forming a combined set of instructions, and transmitting the combined set of instructions to the implant. The previously transmitted set of instructions, or a representation thereof, may be stored in memory 2070 of the external device 2000.

The combined set of instructions may have a data format which facilitates such extraction, for example including metadata identifying data relating to the previously transmitted set of instructions in the combined set of instructions. In some embodiments, the combined set of instructions comprises the first set of instructions and a cryptographic hash of the previously transmitted set of instructions. Consequently, the method comprises combining, at the external device, a first set of instructions with a previously transmitted set of instructions, forming a first combined set of instructions. A cryptographic hash function is a special class of hash function that has certain properties which make it suitable for use in cryptography. It is a mathematical algorithm that maps data of arbitrary size to a bit string of a fixed size (a hash) and is designed to be a one-way function, that is, a function which is infeasible to invert. Examples include MD5, SHA1, SHA 256, etc. Increased security is thus achieved.

The first combined set of instructions is then transmitted to the implant 100, where it is received by e.g. the transceiver 1030, 1080. The first combined set of instructions may be transmitted to the implant using a proprietary network protocol. The first combined set of instructions may be transmitted to the implant using a standard network protocol. In these cases, the implant and/or external device(s) comprises the necessary features and functionality (described in the respective sections of this document) for performing transmission of data. By using different communication protocols, at the external device 2000, for communication to the implant 100 and a second external device 3000, an extra layer of security is added as the communication between implant and the external device may be made less directly accessible to remote third parties.

At the implant 100, the computing unit verifies the authenticity of the received first combined set of instructions, by: extracting the previously transmitted set of instructions from the first combined set of instructions, and comparing the extracted previously transmitted set of instructions with previously received instructions stored in the implant.

Upon determining that the extracted previously transmitted set of instructions equals the previously received instructions stored in the implant, the authenticity of the received first combined set of instructions may be determined as valid, and consequently, the first set of instructions may be safely run at the implant, and the first combined set of instructions may be stored in memory 107 of the implant, to be used for verifying a subsequent received set of instructions.

In some embodiments, upon determining by the internal computing unit 106 that the extracted previously transmitted set of instructions differs from the previously received instructions stored in the implant, feedback related to an unauthorized attempt to instruct the implant may be provided. For example, the transceiver 1080, 1030 may send out a distress signal to e.g. the external device 2000 or to any other connected devices. The implant 100 may otherwise inform the patient that something is wrong by e.g. vibration or audio. The implant 100 may be run in safe mode, using a preconfigured control program which is stored in memory 1070 and specifically set up for these situations, e.g. by requiring specific encoding to instruct the implant, or only allow a predetermined device (e.g. provided by the manufacturer) to instruct the implant 100. In some embodiments, when receiving such feedback at the external device 2000, the external device 2000 retransmits the first combined set of instructions again, since the unauthorized attempt may in reality be an error in transmission (where bits of the combined set of instructions are lost in transmission), and where the attempt to instruct the implant is indeed authorized.

The step of comparing the extracted previously transmitted set of instructions with previously received instructions stored in the implant may be done in different ways. For example, the step of comparing the extracted previously transmitted set of instructions with previously received instructions stored in the implant comprises calculating a difference between the extracted previously transmitted set of instructions with previously received instructions stored in the implant, and comparing the difference with a threshold value, wherein the extracted previously transmitted set of instructions is determined to equal the previously received instructions stored in the implant in the case of the difference value not exceeding the threshold value. This embodiment may be used when received instructions is stored in clear text, or a representation thereof, in the implant, and where the combined set of instructions, transmitted from the external device also includes such a representation of the previously transmitted instructions. This embodiment may be robust against error in transmission where bits of information are lost or otherwise scrambled.

In other embodiments, the combined set of instructions comprises the first set of instructions and a cryptographic hash of the previously transmitted set of instructions, wherein the method further comprises, at the implant, calculating a cryptographic hash of the previously received instructions stored in the implant and comparing the calculated cryptographic hash to the cryptographic hash included in the first combined set of instructions. This embodiment provides increased security since the cryptographic hash is difficult to decode or forge.

The above way of verifying the authenticity of received instructions at the implant may be iteratively employed for further sets if instructions.

To further increase security, the transmission of a first set of instructions, to be stored at the implant 100 for verifying subsequent sets of combined instructions, where each set of received combined instructions will comprise data which in some form will represent, or be based on, the first set of instruction, may be performed.

In one example, the external device 2000 may be adapted to communicate with the implant 100 using two separate communication methods. A communication range of a first communication method W1 may be less than a communication range of a second communication method W2.

The method may comprise the steps of:
Sending a first part of a key from the external device 2000 to the implant 100, using the first communication method W1.
Sending a second part of the key from the external device 200 to the implant 100, using the second communication method W2.
Sending encrypted data from the external device 2000 to the implant 100 using the second communication method W2.
Deriving, in the implant a combined key from the first part of the key and the second part of the key.
Decrypting the encrypted data, in the implant 100, using the combined key.

The external device 2000 may be adapted to be in electrical connection C1 with the implant 100 (and vice versa), using the body as a conductor. The method may then further comprise confirming the electrical connection C1 between the implant 100 and the external device 2000 and as a result of the confirmation, decrypting the encrypted data in the implant 100 and using the decrypted data for instructing the implant 100.

The method may also comprise placing a conductive member 2010, configured to be in connection with the external device 2000, in electrical connection with a skin of the patient for conductive communication with the implant 100. By means of the electrical connection an extra layer of security is added as a potential hacker would have to be in contact with the patient to access or affect the operation of an implant.

Using a plurality of communication methods, may increase the security of the authentication and the communication with the implant as more than one channel for communication may need to be hacked or hijacked by an unauthorized entity to gain access to the implant or the communication.

The electrical connection C1 the conductive member 2010 and conductive communication may be further described herein in the general definitions section. In these cases, the implant 100 and/or external device 2000 comprise the necessary features and functionality (described in the respective sections of this document).

It should also be noted that any one of the first and second communication methods W1, W2 may be needed to be confirmed in order to decrypt the encrypted data in the implant 100 and using the decrypted data for instructing the implant 100.

The method may further comprise the step of wirelessly receiving, at the implant 100, a third part of the key from the second external device 3000. In this case, the combined key may be derived from the first part of the key, the second part of the key and the third part of the key.

The first communication method W1 may be a wireless form of communication. The first communication method W1 may preferably be a form of electromagnetic or radio-based communication however, other forms of communication are not excluded. The first communication method W1 may comprise or be related to the items of the following list: Radio-frequency identification (RFID), Bluetooth, Bluetooth 5, Bluetooth Low Energy (BLE), Near Field Communication (NFC), NFC-V, Infrared (IR) based communication, Ultrasound based communication.

RFID communication may enable the use of a passive receiver circuit such as those in a RFID access/key or payment card. IR based communication may comprise fiber optical communication and IR diodes. IR diodes may alternatively be used directly, without a fiber, such as in television remote control devices. Ultrasound based communication may be based on the non-invasive, ultrasound imaging found in use for medical purposes such as monitoring the development of mammal fetuses.

The first communication method W1 may use a specific frequency band. The frequency band of the first communication method W1 may have a center frequency of 13.56 MHz or 27.12 MHz These bands may be referred to as industrial, scientific, and medical (ISM) radio bands. Other ISM bands not mentioned here may also be utilized for the communication methods W1, W2. A bandwidth of the 13.56 MHz centered band may be 14 kHz and A bandwidth of the 27.12 MHz centered band may be 326 kHz.

The communication range of the first communication method W1 may be less than 10 meters, preferably less than 2 meters, more preferably less than 1 meter and most preferably less than 20 centimeters. The communication range of the first communication method W1 may be limited by adjusting a frequency and/or a phase of the communication. Different frequencies may have different rates of attenuation. By implementing a short communication range of the first communication method, security may be increased since it may be ensured or made probable that the external device is under control of the patient (holding the external device close to the implant)

The communication range of the first communication method W1 should be evaluated by assuming that a patient's body, tissue, and bones present the propagation medium. Such a propagation medium may present different attenuation rates as compared to a free space of an air-filled atmosphere or a vacuum.

By restricting the communication range, it may be established that the external device communicating with the implant is in fact on, or at least proximal to, the patient. This may add extra security to the communication.

The second communication method W2 may be a wireless form of communication. The second communication method W2 may preferably be a form of electromagnetic or radio-based communication. The second communication method W2 may be based on telecommunication methods. The second communication method W2 may comprise or be related to the items of the following list: Wireless Local Area Network (WLAN), Bluetooth, Bluetooth 5, BLE, GSM or 2G (2nd generation cellular technology), 3G, 4G, 5G.

The second communication method W2 may utilize the ISM bands as mentioned in the above for the first communication method W1.

A communication range of the second communication method W2 may be longer than the communication range of the first communication method W1. The communication range of the second communication method W2 may preferably be longer than 10 meters, more preferably longer than 50 meters, and most preferably longer than 100 meters.

Encrypted data may comprise instructions for updating a control program 110 running in the implant 100. Encrypted data may further comprise instructions for operating the implant 100.

In one embodiment, the implant 100 may transmit data to an external device 2000 which may add an additional layer of encryption and transmit the data to a second external device 3000, described with reference to FIGS. 46A-C. By having the external device add an additional layer of encryption, less computing resources may be needed in the implant, as the implant may transmit unencrypted data or data encrypted using a less secure or less computing resource requiring encryption. In this way, data can still be relatively securely transmitted to a third device. The transmission of data can be performed using any of the method described herein in addition to the method or in the system described below.

Thus, in an embodiment, a system is provided. The system comprises an implant 100 having a communication unit 1020 configured to transmit data from the body of the patient to an external device 2000, and an encryption unit 1820 for encrypting the data to be transmitted. The system further comprises an external device 2000 configured to receive the data transmitted by the communication unit 1020, encrypt the received data using a first key and transmit the encrypted received data to a third external device 3000. The encryption can be performed using any of the keys described above or below. In some embodiments, the external device 2000 is configured to decrypt the data received from the internal communication unit 1020 before encrypting and transmitting the data. Alternatively, the external device 2000 may encrypt and transmit the data received from the internal communication unit 1020 without decrypting it first.

In one example, the encryption unit 1820 is configured to encrypt the data to be transmitted using a second key. The first key or the second key may, for example, implant specific information, a secret key associated with the external device, an identifier of the implant or an identifier of the communication unit 1020. The second key could be a key transmitted by the external device 2000 to the internal communication unit 1020. In some examples, the second key is a combined key comprising a third key received by the implant from the external device 2000.

The first key may be a combined key comprising a fourth key, wherein the fourth key is received by the external device 2000 from a fourth device. The fourth device may be a verification unit, either comprised in the external device, or external to the external device and connected to it. The verification unit may have a sensor 2500 for verification, such as a fingerprint sensor. More details in regard to this will be described below. Alternatively, the verification unit may be a generator, as described above.

The system may be configured to perform a method for transmitting data using a sensed parameter. The method may comprise transmitting a parameter measured by the external device 2000 from the external device 2000 to the implant 100. In this case, the comparison of the parameter of the patient measured by the external device 2000 and the parameter of the patient measured by the implant 100 may be performed by the implant 100. The implant 100 may comprise a first sensor 1500 for measuring the parameter of the patient at the implant 100. The external device 2000 may comprise an external sensor 2500 for measuring the parameter of the patient at the external device 2000.

Authentication of the connection between the implant 100 and the external device 2000 may be performed automatically without input, authentication, or verification from a user or patient. This is because the comparison of parameters measured internally and externally, by the internal and external sensors 1500, 2500 respectively may be enough to authenticate the connection. This may typically be the case when the parameter of the patient is related to an automatically occurring physiological function of the patient such as e.g. a pulse of the patient. Certain types of authentication may however require actions from the patient, e.g. having the patient perform specific movements.

In the embodiments described herein, the implant 100 may comprise or be connected to a sensation generator 1810 as described above. In response to an event in the implant, such as a reset, a restart, receipt of new instructions, receipt of a new configuration or update, installation or activation of new instructions or configuration or update, the implant 100 may be configured to cause the sensation generator 1810 to generate a sensation detectable by the patient in which the implant is implanted. In some examples, the user may after the sensation verify an action, for example via a user interface of an external device 2000.

The implant may further implement a method for improving the security of the data transmitted from the implant. The method, for encrypted communication between an implant 100, when implanted in a patient's body, and an external device 2000, comprises encoding or encrypting, by the implant 100 or a processor 1060 comprised in or connected to the implant 100, data relating to the implant 100 or the operation thereof; transmitting, by a first communication unit 1020 comprised in the implant 100, the data; receiving, by a second communication unit comprised the external device 2000, the data; encrypting, by the external device 2000, the data using an encryption key to obtain encrypted data; and transmitting the encrypted data to a third external device 3000. In this way, the external device 2000 may add or exchange the encryption, or add an extra layer of encryption, to the data transmitted by the implant 100. When the implant encodes the data to be transmitted it may be configured to not encrypt the data before transmitting, or only using a light weight encryption, thus not needing as much processing power as if the implant were to fully encrypt the data before the transmission.

The encrypting, by the implant 100, may comprise encrypting the data using a second key. The encryption using the second key may be a more light weight encryption than the encryption performed by the external device using the second key, i.e. an encryption that does not require as much computing resources as the encryption performed by the external device 2000.

The first or the second key may comprise a private key exchanged as described above with reference to encryption and authentication, or the first or the second key may comprise an implant specific information, a secret key associated with the external device, an identifier of the implant 100 or an identifier of the communication unit 1020. They may be combined keys as described in this description, and the content of the keys, any combination of keys, and the exchange of a key or keys is described in the encryption and/or authentication section.

Figure 47:
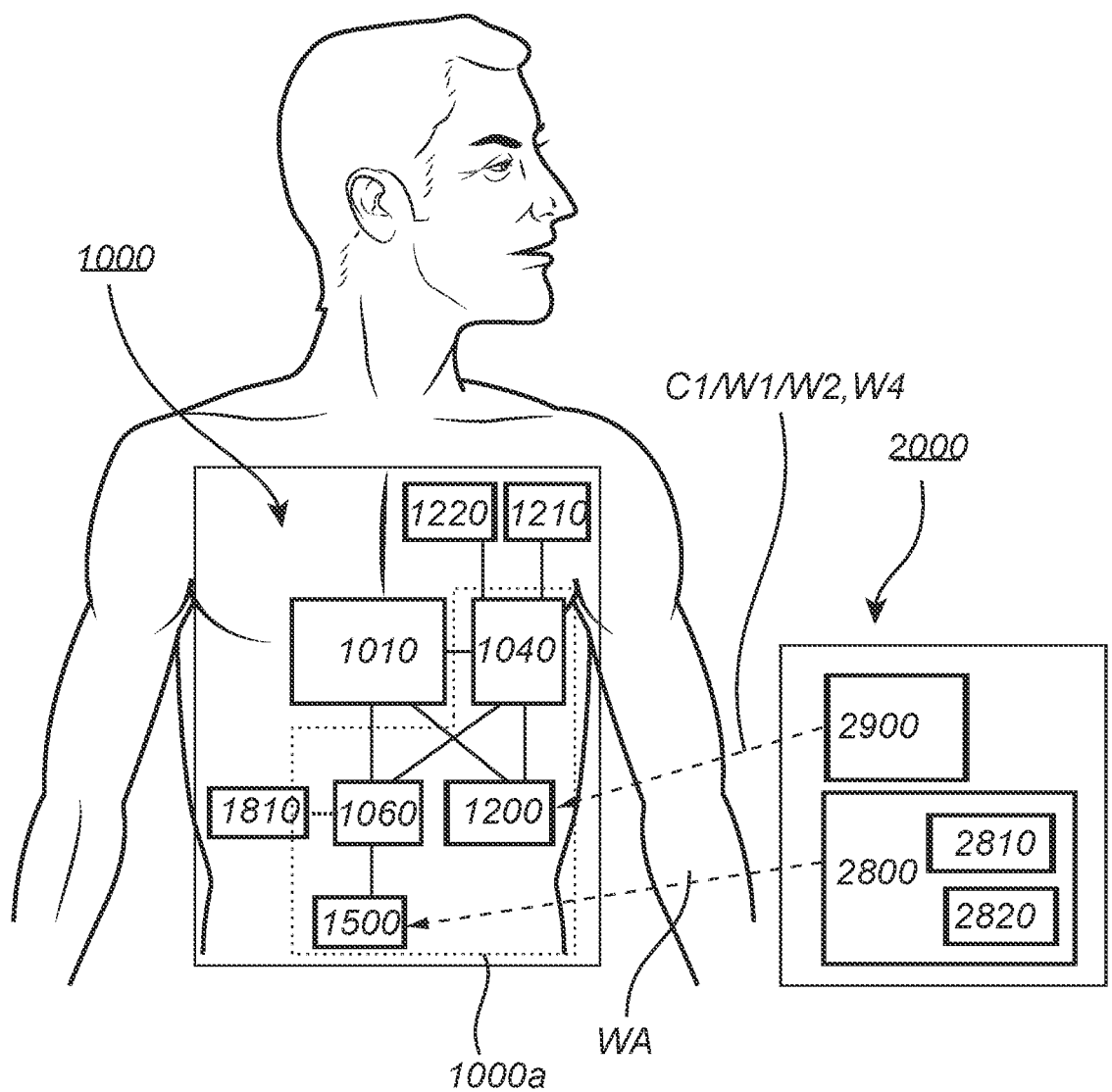
Figure 48:
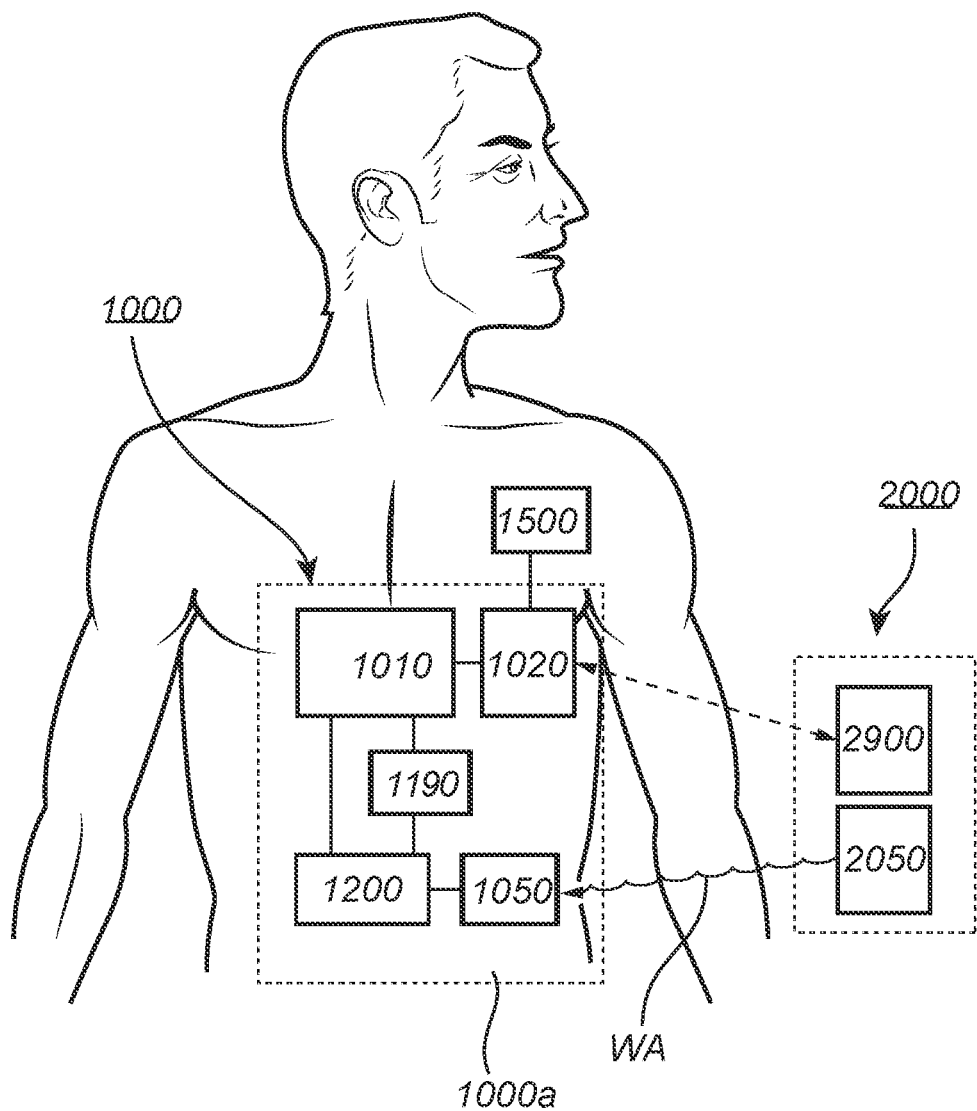

In an embodiment, the implant comprises at least one sensor for sensing at least one physiological parameter of the patient or a functional parameter of the implant, now described with reference to FIG. 47. The devices shown in FIG. 47 may further comprise the features described with reference to FIGS. 46A-C. The sensor 1500 may, for example, be a pressure sensor, an electrical sensor, a clock, a temperature sensor, a motion sensor, an optical sensor, a sonic sensor, an ultrasonic sensor. The sensor 1500 is configured to periodically sense the parameter and the communication unit 1020 is configured to, in response to the sensed parameter being differing from a predetermined threshold (such as being less than a predetermined value or exceeding a predetermined value) or predetermined interval, wirelessly broadcast information relating to the sensed parameter. The internal communication unit 1020 may be configured to broadcast the information using a short- to mid-range transmitting protocol, such as a Radio Frequency type protocol, a RFID type protocol, a WLAN type protocol, a Bluetooth type protocol, a BLE type protocol, a NFC type protocol, a 3G/4G/5G type protocol, or a GSM type protocol.

The control unit 1000a of the implant may be connected to the sensor 1500 and to the communication unit 1020, and the control unit 1000a may be configured to anonymize the information before it is transmitted. The transmission of data may also be called broadcasting of data.

In addition to or as an alternative to transmitting the data when the sensed parameter is above or below a predetermined threshold or outside of a predetermined interval, the communication unit 1020 may be configured to broadcast the information periodically. The control unit 1000a may be configured to cause the communication unit 1020 to broadcast the information in response to a second parameter being above or below a predetermined threshold, or outside of a predetermined interval. The second parameter may, for example, be related to the control unit 1000a itself, such as a free memory or free storage space parameter, or a battery status parameter. When the implant comprises an implantable energy source and an energy source indicator, the energy source indicator is configured to indicate a functional status of the implantable energy source and the indication may be comprised in the transmitted data. The functional status may indicate at least one of charge level and temperature of the implantable energy source.

In some embodiments the external device 2000 is configured to receive the broadcasted information, encrypt the received information using an encryption key and transmit the encrypted received information. In this way, the external device 2000 may add an additional layer of encryption or exchange the encryption performed by the internal communication unit.

In an embodiment, the internal communication unit 1020 is configured to transmit the data using the body of the patient as a conductor C1, and the external device 2000 is configured to receive the data via the body. Alternatively, or in combination, the communication unit of the implant is configured to transmit the data wirelessly to the external device W2.

Thus, the implant 100 may implement a method for transmitting data from an implant comprising a processor 1060 and a communication unit 1020, comprising: obtaining sensor measurement data via a sensor 1500 connected to or comprised in the implant 100, the sensor measurement relating to at least one physiological parameter of the patient or a functional parameter of the implant 100, and transmitting by the communication unit 1020 the sensor measurement data in response to the sensor measurement being above a predetermined threshold, wherein the sensor 1500 is configured to periodically sense the parameter. The method may further comprise broadcasting the sensor measurement data, to be received by an external device 2000. The transmitting or broadcasting may comprise using at least one of a Radio Frequency type protocol, RFID type protocol, WLAN type protocol, Bluetooth type protocol, BLE type protocol, NFC type protocol, 3G/4G/5G type protocol, or a GSM type protocol.

The method may further comprise, at the processor 1060, anonymizing, by the processor, the sensor measurement data before it is transmitted, or encrypting the sensor measurement data, using an encryptor 1820 comprised in the processing unit, before it is transmitted. The transmitting of the data may further comprise to encode the data before the transmitting. The type of encoding may be dependent on the communication channel or the protocol used for the transmission.

The transmitting may be performed periodically, or in response to a signal received by the processor, for example, by an internal part of the implant such as a sensor 1500, or by an external device 2000.

The parameter may, for example, be at least one of a functional parameter of the implant (such as a battery parameter, a free memory parameter, a temperature, a pressure, an error count, a status of any of the control programs, or any other functional parameter mentioned in this description) or a parameter relating to the patient (such as a temperature, a blood pressure, or any other parameter mentioned in this description). In an example, the implant 100 comprises an implantable energy source 1040 and an energy source indicator 1040c, and the energy source indicator 1040c is configured to indicate a functional status of the implantable energy source 1040, and the sensor measurement comprises data related to the energy source indicator.

In one example, the transmitting comprises transmitting the sensor measurement to an internal processor 1060 configured to cause a sensation generator 1810 to cause a sensation detectable by the patient in which the implant 100 is implanted.

The method may be implemented in a system comprising the implant 100 and an external device 2000, and further comprise receiving the sensor measurement data at the external device 2000, and, at the external device 2000, encrypting the sensor measurement data using a key to obtain encrypted data, and, transmitting the encrypted data. The transmitting may, for example, be performed wirelessly W3 or conductively C1.

In the examples or embodiments transmitting data from or to the implant 100, the following method may be implanted in order to verify the integrity of the data, described with reference to FIGS. 46A-B. By verifying the integrity of the data, an external device 2000 or a processor 1060 comprised in the implant may verify that the data has not been corrupted or tampered with during the transmission. In some examples, data integrity for data communicated between an implant 100 and an external device 2000 or between an external device 2000 and an implant 100 may be performed using a cyclic redundancy check.

Thus, in a first example, a method for evaluating a parameter of an implant 100 implanted in a patient is described. The implant 100 comprises a processor 1060, a sensor 1500 for measuring the parameter, and an internal communication unit 1020. The method comprises measuring, using the sensor 1500, the functional parameter to obtain measurement data; establishing a connection between the internal communication unit 1020 and an external device 2000 configured to receive data from the implant; determining, by the processor 1060, a cryptographic hash or a metadata relating to the measurement data and adapted to be used by the external device 2000 to verify the integrity of the received data; transmitting the cryptographic hash or metadata; and transmitting, from the communication unit 1020, the measurement data.

The parameter may, for example, be a parameter of the implant, such as a temperature or a battery status indicator, or a characteristics of the stimulation signal comprising e.g. amplitude, frequency, pulse duration, or a biological response from the stimulated muscle tissue such as contraction or temperature. In some examples, multiple parameters may be used.

The method may further comprise evaluating the measurement data relating to the functional parameter. By evaluating it may be meant to determine if the parameter is exceeding or less than a predetermined value, to extract another parameter from the measurement data, compare the another parameter to a predetermined value, or displaying the another parameter to a user. For example, the method may further comprise, at the external device 2000, to determining, based on the evaluating, that the implant 100 is functioning correctly, or determining based on the evaluating that the implant 100 is not functioning correctly.

If it is determined that the implant 100 is not functioning correctly, the method may further comprise sending, from the external device 2000, a corrective command to the implant 100, receiving the corrective command at the implant 100, and by running the corrective command correcting the functioning of the implant 100 according to the corrective command.

The method may further comprise, at the external device 2000, receiving the transmitted cryptographic hash or metadata, receiving the measurement data, and verifying the integrity of the measurement data using the cryptographic hash or metadata. The cryptographic hash algorithm be any type of hash algorithm, i.e. an algorithm comprising a one-way function configured to have an input data of any length as input and produce a fixed-length hash value. For example, the cryptographic hash algorithm may be MD5, SHA1, SHA 256, etc.

In some examples, the cryptographic hash is a signature obtained by using a private key of the implant, and wherein the verifying, by the external device 2000, comprises verifying the signature using a public key corresponding to the private key.

When using a cryptographic hash, the method may further comprise calculating a second cryptographic hash for the received measurement data using a same cryptographic hash algorithm as the processor, and determining that the measurement data has been correctly received based on that the cryptographic hash and the second cryptographic hash are equal (i.e. have the same value).

When using a metadata the verifying the integrity of the data may comprises obtaining a second metadata for the received measurement data relating to the functional parameter, and determining that the data has been correctly received based on that metadata and the second metadata are equal. The metadata may, for example, be a length of the data, or a timestamp.

In some examples the measurement data is transmitted in a plurality of data packets. In those examples, the cryptographic hash or metadata comprises a plurality of cryptographic hashes or metadata each corresponding to a respective data packet, and the transmitting of each the cryptographic hashes or metadata is performed for each of the corresponding data packets.

A similar method may be utilized for communicating instructions from an external device 2000 to an implant 100 implanted in a patient. The method comprises establishing a first connection between the external device 2000 and the implant 100, establishing a second connection between a second external device 3000 and the implant 100, transmitting, from the external device 2000, a first set of instructions to the implant 100 over the first connection, transmitting, from the second external device 3000, a first cryptographic hash or metadata corresponding to the first set of instructions to the implant, and, at the implant 100, verifying the integrity of the first set of instructions and the first cryptographic hash or metadata, based on the first cryptographic hash or metadata. The external device 2000 may be separate from the second external device 3000.

The first connections may be established between the internal communication unit 1020 and a transceiver of the external communication unit 2010, 2030. In some examples, the communication using the second connection is performed using a different protocol than a protocol used for communication using the first communication channel. In some examples, the first connection is a wireless connection and the second connection is an electrical connection. The second connection may, for example, be an electrical connection using the patient's body as a conductor. The protocols and ways of communicating may be any communication protocols described in this description with reference to C1, and W1-W4. The establishing of the first and second connections are performed according to the communication protocol used for each of the first and the second connections.

When using a cryptographic hash, the verifying the integrity of the first set of instructions may comprise calculating a second cryptographic hash for the received first set of instructions using a same cryptographic hash algorithm as the processor 1060, and determining that the first set of instructions has been correctly received based on that the cryptographic hash and the second cryptographic hash are equal. The cryptographic hash may, for example, be a signature obtained by using a private key of the implant 100, and wherein the verifying comprises verifying the signature using a public key corresponding to the private key. In some examples, the cryptographic hash is a signature obtained by using a private key of the implant, and wherein the verifying comprises verifying the signature using a public key corresponding to the private key. The private keys and public keys, as well as the exchange or transmittal of keys have been described in this description. Alternatively, other well-known methods can be used for transmitting or exchanging a key or keys between the external device 2000 and the implant 100.

When using a metadata, and wherein the verifying the integrity of the data may comprise obtaining a second metadata for the received first set of instructions, and determining that the first set of instructions has been correctly received based on that metadata and the second metadata are equal. The metadata may, for example, be any type of data relating to the data to be transmitted, in this example the first set of instructions. For example, the metadata may be a length of the data to be transmitted, a timestamp on which the data was transmitted or retrieved or obtained, a size, a number of packets, or a packet identifier.

In some examples, the implant 100 may transmit data to an external device 2000 relating to the data information in order to verify that the received data is correct. The method may thus further comprise, transmitting, by the implant 100, information relating to the received first set of instructions, receiving, by the external device 2000, the information, and verifying, by the external device 2000, that the information corresponds to the first set of instructions sent by the external device 2000. The information may, for example, comprise a length of the first set of instructions.

The method may further comprise, at the implant 100, verifying the authenticity of the first set of instructions by i. calculating a second cryptographic hash for the first set of instructions, ii. comparing the second cryptographic hash with the first cryptographic hash, iii. determining that the first set of instructions are authentic based on that the second cryptographic hash is equal to the first cryptographic hash, and upon verification of the authenticity of the first set of instructions, storing them at the implant.

In some examples, the first set of instructions comprises a cryptographic hash corresponding to a previous set of instruction, as described in other parts of this description.

In some examples, the first set of instructions may comprise a measurement relating to the patient of the body for authentication, as described in other parts of this description.

A system and a method for transmitting an instruction or a control signal from an external device 200 to an implant 100 is provided and will now be described with reference to FIGS. 46A-C.

The system shown in FIGS. 46A-C comprises an implant 1000, a first external device 2000, and a second external device 3000. The implant comprises a controller 1020 (which could also be called an internal control unit, or a communication unit) and an active unit 101, such as an implantable movement restriction device, an electrode arrangement, an elongated core, a tubular cover, an implantable first and second portion, or an elongated support device as disclosed in the present application. The controller 1020 is in this example adapted to receive an instruction from an external device 2000 over the communication channel W1 or W4 and run the instruction to control a function of the implant 1000, such as a function of the active unit 101. The communication channel may be any type of communication channel, such as any of the wireless connection W1-W4 or the conductive connection C1 described herein. For example, the wireless connection may comprise at least one of the following protocols:
Radio Frequency type protocol
RFID type protocol
WLAN type protocol
Bluetooth type protocol
BLE type protocol
NFC type protocol
3G/4G/5G type protocol
GSM type protocol
Bluetooth 5.

The first external device 2000 is adapted to receive, such as through a user interface, or determine an instruction to be transmitted to the implant 1000. The determination of the instruction may, for example, be based on received data from the implant 1000, such as measurement data or data relating to a state of the implant 1000. The measurement data may, for example be a battery status or a free memory status, or an electrical stimulation pattern. The first external device 2000 may be any type of device capable of transmitting information to the implant 1000 and capable of determining or receiving an instruction to be transmitted to the implant 1000. In a preferred embodiment, the first external device 2000 is a hand-held device, such as a smartphone, smartwatch, tablet etc. handled by the patient, having a user interface for receiving an instruction from a user, such as the patient or a caregiver.

The first external device 2000 is further adapted to transmit the instruction to the second external device 3000 via communication channel W3. The second external device 3000 is adapted to receive the instruction, encrypt the instruction using an encryption key, and then transmit the encrypted instruction to the implant 1000. The implant 1000 is configured to receive the instruction at the controller 1020. The controller thus comprises a wired transceiver 1030 or a wireless transceiver 1080 for receiving the instruction. The implant 1000 is configured to decrypt the received instruction at the controller 1020. The decryption may be performed using a decryption key corresponding to the encryption key. The encryption key, the decryption key, and methods for encryption and/or decryption and exchange of keys may be performed as described herein. Further, there are many known methods for encrypting data which the skilled person would understand to be usable in this example.

The second external device 3000 may be any computing device capable of receiving, encrypting, and transmitting data as described above. For example, the second external device 3000 may be a network device, such as a network server, or it may be an encryption device communicatively coupled to the first external device 2000.

The instruction may be a single instruction for running a specific function or method in the implant 1000, a value for a parameter of the implant, or a set of program steps to be performed by a processor 1060 or computing unit 1060 comprised in the implant.

In this way, the instruction for controlling a function of the implant 1000 may be received at the first external device 2000 but transmitted to the implant via the second external device 3000. By having a second external device 3000 encrypting the instruction before transmitting it to the implant 1000, the instruction may be verified by the second external device 3000 and the first external device 2000 may function so as to relay the instruction to the implant 1000. This may provide an increased security as the instruction sent to the implant 1000 may be verified by the second external device 3000, which, for example, may be a proprietary device managed by the medical professional responsible for the implant 1000. Further, by having the second medical device 3000 verifying and encrypting the instruction, the responsibility authenticity and/or correctness of the instruction may lie with the second external device 3000, which may be beneficial for regulatory purposes, as the first external device 2000 may not be considered as the instructor of the implant.

Further, the second external device 3000 may verify that the instruction is correct before encrypting or signing and transmitting it to the implant 1000. The second external device 3000 may, for example, verify that the instruction is correct by comparing the instruction with a predetermined set of instructions, and if the instruction is comprised in the predetermined set of instructions determine that the instruction is correct. If the instruction comprises a plurality of sub-steps, the second external device may determine that the instruction is correct if all the sub-steps are comprised in the predetermined set of instructions. If the instruction comprises a value for a parameter of the implant, the second external device may verify that the value is within a predetermined range for the parameter. The second external device 3000 may thus comprise a predetermined set of instructions, or a predetermined interval or threshold value for a value of a parameter, stored at an internal or external memory.

The second external device 3000 may be configured to reject the instruction, i.e. to not encrypt and transmit the instruction to the implant 1000, if the verification of the instruction would fail. For example, the second external device 3000 determines that the instruction or any sub-step of the instruction is not comprised in the predetermined set of instructions, or if a value for a parameter is not within a predetermined interval, the second external device 3000 may determine that the verification has failed.

In some embodiments, the implant 1000 may be configured to verify the instruction. The verification of the instruction may be performed in the same way as described with reference to the second external device 3000 above. If the verification is performed by comparing the instruction or any sub-steps of the instruction with a predetermined set of instructions, the implant 1000 may comprise a predetermined set of instructions. The predetermined set of instructions may, for example, be stored in an internal memory 1070 of the implant 1000. Similarly, the implant 1000 may store predetermined reference intervals for any parameter that can be set, and the implant may be configured to compare a received value for a parameter to such a predetermined reference interval. If the verification of the instruction would fail, the implant may be configured to reject the instruction, i.e. not run the instruction at the implant 1000.

In an alternative to encrypting and decrypting the instruction, the instruction may be signed by the second external device 3000 using a cryptographic hash, and the implant 1000 may be configured to verify, using the controller, that the signature is correct before running the instruction.

A corresponding method for transmitting instructions from a first external device 3000 to an implant 1000 will now be described. The instruction may relate to a function of the implant 1000, such as an instruction to run a function or method of the implant, or to set a value of a parameter of the implant.

The method comprises:
transmitting an instruction for the implant from the first external device 2000 to a second external device 3000, the instruction relating to a function of the implant 1000,
encrypting, at the second external device 3000 using a first encryption key, the instruction into an encrypted instruction, and
transmitting the encrypted instruction from the second external device 3000 to the implant 1000,
decrypting, by the controller 1020, the instructions using a second encryption key corresponding to the first encryption key.

The instruction may be any type of instruction for controlling a function of the implant. For example, the instruction may be an instruction to run a function or method of the implant 1000, an instruction comprising a plurality of sub-steps to be run at the controller 1020, or a value for a parameter at the implant. The instruction may relate to an electrical stimulation pattern or an electrical stimulation signal. The first external device 2000 may, for example, receive the instruction from a user via a user interface displayed at or connected to the first external device 2000. In another example, the first external device 2000 may determine the instruction in response to data received from the implant 1000, such as measurement data, or from another external device. Thus, in some examples, the method may further comprise receiving, at the first external device 2000, an instruction to be transmitted to the implant 1000. The method may further comprise displaying a user interface for receiving the instruction. In another example, the method comprises determining, at the first external device 2000, an instruction to be transmitted to the implant 1000.

In some embodiments, the transmitting of the encrypted instruction from the second external device 3000 to the implant 2000 comprises transmitting the encrypted instruction from the second external device 3000 to the first external device 2000, and transmitting the encrypted instruction from the first external device 2000 to the implant 1000. In other words, the first external device 2000 may relay the encrypted instruction from the second external device 3000 to the implant 1000, preferably without decrypting the instruction before transmitting it.

The method may further comprise to, at the controller, running the instruction or performing the instruction. The running of the instruction may be performed by a processor comprised in the controller, and may, for example, cause the internal computing unit or processor to instruct an active unit of the implant to perform an action.

The method may further comprise verifying, at the second external device 3000, that the instructions are correct. The verifying may be performed as described above with reference to the system.

The method may further comprise verifying, by the controller 1020, that the instructions are correct. The verifying may be performed as described above with reference to the system.

The method may further comprise authenticating the connection between the first external device 2000 and the controller 102 of the implant 1000 over which the encrypted instruction is to be transmitted. The authentication may be performed as described herein.

As described above, a control program of the implant may be updatable, configurable, or replaceable. A system and a method for updating or configuring a control program of the implant is now described with reference to FIGS. 46A-C. The implant 100 may comprise an internal computing unit 1060 configured to control a function of said implant 100, the internal computing unit 1060 comprises an internal memory configured to store: i. a first control program 1100 for controlling the internal computing unit, and ii. a second, configurable or updatable, with predefined program steps, control program 1120 for controlling said function of said implant 100, and iii. a set of predefined program steps for updating the second control program 1120. The internal computing unit 1060 may further comprise or be connected to an internal communication unit 1020, the internal communication unit being configured to communicate with an external device 2000, wherein said internal computing unit 1060 is configured to receive an update to the second control program 1120 via said internal communication unit 1020, and a verification function of, connected to, or transmitted to said internal computing unit 1020, said verification function being configured to verify that the received update to the second control program 1120 comprises program steps comprised in the set of predefined program steps. In this way, the updating or programming of the second control program may be performed using predefined program steps, which may decrease the risk that the new or updated control program is incorrect or comprises malicious software, such as a virus, spyware or a malware.

The predefined program steps may comprise setting a variable related to a time, a minimum or maximum temperature, a current, a voltage, an intensity, a frequency, an amplitude of electrical stimulation, a feedback mode (sensorics or other), and a post-operative mode or a normal mode.

The verification function may be configured to reject the update in response to the update comprising program steps not comprised in the set of predefined program steps and/or be configured to allow the update in response to the update only comprising program steps comprised in the set of predefined program steps.

The internal computing unit may be configured to install the update in response to a positive verification, for example by a user using an external device, by a button or similarly pressed by a user, or by another external signal.

The authentication or verification of communications between the implant and an external device has been described above.

When updating a control program of the internal computing unit, it may be beneficial to transmit a confirmation to a user or to an external device or system. Such a method is now described with reference to FIGS. 46A-B.

The method for updating a control program of an internal computing unit comprised in an implant according to any of the embodiments described herein, wherein the implant is adapted for communication with a first external device and a second external device, which may comprise receiving, by the internal computing unit, an update or configuration to the control program from the first external device, wherein the update is received using a first communication channel; installing, by the internal computing unit, the update; and transmitting, by the internal computing unit, logging data relating to the receipt of the update or configuration and/or logging data relating to an installation of the update to the second external device using the second communication channel; wherein the first and the second communication channels are different communication channels. By using a first and a second communication channels, in comparison to only using one, the security of the updating may be improved as any attempts to update the control program will be logged via the second communication channel, and thus, increasing the chances of finding incorrect or malicious update attempts.

The update or configuration comprises a set of instructions for the control program, and may, for examples comprise a set of predefined program steps as described above. The configuration or update may comprise a value for a predetermined parameter.

In some examples, the method further comprises confirming, by a user or by an external control unit, that the update or configuration is correct based on the received logging data.

The logging data may be related to the receipt of the update or configuration, and the internal computing unit is configured to install the update or configuration in response to receipt of a confirmation that the logging data relates to a correct set of instructions. In this way, the internal computing unit may receive data, transmit a logging entry relating to the receipt, and then install the data in response to a positive verification that the data should be installed.

In another example, or in combination with the one described above, the logging data is related to the installation or the update or configuration. In this example the logging data may be for information purposes only and not affect the installation, or the method may further comprise activating the installation in response to the confirmation that the update or configuration is correct.

If the update or configuration is transmitted to the internal computing unit in one or more steps, the verification as described above may be performed for each of the steps.

The method may further comprise, after transmitting the logging data to the second external device, verifying the update via a confirmation from the second external device via the second communication channel.

Embodiments relating to an implant having an internal control unit having a processor with a sleep mode and an active mode will now be described with reference to FIG. 47. The implant, the internal communication unit and the external device(s) may have the features described above with reference to FIGS. 46A-C.

In an embodiment in which the internal control unit 1000a comprises a processor 1060 having a sleep mode and an active mode, the internal control unit 1000a (the internal control unit may also called a controller) comprises a sensor 1500 and a processing unit 1060 having a sleep mode and an active mode, wherein the sensor 1500 is configured to periodically measure a physical parameter of the patient, and wherein the internal control unit 1000a is further configured to, in response to a sensor measurement preceding a predetermined value, setting the processing unit 1060 in an active mode. That is, the internal control unit 1000a may "wake up" or be set in an active mode in response to a measurement from, for example, the body. A physical parameter of the patient could for example be a local or systemic temperature, saturation/oxygenation, blood pressure or a parameter related to an ischemia marker such as lactate.

By sleeping mode it is meant a mode with less battery consumption and/or processing power used in the processing unit 1060, and by "active mode" it may be meant that the processing unit 1060 is not restricted in its processing.

The sensor 1500 may, for example, be a pressure sensor. The pressure sensor may be adapted to measure a pressure in an organ of a patient, a reservoir of the implant or a restriction device of the active unit 1010. The sensor 1500 may be an analog sensor or a digital sensor, i.e. a sensor 1500 implemented in part in software. In some examples, the sensor is adapted to measure one or more of a battery or energy storage status of the implant and a temperature of the implant. In this way, the sensor 1500 may periodically sense a pressure of the implant or of the patient and set the processing unit 1060 in an active mode if the measured pressure is above a predetermined value. Thus, less power, i.e. less of for example a battery or energy storage comprised in the implant, may be used, thereby prolonging the lifetime of the implant 100 or increasing the time between charging occasions of the implant 100.

In some examples, the processor, when in set in the active mode, may cause a sensation generator 1810 connected to the implant, comprised in the implant or comprised in an external device 2000, 3000, to generate a sensation detectable by a sense of the patient. For example, the processor may cause the sensation generator to generate a sensation in response to a measure battery status, for example that the battery is above or below a predetermined level, that a measured pressure is above or below a predetermined level, or that another measured parameter has an abnormal value, i.e. less than or exceeding a predetermined interval or level. The sensation generator has been described in further detail earlier in this description.

The processing unit 1060 may be configured to perform a corrective action in response to a measurement being below or above a predetermined level. Such a corrective action may, for example, be increasing or decreasing the electrical stimulation in terms of amplitude, periodicity, frequency, pause periods and the like.

The internal control unit 1000a may comprise an internal communication unit 1020 or a signal transmitter 1040 connected to the processing unit, and wherein the processing unit is configured to transmit data relating to the measurement via the internal communication unit 1020 or the internal signal transmitter 1040. The transmitted data may be received by an external device 2000.

The external device may have an external communication unit 2900. The external device may comprise a signal provider 2800 for providing a wake signal to the internal control unit. In some examples, the signal provider comprises a coil or magnet 2810 for providing a magnetic wake signal.

The implant may implement a corresponding method for controlling a medical implant when implanted in a patient. The method comprises measuring, with a sensor of a controller connected to or comprised in the medical implant, a physiological parameter of the patient or a parameter of the medical implant, and, in response to a sensor measurement having an abnormal value, setting, by the controller, a processor of the controller from a sleep mode to an active mode. The measuring may be carried out periodically. By "abnormal value" it may be meant a measured value exceeding or being less than a predetermined value, or a measured value being outside a predetermined interval. The method may further comprise generating, with a sensation generator as described above, a sensation detectable by the patient. In some examples, the generating comprises requesting, by the processor, the sensation generator to generate the sensation.

The method may further comprise to perform a medical intervention in response to a sensor measurement having an abnormal value, preferably after the processing unit has been set in the active mode.

A system comprising an implant having an internal control unit having a sleep mode and an active mode will now be described with reference to FIG. 47. In an embodiment, the internal control unit 1000a comprises a sensor 1500 adapted to detect a magnetic field and a processing unit having a sleep mode and an active mode, now described with reference to FIGS. 46A-C. The external control unit 2000 comprises a signal provider 2800 adapted to provide a magnetic field detectable by the internal sensor 1500. The internal control unit 1000a is further configured to, in response to a detected magnetic field exceeding a predetermined value, setting the processing unit 1060 in an active mode. In this way, the external device 2000 may cause a sleeping internal control unit 1000a or processor 1060 to "wake up".

The sensor 1500 may, for example, be a hall effect sensor, a fluxgate sensor, an ultra-sensitive magnetic field sensor, a magneto-resistive sensor, an AMR or GMR sensor, or the sensor may comprise a third coil having an iron core.

The magnetic field provider 2800 may have an off state, wherein it does not provide any magnetic field, and an on state, wherein it provides a magnetic field. For example, the magnetic field provider 2800 may comprise a magnet 2810, a coil 2810, a coil having a core 2810, or a permanent magnet 2810. In some embodiments, the magnetic field provider 2800 may comprise a shielding means for preventing a magnet 2810 or permanent magnet 2810 from providing a magnetic field in the off state. In order to provide a substantially even magnetic field, the magnetic field provider may comprise a first and a second coil arranged perpendicular to each other.

After the processing unit 1060 has been set in an active mode, i.e. when the processing unit 1060 has been woken, the implant may determine a frequency for further communication between the internal communication unit 1020 and the external device 2000. The implant 100 may thus comprise a frequency detector 1210 for detecting a frequency for communication between the first 1020 and the second communication units 2900. The frequency detector 1210 is, for example, an antenna. The external device 2000 may comprise a frequency indicator 2820, for transmitting a signal indicative of a frequency. The frequency indicator 2820, may, for example, be a magnetic field provider capable of transmitting a magnetic field with a specific frequency. In some examples the frequency indicator is comprised in or the same as the magnetic field provider 2810. In this way, the frequency signal is detected using means separate from the sensor, and can, for example, be detected using a pin on a chip.

Alternatively, the internal communication unit 1020 and the external device 2000 may communicate using a predetermined frequency or a frequency detected by means defined by a predetermined method according to a predetermined protocol to be used for the communication between the internal communication unit 1020 and the external device 2000.

In some embodiments, the sensor 1500 may be used for the communication. The communication may in these embodiments be performed with such that a frequency of the magnetic field generated by the coil is 9-315 kHz, or the magnetic field generated by the coil is less than or equal to 125 kHz, preferably less than 58 kHz. The frequency may be less than 50 Hz, preferably less than 20 Hz, more preferably less than 10 Hz, in order to be transmittable through a titan box.

In some embodiments, the internal control unit 1000a comprises a receiver unit 1220, and the internal control unit and the external control unit are configured to transmit and/or receive data via the receiver unit 1220 via magnetic induction. The receiver unit 1220 may comprise a high-sensitivity magnetic field detector, or the receiver unit may comprise a fourth coil for receiving the magnetic induction.

The system may implement a method for controlling a medical implant implanted in a patient. The method comprises monitoring for signals by a sensor 1500 comprised in an internal control unit 1000a communicatively coupled to the active unit 1010, providing, from a signal provider 2800 comprised in an external device 2000, a wake signal, the external device 2000 being adapted to be arranged outside of the patient's body, and setting, by the internal control unit 1000a and in response to a detected wake signal WS, a mode of a processing unit 1060 comprised in the internal control unit from a sleep mode to an active mode.

The method may also comprise detecting, using a frequency detector 1210, a frequency for data communication between a first communication unit 1020 and a second communication unit 2900, the first communication unit 1020 being associated with the internal control unit 1000a and the second communication unit 2900 being associated with the external device 2000, wherein the frequency detector 1210 is communicatively coupled to the internal control unit 1000a or the external device 2000. The detection may be performed using a detection sequence for detecting the frequency. This detection sequence may, for example, be a detection sequence defined in the protocol to be used for communication between the first and the second communication units. Potential protocols that may be used for communication between an internal communication unit 1020 and an external device 2000 has been described earlier in this description. Thus, the method may comprise determining, using the frequency detector 1210, the frequency for data communication, and initiating data communication between the first communication unit 1020 and the second communication unit 2900. The data communication can, for example, comprise one or more control instructions for controlling the medical implant 100 transmitted from the external device, or, for example, comprise data related to the operation of the medical implant 100 and be transmitted from the internal control unit 1020.

In some examples, the medical implant may comprise or be connected to a power supply for powering the medical implant. This will now be described with reference to FIG. 48. The medical implant, the internal control unit, and the external device(s) may comprise all elements described above with reference to FIGS. 46A-C and FIG. 47. The power supply may comprise an implantable energy source 1200 for providing energy to the medical implant, an energy provider 1190 connected to the implantable energy source 1200 and connected to an energy consuming part 1010 of the medical implant, the energy provider 1190 being configured to store energy to provide a burst of energy to the energy consuming part 1010, wherein the energy provider 1190 is configured to be charged by the implantable energy source 120 and to provide the energy consuming part with electrical power during startup of the energy consuming part 1010.

Alternatively, the implant 100 may comprise a first implantable energy source 1200 for providing energy to an energy consuming part 1010 of the medical implant 100, a second implantable energy source 1190 connected to the implantable energy source 1200 and connected to the energy consuming part, wherein the second implantable energy source 1190 is configured to be charged by the implantable energy source 1200 and to provide the energy consuming part 1010 with electrical power during startup of the energy consuming part 1010, wherein the second implantable energy source 1190 has a higher energy density than the first implantable energy source 1200. By having a "higher energy density" it may be meant that the second implantable energy source 1190 has a higher maximum energy output per time unit than the first implantable energy source 1200. The second energy storage 1190 may be an energy provider as discussed below.

The energy consuming part 1010 may be any part of an implant requiring energy, such as an electrode arrangement for providing electrical stimulation to tissue of the patient, a processing or computing unit, a communication unit, a CPU for encrypting information, a transmitting and/or receiving unit for communication with an external unit (not shown as part of the energy consuming part in the drawings, that is, the communication unit may be connected to the energy storage 1200 and to the energy provider 1190), a measurement unit or a sensor, a data collection unit, a solenoid, a vibrator, or a feedback unit.

In this way, an energy consuming part requiring a quick start or an energy consuming part which requires a high level or burst of energy for a start may be provided with sufficient energy. This may be beneficial as instead of having an idle component using energy, the component may be completely turned off and quickly turned on when needed. Further, this may allow the use of energy consuming parts needing a burst of energy for a startup while having a lower energy consumption when already in use. In this way, a battery or an energy source having a slower discharging (or where a slower discharging is beneficial for the lifetime or health of the battery) may be used for the implant, as the extra energy needed for the startup is provided by the energy provider.

Energy losses may occur in a battery or energy source of an implant if the battery or energy source is discharged too fast. These energy losses may for example be in the form of heat, which may damage the battery or energy source. By the apparatus described in these examples, energy may be provided from the battery or energy source in a way that does not damage the battery or energy source, which may improve the lifetime of the battery or energy source and thereby the lifetime of the medical implant.

In some examples, the discharging from the implantable energy source 120 during startup of the energy consuming part is slower than the energy needed for startup of the energy consuming part 1010, i.e. the implantable energy source 1200 is configured to have a slower discharging than the energy needed for startup of the energy consuming part. That is, there is a difference between the energy needed by the energy consuming part 1010 and the energy the implantable energy source 1200 is capable of providing without damaging the implantable energy source 1200. In other words, a maximum energy consumption of the energy consuming part 1010 may be higher than the maximum energy capable of being delivered by the implantable energy source 1200 without causing damage to the implantable energy source, and the energy provider 1190 may be adapted to deliver an energy burst corresponding to difference between the required energy consumption and the maximum energy capable of being delivered by the implantable energy source 1200. The implantable energy source 1200 may be configured to store a substantially larger amount of energy than the energy burst provider 1190 but may be slower to charge.

The implantable energy source 1200 may be any type of energy source suitable for an implant 1000, such as a re-chargeable battery or a solid-state battery, such as a tionyl-chlorid battery. The implantable energy source 1200 may be connected to the energy consuming part 1010 and configured to power the energy consuming part 1010 after it has been started using the energy provider 1190.

The energy provider 1990 may be any type of part configured to provide a burst of energy for the energy consuming part 1010. In some examples, the energy provider 1190 is a capacitor, such as a start capacitor, a run capacitor, a dual run capacitor or a supercapacitor. The energy provider 1190 may be connected to the implantable energy source 1200 and be adapted to be charged using the implantable energy source 1200. In some examples, the energy provider may be a second energy provider 1190 configured to be charged by the implantable energy source 1200 and to provide the energy consuming part 1010 with electrical energy.

A corresponding method for powering a medical implant may also be contemplated. The method comprises the steps of initiating an energy consuming part 1010 of the implant, the energy consuming part being connected to an implantable energy source 1200, providing an initial burst of energy to the energy consuming part 1010 using an energy provider 1190 connected to the implantable energy source 1200 and to the energy consuming part 1010, the energy provider 1190 being adapted to provide a burst of energy to the energy consuming part 1010, and subsequently powering the energy consuming part 1010 using the implantable energy source 1200.

In some examples, a maximum energy consumption of the energy consuming part 1010 is higher than the maximum energy capable of being delivered by the implantable energy source 1200 without causing damage to the implantable energy source 1200, and the energy provider 1190 is adapted to deliver an energy burst corresponding to difference between the required energy consumption and the maximum energy capable of being delivered by the implantable energy source 1200.

The method may further comprise the step of charging the energy provider 1190 using the implantable energy source 1200.

Initiating an energy consuming part 1010 may comprise transitioning a control unit of the medical implant from a sleep mode to an operational or active mode.

The implantable energy source 1200 may be adapted to be wirelessly charged and the implantable energy source may be connected to an internal charger 1050 for receiving wireless energy from an external device 2000 via an external charger 2050, and the method may comprise wirelessly charging the implantable energy source 1200. In some examples the method comprises controlling a receipt of electrical power from an external energy source at the internal charger 1050. The internal energy 1200 source may be charged via the receipt of a transmission of electrical power from an external energy source 2050 by the internal charger 1050.

The embodiments described herein may advantageously be combined. A computer program product of, or adapted to be run on, an internal computing unit or an external device is also provided, which comprises a computer-readable storage medium with instructions adapted to make the internal computing unit and/or the external device perform the actions as described in any embodiment or example above.

The different aspects or any part of an aspect or different embodiments or any part of an embodiment may all be combined in any possible way. For example, all the embodiments relating to the communication and controlling of the implant may be combined with the embodiments relating to the programming of the implant, the methods, and systems for improving energy consumption or the power supply. The embodiments relating to the programming of the implant may be combined with any of the embodiments relating to improving the energy consumption or the power supply. The embodiments relating to the power supply may be combined with the methods and systems for improving the energy consumption. Any method or any step of method may be seen also as an apparatus description, as well as, any apparatus embodiment, aspect or part of aspect or part of embodiment may be seen as a method description and all may be combined in any possible way down to the smallest detail. Any detailed description should be interpreted in its broadest outline as a general summary description, and please note that any embodiment or part of embodiment as well as any method or part of method could be combined in any way within the scope of the inventive concept, as defined by the appended claims. All examples herein should be seen as part of the general description and therefore possible to combine in any way in general terms.

In the following, numbered aspect groups 260SE-274SE of the present invention are provided. The different aspects are numbered individually within the groups and the references to other aspects relate to aspects within the same group. The scope of protection is however defined by the appended claims.

Aspect Group 260SE: Reflux_Stop_Exercise_General
1. An apparatus (100) for treating reflux disease of a human patient, comprising:
    an implantable movement restriction device (110) having a shape and size allowing it to be arranged to rest against a fundus wall portion (14) of the patient's stomach (10) and to be at least partly invaginated by the fundus wall portion, such that the movement restriction device is implanted at a position between the patient's diaphragm (30) and a lower portion of the fundus wall, and such that movement of the cardia (22) of the patient's stomach towards the diaphragm is restricted to hinder the cardia from sliding through the diaphragm opening (32) into the patient's thorax; and an electrode arrangement (150) configured to engage and electrically stimulate muscle tissue of the fundus wall portion to exercise the muscle tissue to improve the conditions for long term implantation of the movement restriction device.
2. The apparatus according to aspect 1, wherein the electrode arrangement is arranged on an outer surface of the movement restriction device.
3. The apparatus according to aspect 1 or 2, wherein the electrode arrangement comprises a plurality of electrode elements (152), each of which being configured to engage and electrically stimulate the muscle tissue.
4. The apparatus according to any of the preceding aspects, wherein the electrode arrangement comprises a coiled wire for increasing a contact surface between the electrode arrangement and the muscle tissue and for allowing the electrode arrangement to follow contraction and relaxation of the muscle tissue.
5. The apparatus according to any of the preceding aspects, wherein the electrode arrangement comprises a bare electrode portion (155) configured to form a metal-tissue interface with the muscle tissue, thereby allowing faradaic charge transfer to the be predominant charge transfer mechanism over said interface.
6. The apparatus according to any of the preceding aspects, wherein the electrode arrangement comprises an electrode portion at least partly covered by a dielectric material (157) configured to form a dielectric-tissue interface with the muscle tissue, thereby allowing for a faradaic portion of the charge transfer mechanism over said interface to be reduced.
7. The apparatus according to any of the preceding aspects, wherein the electrode arrangement is further configured to be arranged to electrically stimulate the cardiac sphincter to cause the cardiac sphincter (26) to contract.

8. The apparatus according to aspect 7, wherein the electrode arrangement comprises at least two electrode elements (154) configured to be arranged on opposing sides of the cardiac sphincter.
9. The apparatus according to aspect 8, further comprising a holder configured to support the at least two electrode elements at the opposing sides of the cardiac sphincter.
10. The apparatus according to any of the preceding aspects, further comprising an implantable energy source (160) configured to provide the electrode with electrical power.
11. The apparatus according to aspect 10, wherein the implantable energy source is arranged inside the movement restriction device.
12. The apparatus according to aspect 10, wherein the implantable energy source is configured to be arranged outside the movement restriction device.
13. The apparatus according to aspect 12, wherein the implantable energy source is configured to be implanted subcutaneously.
14. The apparatus according to any of aspects 10-13, wherein the implantable energy source comprises a primary cell.
15. The apparatus according to any of aspects 10-14, wherein the implantable energy source comprises a secondary cell.
16. The apparatus according to aspect 14 or 15, further comprising a controller (170) configured to indicate a functional status of the implantable energy source.
17. The apparatus according to aspect 16, wherein the functional status indicates a charge level of the implantable energy source.
18. The apparatus according to aspect 16 or 17, wherein the functional status indicates a temperature of at least one of the implantable energy source, the muscle tissue and the electrode arrangement.
19. The apparatus according to any of aspects 16-18, wherein the implantable energy source is configured to be charged by an external energy source (165) arranged outside the patient's body.
20. The apparatus according to aspect 19, further comprising an implantable charger (190) configured to be electrically connected to the implantable energy source and enable charging of the implantable energy source by the external energy source.
21. The apparatus according to aspect 20, wherein the charger comprises an electromagnetic coil configured to receive electrical power wirelessly from the external energy source.
22. The apparatus according to aspect 19 or 20, wherein the charger is configured to control the charging of the implantable energy source based on the functional status.
23. The apparatus according to any of aspects 20-22, wherein the charger is configured to control the charging of the implantable energy source by controlling a receipt of electrical power from the external energy source at the implantable charger.
24. The apparatus according to any of aspects 20-22, wherein the charger is configured to control the charging of the implantable energy source by controlling a transmission of electrical power from the external energy source to the implantable charger.
25. The apparatus according to any of aspects 1-15, further comprising a controller (170) configured to be operably connected to the electrode arrangement for controlling the electrical stimulation of the muscle tissue.
26. The apparatus according to aspect 25, wherein the controller is configured to control the electrical stimulation such that the muscle tissue is stimulated by a series of electrical pulses (PL1, PL2, PL3, PL4).
27. The apparatus according to aspect 26, wherein the controller is configured to control the electrical stimulation such that a pulse of a first polarity is followed by a pulse of a second, reversed polarity.
28. The apparatus according to any of aspects 25-27, wherein the controller is configured to generate a pulsed electrical stimulation signal comprising a pulse frequency (F) of 0.01-150 Hz.
29. The apparatus according to aspect 28, wherein the electrical stimulation signal comprises a pulse duration (D) of 0.01-100 ms.
30. The apparatus according to aspect 28 or 29, wherein the electrical stimulation signal comprises a pulse amplitude (A) of 1-15 mA.
31. The apparatus according to any of aspects 28-30, wherein the electrical stimulation signal comprises a pulse frequency of 0.15-0.25 Hz, a pulse duration of 20-30 ms and a pulse amplitude of 3-10 mA.
32. The apparatus according to any of aspects 28-31, wherein the electrical stimulation signal comprises a build-up period (X1) of 0.01-2 s in which the amplitude is gradually increasing, a stimulation period (X2) of 1-60 s, and a stimulation pause (X4) of 0.01-60 s, wherein the electrical signal comprises a pulse frequency of 1-50 Hz and a pulse duration of 0.1-10 ms.
33. The apparatus according to any of aspects 25-32, wherein the controller comprises a wireless remote control (175).
34. The apparatus according to aspect 33, wherein the wireless remote control comprises an external signal transmitter, and wherein the controller comprises an implantable controller configured to receive a signal transmitted by the external signal transmitter and to control an operation of the apparatus based on said signal.
35. The apparatus according to aspect 35, wherein the signal is selected from the group consisting of: a sound signal, an ultrasound signal, an electromagnetic signal, and infrared signal, a visible light signal, an ultra violet light signal, a laser signal, a microwave signal, a radio wave signal, an X-ray radiation signal and a gamma radiation signal.
36. The apparatus according to any of aspects 25-35, further comprising an implantable sensor (S1) configured to sense actions potentials generated by pacemaker cells of the muscle tissue, and wherein the controller is configured to control the electrical simulation based at least partly on the sensed action potentials.
37. The apparatus according to aspect 36, wherein the controller is configured to generate electrical pulses amplifying the sensed action potentials.
38. The apparatus according to any of the preceding aspects, wherein a volume of the movement restriction device is non-adjustable after implantation.
39. The apparatus according to any of aspects 1-37, wherein a volume of the movement restriction device is adjustable after implantation.

40. The apparatus according to aspect 39, wherein the volume of the movement restriction device is adjustable invasively or non-invasively.
41. The apparatus according to aspect 39 or 40, wherein the movement restriction device comprises an injection port (115) for allowing a fluid to be injected or extracted from the inside of the movement restriction device so as to vary a volume of the movement restriction device after implantation.
42. The apparatus according to any of the preceding aspects, wherein the movement restriction device comprises a biocompatible outer surface configured to rest against the fundus wall portion.
43. The apparatus according to any of the preceding aspects, wherein the movement restriction device is substantially spherical or egg-shaped.
44. The apparatus according to any of aspects 1-42, wherein the movement restriction device has a portion configured to be arranged to point away from the esophagus when implanted.
45. The apparatus according to any of the preceding aspects, wherein the movement restriction device is configured to be invaginated when placed on the outside of the fundus wall portion.
46. The apparatus according to any of aspects 1-44, wherein the movement restriction device is configured to be invaginated when placed on the inside of the fundus wall portion.
47. The apparatus according to any of the preceding aspects, wherein the movement restriction device is configured to be introduced in the patient's body by means of a gastroscope or an intraluminal instrument.
48. The apparatus according to aspect 47, wherein the movement restriction device is configured to change its shape to allow it to pass through a trocar during insertion into the patient's body.
49. The apparatus according to any of the preceding aspects, wherein the movement restriction device is formed of at least two distinct and separable pieces (111, 112, 113) configured to be assembled into the movement restriction device after insertion in the patient's body.
50. The apparatus according to any of the preceding aspects, wherein a minimum width of the movement restriction device, as measured from side to side, is 30 mm or larger, such as 40 mm or larger.
51. The apparatus according to any of the preceding aspects, wherein a minimum outer circumference of the movement restriction device is 150 mm or less, such as 130 mm or less, such as 110 mm or less, such as 90 mm or less, such as 70 mm or less, such as 50 mm or less, such as 30 mm or less.

Aspect Group 261SE: Reflux_Stop_Exercise_Torus
1. An apparatus (100) for treating reflux disease of a human patient, comprising:
an at least partly ring-shaped implantable movement restriction device comprising a first portion (110) configured to be at least partly invaginated by a first wall portion of the patient's stomach (10) and arranged such that at least a part of the first portion is arranged above the cardiac notch (24) of the patient's stomach, and such that movement of the cardia (22) towards the diaphragm (30) is restricted to prevent the cardia from sliding through the diaphragm opening (32) into the patient's thorax; and
an electrode arrangement (150) configured to electrically stimulate muscle tissue of the first wall portion to exercise the muscle tissue to improve the conditions for long term implantation of the movement restriction device.
2. The apparatus according to aspect 1, wherein the electrode arrangement is arranged on an outer surface of the movement restriction device.
3. The apparatus according to aspect 1 or 2, wherein the electrode arrangement comprises a plurality of electrode elements (152), each of which being configured to engage and electrically stimulate the muscle tissue.
4. The apparatus according to any of the preceding aspects, wherein the electrode arrangement comprises a coiled wire for increasing a contact surface between the electrode arrangement and the muscle tissue and for allowing the electrode arrangement to follow contraction and relaxation of the muscle tissue.
5. The apparatus according to any of the preceding aspects, wherein the electrode arrangement comprises a bare electrode portion (155) configured to form a metal-tissue interface with the muscle tissue, thereby allowing faradaic charge transfer to the be predominant charge transfer mechanism over said interface.
6. The apparatus according to any of the preceding aspects, wherein the electrode arrangement comprises an electrode portion at least partly covered by a dielectric material (157) configured to form a dielectric-tissue interface with the muscle tissue, thereby allowing for a faradaic portion of the charge transfer mechanism over said interface to be reduced.
7. The apparatus according to any of the preceding aspects, wherein the electrode arrangement is further configured to be arranged to electrically stimulate the cardiac sphincter (26) of the patient to cause the cardiac sphincter to contract.
8. The apparatus according to aspect 7, wherein the electrode arrangement comprises at least two electrode elements (154) configured to be arranged on opposing sides of the cardiac sphincter.
9. The apparatus according to aspect 8, further comprising a holder (120) configured to support the at least two electrode elements at the opposing sides of the cardiac sphincter.
10. The apparatus according to any of the preceding aspects, further comprising an implantable energy source (160) configured to provide the electrode with electrical power.
11. The apparatus according to aspect 10, wherein the implantable energy source is arranged inside the movement restriction device.
12. The apparatus according to aspect 10, wherein the implantable energy source is configured to be arranged outside the movement restriction device.
13. The apparatus according to aspect 12, wherein the implantable energy source is configured to be implanted subcutaneously.
14. The apparatus according to any of aspects 10-13, wherein the implantable energy source comprises a primary cell.
15. The apparatus according to any of aspects 10-14, wherein the implantable energy source comprises a secondary cell.
16. The apparatus according to aspect 14 or 15, further comprising a controller (170) configured to indicate a functional status of the implantable energy source.
17. The apparatus according to aspect 16, wherein the functional status indicates a charge level of the implantable energy source.

18. The apparatus according to aspect 16 or 17, wherein the functional status indicates a temperature of at least one of the implantable energy source, the muscle tissue, and the electrode arrangement.
19. The apparatus according to any of aspects 16-18, wherein the implantable energy source is configured to be charged by an external energy source (165) arranged outside the patient's body.
20. The apparatus according to aspect 19, further comprising an implantable charger (190) configured to be electrically connected to the implantable energy source and enable charging of the implantable energy source by the external energy source.
21. The apparatus according to aspect 20, wherein the charger comprises an electromagnetic coil configured to receive electrical power wirelessly from the external energy source.
22. The apparatus according to aspect 20 or 21, wherein the charger is configured to control the charging of the implantable energy source based on the functional status.
23. The apparatus according to any of aspects 20-22, wherein the charger is configured to control the charging of the implantable energy source by controlling a receipt of electrical power from the external energy source at the implantable charger.
24. The apparatus according to any of aspects 20-22, wherein the charger is configured to control the charging of the implantable energy source by controlling a transmission of electrical power from the external energy source to the implantable charger.
25. The apparatus according to aspect 1, further comprising controller (170) configured to be operably connected to the electrode arrangement for controlling the electrical stimulation of the muscle tissue.
26. The apparatus according to aspect 25, wherein the controller is configured to control the electrical stimulation such that the muscle tissue is stimulated by a series of electrical pulses (PL1, PL2, PL3, PL4).
27. The apparatus according to aspect 26, wherein the controller is configured to control the electrical stimulation such that a pulse of a first polarity is followed by a pulse of a second, reversed polarity.
28. The apparatus according to any of aspects 25-27, wherein the controller is configured to generate a pulsed electrical stimulation signal comprising a pulse frequency (F) of 0.01-150 Hz.
29. The apparatus according to aspect 28, wherein the electrical stimulation signal comprises a pulse duration (D) of 0.01-100 ms.
30. The apparatus according to aspect 28 or 29, wherein the electrical stimulation signal comprises a pulse amplitude (A) of 1-15 mA.
31. The apparatus according to any of aspects 28-30, wherein the electrical stimulation signal comprises a pulse frequency of 0.15-0.25 Hz, a pulse duration of 20-30 ms and a pulse amplitude of 3-10 mA.
32. The apparatus according to any of aspects 28-31, wherein the electrical stimulation signal comprises a build-up period (X1) of 0.01-2 s in which the amplitude is gradually increasing, a stimulation period (X2) of 1-60 s, and a stimulation pause (X4) of 0.01-60 s, wherein the electrical signal comprises a pulse frequency of 1-50 Hz and a pulse duration of 0.1-10 ms.
33. The apparatus according to any of aspects 25-32, wherein the controller comprises a wireless remote control (175).
34. The apparatus according to aspect 33, wherein the wireless remote control comprises an external signal transmitter, and wherein the apparatus further comprises an implantable controller configured to receive a signal transmitted by the external signal transmitter and to control an operation of the apparatus based on said signal.
35. The apparatus according to aspect 35, wherein signal is selected from the group consisting of: a sound signal, an ultrasound signal, an electromagnetic signal, and infrared signal, a visible light signal, an ultra violet light signal, a laser signal, a microwave signal, a radio wave signal, an X-ray radiation signal and a gamma radiation signal.
36. The apparatus according to any of aspects 25-35, further comprising an implantable sensor (S1) configured to sense actions potentials generated by pacemaker cells of the muscle tissue, and wherein the controller is configured to control the electrical simulation based at least partly on the sensed action potentials.
37. The apparatus according to aspect 36, wherein the controller is configured to generate electrical pulses amplifying the sensed action potentials.
38. The apparatus according to any of the preceding aspects, wherein a volume of the movement restriction device is non-adjustable after implantation.
39. The apparatus according to any of aspects 1-37, wherein a volume of the movement restriction device is adjustable after implantation.
40. The apparatus according to aspect 39, wherein the volume of the movement restriction device is adjustable invasively or non-invasively.
41. The apparatus according to aspect 39 or 40, wherein the movement restriction device comprises an injection port (115) for allowing a fluid to be injected or extracted from the inside of the movement restriction device so as to vary a volume of the movement restriction device after implantation.
42. The apparatus according to any of the preceding aspects, wherein the movement restriction device comprises a biocompatible outer surface configured to rest against the first wall portion.
43. The apparatus according to any of the preceding aspects, wherein the first wall portion is a fundus wall portion (14).
44. The apparatus according to aspect any of the preceding aspects, wherein the movement restriction device further comprises a second portion (120), and wherein the first and second portions of the movement restriction device are configured to be arranged on opposite sides of the cardia (26).
45. The apparatus according to aspect 44, wherein the movement restriction device is configured to be arranged such that a gap is formed between the second portion of the movement restriction device and the esophagus.
46. The apparatus according to aspect 44, wherein the second portion of the movement restriction device is configured to be at least partly invaginated by a second wall portion of the stomach.
47. The apparatus according to any of the preceding aspects, wherein the movement restriction device is configured to be arranged such that a portion of the first wall portion is arranged between the first portion of the movement restriction device and the esophagus.

48. The apparatus according to any of the preceding aspects, wherein the movement restriction device is configured to be at least partly invaginated by the first wall portion along at least half of the toroidal length of the movement restriction device.
49. The apparatus according to any of the preceding aspects, wherein the movement restriction device is configured to be invaginated when placed on the outside of the stomach wall.
50. The apparatus according to any of the preceding aspects, wherein the movement restriction device comprises two end portions configured to be coupled to each other to form a closed ring.
51. The apparatus according to aspect 50, wherein the end portions are configured to be releasably attached to each other.
52. The apparatus according to aspect 44, wherein a poloidal circumference of the movement restriction device is larger for the first portion and for the second portion.
53. The apparatus according to aspect 52, wherein a minimum width of the first portion of the movement restriction device, as measured from side to side, is 30 mm or larger, such as 40 mm or larger.
54. The apparatus according to aspect 52, wherein a minimum poloidal circumference of the first portion of the movement restriction device is 150 mm or less, such as 130 mm or less, such as 110 mm or less, such as 90 mm or less, such as 70 mm or less, such as 50 mm or less, such as 30 mm or less.
55. The apparatus according to any of the preceding aspects, wherein the movement restriction device has a shape conforming to a torus.

Aspect Group 262SE: Reflux_Constricting-Band_Cover

1. An apparatus (100) for treating reflux disease of a human patient, comprising:
    an elongated core (210) having a length allowing the core to at least partly encircle the esophagus (20) of the patient, wherein the length is variable to allow the core to be arranged in a constricting state for hindering fluid from passing from the stomach (10) into the esophagus and in an expanded state for allowing food to pass into the stomach in response to the patient swallowing; and
    a tubular cover (220) enclosing at least a part of the core and comprising a plurality of portions (224, 225, 226) adapted to bend relative to each other to allow the core to change between the constricting state and the expanded state, when the cover is at least partly covered by fibrotic tissue, without being substantially hindered or impeded by the presence of said fibrotic tissue.
2. The apparatus according to aspect 1, wherein the core is configured to allow a transition from the constricting state into the expanded state caused by the food passing through esophagus.
3. The apparatus according to aspect 1 or 2, wherein the core is configured to exert an encircling pressure on the esophagus in the constricting state.
4. The apparatus according to aspect 3, further comprising an attractor (212, 213) for resiliently attracting adjacent portions of the core to one another to generate the encircling pressure.
5. The apparatus according to aspect 4, wherein the attractor comprises an elastic element (212).
6. The apparatus according to aspect 4 or 5, wherein the attractor comprises at least two mutually attracting magnets (213).
7. The apparatus according to aspect 6, further comprising a link (214) connecting a first and a second one of said at least two magnets to each other.
8. The apparatus according to aspect 7, wherein the link is configured to extend into at least one of said magnets in response to said magnets moving towards each other.
9. The apparatus according to any of the preceding aspects, wherein the cover comprises an array of tubular segments (222).
10. The apparatus according to any of the preceding aspects, wherein the cover comprises a biocompatible outer surface for long-term implantation.
11. The apparatus according to any of the preceding aspects, wherein the cover is configured to rest against an outer surface of the esophagus.
12. The apparatus according to any of the preceding aspects, wherein the cover comprises a surface promoting tissue growth.
13. The apparatus according to any of the preceding aspects, wherein the cover is formed of a polymer material, such as silicone.
14. The apparatus according to any of the preceding aspects, wherein the cover is formed of a material having a thickness of 0.1 to 10 mm, such as 1-5 mm.
15. The apparatus according to any of the preceding aspects, wherein the cover comprises at least one predefined fold (224) along which the cover is allowed to fold in response to the core varying its length.
16. The apparatus according to any of the preceding aspects, wherein the cover comprises lowered and elevated portions (225, 226) allowing the cover to vary its length while maintaining its surface area.
17. The apparatus according to any of the preceding aspects, wherein the cover is configured to be compressible and expandable in its length direction.
18. The apparatus according to any of the preceding aspects, wherein a length of the cover enclosing said at least a part of the core exceeds a length of said at least a part of the core when said at least a part of the core is arranged in the constricting state.
19. The apparatus according to any of the preceding aspects, wherein the core comprises two end portions (216) configured to be coupled to each other to form a closed ring around the esophagus.
20. The apparatus according to aspect 21, wherein the end portions are configured to be releasably attached to each other.
21. The apparatus according to aspect 20 or 21, wherein the end portions comprise a respective interlockable attacher.
22. The apparatus according to aspect 1, wherein the core comprises a plurality of core elements configured to be arranged in an annular array around the esophagus.
23. The apparatus according to aspect 22, wherein the core further comprises a plurality of links, each of which extending between a respective pair of core elements arranged adjacent to each other.
24. The apparatus according to aspect 23, wherein each of the links is configured to allow the respective core elements to move towards and away from each other.
25. The apparatus according to aspect 24, wherein each of the links is configured to extend into at least one of the core elements of the respective pair of core elements as said core elements move towards each other.

26. The apparatus according to aspects 22-25, further comprising an attractor for resiliently attracting adjacent core elements of the annular array to each other.
27. The apparatus according to aspect 26, wherein the attractor comprises at least one of a magnet, an elastic member, and a spring.
28. The apparatus according to any of the preceding aspects, further comprising an electrode arrangement (150) configured to be arranged between the apparatus and the esophagus and to electrically stimulate muscle tissue of the outer wall of the esophagus to exercise the muscle tissue to improve the conditions for long term implantation of the movement restriction device.
29. The apparatus according to aspect 28, wherein the electrode arrangement is arranged on an outer surface of the cover.
30. The apparatus according to aspect 28 or 29, wherein the electrode arrangement comprises a plurality of electrode elements (154), each of which being configured to electrically stimulate the muscle tissue.
31. The apparatus according to any of aspects 28-30, wherein the electrode arrangement comprises a coiled wire for increasing a contact surface between the electrode arrangement and the muscle tissue and for allowing the electrode arrangement to follow contraction and relaxation of the muscle tissue.
32. The apparatus according to any of aspects 28-31, wherein the electrode arrangement comprises a bare electrode portion (155) configured to form a metal-tissue interface with the muscle tissue, thereby allowing faradaic charge transfer to the be predominant charge transfer mechanism over said interface.
33. The apparatus according to any of aspects 28-31, wherein the electrode arrangement comprises an electrode portion at least partly covered by a dielectric material (157) configured to form a dielectric-tissue interface with the muscle tissue, thereby allowing for a faradaic portion of the charge transfer mechanism over said interface to be reduced.
34. The apparatus according to any of aspects 28-33, wherein the electrode arrangement is configured to be to electrically stimulate the cardiac sphincter (26) of the patient to cause the cardiac sphincter to contract.
35. The apparatus according to aspect 34, wherein the electrode arrangement comprises at least two electrode elements (154) configured to be arranged on opposing sides of the cardiac sphincter.
36. The apparatus according to any of aspects 28-35, further comprising an implantable energy source (160) configured to provide the electrode arrangement with electrical power.
37. The apparatus according to aspect 36, wherein the implantable energy source is arranged inside the cover.
38. The apparatus according to aspect 36, wherein the implantable energy source is configured to be arranged outside the cover.
39. The apparatus according to aspect 38, wherein the implantable energy source is configured to be implanted subcutaneously.
40. The apparatus according to any of aspects 36-39, wherein the implantable energy source comprises a primary cell.
41. The apparatus according to any of aspects 36-40, wherein the implantable energy source comprises a secondary cell.
42. The apparatus according to aspect 36-41, further comprising a controller (170) configured to indicate a functional status of the implantable energy source.
43. The apparatus according to aspect 42, wherein the functional status indicates a charge level of the implantable energy source.
44. The apparatus according to aspect 42 or 43, wherein the functional status indicates a temperature of at least one of the implantable energy source, the muscle tissue, and the electrode arrangement.
45. The apparatus according to any of aspects 36-44, wherein the implantable energy source is configured to be charged by an external energy source (165) arranged outside the patient's body.
46. The apparatus according to aspect 45, further comprising an implantable charger (190) configured to be electrically connected to the implantable energy source and enable charging of the implantable energy source by the external energy source.
47. The apparatus according to aspect 46, wherein the charger comprises an electromagnetic coil configured to receive electrical power wirelessly from the external energy source.
48. The apparatus according to aspect 46 or 47, wherein the charger is configured to control the charging of the implantable energy source based on the functional status.
49. The apparatus according to any of aspects 46-48, wherein the charger is configured to control the charging of the implantable energy source by controlling a receipt of electrical power from the external energy source at the implantable charger.
50. The apparatus according to any of aspects 46-48, wherein the charger is configured to control the charging of the implantable energy source by controlling a transmission of electrical power from the external energy source to the implantable charger.
51. The apparatus according to aspect 28, further comprising controller (170) configured to be operably connected to the electrode arrangement for controlling the electrical stimulation of the muscle tissue.
52. The apparatus according to aspect 51, wherein the controller is configured to control the electrical stimulation such that the muscle tissue is stimulated by a series of electrical pulses (PL1, PL2, PL3, PL4).
53. The apparatus according to aspect 52, wherein the controller is configured to control the electrical stimulation such that a pulse of a first polarity is followed by a pulse of a second, reversed polarity.
54. The apparatus according to any of aspects 51-53, wherein the controller is configured to generate a pulsed electrical stimulation signal comprising a pulse frequency (F) of 0.01-150 Hz.
55. The apparatus according to aspect 54, wherein the electrical stimulation signal comprises a pulse duration (D) of 0.01-100 ms.
56. The apparatus according to aspect 54 or 55, wherein the electrical stimulation signal comprises a pulse amplitude (A) of 1-15 mA.
57. The apparatus according to any of aspects 54-56, wherein the electrical stimulation signal comprises a pulse frequency of 0.15-0.25 Hz, a pulse duration of 20-30 ms and a pulse amplitude of 3-10 mA.
58. The apparatus according to any of aspects 54-57, wherein the electrical stimulation signal comprises a build-up period (X1) of 0.01-2 s in which the amplitude is gradually increasing, a stimulation period (X2) of 1-60 s, and a stimulation pause (X4) of 0.01-60 s, wherein the electrical signal comprises a pulse frequency of 1-50 Hz and a pulse duration of 0.1-10 ms.

59. The apparatus according to any of aspects 51-58, wherein the controller comprises a wireless remote control (175).

60. The apparatus according to aspect 59, wherein the wireless remote control comprises an external signal transmitter, and wherein the apparatus further comprises an implantable controller configured to receive a signal transmitted by the external signal transmitter and to control an operation of the apparatus based on said signal.

61. The apparatus according to aspect 60, wherein signal is selected from the group consisting of: a sound signal, an ultrasound signal, an electromagnetic signal, and infrared signal, a visible light signal, an ultra violet light signal, a laser signal, a microwave signal, a radio wave signal, an X-ray radiation signal and a gamma radiation signal.

62. The apparatus according to any of aspects 51-61, further comprising an implantable sensor (S1) configured to sense actions potentials generated by pacemaker cells of the muscle tissue, and wherein the controller is configured to control the electrical simulation based at least partly on the sensed action potentials.

63. The apparatus according to aspect 62, wherein the controller is configured to generate electrical pulses amplifying the sensed action potentials.

Aspect Group 263SE: Reflux_Constricting-Band_Stimulation

1. An apparatus (100) for treating reflux disease of a human patient, comprising:
   an elongated core (210) having a length allowing the core to at least partly encircle the esophagus (20) of the patient, wherein the length is variable to allow the core to be arranged in a constricting state for hindering fluid from passing from the stomach (10) into the esophagus and in an expanded state for allowing food to pass into the stomach in response to the patient swallowing; and
   an electrode arrangement (150) comprising an electrode element (154) supported by the core and configured to electrically stimulate muscle tissue of the esophagus.

2. The apparatus according to aspect 1, wherein the core is configured to allow a transition from the constricting state into the expanded state caused by the food passing through esophagus.

3. The apparatus according to aspect 1 or 2, wherein the core is configured to exert an encircling pressure on the esophagus in the constricting state.

4. The apparatus according to aspect 3, further comprising an attractor (212) for resiliently attracting adjacent portions (213) of the core to one another to generate the encircling pressure.

5. The apparatus according to aspect 4, wherein the attractor comprises an elastic element.

6. The apparatus according to aspect 4 or 5, wherein the attractor comprises at least two mutually attracting magnets.

7. The apparatus according to aspect 6, further comprising a link (214) connecting a first and a second one of said at least two magnets to each other.

8. The apparatus according to aspect 7, wherein the link is configured to extend into at least one of said magnets in response to said magnets moving towards each other.

9. The apparatus according to any of the preceding aspects, wherein the core comprises a biocompatible outer surface for long-term implantation.

10. The apparatus according to any of the preceding aspects, wherein the core comprises two end portions (216) configured to be coupled to each other to form a closed ring around the esophagus.

11. The apparatus according to aspect 10, wherein the end portions are configured to be releasably attached to each other.

12. The apparatus according to aspect 10 or 11, wherein the end portions comprise a respective interlockable attacher.

13. The apparatus according to aspect 1, wherein the core comprises a plurality of core elements configured to be arranged in an annular array around the esophagus.

14. The apparatus according to aspect 13, wherein the core further comprises a plurality of links, each of which extending between a respective pair of core elements arranged adjacent to each other.

15. The apparatus according to aspect 14, wherein each of the links is configured to allow the respective core elements to move towards and away from each other.

16. The apparatus according to aspect 15, wherein each of the links is configured to extend into at least one of the core elements of the respective pair of core elements as said core elements move towards each other.

17. The apparatus according to aspects 13-16, further comprising an attractor for resiliently attracting adjacent core elements of the annular array to each other.

18. The apparatus according to aspect 17, wherein the attractor comprises at least one of a magnet, an elastic member, and a spring.

19. The apparatus according to any of the preceding aspects, wherein the electrode arrangement is configured to electrically stimulate the muscle tissue so as to exercise the muscle tissue to improve the conditions for long term implantation of the core.

20. The apparatus according to any of the preceding aspects, wherein the electrode arrangement comprises a plurality of electrode elements (154), each of which being configured to electrically stimulate the muscle tissue.

21. The apparatus according to any of the preceding aspects, wherein the electrode arrangement comprises a coiled wire for allowing the electrode arrangement to follow a variation of the length of the core.

22. The apparatus according to any of the preceding aspects, wherein the electrode arrangement comprises a bare electrode portion (155) configured to form a metal-tissue interface with the muscle tissue, thereby allowing faradaic charge transfer to the be predominant charge transfer mechanism over said interface.

23. The apparatus according to any of aspects 1-21, wherein the electrode arrangement comprises an electrode portion at least partly covered by a dielectric material (157) configured to form a dielectric-tissue interface with the muscle tissue, thereby allowing for a faradaic portion of the charge transfer mechanism over said interface to be reduced.

24. The apparatus according to any of the preceding aspects, wherein the electrode arrangement is configured to be to electrically stimulate the cardiac sphincter of the patient to cause the cardiac sphincter to contract.

25. The apparatus according to aspect 24, wherein the electrode arrangement comprises at least two electrode elements configured to be arranged on opposing sides of the cardiac sphincter.
26. The apparatus according to any of the preceding aspects, further comprising an implantable energy source (160) configured to provide the electrode arrangement with electrical power.
27. The apparatus according to aspect 26, wherein the implantable energy source is arranged inside the core.
28. The apparatus according to aspect 26, wherein the implantable energy source is configured to be arranged outside the core.
29. The apparatus according to aspect 28, wherein the implantable energy source is configured to be implanted subcutaneously.
30. The apparatus according to any of aspects 26-29, wherein the implantable energy source comprises a primary cell.
31. The apparatus according to any of aspects 26-30, wherein the implantable energy source comprises a secondary cell.
32. The apparatus according to aspect 26-31, further comprising a controller (170) configured to indicate a functional status of the implantable energy source.
33. The apparatus according to aspect 32, wherein the functional status indicates a charge level of the implantable energy source.
34. The apparatus according to aspect 32 or 33, wherein the functional status indicates a temperature of at least one of the implantable energy source, the muscle tissue, and the electrode arrangement.
35. The apparatus according to any of aspects 26-34, wherein the implantable energy source is configured to be charged by an external energy source (165) arranged outside the patient's body.
36. The apparatus according to aspect 35, further comprising an implantable charger (190) configured to be electrically connected to the implantable energy source and enable charging of the implantable energy source by the external energy source.
37. The apparatus according to aspect 36, wherein the charger comprises an electromagnetic coil configured to receive electrical power wirelessly from the external energy source.
38. The apparatus according to aspect 36 or 37, wherein the charger is configured to control the charging of the implantable energy source based on the functional status.
39. The apparatus according to any of aspects 36-38, wherein the charger is configured to control the charging of the implantable energy source by controlling a receipt of electrical power from the external energy source at the implantable charger.
40. The apparatus according to any of aspects 36-38, wherein the charger is configured to control the charging of the implantable energy source by controlling a transmission of electrical power from the external energy source to the implantable charger.
41. The apparatus according to any of the preceding aspects, further comprising a controller (170) configured to be operably connected to the electrode arrangement for controlling the electrical stimulation of the muscle tissue.
42. The apparatus according to aspect 41, wherein the controller is configured to control the electrical stimulation such that the muscle tissue is stimulated by a series of electrical pulses (PL1, PL2, PL3, PL4).
43. The apparatus according to aspect 42, wherein the controller is configured to control the electrical stimulation such that a pulse of a first polarity is followed by a pulse of a second, reversed polarity.
44. The apparatus according to any of aspects 41-43, wherein the controller is configured to generate a pulsed electrical stimulation signal comprising a pulse frequency (F) of 0.01-150 Hz.
45. The apparatus according to aspect 44, wherein the electrical stimulation signal comprises a pulse duration (D) of 0.01-100 ms.
46. The apparatus according to aspect 44 or 45, wherein the electrical stimulation signal comprises a pulse amplitude (A) of 1-15 mA.
47. The apparatus according to any of aspects 44-46, wherein the electrical stimulation signal comprises a pulse frequency of 0.15-0.25 Hz, a pulse duration of 20-30 ms and a pulse amplitude of 3-10 mA.
48. The apparatus according to any of aspects 44-47, wherein the electrical stimulation signal comprises a build-up period of 0.01-2 s in which the amplitude is gradually increasing, a stimulation period of 1-60 s, and a stimulation pause of 0.01-60 s, wherein the electrical signal comprises a pulse frequency of 1-50 Hz and a pulse duration of 0.1-10 ms.
49. The apparatus according to any of aspects 41-48, wherein the controller comprises a wireless remote control (175).
50. The apparatus according to aspect 49, wherein the wireless remote control comprises an external signal transmitter, and wherein the apparatus further comprises an implantable controller configured to receive a signal transmitted by the external signal transmitter and to control an operation of the apparatus based on said signal.
51. The apparatus according to aspect 50, wherein signal is selected from the group consisting of: a sound signal, an ultrasound signal, an electromagnetic signal, and infrared signal, a visible light signal, an ultra violet light signal, a laser signal, a microwave signal, a radio wave signal, an X-ray radiation signal and a gamma radiation signal.
52. The apparatus according to any of aspects 41-51, further comprising an implantable sensor (S1) configured to sense actions potentials generated by pacemaker cells of the muscle tissue, and wherein the controller is configured to control the electrical simulation based at least partly on the sensed action potentials.
53. The apparatus according to aspect 52, wherein the controller is configured to generate electrical pulses amplifying the sensed action potentials.

Aspect Group 264SE: Reflux_Constricting-Band_No_Core
1. An apparatus (100) for treating reflux disease of a human patient, comprising:
    a tubular device (220) having a length allowing the tubular device to at least partly encircle the esophagus (20) of the patient, wherein the length is variable to allow the tubular cover to be arranged in a constricting state for hindering fluid from passing from the stomach (10) into the esophagus and in an expanded state for allowing food to pass into the stomach in response to the patient swallowing;
    wherein the outer surface of the tubular device comprises a plurality of portions (224, 225, 226) adapted to bend relative to each other to allow the tubular device to change between the constricting state and the expanded state, when the outer surface is at least partly covered by fibrotic tissue, without being substantially hindered or impeded by the presence of said fibrotic tissue.

2. The apparatus according to aspect 1, wherein the tubular device is configured to allow a transition from the constricting state into the expanded state caused by the food passing through esophagus.

3. The apparatus according to aspect 1 or 2, wherein the tubular device is configured to exert an encircling pressure on the esophagus in the constricting state.

4. The apparatus according to aspect 3, further comprising an attractor (212, 213) for resiliently attracting adjacent portions of the tubular device to one another to generate the encircling pressure.

5. The apparatus according to aspect 4, wherein the attractor comprises an elastic element (212).

6. The apparatus according to aspect 4 or 5, wherein the attractor comprises at least two mutually attracting magnets (213).

7. The apparatus according to aspect 6, further comprising a link (214) connecting a first and a second one of said at least two magnets to each other.

8. The apparatus according to aspect 7, wherein the link is configured to extend into at least one of said magnets in response to said magnets moving towards each other.

9. The apparatus according to any of the preceding aspects, wherein the tubular device comprises an array of tubular segments (222).

10. The apparatus according to any of the preceding aspects, wherein the tubular device comprises a biocompatible outer surface for long-term implantation.

11. The apparatus according to any of the preceding aspects, wherein the tubular device is configured to rest against an outer surface of the esophagus.

12. The apparatus according to any of the preceding aspects, wherein the tubular device comprises a surface promoting tissue growth.

13. The apparatus according to any of the preceding aspects, wherein the tubular device is formed of a polymer material, such as silicone.

14. The apparatus according to any of the preceding aspects, wherein the tubular device is formed of a material having a thickness of 0.1 to 10 mm, such as 1 to 5 mm.

15. The apparatus according to any of the preceding aspects, wherein the tubular device comprises at least one predefined fold (224) along which the tubular device is allowed to fold in response to the tubular device varying its length.

16. The apparatus according to any of the preceding aspects, wherein the tubular device comprises lowered and elevated portions (225, 226) allowing the tubular device to vary its length while maintaining its surface area.

17. The apparatus according to any of the preceding aspects, wherein the tubular device is configured to be compressible and expandable in its length direction.

18. The apparatus according to any of the preceding aspects, wherein the tubular device comprises two end portions (216) configured to be coupled to each other to form a closed ring around the esophagus.

19. The apparatus according to aspect 18, wherein the end portions are configured to be releasably attached to each other.

20. The apparatus according to aspect 18 or 19, wherein the end portions comprise a respective interlockable attacher.

21. The apparatus according to any of the preceding aspects, further comprising an elongated core (210) configured to be enclosed by the tubular device, and to vary its length in accordance with the varying length of the tubular device.

22. The apparatus according to aspect 21, wherein the core comprises a plurality of core elements configured to be arranged in an annular array around the esophagus.

23. The apparatus according to aspect 22, wherein the core further comprises a plurality of links, each of which extending between a respective pair of core elements arranged adjacent to each other.

24. The apparatus according to aspect 23, wherein each of the links is configured to allow the respective core elements to move towards and away from each other.

25. The apparatus according to aspect 24, wherein each of the links is configured to extend into at least one of the core elements of the respective pair of core elements as said core elements move towards each other.

26. The apparatus according to aspects 22-25, further comprising an attractor for resiliently attracting adjacent core elements of the annular array to each other.

27. The apparatus according to aspect 26, wherein the attractor comprises at least one of a magnet, an elastic member, and a spring.

28. The apparatus according to any of the preceding aspects, further comprising an electrode arrangement (150) configured to be arranged between the apparatus and the esophagus and to electrically stimulate muscle tissue of the outer wall of the esophagus to exercise the muscle tissue to improve the conditions for long term implantation of the movement restriction device.

29. The apparatus according to aspect 28, wherein the electrode arrangement is arranged on the outer surface of the tubular device.

30. The apparatus according to aspect 28 or 29, wherein the electrode arrangement comprises a plurality of electrode elements (154), each of which being configured to electrically stimulate the muscle tissue.

31. The apparatus according to any of aspects 28-30, wherein the electrode arrangement comprises a coiled wire for increasing a contact surface between the electrode arrangement and the muscle tissue and for allowing the electrode arrangement to follow contraction and relaxation of the muscle tissue.

32. The apparatus according to any of aspects 28-31, wherein the electrode arrangement comprises a bare electrode portion (155) configured to form a metal-tissue interface with the muscle tissue, thereby allowing faradaic charge transfer to the be predominant charge transfer mechanism over said interface.

33. The apparatus according to any of aspects 28-31, wherein the electrode arrangement comprises an electrode portion at least partly covered by a dielectric material (157) configured to form a dielectric-tissue interface with the muscle tissue, thereby allowing for a faradaic portion of the charge transfer mechanism over said interface to be reduced.

34. The apparatus according to any of aspects 28-33, wherein the electrode arrangement is configured to be to electrically stimulate the cardiac sphincter (26) of the patient to cause the cardiac sphincter to contract.

35. The apparatus according to aspect 34, wherein the electrode arrangement comprises at least two electrode elements (154) configured to be arranged on opposing sides of the cardiac sphincter.
36. The apparatus according to any of aspects 28-35, further comprising an implantable energy source (160) configured to provide the electrode arrangement with electrical power.
37. The apparatus according to aspect 36, wherein the implantable energy source is arranged inside the cover.
38. The apparatus according to aspect 36, wherein the implantable energy source is configured to be arranged outside the cover.
39. The apparatus according to aspect 38, wherein the implantable energy source is configured to be implanted subcutaneously.
40. The apparatus according to any of aspects 36-39, wherein the implantable energy source comprises a primary cell.
41. The apparatus according to any of aspects 36-40, wherein the implantable energy source comprises a secondary cell.
42. The apparatus according to aspect 36-41, further comprising a controller (170) configured to indicate a functional status of the implantable energy source.
43. The apparatus according to aspect 42, wherein the functional status indicates a charge level of the implantable energy source.
44. The apparatus according to aspect 42 or 43, wherein the functional status indicates a temperature of at least one of the implantable energy source, the muscle tissue, and the electrode arrangement.
45. The apparatus according to any of aspects 36-44, wherein the implantable energy source is configured to be charged by an external energy source (165) arranged outside the patient's body.
46. The apparatus according to aspect 45, further comprising an implantable charger (190) configured to be electrically connected to the implantable energy source and enable charging of the implantable energy source by the external energy source.
47. The apparatus according to aspect 46, wherein the charger comprises an electromagnetic coil configured to receive electrical power wirelessly from the external energy source.
48. The apparatus according to aspect 46 or 47, wherein the charger is configured to control the charging of the implantable energy source based on the functional status.
49. The apparatus according to any of aspects 46-48, wherein the charger is configured to control the charging of the implantable energy source by controlling a receipt of electrical power from the external energy source at the implantable charger.
50. The apparatus according to any of aspects 46-48, wherein the charger is configured to control the charging of the implantable energy source by controlling a transmission of electrical power from the external energy source to the implantable charger.
51. The apparatus according to aspect 28, further comprising controller (170) configured to be operably connected to the electrode arrangement for controlling the electrical stimulation of the muscle tissue.
52. The apparatus according to aspect 51, wherein the controller is configured to control the electrical stimulation such that the muscle tissue is stimulated by a series of electrical pulses (PL1, PL2, PL3, PL4).
53. The apparatus according to aspect 52, wherein the controller is configured to control the electrical stimulation such that a pulse of a first polarity is followed by a pulse of a second, reversed polarity.
54. The apparatus according to any of aspects 51-53, wherein the controller is configured to generate a pulsed electrical stimulation signal comprising a pulse frequency (F) of 0.01-150 Hz.
55. The apparatus according to aspect 54, wherein the electrical stimulation signal comprises a pulse duration (D) of 0.01-100 ms.
56. The apparatus according to aspect 54 or 55, wherein the electrical stimulation signal comprises a pulse amplitude (A) of 1-15 mA.
57. The apparatus according to any of aspects 54-56, wherein the electrical stimulation signal comprises a pulse frequency of 0.15-0.25 Hz, a pulse duration of 20-30 ms and a pulse amplitude of 3-10 mA.
58. The apparatus according to any of aspects 54-57, wherein the electrical stimulation signal comprises a build-up period (X1) of 0.01-2 s in which the amplitude is gradually increasing, a stimulation period (X2) of 1-60 s, and a stimulation pause (X4) of 0.01-60 s, wherein the electrical signal comprises a pulse frequency of 1-50 Hz and a pulse duration of 0.1-10 ms.
59. The apparatus according to any of aspects 51-58, wherein the controller comprises a wireless remote control (175).
60. The apparatus according to aspect 59, wherein the wireless remote control comprises an external signal transmitter, and wherein the apparatus further comprises an implantable controller configured to receive a signal transmitted by the external signal transmitter and to control an operation of the apparatus based on said signal.
61. The apparatus according to aspect 60, wherein signal is selected from the group consisting of: a sound signal, an ultrasound signal, an electromagnetic signal, and infrared signal, a visible light signal, an ultra violet light signal, a laser signal, a microwave signal, a radio wave signal, an X-ray radiation signal and a gamma radiation signal.
62. The apparatus according to any of aspects 51-61, further comprising an implantable sensor (S1) configured to sense actions potentials generated by pacemaker cells of the muscle tissue, and wherein the controller is configured to control the electrical simulation based at least partly on the sensed action potentials.
63. The apparatus according to aspect 62, wherein the controller is configured to generate electrical pulses amplifying the sensed action potentials.

Aspect Group 265SE: Reflux_Constricting-Band_Stop
1. An apparatus (100) for treating reflux disease of a human patient, comprising an elongated core (210) having a length allowing the core to at least partly encircle the esophagus (20) of the patient;
    wherein the length is variable to allow the core to be arranged in a constricting state for hindering fluid from passing from the stomach (10) into the esophagus and in an expanded state for allowing food to pass into the stomach in response to the patient swallowing; and
    wherein the elongated core has a size allowing at least a portion of the elongated core to protrude above the cardiac sphincter of the patient, when implanted, such that movement of the cardia towards the diaphragm is restricted to hinder the cardia from sliding through the diaphragm opening (32) into the patient's thorax.
2. The apparatus according to aspect 1, wherein the elongated core has a maximum height exceeding 2 cm, as measured in a normal direction to the plane in which the elongated core extends when encircling the esophagus.
3. The apparatus according to aspect 2, wherein the maximum height is 3 cm or more, such as 4 cm or more, such as 5 cm or more.
4. The apparatus according to aspect 2 of 3, wherein the elongated core is configured to be implanted such that a portion of the elongated core having the maximum height is arranged at the fundus side of the esophagus.
5. The apparatus according to any of the preceding aspects, wherein the elongated core comprises a plurality of portions that are movable relative to each other.
6. The apparatus according to aspect 5, wherein the elongated core is configured to exert an encircling pressure on the esophagus in the constricting state.
7. The apparatus according to aspect 6, further comprising an attractor (212) for resiliently attracting adjacent portions (213) of the elongated core to one another to generate the encircling pressure.
8. The apparatus according to aspect 7, wherein the attractor comprises an elastic element.
9. The apparatus according to aspect 7, wherein the attractor comprises at least two mutually attracting magnets.
10. The apparatus according to aspect 9, further comprising a link (214) connecting a first and a second one of said at least two magnets to each other.
11. The apparatus according to any of the preceding aspects, further comprising a tubular cover (220) enclosing at least a part of the elongated core and comprising a plurality of cover portions (224, 225, 226) adapted to bend relative to each other to allow the elongated core to change between the constricting state and the expanded state, when the cover is at least partly covered by fibrotic tissue, without being substantially hindered or impeded by the presence of said fibrotic tissue.
12. The apparatus according to aspect 11, wherein the elongated core comprises an array of tubular segments (222).
13. The apparatus according to aspect 11 or 12, wherein the cover is formed of an inelastic material.
14. The apparatus according to any of aspects 11-13, wherein the cover comprises a biocompatible outer surface for long-term implantation.
15. The apparatus according to any of aspects 11-14, wherein the cover is configured to rest against an outer surface of the esophagus.
16. The apparatus according to any of aspects 11-15, wherein the cover comprises a surface promoting tissue growth.
17. The apparatus according to any of aspects 11-16, wherein the cover is formed of a polymer material, such as silicone.
18. The apparatus according to any of aspects 11-17, wherein the cover is formed of a material having a thickness of 0.1 to 10 mm, such as 1 to 5 mm.
19. The apparatus according to any of aspects 11-18, wherein the cover comprises at least one predefined fold (224) along which the cover is allowed to fold in response to the elongated core varying its length.
20. The apparatus according to any of aspects 11-19, wherein the cover comprises lowered and elevated portions (224, 225) allowing the cover to vary its length while maintaining its surface area.
21. The apparatus according to any of aspects 11-20, wherein the cover is configured to be compressible and expandable in its length direction.
22. The apparatus according to any of aspects 11-21, wherein a length of the cover enclosing said at least a part of elongated core exceeds a length of said at least a part of the elongated core when said at least a part of the second implantable portion is arranged in the constricting state.
23. The apparatus according to any of the preceding aspects, comprising two end portions (216) configured to be coupled to each other to form a closed ring around the esophagus.
24. The apparatus according to aspect 23, wherein the end portions are configured to be releasably attached to each other.
25. The apparatus according to aspect 23 or 24, wherein the end portions comprise a respective interlockable attacher.
26. The apparatus according to aspect 1, wherein the elongated core comprises a plurality of bodies (213) configured to be arranged in an annular array around the esophagus.
27. The apparatus according to aspect 26, wherein the elongated core further comprises a plurality of links (214), each of which extending between a respective pair of bodies arranged adjacent to each other.
28. The apparatus according to aspect 27, wherein the elongated core comprises at least some of the plurality bodies and at least some of the plurality of links, and wherein each of said links is configured to allow the respective ones of said bodies to move towards and away from each other.
29. The apparatus according to aspect 28, wherein each of said links is configured to extend into at least one of the respective ones of said bodies as said bodies move towards each other.
30. The apparatus according to aspects 26, wherein the elongated core comprises at least some of the plurality of bodies and at least some of the plurality of links, and wherein the apparatus further comprises an attractor for resiliently attracting adjacent ones of said bodies to each other.
31. The apparatus according to aspect 30, wherein the attractor comprises at least one of a magnet, an elastic member, and a spring.
32. The apparatus according to any of the preceding aspects, wherein the elongated core comprises a biocompatible outer surface configured to rest against the fundus wall portion.
33. The apparatus according to any of the preceding aspects, further comprising an electrode arrangement (150) configured to be arranged between the apparatus and the esophagus and to electrically stimulate muscle tissue of the outer wall of the esophagus to exercise the muscle tissue to improve the conditions for long term implantation of the movement restriction device.
34. The apparatus according to aspect 33, wherein the electrode arrangement is arranged on an outer surface of the elongated core.

35. The apparatus according to aspect 33 or 34, wherein the electrode arrangement comprises a plurality of electrode elements (152, 154), each of which being configured to electrically stimulate the muscle tissue.
36. The apparatus according to any of aspects 33-35, wherein the electrode arrangement comprises a coiled wire for increasing a contact surface between the electrode arrangement and the muscle tissue and for allowing the electrode arrangement to follow contraction and relaxation of the muscle tissue.
37. The apparatus according to any of aspects 33-36, wherein the electrode arrangement comprises a bare electrode portion (155) configured to form a metal-tissue interface with the muscle tissue, thereby allowing faradaic charge transfer to the be predominant charge transfer mechanism over said interface.
38. The apparatus according to any of aspects 33-36, wherein the electrode arrangement comprises an electrode portion at least partly covered by a dielectric material (157) configured to form a dielectric-tissue interface with the muscle tissue, thereby allowing for a faradaic portion of the charge transfer mechanism over said interface to be reduced.
39. The apparatus according to any of aspects 33-38, wherein the electrode arrangement is configured be arranged to electrically stimulate the cardiac sphincter (26) of the patient to cause the cardiac sphincter to contract.
40. The apparatus according to aspect 39, wherein the electrode arrangement comprises at least two electrode elements (154) configured to be arranged on opposing sides of the cardiac sphincter.
41. The apparatus according to any of aspects 33-40, further comprising an implantable energy source (160) configured to provide the electrode arrangement with electrical power.
42. The apparatus according to aspect 41, wherein the implantable energy source comprises a primary cell and/or a secondary cell.
43. The apparatus according to aspect 41-42, further comprising a controller (170) configured to indicate a functional status of the implantable energy source.
44. The apparatus according to aspect 43, wherein the functional status indicates a charge level of the implantable energy source.
45. The apparatus according to aspect 43 or 44, wherein the functional status indicates a temperature of at least one of the implantable energy source, the muscle tissue, and the electrode arrangement.
46. The apparatus according to any of aspects 37-45, wherein the implantable energy source is configured to be charged by an external energy source (165) arranged outside the patient's body.
47. The apparatus according to aspect 46, further comprising an implantable charger (190) configured to be electrically connected to the implantable energy source and enable charging of the implantable energy source by the external energy source.
48. The apparatus according to aspect 47, wherein the charger comprises an electromagnetic coil configured to receive electrical power wirelessly from the external energy source.
49. The apparatus according to aspect 47 or 48, wherein the charger is configured to receive the functional status from the energy source indicator and control the charging of the implantable energy source based on the functional status.
50. The apparatus according to any of aspects 47-49, wherein the charger is configured to control the charging of the implantable energy source by controlling a receipt of electrical power from the external energy source at the implantable charger.
51. The apparatus according to any of aspects 47-49, wherein the charger is configured to control the charging of the implantable energy source by controlling a transmission of electrical power from the external energy source to the implantable charger.
52. The apparatus according to any of aspects 29-51, further comprising controller (170) configured to be operably connected to the electrode arrangement for controlling the electrical stimulation of the muscle tissue.
53. The apparatus according to aspect 52, wherein the controller is configured to control the electrical stimulation such that the muscle tissue is stimulated by a series of electrical pulses (PL1, PL2, PL3, PL4).
54. The apparatus according to aspect 53, wherein the controller is configured to control the electrical stimulation such that a pulse of a first polarity is followed by a pulse of a second, reversed polarity.
55. The apparatus according to any of aspects 52-54, wherein the controller is configured to generate a pulsed electrical stimulation signal comprising a pulse frequency (F) of 0.01-150 Hz.
56. The apparatus according to aspect 55, wherein the electrical stimulation signal comprises a pulse duration (D) of 0.01-100 ms.
57. The apparatus according to aspect 55 or 56, wherein the electrical stimulation signal comprises a pulse amplitude (A) of 1-15 mA.
58. The apparatus according to any of aspects 55-57, wherein the electrical stimulation signal comprises a pulse frequency of 0.15-0.25 Hz, a pulse duration of 20-30 ms and a pulse amplitude of 3-10 mA.
59. The apparatus according to any of aspects 55-58, wherein the electrical stimulation signal comprises a build-up period of 0.01-2 s in which the amplitude is gradually increasing, a stimulation period of 1-60 s, and a stimulation pause of 0.01-60 s, wherein the electrical signal comprises a pulse frequency of 1-50 Hz and a pulse duration of 0.1-10 ms.
60. The apparatus according to any of aspects 52-59, wherein the controller comprises a wireless remote control (175).
61. The apparatus according to aspect 60, wherein the wireless remote control comprises an external signal transmitter, and wherein the apparatus further comprises an implantable controller configured to receive a signal transmitted by the external signal transmitter and to control an operation of the apparatus based on said signal.
62. The apparatus according to aspect 61, wherein signal is selected from the group consisting of: a sound signal, an ultrasound signal, an electromagnetic signal, and infrared signal, a visible light signal, an ultra violet light signal, a laser signal, a microwave signal, a radio wave signal, an X-ray radiation signal and a gamma radiation signal.
63. The apparatus according to any of aspects 52-62, further comprising an implantable sensor (S1) configured to sense actions potentials generated by pacemaker cells of the muscle tissue, and wherein the controller is configured to control the electrical simulation based at least partly on the sensed action potentials.
64. The apparatus according to aspect 63, wherein the controller is configured to generate electrical pulses amplifying the sensed action potentials.

Aspect Group 266SE: Reflux_Constricting-Band_Stop_Invaginated

1. An apparatus (100) for treating reflux disease of a human patient, adapted to at least partly encircle the esophagus (20) of the patient, comprising:
   a first implantable portion (110) having a shape and size allowing it to be arranged to rest against a fundus wall portion (14) of the patient's stomach (10) and to be at least partly invaginated by the fundus wall portion, such that the first implantable portion is implanted at a position between the patient's diaphragm (30) and a lower portion of the fundus wall, and such that movement of the cardia (22) of the patient's stomach towards the diaphragm is restricted to hinder the cardia from sliding through the diaphragm opening into the patient's thorax;
   a second implantable portion (120) being elongated to at least partly encircle the esophagus and having a variable length for allowing the apparatus be arranged in a constricting state for hindering fluid from passing from the stomach into the esophagus and in an expanded state for allowing food to pass into the stomach in response to the patient swallowing.
2. The apparatus according to aspect 1, wherein the first portion has a substantially fixed shape during operation of the apparatus.
3. The apparatus according to aspect 1 or 2, wherein a maximum width of a cross section taken across a length direction of the first implantable portion is larger than a maximum width of a cross section taken across a length direction of the second implantable portion.
4. The apparatus according to any of the preceding aspects, wherein the second implantable portion is configured to allow a transition from the constricting state into the expanded state caused by the food passing through esophagus.
5. The apparatus according to any of the preceding aspects, wherein the second implantable portion is configured to exert an encircling pressure on the esophagus in the constricting state.
6. The apparatus according to aspect 5, further comprising an attractor (212) for resiliently attracting adjacent portions (213) of the second implantable portion to one another to generate the encircling pressure.
7. The apparatus according to aspect 6, wherein the attractor comprises an elastic element.
8. The apparatus according to aspect 6, wherein the attractor comprises at least two mutually attracting magnets.
9. The apparatus according to aspect 8, further comprising a link (214) connecting a first and a second one of said at least two magnets to each other.
10. The apparatus according to aspect 9, wherein the link is configured to extend into at least one of said magnets in response to said magnets moving towards each other.
11. The apparatus according to any of the preceding aspects, further comprising a tubular cover (220) enclosing at least a part of the second implantable portion and comprising a plurality of cover portions (224, 225, 226) adapted to bend relative to each other to allow the second implantable portion to change between the constricting state and the expanded state, when the cover is at least partly covered by fibrotic tissue, without being substantially hindered or impeded by the presence of said fibrotic tissue.
12. The apparatus according to aspect 11, wherein the second implantable portion comprises an array of tubular segments (222).
13. The apparatus according to aspect 11 or 12, wherein the cover is formed of an inelastic material.
14. The apparatus according to any of aspects 11-13, wherein the cover comprises a biocompatible outer surface for long-term implantation.
15. The apparatus according to any of aspects 11-14, wherein the cover is configured to rest against an outer surface of the esophagus.
16. The apparatus according to any of aspects 11-15, wherein the cover comprises a surface promoting tissue growth.
17. The apparatus according to any of aspects 11-16, wherein the cover is formed of a polymer material, such as silicone.
18. The apparatus according to any of aspects 11-17, wherein the cover is formed of a material having a thickness of 0.1 to 10 mm, such as 1 to 5 mm.
19. The apparatus according to any of aspects 11-18, wherein the cover comprises at least one predefined fold (224) along which the cover is allowed to fold in response to the second implantable portion varying its length.
20. The apparatus according to any of aspects 11-19, wherein the cover comprises lowered and elevated portions (224, 225) allowing the cover to vary its length while maintaining its surface area.
21. The apparatus according to any of aspects 11-20, wherein the cover is configured to be compressible and expandable in its length direction.
22. The apparatus according to any of aspects 11-21, wherein a length of the cover enclosing said at least a part of the second implantable portion exceeds a length of said at least a part of the second implantable portion when said at least a part of the second implantable portion is arranged in the constricting state.
23. The apparatus according to any of the preceding aspects, comprising two end portions (216) configured to be coupled to each other to form a closed ring around the esophagus.
24. The apparatus according to aspect 23, wherein the end portions are configured to be releasably attached to each other.
25. The apparatus according to aspect 23 or 24, wherein the end portions comprise a respective interlockable attacher.
26. The apparatus according to aspect 1, wherein at least one of the first and the second implantable portion comprises a plurality of bodies (213) configured to be arranged in an annular array around the esophagus.
27. The apparatus according to aspect 26, wherein at least one of the first and the second implantable portion further comprises a plurality of links (214), each of which extending between a respective pair of bodies arranged adjacent to each other.
28. The apparatus according to aspect 27, wherein the second implantable portion comprises at least some of the plurality bodies and at least some of the plurality of links, and wherein each of said links is configured to allow the respective ones of said bodies to move towards and away from each other.

29. The apparatus according to aspect 28, wherein each of said links is configured to extend into at least one of the respective ones of said bodies as said bodies move towards each other.

30. The apparatus according to aspects 26, wherein the second implantable portion comprises at least some of the plurality of bodies and at least some of the plurality of links, and wherein the apparatus further comprises an attractor for resiliently attracting adjacent ones of said bodies to each other.

31. The apparatus according to aspect 30, wherein the attractor comprises at least one of a magnet, an elastic member, and a spring.

32. The apparatus according to aspect 1, wherein the first implantable portion is formed of a single body and the second implantable portion is formed of an array of bodies, wherein the array of bodies is movable towards and away from each other.

33. The apparatus according to any of the preceding aspects, wherein a volume of the first implantable portion is non-adjustable.

34. The apparatus according to any of aspects 1-32, wherein a volume of the first implantable portion is adjustable after implantation.

35. The apparatus according to any of the preceding aspects, wherein the first implantable portion comprises a biocompatible outer surface configured to rest against the fundus wall portion.

36. The apparatus according to any of the preceding aspects, wherein the first implantable portion is configured to be arranged such that a part of the fundus wall portion is arranged between the first implantable portion of the apparatus and the esophagus.

37. The apparatus according to any of the preceding aspects, wherein the first implantable portion is configured to be at least partly invaginated by the fundus wall portion along at least half of a length of the apparatus.

29. The apparatus according to any of aspects 11-22, further comprising an electrode arrangement (150) configured to be arranged between the apparatus and the esophagus and to electrically stimulate muscle tissue of the outer wall of the esophagus to exercise the muscle tissue to improve the conditions for long term implantation of the movement restriction device.

30. The apparatus according to aspect 29, wherein the electrode arrangement is arranged on an outer surface of the cover.

31. The apparatus according to aspect 29 or 30, wherein the electrode arrangement comprises a plurality of electrode elements (152, 154), each of which being configured to electrically stimulate the muscle tissue.

32. The apparatus according to any of aspects 29-31, wherein the electrode arrangement comprises a coiled wire for increasing a contact surface between the electrode arrangement and the muscle tissue and for allowing the electrode arrangement to follow contraction and relaxation of the muscle tissue.

33. The apparatus according to any of aspects 29-32, wherein the electrode arrangement comprises a bare electrode portion (155) configured to form a metal-tissue interface with the muscle tissue, thereby allowing faradaic charge transfer to the be predominant charge transfer mechanism over said interface.

34. The apparatus according to any of aspects 29-33, wherein the electrode arrangement comprises an electrode portion at least partly covered by a dielectric material (157) configured to form a dielectric-tissue interface with the muscle tissue, thereby allowing for a faradaic portion of the charge transfer mechanism over said interface to be reduced.

35. The apparatus according to any of aspects 29-34, wherein the electrode arrangement is configured be arranged to electrically stimulate the cardiac sphincter (26) of the patient to cause the cardiac sphincter to contract.

36. The apparatus according to aspect 35, wherein the electrode arrangement comprises at least two electrode elements (154) configured to be arranged on opposing sides of the cardiac sphincter.

37. The apparatus according to any of aspects 29-36, further comprising an implantable energy source (160) configured to provide the electrode arrangement with electrical power.

38. The apparatus according to aspect 37, wherein the implantable energy source is arranged inside the cover.

39. The apparatus according to aspect 37, wherein the implantable energy source is configured to be arranged outside the cover.

40. The apparatus according to aspect 39, wherein the implantable energy source is configured to be implanted subcutaneously.

41. The apparatus according to any of aspects 37-40, wherein the implantable energy source comprises a primary cell.

42. The apparatus according to any of aspects 37-41, wherein the implantable energy source comprises a secondary cell.

43. The apparatus according to aspect 37-42, further comprising a controller (170) configured to indicate a functional status of the implantable energy source.

44. The apparatus according to aspect 43, wherein the functional status indicates a charge level of the implantable energy source.

45. The apparatus according to aspect 43 or 44, wherein the functional status indicates a temperature of at least one of the implantable energy source, the muscle tissue, and the electrode arrangement.

46. The apparatus according to any of aspects 37-45, wherein the implantable energy source is configured to be charged by an external energy source (165) arranged outside the patient's body.

47. The apparatus according to aspect 46, further comprising an implantable charger (190) configured to be electrically connected to the implantable energy source and enable charging of the implantable energy source by the external energy source.

48. The apparatus according to aspect 47, wherein the charger comprises an electromagnetic coil configured to receive electrical power wirelessly from the external energy source.

49. The apparatus according to aspect 47 or 48, wherein the charger is configured to receive the functional status from the energy source indicator and control the charging of the implantable energy source based on the functional status.

50. The apparatus according to any of aspects 47-49, wherein the charger is configured to control the charging of the implantable energy source by controlling a receipt of electrical power from the external energy source at the implantable charger.

51. The apparatus according to any of aspects 47-49, wherein the charger is configured to control the charging of the implantable energy source by controlling a transmission of electrical power from the external energy source to the implantable charger.

52. The apparatus according to any of aspects 29-51, further comprising controller (170) configured to be operably connected to the electrode arrangement for controlling the electrical stimulation of the muscle tissue.

53. The apparatus according to aspect 52, wherein the controller is configured to control the electrical stimulation such that the muscle tissue is stimulated by a series of electrical pulses (PL1, PL2, PL3, PL4).

54. The apparatus according to aspect 53, wherein the controller is configured to control the electrical stimulation such that a pulse of a first polarity is followed by a pulse of a second, reversed polarity.

55. The apparatus according to any of aspects 52-54, wherein the controller is configured to generate a pulsed electrical stimulation signal comprising a pulse frequency (F) of 0.01-150 Hz.

56. The apparatus according to aspect 55, wherein the electrical stimulation signal comprises a pulse duration (D) of 0.01-100 ms.

57. The apparatus according to aspect 55 or 56, wherein the electrical stimulation signal comprises a pulse amplitude (A) of 1-15 mA.

58. The apparatus according to any of aspects 55-57, wherein the electrical stimulation signal comprises a pulse frequency of 0.15-0.25 Hz, a pulse duration of 20-30 ms and a pulse amplitude of 3-10 mA.

59. The apparatus according to any of aspects 55-58, wherein the electrical stimulation signal comprises a build-up period of 0.01-2 s in which the amplitude is gradually increasing, a stimulation period of 1-60 s, and a stimulation pause of 0.01-60 s, wherein the electrical signal comprises a pulse frequency of 1-50 Hz and a pulse duration of 0.1-10 ms.

60. The apparatus according to any of aspects 52-59, wherein the controller comprises a wireless remote control (175).

61. The apparatus according to aspect 60, wherein the wireless remote control comprises an external signal transmitter, and wherein the apparatus further comprises an implantable controller configured to receive a signal transmitted by the external signal transmitter and to control an operation of the apparatus based on said signal.

62. The apparatus according to aspect 61, wherein signal is selected from the group consisting of: a sound signal, an ultrasound signal, an electromagnetic signal, and infrared signal, a visible light signal, an ultra violet light signal, a laser signal, a microwave signal, a radio wave signal, an X-ray radiation signal and a gamma radiation signal.

63. The apparatus according to any of aspects 52-62, further comprising an implantable sensor (S1) configured to sense actions potentials generated by pacemaker cells of the muscle tissue, and wherein the controller is configured to control the electrical simulation based at least partly on the sensed action potentials.

64. The apparatus according to aspect 63, wherein the controller is configured to generate electrical pulses amplifying the sensed action potentials.

Aspect Group 267SE: Reflux_Stimulating-Band_Stop_Invaginated

1. An apparatus (100) for treating reflux disease of a human patient, adapted to at least partly encircle the esophagus (20) of the patient, comprising:

a movement restriction device (110) having a shape and size allowing it to be arranged to rest against a fundus wall portion (14) of the patient's stomach (10) and to be at least partly invaginated by the fundus wall portion, such that the first implantable portion is implanted at a position between the patient's diaphragm (30) and a lower portion of the fundus wall, and such that movement of the cardia (22) of the patient's stomach towards the diaphragm is restricted to hinder the cardia from sliding through the diaphragm opening (32) into the patient's thorax; and an elongated support device (120) connected to the movement restriction device and configured to at least partly encircle the esophagus;

wherein the apparatus further comprises an electrode arrangement (150) comprising an electrode element (154) supported by the support device and configured to electrically stimulate muscle tissue of the esophagus; and wherein the support device comprises a rigidity that allows the position of the electrode element relative to the esophagus to be determined mainly by the position and orientation of the movement restriction device.

2. The apparatus according to aspect 1, wherein electrode arrangement comprises a plurality of electrode elements.

3. The apparatus according to aspect 1 or 2, wherein the electrode arrangement is configured to electrically stimulate the cardiac sphincter (26) of the patient to cause the cardiac sphincter to contract.

4. The apparatus according to aspect 3, wherein the electrode arrangement is configured to stimulate opposing sides of the cardiac sphincter.

5. The apparatus according to any of the preceding aspects, wherein the electrode arrangement is configured to exercise muscle tissue in contact with the apparatus to improve the conditions for long term implantation of the apparatus.

6. The apparatus according to aspect 2, wherein an electrode element of the plurality of electrode elements is configured to be arranged between the movement restriction device and the fundus wall portion to electrically stimulate muscle tissue of the fundus wall portion.

7. The apparatus according to any of the preceding aspects, wherein the electrode arrangement comprises a coiled wire for increasing a contact surface between the electrode arrangement and the muscle tissue.

8. The apparatus according to any of the preceding aspects, wherein a maximum width of a cross section taken across a length direction of the movement restriction device is larger than a maximum width of a cross section taken across a length direction of the support device.

9. The apparatus according to any of the preceding aspects, wherein the support device is formed as a band configured to be arranged around at least a part of the esophagus, and wherein a first and a second end portion of the band is coupled to the first implantable portion.

10. The apparatus according to any of the preceding aspects, wherein the apparatus comprises a biocompatible outer surface for long-term implantation.
11. The apparatus according to any of the preceding aspects, wherein the apparatus is formed of a polymer material, such as silicone.
12. The apparatus according to any of the preceding aspects, wherein the movement restriction device is configured to be arranged such that a part of the fundus wall portion is arranged between the movement restriction device and the esophagus.
13. The apparatus according to any of the preceding aspects, wherein the movement restriction device is configured to be fully invaginated by the fundus wall portion.
14. The apparatus according to any of the preceding aspects, wherein the apparatus is ring-shaped and configured to be at least partly invaginated by the fundus wall portion along at least half of a circumference of the apparatus.
15. The apparatus according to any of the preceding aspects, wherein the electrode arrangement comprises a bare electrode portion (155) configured to form a metal-tissue interface with the muscle tissue, thereby allowing faradaic charge transfer to the be predominant charge transfer mechanism over said interface.
16. The apparatus according to any of aspects 1-14, wherein the electrode arrangement comprises an electrode portion at least partly covered by a dielectric material (157) configured to form a dielectric-tissue interface with the muscle tissue, thereby allowing for a faradaic portion of the charge transfer mechanism over said interface to be reduced.
17. The apparatus according to any of the preceding aspects, further comprising an implantable energy source (160) configured to provide the electrode arrangement with electrical power.
18. The apparatus according to aspect 17, wherein the implantable energy source is arranged within the movement restriction device or the support device.
19. The apparatus according to aspect 17, wherein the implantable energy source is configured to be arranged outside movement restriction device and the support device.
20. The apparatus according to aspect 19, wherein the implantable energy source is configured to be implanted subcutaneously.
21. The apparatus according to any of aspects 17-20, wherein the implantable energy source comprises a primary cell.
22. The apparatus according to any of aspects 17-31, wherein the implantable energy source comprises a secondary cell.
23. The apparatus according to aspect 17-22, further comprising a controller (170) configured to indicate a functional status of the implantable energy source.
24. The apparatus according to aspect 23, wherein the functional status indicates a charge level of the implantable energy source.
25. The apparatus according to aspect 23 or 24, wherein the functional status indicates a temperature of at least one of the implantable energy source, the muscle tissue, and the electrode arrangement.
26. The apparatus according to any of aspects 17-25, wherein the implantable energy source is configured to be charged by an external energy source arranged outside the patient's body.
27. The apparatus according to aspect 26, further comprising an implantable charger (190) configured to be electrically connected to the implantable energy source and enable charging of the implantable energy source by the external energy source.
28. The apparatus according to aspect 27, wherein the charger comprises an electromagnetic coil configured to receive electrical power wirelessly from the external energy source.
29. The apparatus according to aspect 27 or 28, wherein the charger is configured to receive the functional status from the energy source indicator and control the charging of the implantable energy source based on the functional status.
30. The apparatus according to any of aspects 27-29, wherein the charger is configured to control the charging of the implantable energy source by controlling a receipt of electrical power from the external energy source at the implantable charger.
31. The apparatus according to any of aspects 27-29, wherein the charger is configured to control the charging of the implantable energy source by controlling a transmission of electrical power from the external energy source to the implantable charger.
32. The apparatus according to any of the preceding aspects, further comprising controller (170) configured to be operably connected to the electrode arrangement for controlling the electrical stimulation of the muscle tissue.
33. The apparatus according to aspect 32, wherein the controller is configured to control the electrical stimulation such that the muscle tissue is stimulated by a series of electrical pulses (PL1, PL2, PL3, PL4).
34. The apparatus according to aspect 33, wherein the controller is configured to control the electrical stimulation such that a pulse of a first polarity is followed by a pulse of a second, reversed polarity.
35. The apparatus according to any of aspects 32-34, wherein the controller is configured to generate a pulsed electrical stimulation signal comprising a pulse frequency (F) of 0.01-150 Hz.
36. The apparatus according to aspect 35, wherein the electrical stimulation signal comprises a pulse duration (D) of 0.01-100 ms.
37. The apparatus according to aspect 35 or 36, wherein the electrical stimulation signal comprises a pulse amplitude (A) of 1-15 mA.
38. The apparatus according to any of aspects 35-37, wherein the electrical stimulation signal comprises a pulse frequency of 0.15-0.25 Hz, a pulse duration of 20-30 ms and a pulse amplitude of 3-10 mA.
39. The apparatus according to any of aspects 35-38, wherein the electrical stimulation signal comprises a build-up period of 0.01-2 s in which the amplitude is gradually increasing, a stimulation period of 1-60 s, and a stimulation pause of 0.01-60 s, wherein the electrical signal comprises a pulse frequency of 1-50 Hz and a pulse duration of 0.1-10 ms.
40. The apparatus according to any of aspects 32-39, wherein the controller comprises a wireless remote control (175).
41. The apparatus according to aspect 40, wherein the wireless remote control comprises an external signal transmitter, and wherein the apparatus further comprises an implantable controller configured to receive a signal transmitted by the external signal transmitter and to control an operation of the apparatus based on said signal.
42. The apparatus according to aspect 41, wherein signal is selected from the group consisting of: a sound signal, an ultrasound signal, an electromagnetic signal, and infrared signal, a visible light signal, an ultra violet light signal, a laser signal, a microwave signal, a radio wave signal, an X-ray radiation signal and a gamma radiation signal.
43. The apparatus according to any of aspects 32-42, further comprising an implantable sensor (S1) configured to sense actions potentials generated by pacemaker cells of the muscle tissue, and wherein the controller is configured to control the electrical simulation based at least partly on the sensed action potentials.
44. The apparatus according to aspect 43, wherein the controller is configured to generate electrical pulses amplifying the sensed action potentials.

Aspect Group 268SE: Reflux_Stop_His_Method
1. A method for treating reflux disease of a human patient by implanting a movement restriction device (100) such that the movement restriction device is arranged to restrict movement of the cardia (22) of the patient's stomach (10) towards the diaphragm (30) to hinder the cardia from sliding through the diaphragm opening (32) into the patient's thorax, wherein the method comprises:
    placing the movement restriction device such that a lower portion of the movement restriction device rests against the serosa at the angle of His (24), and such that an upper portion of the movement restriction device defines a gap between the movement restriction device and the patient's esophagus (20), when the lower portion rests against the angle of His;
    arranging a portion of the fundus (12) of the stomach in the gap; and
    attaching the fundus to the patient's esophagus to at least partly enclose the movement restriction device by the portion of the fundus.
2. The method according to aspect 1, wherein the movement restriction device has a rounded shape.
3. The method according to aspect 1 or 2, comprising arranging the upper portion to point away from the esophagus.
4. The method according to any of the preceding aspects, wherein the lower portion is wider that the upper portion.
5. The method according to any of the preceding aspects, wherein the movement restriction device has a C-shaped cross section.
6. The method according to any of the preceding aspects, wherein the upper portion comprises a recess defined in the outer surface of the movement restriction device.
7. The method according to any of the preceding aspects, wherein the lower portion comprises a curved outer surface, wherein the method further comprises arranging the curved outer surface to face the esophagus, and wherein the curved outer surface comprises a radius of curvature corresponding to or exceeding the radius of curvature of the esophagus.
8. The method according to any of the preceding aspects, further comprising at least partly invaginating an elongated support (117), protruding from the movement restriction device, in the portion of the fundus before attaching the fundus to the esophagus.
9. The method according to aspect 8, wherein the support is shaped as a lever, wherein the method further comprises orienting the support along the esophagus.
10. The method according to any of the preceding aspects, further comprising arranging an electrode arrangement (150) between the movement restriction device and the portion of the fundus and/or the serosa, wherein the electrode arrangement is configured to electrically stimulate muscle tissue of the portion of the fundus and/or the serosa to improve the conditions for long term implantation of the movement restriction device.
11. The method according to aspect 10, wherein the electrode arrangement comprises a plurality of electrode elements (152), each of which being configured to engage and electrically stimulate the muscle tissue.
12. The method according to aspect 10 or 11, wherein the electrode arrangement comprises a coiled wire for increasing a contact surface between the electrode arrangement and the muscle tissue and for allowing the electrode arrangement to follow contraction and relaxation of the muscle tissue.
13. The method according to any of aspects 10-12, wherein the electrode arrangement comprises a bare electrode portion (155) configured to form a metal-tissue interface with the muscle tissue, thereby allowing faradaic charge transfer to the be predominant charge transfer mechanism over said interface.
14. The method according to any aspects 10-12, wherein the electrode arrangement comprises an electrode portion at least partly covered by a dielectric material (157) configured to form a dielectric-tissue interface with the muscle tissue, thereby allowing for a faradaic portion of the charge transfer mechanism over said interface to be reduced.
15. The method according to any of aspects 10-14, wherein the electrode arrangement is further configured to be arranged to electrically stimulate the cardiac sphincter (26) to cause the cardiac sphincter to contract.
16. The method according to aspect 15, wherein the electrode arrangement comprises at least two electrode elements (154), wherein the method further comprises arranging said electrode elements on opposing sides of the cardiac sphincter.
17. The method according to aspect 16, wherein the movement restriction device further comprises a holder (120) configured to support the at least two electrode elements at the opposing sides of the cardiac sphincter.
18. The method according to any of aspects 10-17, further comprising implanting an implantable energy source (160) configured to provide the electrode with electrical power.
19. The method according to aspect 18, wherein the implantable energy source is arranged inside the movement restriction device.
20. The method according to aspect 18, wherein the implantable energy source is configured to be arranged outside the movement restriction device, and wherein the method further comprises implanting the implantable energy source in the patient's body.
21. The method according to aspect 20, further comprising implanting the implantable energy source subcutaneously.
22. The method according to any of aspects 18-21, wherein the implantable energy source comprises a primary cell.

23. The method according to any of aspects 18-22, wherein the implantable energy source comprises a secondary cell.
24. The method according to aspect 18-23, further comprising implanting a controller (170) configured to indicate a functional status of the implantable energy source.
25. The method according to aspect 24, wherein the functional status indicates a charge level of the implantable energy source.
26. The method according to aspect 24 or 25, wherein the functional status indicates a temperature of at least one of the implantable energy source, the muscle tissue, and the electrode arrangement.
27. The method according to any of aspects 24-26, wherein the implantable energy source is configured to be charged by an external energy source (165) arranged outside the patient's body.
28. The method according to aspect 27, further comprising implanting an implantable charger (190) configured to be electrically connected to the implantable energy source and enable charging of the implantable energy source by the external energy source.
29. The method according to aspect 28, wherein the charger comprises an electromagnetic coil configured to receive electrical power wirelessly from the external energy source.
30. The method according to aspect 28 or 29, wherein the charger is configured to control the charging of the implantable energy source based on the functional status.
31. The method according to any of aspects 28-30, wherein the charger is configured to control the charging of the implantable energy source by controlling a receipt of electrical power from the external energy source at the implantable charger.
32. The method according to any of aspects 28-31, wherein the charger is configured to control the charging of the implantable energy source by controlling a transmission of electrical power from the external energy source to the implantable charger.
33. The method according to any of aspects 10-23, further comprising implanting a controller (170) configured to be operably connected to the electrode arrangement for controlling the electrical stimulation of the muscle tissue.
34. The method according to aspect 33, wherein the controller is configured to control the electrical stimulation such that the muscle tissue is stimulated by a series of electrical pulses (PL1, PL2, PL3, PL4).
35. The method according to aspect 34, wherein the controller is configured to control the electrical stimulation such that a pulse of a first polarity is followed by a pulse of a second, reversed polarity.
36. The method according to aspect 34 or 35, wherein the controller is configured to generate a pulsed electrical stimulation signal comprising a pulse frequency (F) of 0.01-150 Hz.
37. The method according to aspect 36, wherein the electrical stimulation signal comprises a pulse duration (D) of 0.01-100 ms.
38. The method according to aspect 36 or 37, wherein the electrical stimulation signal comprises a pulse amplitude (A) of 1-15 mA.
39 The method according to any of aspects 36-38, wherein the electrical stimulation signal comprises a pulse frequency of 0.15-0.25 Hz, a pulse duration of 20-30 ms and a pulse amplitude of 3-10 mA.
40. The method according to any of aspects 36-39, wherein the electrical stimulation signal comprises a build-up period of 0.01-2 s in which the amplitude is gradually increasing, a stimulation period of 1-60 s, and a stimulation pause of 0.01-60 s, wherein the electrical signal comprises a pulse frequency of 1-50 Hz and a pulse duration of 0.1-10 ms.
41. The method according to any of aspects 33-43, further comprising implanting an implantable sensor (S1) configured to sense actions potentials generated by pacemaker cells of the muscle tissue, and wherein the controller is configured to control the electrical simulation based at least partly on the sensed action potentials.
42. The method according to aspect 44, wherein the controller is configured to generate electrical pulses amplifying the sensed action potentials.

Aspect Group 269SE: Reflux_Stop_Gastric-Sleeve

1. An apparatus (100) for treating reflux disease of a human patient, comprising:
   an implantable movement restriction device (110); and
   an elongated attacher (117) configured to be attached to the movement restriction device and to be at least partly invaginated by a wall portion of the patient's stomach (10);
   wherein the attacher comprises a shape and size allowing it to be invaginated by the wall portion to hinder rotation of the movement restriction device; and
   wherein the attacher is configured to be invaginated by the wall portion such that the movement restriction device is arranged at a position between the patient's diaphragm (30) and the wall portion, distant from the patient's esophagus (20), to restrict movement of the cardia (22) of the patient's stomach towards the diaphragm to hinder the cardia from sliding through the diaphragm opening (32) into the patient's thorax.
2. The apparatus according to aspect 1, wherein a first end portion of the attacher is configured to be invaginated by the wall portion and a second end portion is configured to be attached to the movement restriction device.
3. The apparatus according to aspect 1 or 2, wherein the attacher comprises a first portion (118) and a second portion (119) extending in different directions relative to each other, wherein the first portion is configured to be invaginated by the wall portion to hinder rotation of the movement restriction device around a first axis, and wherein the second portion is configured to be invaginated by the wall portion to hinder rotation of the movement restriction device around a second axis, different from the first axis.
4. The apparatus according to aspect 3, wherein the first and second portions of the attacher are curved to follow a curvature of the wall portion.
5. The apparatus according to aspect 3 or 4, wherein the first portion and second portion are arranged at an angle to each other, the angle being in the interval of 60-120 degrees.
6. The apparatus according to any of the preceding aspects, wherein the attacher is configured to be releasably attached to the movement restriction device.
7. The apparatus according to any of the preceding aspects, wherein the movement restriction device has a rounded shape.

8. The apparatus according to any of the preceding aspects, wherein the movement restriction device has a shape conforming to a sphere.
9. The apparatus according to any of the preceding aspects, wherein the attacher is configured to allow a position of the movement restriction device to be adjusted after invagination of the attachment means.
10. The apparatus according to any of the preceding aspects, configured to allow a distance between the movement restriction device and the attacher to be varied to allow the position of the movement restriction device relative to the diaphragm to be adjusted.
11. The apparatus according to any of the preceding aspects, configured to allow an orientation of the movement restriction device relative to the attachments means to be varied to allow the position of the movement restriction device relative to the diaphragm to the adjusted.
12. The apparatus according to aspect 3, wherein the attacher comprises a third portion, configured to be arranged to protrude from the wall portion when implanted, and to define a distance between the wall portion and the movement restriction device.
13. The apparatus according to aspect 12, wherein the third portion comprises a curvature allowing the third portion to be arranged to point away from the esophagus when implanted.
14. The apparatus according to aspect 1, wherein the movement restriction device and the attacher are integrally formed into a single piece.
15. The apparatus according to any of the preceding aspects, wherein each of the movement restriction device and the attachments means comprises a biocompatible outer surface.
16. The apparatus according to any of the preceding aspects, wherein the attacher comprises an outer surface configured to promote tissue growth.
17. The apparatus according to any of the preceding aspects, wherein the attacher is formed of a metal.
18. The apparatus according to any of aspects 1-16, wherein the movement restriction device is formed of a polymer.
19. The apparatus according to any of the preceding aspects, wherein a minimum width of the movement restriction device, as measured from side to side, is 30 mm or larger, such as 40 mm or larger.
20. The apparatus according to any of the preceding aspects, wherein an outer surface of the movement restriction device comprises a material for hindering growth of fibrotic tissue.
22. The apparatus according to any of the preceding aspects, further comprising an electrode arrangement (150) configured to be arranged between the apparatus and muscle tissue of at least one of the diaphragm and the wall portion, and to electrically stimulate muscle tissue to exercise the muscle tissue to improve the conditions for long term implantation of the apparatus.
23. The apparatus according to aspect 22, wherein the electrode arrangement comprises a plurality of electrode elements (152), each of which being configured to engage and electrically stimulate the muscle tissue.
24. The apparatus according to any of aspects 22 or 23, wherein the electrode arrangement comprises a bare electrode portion (155) configured to form a metal-tissue interface with the muscle tissue, thereby allowing faradaic charge transfer to the be predominant charge transfer mechanism over said interface.
25. The apparatus according to any aspects 22 or 23, wherein the electrode arrangement comprises an electrode portion at least partly covered by a dielectric material (157) configured to form a dielectric-tissue interface with the muscle tissue, thereby allowing for a faradaic portion of the charge transfer mechanism over said interface to be reduced.
26. The apparatus according to any of aspects 22-25, further comprising an implantable energy source (160) configured to provide the electrode arrangement with electrical power.
27. The apparatus according to aspect 26, wherein the implantable energy source is arranged inside the movement restriction device or the attachment means.
28. The apparatus according to aspect 26, wherein the implantable energy source is configured to be arranged outside the movement restriction device and the attachment means.
29. The apparatus according to aspect 28, wherein the implantable energy source is configured to be implanted subcutaneously.
30. The apparatus according to any of aspects 26-29, wherein the implantable energy source comprises a primary cell.
31. The apparatus according to any of aspects 26-30, wherein the implantable energy source comprises a secondary cell.
32. The apparatus according to aspect 26-31, further comprising a controller (170) configured to indicate a functional status of the implantable energy source.
33. The apparatus according to aspect 32, wherein the functional status indicates a charge level of the implantable energy source.
34. The apparatus according to aspect 32 or 33, wherein the functional status indicates a temperature of at least one of the implantable energy source, the muscle tissue, and the electrode arrangement.
35. The apparatus according to any of aspects 32-34, wherein the implantable energy source is configured to be charged by an external energy source (165) arranged outside the patient's body.
36. The apparatus according to aspect 35, further comprising an implantable charger (190) configured to be electrically connected to the implantable energy source and enable charging of the implantable energy source by the external energy source.
37. The apparatus according to aspect 33, wherein the charger comprises an electromagnetic coil configured to receive electrical power wirelessly from the external energy source.
38. The apparatus according to aspect 36 or 37, wherein the charger is configured to control the charging of the implantable energy source based on the functional status.
39. The apparatus according to any of aspects 33-38, wherein the charger is configured to control the charging of the implantable energy source by controlling a receipt of electrical power from the external energy source at the implantable charger.
40. The apparatus according to any of aspects 36-39, wherein the charger is configured to control the charging of the implantable energy source by controlling a transmission of electrical power from the external energy source to the implantable charger.
41. The apparatus according to any of aspects 22-40, further comprising controller (170) configured to be operably connected to the electrode arrangement for controlling the electrical stimulation of the muscle tissue.

42. The apparatus according to aspect 41, wherein the controller is configured to control the electrical stimulation such that the muscle tissue is stimulated by a series of electrical pulses (PL1, PL2, PL3, PL4).
43. The apparatus according to aspect 42, wherein the controller is configured to control the electrical stimulation such that a pulse of a first polarity is followed by a pulse of a second, reversed polarity.
44. The apparatus according to aspect 42 or 43, wherein the controller is configured to generate a pulsed electrical stimulation signal comprising a pulse frequency (F) of 0.01-150 Hz.
45. The apparatus according to aspect 44, wherein the electrical stimulation signal comprises a pulse duration (D) of 0.01-100 ms.
46. The apparatus according to aspect 44 or 45, wherein the electrical stimulation signal comprises a pulse amplitude (A) of 1-15 mA.
47. The apparatus according to any of aspects 44-46, wherein the electrical stimulation signal comprises a pulse frequency of 0.15-0.25 Hz, a pulse duration of 20-30 ms and a pulse amplitude of 3-10 mA.
48. The apparatus according to any of aspects 44-47, wherein the electrical stimulation signal comprises a build-up period of 0.01-2 s in which the amplitude is gradually increasing, a stimulation period of 1-60 s, and a stimulation pause of 0.01-60 s, wherein the electrical signal comprises a pulse frequency of 1-50 Hz and a pulse duration of 0.1-10 ms.
49. The apparatus according to any of aspects 41-48, wherein the controller comprises a wireless remote control (175).
50. The apparatus according to aspect 49, wherein the wireless remote control comprises an external signal transmitter, and wherein the controller comprises an implantable controller configured to receive a signal transmitted by the external signal transmitter and to control an operation of the apparatus based on said signal.
51. The apparatus according to aspect 50, wherein the signal is selected from the group consisting of: a sound signal, an ultrasound signal, an electromagnetic signal, and infrared signal, a visible light signal, an ultra violet light signal, a laser signal, a microwave signal, a radio wave signal, an X-ray radiation signal and a gamma radiation signal.
52. The apparatus according to any of aspects 41-51, further comprising an implantable sensor (S1) configured to sense actions potentials generated by pacemaker cells of the muscle tissue, and wherein the controller is configured to control the electrical simulation based at least partly on the sensed action potentials.

Aspect Group 270SE: Reflux_Band_Stop_Method

1. A method of treating reflux disease in a human patient by implanting an apparatus (100) comprising a movement restriction device (110) and an elongated support device (120), such that the support device at least partly encircles the esophagus (10) of the patient and such that the movement restriction device is at arranged on the fundus side of the esophagus to restrict the movement of the cardia (22) in relation to the diaphragm (30) to hinder the cardia to from sliding through the diaphragm opening (32) into the patient's thorax, the method comprising the steps of:
   introducing the apparatus into the abdominal cavity;
   placing the apparatus such that the movement restriction device rests against the outside of the stomach's fundus (12);
   wrapping a portion of the fundus around at least a part of the movement restriction device;
   affixing the fundus to the esophagus such that the movement restriction device is arranged at a position between the diaphragm and the cardiac sphincter, and such that a part of the fundus is arranged between the movement restriction device and the esophagus; and
   arranging the support device to at least partly encircle the esophagus;
   wherein the movement restriction device and the second portion form a ring-shaped body extending through the pouch to at least partly encircle the esophagus.
2. The method according to aspect 1, comprising placing the apparatus such that the movement restriction device rests against the outside of the fundus at a position between the cardiac sphincter and the portion of the fundus that is to be affixed to the esophagus.
3. The method according to aspect 1, comprising placing the apparatus such that the portion of the fundus that is affixed to the esophagus is arranged between the cardiac sphincter (26) and the movement restriction device.
4. The method according to any of the preceding aspects, wherein the pouch is formed to be open in a least two positions to form a tunnel through which the apparatus extends.
5. The method according to any of the preceding aspects, further comprising affixing the portion of the fundus to the patient's diaphragm.
6. The method according to any of the preceding aspects, wherein affixing the portion of the fundus to the esophagus includes suturing or stapling.
7. The method according to any of the preceding aspects, wherein the support device comprises a first and a second end portion between which the esophagus can be introduced, and wherein the first and second end portions can be coupled to each other so as to fixate the support device to the esophagus in an encircling manner.
8. The method according to any of the preceding aspects, further comprising:
   inserting a needle or a tube-like instrument into the patient's abdomen;
   using the needle or tube-like instrument to fill the abdomen with a gas;
   placing at least two laparoscopic trocars in the abdomen;
   inserting a camera through one of the laparoscopic trocars into the abdomen;
   inserting at least one dissecting tool through one the laparoscopic trocars;
   dissecting a portion of the stomach; and
   at least partly closing the pouch by means of sutures, such as barbed sutures, or staples.
9. The method according to any of the preceding aspects, wherein the support device comprises a variable length for allowing the apparatus be arranged in a constricting state for hindering fluid from passing from the stomach into the esophagus and in an expanded state for allowing food to pass into the stomach in response to the patient swallowing.
10. The method according to aspect 9, wherein the movement restriction device has a substantially fixed shape during operation of the apparatus.
11. The method according to aspect 9 or 10, wherein the support device is configured to allow a transition from the constricting state into the expanded state caused by the food passing through esophagus.
12. The method according to any of aspects 9-11, wherein the support device is configured to exert an encircling pressure on the esophagus in the constricting state.
13. The method according to aspect 12, further comprising an attractor (212) for resiliently attracting adjacent portions (213) of the support device to one another to generate the encircling pressure.
14. The method according to aspect 13, wherein the attractor comprises an elastic element.
15. The method according to aspect 13, wherein the attractor comprises at least two mutually attracting magnets.
16. The method according to aspect 15, further comprising a link (214) connecting a first and a second one of said at least two magnets to each other.
17. The method according to aspect 16, wherein the link is configured to extend into at least one of said magnets in response to said magnets moving towards each other.
18. The method according to any of aspects 9-17, further comprising a tubular cover (220) enclosing at least a part of the support device and comprising a plurality of cover portions (224, 225, 226) adapted to bend relative to each other to allow the second support device to change between the constricting state and the expanded state, when the cover is at least partly covered by fibrotic tissue, without being substantially hindered or impeded by the presence of said fibrotic tissue.
19. The method according to aspect 18, wherein the cover comprises at least one predefined fold (224) along which the cover is allowed to fold in response to the support device varying its length.
20. The apparatus according to any of aspects 18-20, wherein the cover comprises lowered and elevated portions (225, 226) allowing the cover to vary its length while maintaining its surface area.
21. The method according to any of aspects 1-8, wherein the apparatus further comprises an electrode arrangement (150) comprising an electrode element (154) supported by the support device and configured to electrically stimulate muscle tissue of the esophagus.
22. The method according to aspect 21, wherein the electrode arrangement is configured to electrically stimulate the cardiac sphincter of the patient to cause the cardiac sphincter to contract.
23. The method according to aspect 22, wherein the electrode arrangement is configured to stimulate opposing sides of the cardiac sphincter.
24. The method according to any aspects 1-8, further comprising an electrode arrangement (150) configured to be arranged between the movement restriction device and the portion of the fundus to electrically stimulate muscle tissue of the portion of the fundus to exercise the muscle tissue to improve the conditions for long term implantation of the movement restriction device.
25. The method according to any of aspects 21-24, wherein the electrode arrangement comprises a bare electrode portion (155) configured to form a metal-tissue interface with the muscle tissue, thereby allowing faradaic charge transfer to the be predominant charge transfer mechanism over said interface.
26. The method according to any of aspects 21-24, wherein the electrode arrangement comprises an electrode portion at least partly covered by a dielectric material (157) configured to form a dielectric-tissue interface with the muscle tissue, thereby allowing for a faradaic portion of the charge transfer mechanism over said interface to be reduced.
27. The method according to any of aspects 21-26, further comprising implanting an implantable energy source (160) in the patient's body, wherein the implantable energy source is configured to provide the electrode arrangement with electrical power.
28. The method according to aspect 27, wherein the implantable energy source is arranged inside the movement restriction device.
29. The method according to 27, comprising placing the implantable energy source outside the movement restriction device and the support device.
30. The method according to aspect 27, comprising implanting the implantable energy source subcutaneously.
31. The method according to any of aspects 27-30, further comprising implanting a controller (170) in the patient's body, wherein the controller is configured to indicate a functional status of the implantable energy source.
32. The method according to 31, wherein the functional status indicates a charge level of the implantable energy source.
33. The method according to aspect 32, wherein the functional status indicates a temperature of at least one of the implantable energy source, the muscle tissue, and the electrode arrangement.
34. The method according to any of aspects 31-33, further comprising implanting an implantable charger (190) in the patient's body, wherein the implantable charger is configured to be electrically connected to the implantable energy source and enable charging of the implantable energy source by an external energy source (165) arranged outside the body.
35. The method according to aspect 34, wherein the charger is configured to control the charging of the implantable energy source based on the functional status.
36. The method according to aspect 34 or 35, wherein the charger is configured to control the charging of the implantable energy source by controlling a receipt of electrical power from the external energy source at the implantable charger.
37. The method according to aspect 34 or 35, wherein the charger is configured to control the charging of the implantable energy source by controlling a transmission of electrical power from the external energy source to the implantable charger.
38. The method according to any of aspects 21-37, further comprising implanting a controller (170) in the patient's body, wherein the controller is configured to be operably connected to the electrode arrangement for controlling the electrical stimulation of the muscle tissue.
39. The method according to aspect 38, wherein the controller is configured to control the electrical stimulation such that the muscle tissue is stimulated by a series of electrical pulses (PL1, PL2, PL3, PL4).

40. The method according to aspect 39, wherein the controller is configured to control the electrical stimulation such that a pulse of a first polarity is followed by a pulse of a second, reversed polarity.

41. The method according to any of aspects 38-40, wherein the controller is configured to generate a pulsed electrical stimulation signal comprising a pulse frequency (F) of 0.01-150 Hz.

42. The method according to aspect 41, wherein the electrical stimulation signal comprises a pulse duration (D) of 0.01-100 ms.

43. The method according to aspect 41 or 42, wherein the electrical stimulation signal comprises a pulse amplitude (A) of 1-15 mA.

44. The method according to any of aspects 41-43, wherein the electrical stimulation signal comprises a pulse frequency of 0.15-0.25 Hz, a pulse duration of 20-30 ms and a pulse amplitude of 3-10 mA.

45. The method according to any of aspects 41-44, wherein the electrical stimulation signal comprises a build-up period of 0.01-2 s in which the amplitude is gradually increasing, a stimulation period of 1-60 s, and a stimulation pause of 0.01-60 s, wherein the electrical signal comprises a pulse frequency of 1-50 Hz and a pulse duration of 0.1-10 ms.

Aspect Group 271SE: Reflux_Modum-Forsell_Method

1. A method for affixing a fundus portion (14) of the stomach (10) of a human patient to the patient's esophagus (20), wherein the fundus portion extends from the angle of His (28) and in a direction away from the esophagus, the method comprising:
   folding the fundus portion towards the esophagus such that the fundus portion rests against the esophagus, from the angle of His and upwards along the esophagus; and
   affixing the fundus portion to the esophagus by means of fasteners (230) arranged along a first line (231) and a second line (232);
   wherein the first line and the second line extend along the esophagus and are arranged such that a distance between the first line and the second line increases with an increasing distance from the angle of His.
2. The method according to aspect 1, wherein the abdominal part of the esophagus and the fundus are divided by a plane into a ventral and a dorsal side, and wherein the method comprises providing the first line on the dorsal side of the plane and the second line on the ventral side of the plane.
3. The method according to aspect 1 or 2, comprising beginning the first line less than 1 cm above the angle of His and beginning the second line less than 3 cm above the angle of His.
4. The method according to any of the preceding aspects, comprising beginning the second line at a distance less than 2 cm from the first line.
5. The method according to any of the preceding aspects, wherein a separating angle between the first line and the second line is in the range of 90-150 degrees.
6. The method according to any of the preceding aspects, further comprising providing an additional fastener (233) between the first line and the second line, at the top of the fundus portion.
7. The method according to any of the preceding aspects, wherein the fasteners comprise staples.
8. The method according to any of aspects 1-6, wherein the fasteners comprise sutures, such as barbed sutures.
9. The method according to aspect 8, wherein the first line of fasteners comprises a first continuous suture, and wherein the second line of fasteners comprises a second continuous suture.
10. The method according to any of the preceding aspects, further comprising:
    placing a movement restriction device (110) on the fundus;
    forming a pouch in the fundus;
    arranging the movement restriction device at least partly in the pouch;
    invaginating the movement restriction device by the fundus by at least partly closing the pouch by fasteners;
    wherein the movement restriction device is arranged at a position between the diaphragm (30) and the cardiac sphincter (26) to hinder the cardia (22) from sliding through the diaphragm opening (32) into the patient's thorax.
11. The method according to aspect 10, wherein the movement restriction device is invaginated after affixing the fundus portion to the esophagus.
12. The method according to aspect 10 or 11, wherein the pouch is formed to be open in a least two positions to form a tunnel through which the movement restriction device extends.
13. The method according to any of aspects 10-12, further comprising affixing the fundus to the diaphragm.
14. The method according to any of aspects 10-13, further comprising arranging an elongated support device (120) to at least partly encircle the esophagus, wherein the elongated support device and the movement restriction device form a respective portion of an implantable apparatus for treating reflux disease.
15. The method according to aspect 14, wherein the support device comprises a variable length for allowing the apparatus to be arranged in a constricting state for hindering fluid from passing from the stomach into the esophagus and in an expanded state for allowing food to pass into the stomach in response to the patient swallowing.
16. The method according to aspect 15, wherein the support device is configured to allow a transition from the constricting state into the expanded state caused by the food passing through the esophagus.
17. The method according to aspect 16, further comprising an attractor (212) for resiliently attracting adjacent portions (213) of the support device to one another to generate an encircling pressure on the esophagus.
18. The method according to aspect 17, wherein the attractor comprises an elastic element.
19. The method according to aspect 17, wherein the attractor comprises at least two mutually attracting magnets.
20. The method according to any of aspects 15-19, further comprising a tubular cover (220) enclosing at least a part of the support device and comprising a plurality of cover portions (224, 225, 226) adapted to bend relative to each other to allow the second support device to change between the constricting state and the expanded state, when the cover is at least partly covered by fibrotic tissue, without being substantially hindered or impeded by the presence of said fibrotic tissue.
21. The method according to aspect 20, wherein the cover comprises at least one predefined fold (224) along which the cover is allowed to fold in response to the support device varying its length.
22. The method according to any of aspects 15-21, wherein the apparatus further comprises an electrode arrangement (150) comprising an electrode element (154) supported by the support device and configured to electrically stimulate muscle tissue of the esophagus.
23. The method according to aspect 22, wherein the electrode arrangement is configured to electrically stimulate the cardiac sphincter of the patient to cause the cardiac sphincter to contract.
24. The method according to any aspects 10-14, further comprising an electrode arrangement (150) configured to be arranged between the movement restriction device and the fundus portion to electrically stimulate muscle tissue of the fundus portion to exercise the muscle tissue to improve the conditions for long term implantation of the movement restriction device.
25. The method according to any of aspects 10-24, wherein the electrode arrangement comprises a bare electrode portion (155) configured to form a metal-tissue interface with the muscle tissue, thereby allowing faradaic charge transfer to the be predominant charge transfer mechanism over said interface.
26. The method according to any of aspects 10-24, wherein the electrode arrangement comprises an electrode portion at least partly covered by a dielectric material (157) configured to form a dielectric-tissue interface with the muscle tissue, thereby allowing for a faradaic portion of the charge transfer mechanism over said interface to be reduced.
27. The method according to any of aspects 24-26, further comprising implanting an implantable energy source (160) in the patient's body, wherein the implantable energy source is configured to provide the electrode arrangement with electrical power.
28. The method according to aspect 27, wherein the implantable energy source is arranged inside the movement restriction device.
29. The method according to 27, comprising placing the implantable energy source outside the movement restriction device and the support device.
30. The method according to aspect 27, comprising implanting the implantable energy source subcutaneously.
31. The method according to any of aspects 27-30, further comprising implanting a controller (170) in the patient's body, wherein the controller is configured to indicate a functional status of the implantable energy source.
32. The method according to 31, wherein the functional status indicates a charge level of the implantable energy source.
33. The method according to aspect 32, wherein the functional status indicates a temperature of at least one of the implantable energy source, the muscle tissue, and the electrode arrangement.
34. The method according to any of aspects 31-33, further comprising implanting an implantable charger (190) in the patient's body, wherein the implantable charger is configured to be electrically connected to the implantable energy source and enable charging of the implantable energy source by an external energy source (165) arranged outside the body.
35. The method according to aspect 34, wherein the charger is configured to control the charging of the implantable energy source based on the functional status.
36. The method according to aspect 34 or 35, wherein the charger is configured to control the charging of the implantable energy source by controlling a receipt of electrical power from the external energy source at the implantable charger.
37. The method according to aspect 34 or 35, wherein the charger is configured to control the charging of the implantable energy source by controlling a transmission of electrical power from the external energy source to the implantable charger.
38. The method according to any of aspects 24-37, further comprising implanting a controller (170) in the patient's body, wherein the controller is configured to be operably connected to the electrode arrangement for controlling the electrical stimulation of the muscle tissue.
39. The method according to aspect 38, wherein the controller is configured to control the electrical stimulation such that the muscle tissue is stimulated by a series of electrical pulses (PL1, PL2, PL3, PL4).
40. The method according to aspect 39, wherein the controller is configured to control the electrical stimulation such that a pulse of a first polarity is followed by a pulse of a second, reversed polarity.
41. The method according to any of aspects 38-40, wherein the controller is configured to generate a pulsed electrical stimulation signal comprising a pulse frequency (F) of 0.01-150 Hz.
42. The method according to aspect 41, wherein the electrical stimulation signal comprises a pulse duration (D) of 0.01-100 ms.
43. The method according to aspect 41 or 42, wherein the electrical stimulation signal comprises a pulse amplitude (A) of 1-15 mA.
44. The method according to any of aspects 41-43, wherein the electrical stimulation signal comprises a pulse frequency of 0.15-0.25 Hz, a pulse duration of 20-30 ms and a pulse amplitude of 3-10 mA.
45. The method according to any of aspects 41-44, wherein the electrical stimulation signal comprises a build-up period of 0.01-2 s in which the amplitude is gradually increasing, a stimulation period of 1-60 s, and a stimulation pause of 0.01-60 s, wherein the electrical signal comprises a pulse frequency of 1-50 Hz and a pulse duration of 0.1-10 ms.

Aspect Group 272SE: Reflux_Muscle_Stimulation_Kit
1. An apparatus (100) for treating reflux disease in a human patient, comprising an electrode arrangement (150) for electrically stimulating the patient's muscle tissue to exercise the muscle tissue to improve the conditions for long term implantation of the apparatus, further comprising:
    an implantable energy source (160) configured to provide the electrode arrangement with electrical power; and
    a controller (170) operably connected to the electrode arrangement for controlling the electrical stimulation of the muscle tissue.
2. The apparatus according to aspect 1, wherein the electrode arrangement is configured to be arranged between the apparatus and the tissue onto which the apparatus is arranged to rest when implanted.

3. The apparatus according to aspect 1 or 2, wherein the electrode arrangement comprises an electrode element (152, 154, E1, E2) having a bare electrode portion (155) configured to form a metal-tissue interface with the muscle tissue, thereby allowing faradaic charge transfer to the be predominant charge transfer mechanism over said interface.
4. The apparatus according to aspect 1 or 2, wherein the electrode arrangement comprises an electrode element having a portion at least partly covered by a dielectric material (157) configured to form a dielectric-tissue interface with the muscle tissue, thereby allowing for a faradaic portion of the charge transfer mechanism over said interface to be reduced.
5. The apparatus according to any of the preceding aspects, wherein the controller is configured to control the electrical stimulation such that the muscle tissue is stimulated by a series of electrical pulses (PL1, PL2, PL3, PL4).
6. The apparatus according to aspect 5, wherein the controller is configured to control the electrical stimulation such that a pulse of a first polarity is followed by a pulse of a second, reversed polarity.
7. The apparatus according to aspect 5 or 6, wherein the controller is configured to generate a pulsed electrical stimulation signal comprising a pulse frequency (F) of 0.01-150 Hz.
8. The apparatus according to aspect 7, wherein the electrical stimulation signal comprises a pulse duration (D) of 0.01-100 ms.
9. The apparatus according to aspect 7 or 8, wherein the electrical stimulation signal comprises a pulse amplitude (A) of 1-15 mA.
10. The apparatus according to any of aspects 7-9, wherein the electrical stimulation signal comprises a pulse frequency of 0.15-0.25 Hz, a pulse duration of 20-30 ms and a pulse amplitude of 3-10 mA.
11. The apparatus according to any of aspects 7-10, wherein the electrical stimulation signal comprises a build-up period (X1) of 0.01-2 s in which the amplitude is gradually increasing, a stimulation period (X2) of 1-60 s, and a stimulation pause (X4) of 0.01-60 s, wherein the electrical signal comprises a pulse frequency of 1-50 Hz and a pulse duration of 0.1-10 ms.
12. The apparatus according to any of the preceding aspects, wherein the at least one electrode is configured to engage smooth muscle tissue.
13. The apparatus according to aspect 12, further comprising a sensor (S1) configured to sense action potentials generated by pacemaker cells of the muscle tissue, and wherein the controller is configured to control the electrical stimulation based at least partly on the sensed action potentials.
14. The apparatus according to aspect 13, wherein the controller is configured to generate electrical pulses amplifying the sensed action potentials.
15. The apparatus according to any preceding aspect, wherein the implantable energy source is configured to provide the electrode arrangement and/or the controller with electrical power.
16. The apparatus according to any of the preceding aspects, wherein the controller is further configured to indicate a functional status of the implantable energy source.
17. The apparatus according to aspect 16, wherein the functional status indicates at least one of charge level and temperature of the implantable energy source.
18. The apparatus according to aspect 16 or 17, wherein the controller is further configured to include the functional status in a signal transmitted to the outside of the body.
19. The apparatus according to any of the preceding aspects, further comprising a charger (190) configured to control a charging of the implantable energy source by controlling a receipt of electrical power from an external energy source at the implantable charger.
20. The apparatus according to aspect 19, wherein the charger comprises an electromagnetic coil configured to receive electrical power wirelessly from the external energy source.
21. The apparatus according to aspect 19 or 20, wherein the charger is configured to control the charging of the implantable energy source by controlling a transmission of electrical power from the external energy source to the implantable charger.
22. The apparatus according to any of the preceding aspects, wherein the controller comprises a wireless remote control.
23. The apparatus according to aspect 22, wherein the wireless remote control comprises an external signal transmitter, and wherein the controller comprises an implantable controller configured to receive a signal transmitted by the external signal transmitter and to control an operation of the apparatus based on said signal.
24. The apparatus according to aspect 19 wherein signal is selected from the group consisting of: a sound signal, an ultrasound signal, an electromagnetic signal, and infrared signal, a visible light signal, an ultra violet light signal, a laser signal, a microwave signal, a radio wave signal, an X-ray radiation signal and a gamma radiation signal.
25. A method for exercising muscle tissue of a human patient to improve the conditions for long-term implantation of an apparatus for treating reflux disease of a human patient, the method comprises electrically stimulating the muscle against which the apparatus is arranged to rest when implanted.
26. The method according to aspect 25, comprising electrically stimulating the muscle tissue by means of an electrode arrangement arranged between the muscle tissue and the apparatus.
27. The method according to aspect 25 or 26, comprising electrically stimulating the muscle tissue with a pulsed signal (PL1, PL2, PL3, PL4).
28. The method according to aspect 27, wherein the pulsed signal comprises a pulse frequency (F) of 0.01-150 Hz, such as 0.1-150 Hz, such as 1-130 Hz, such as 10-100 Hz, such as 25-75 Hz.
29. The method according to aspect 27 or 28, wherein the pulsed signal comprises a pulse duration (D) of 0.01-100 ms, such as 0.1-50 ms, such as 1-10 ms.
30. The method according to any one of aspects 27-29, wherein the signal comprises a pulse amplitude (A) of 1-15 mA or less, such as 2-10 mA, such as 3-7 mA.
31. The method according to any one of aspects 27-30, wherein the signal comprises a pulse frequency of 0.2 Hz, a pulse duration of 0.3 ms and a pulse amplitude of 5 mA.
32. The method according to any one of aspects 27 to 31, wherein the signal comprises a pulse frequency of 0.15-0.25 Hz, a pulse duration of 20-30 ms and a pulse amplitude of 3-10 mA.

33. The method according to any of aspects 27-32, wherein the pulsed signal comprises a build-up period of 0.01-2 seconds, in which the amplitude is gradually increasing, a stimulation period of 1 to 60 seconds, a stimulation pause of 0.01 to 60 seconds, a pulse frequency of 1 to 50 Hz and a pulse duration of 0.1 to 10 ms.

34. The method according to any one of aspects 27-33, wherein the pulsed signal is applied by using the electrode arrangement as a cathode.

Aspect Group 273SE: Reflux_Charging_Wireless_Kit

1. An apparatus (100) for treating reflux disease of a human patient, comprising an electrode arrangement (150), the apparatus comprising:
    an implantable energy source (160) configured to provide the apparatus with electrical power,
    an external energy source (165) configured be arranged outside of the patient's body and configured to provide energy to the implantable energy source, and
    an implantable charger (190) configured to be electrically connected to the implantable energy source and enable charging of the implantable energy source by the external energy source.

2. The apparatus according to aspect 1, wherein the charger is configured to control the charging of the implantable energy source by controlling a receipt of electrical power from the external energy source at the implantable charger.

3. The apparatus according to aspect 1, wherein the charger is configured to control the charging of the implantable energy source by controlling a transmission of electrical power from the external energy source to the implantable charger.

4. The apparatus according to any preceding aspect, wherein the implantable energy source is configured to provide the electrode arrangement and/or the controller with electrical power.

5. The apparatus according to any of the preceding aspects, wherein the controller is further configured to indicate a functional status of the implantable energy source.

6. The apparatus according to aspect 5, wherein the functional status indicates at least one of charge level and temperature of the implantable energy source.

7. The apparatus according to aspect 5 or 6, wherein the controller is further configured to include the functional status in a signal transmitted to the outside of the body.

8. The apparatus according to aspect 1, wherein the charger comprises an electromagnetic coil configured to receive electrical power wirelessly from the external energy source.

9. The apparatus according to aspect 5-7, wherein the charger is configured to receive the functional status from the energy source indicator and control the charging of the implantable energy source based on the functional status.

10. The apparatus according to any of the preceding aspects, further comprising a controller (170) configured to be operably connected to the electrode arrangement for controlling the electrical stimulation of the muscle tissue.

11. The apparatus according to aspect 10, wherein the controller is configured to control the electrical stimulation such that the muscle tissue is stimulated by a series of electrical pulses (PL1, PL2, PL3, PL4).

12. The apparatus according to aspect 11, wherein the controller is configured to control the electrical stimulation such that a positive pulse is followed by a negative pulse.

13. The apparatus according to any of aspects 10-12, wherein the controller is configured to generate a pulsed electrical stimulation signal comprising a pulse frequency (F) of 0.01-150 Hz.

14. The apparatus according to aspect 13, wherein the electrical stimulation signal comprises a pulse duration (D) of 0.01-100 ms.

15. The apparatus according to aspect 13 or 14, wherein the electrical stimulation signal comprises a pulse amplitude (A) of 1-15 mA.

16. The apparatus according to any of aspects 13-15, wherein the electrical stimulation signal comprises a pulse frequency of 0.15-0.25 Hz, a pulse duration of 20-30 ms and a pulse amplitude of 3-10 mA.

17. The apparatus according to any of aspects 13-16, wherein the electrical stimulation signal comprises a build-up period of 0.01-2 s in which the amplitude is gradually increasing, a stimulation period of 1-60 s, and a stimulation pause of 0.01-60 s, wherein the electrical signal comprises a pulse frequency of 1-50 Hz and a pulse duration of 0.1-10 ms.

18. The apparatus according to any of aspects 10-17, wherein the controller comprises a wireless remote control (175).

19. The apparatus according to aspect 18, wherein the wireless remote control comprises an external signal transmitter (176), and wherein the controller comprises an implantable controller configured to receive a signal transmitted by the external signal transmitter and to control an operation of the apparatus based on said signal.

20. The apparatus according to aspect 19 wherein signal is selected from the group consisting of: a sound signal, an ultrasound signal, an electromagnetic signal, and infrared signal, a visible light signal, an ultra violet light signal, a laser signal, a microwave signal, a radio wave signal, an X-ray radiation signal and a gamma radiation signal.

21. The apparatus according to any of aspects 10-20, further comprising an implantable sensor (S1) configured to sense actions potentials generated by pacemaker cells of the muscle tissue, and wherein the controller is configured to control the electrical simulation based at least partly on the sensed action potentials.

22. The apparatus according to aspect 21, wherein the controller is configured to generate electrical pulses amplifying the sensed action potentials.

Aspect Group 274SE: Reflux_Communication_Kit

1. An apparatus (100) for treating reflux disease of a human patient, comprising an electrode arrangement (150), the apparatus further comprising:
    a controller (170) configured to be operably connected to the electrode arrangement for controlling the electrical stimulation of the muscle tissue, and
    wherein the controller comprises an implantable communicator (171) for transmitting and/or receiving a signal to/from the outside of the patient's body.

2. The apparatus according to aspect 1, wherein the signal comprises a functional status of an implantable energy source (160), wherein the implantable energy source is configured to provide the electrode arrangement and the controller with electrical power.

3. The apparatus according to aspect 2, wherein the functional status indicates a charge level of the implantable energy source.
4. The apparatus according to aspect 2 or 3, wherein the functional status indicates a temperature of at least one of the implantable energy source, the muscle tissue, and the electrode arrangement.
5. The apparatus according to any preceding aspect, wherein the controller further comprises an external controller configured to receive the signal.
6. The apparatus according to any preceding aspect, wherein the controller is configured to control the electrical stimulation such that the muscle tissue is stimulated by a series of electrical pulses (PL1, PL2, PL3, PL4).
7. The apparatus according to aspect 6, wherein the controller is configured to control the electrical stimulation such that a positive pulse is followed by a negative pulse.
8. The apparatus according to any preceding aspect, wherein the controller is configured to generate a pulsed electrical stimulation signal comprising a pulse frequency (F) of 0.01-150 Hz.
9. The apparatus according to any of aspects 6-8, wherein the electrical stimulation signal comprises a pulse duration (D) of 0.01-100 ms.
10. The apparatus according to any of aspects 6-9, wherein the electrical stimulation signal comprises a pulse frequency of 0.15-0.25 Hz, a pulse duration of 20-30 ms and a pulse amplitude of 3-10 mA.
11. The apparatus according to any of aspects 6-10, wherein the electrical stimulation signal comprises a build-up period of 0.01-2 s in which the amplitude is gradually increasing, a stimulation period of 1-60 s, and a stimulation pause of 0.01-60 s, wherein the electrical signal comprises a pulse frequency of 1-50 Hz and a pulse duration of 0.1-10 ms.
12. The apparatus according to any of the preceding aspects, wherein the controller comprises a wireless remote control (175).
13. The apparatus according to aspect 12, the apparatus further comprising an internal controller and an internal signal receiver connected to the internal controller, and wherein the wireless remote control comprises an external signal transmitter (176), and wherein the internal signal receiver implantable in the patient is configured to receive a signal transmitted by the external signal transmitter.
14. The apparatus according to aspect 13 wherein signal is selected from the group consisting of: a sound signal, an ultrasound signal, an electromagnetic signal, and infrared signal, a visible light signal, an ultra violet light signal, a laser signal, a microwave signal, a radio wave signal, an X-ray radiation signal and a gamma radiation signal.
15. The apparatus according to any of the preceding aspects, further comprising an implantable sensor (S1) configured to sense actions potentials generated by pacemaker cells of the muscle tissue, and wherein the controller is configured to control the electrical simulation based at least partly on the sensed action potentials.
16. The apparatus according to aspect 15, wherein the controller is configured to generate electrical pulses amplifying the sensed action potentials.
17. The apparatus according to any of the preceding aspects, further comprising an implantable energy source (160) configured to provide the electrode arrangement and the controller with electrical power.
18. The apparatus according to aspect 17, further comprising an implantable charger (190) configured to be electrically connected to the implantable energy source and enable recharging of the implantable energy source by an external energy source (165), wherein the charger is configured to control the charging of the implantable energy source by controlling the receipt of electrical power from the external energy source.
19. The apparatus according to aspect 18, wherein the charger comprises an electromagnetic coil configured to receive electrical power wirelessly from the external energy source.
20. The apparatus according to aspect 18-19, wherein the charger is configured to receive the functional status from the energy source indicator and control the charging of the implantable energy source based on the functional status.

The invention claimed is:
1. A method for treating reflux disease of a human patient by implanting a movement restriction device such that the movement restriction device is arranged to restrict movement of the cardia of the patient's stomach towards the diaphragm to hinder the cardia from sliding through the diaphragm opening into the patient's thorax, wherein the method comprises:
  placing the movement restriction device such that a lower portion of the movement restriction device rests against the serosa at the angle of His, and such that an upper portion of the movement restriction device defines a gap between the movement restriction device and the patient's esophagus, when the lower portion rests against the angle of His;
  arranging a portion of the fundus of the stomach in the gap; and
  attaching the fundus to the patient's esophagus to at least partly enclose the movement restriction device by the portion of the fundus.
2. The method according to claim 1, comprising arranging the upper portion to point away from the esophagus.
3. The method according to claim 1, wherein the lower portion is wider than the upper portion.
4. The method according to claim 1, wherein the upper portion comprises a recess defined in the outer surface of the movement restriction device.
5. The method according to claim 1, wherein the lower portion comprises a curved outer surface, wherein the method further comprises arranging the curved outer surface to face the esophagus, and wherein the curved outer surface comprises a radius of curvature corresponding to or exceeding the radius of curvature of the esophagus.
6. The method according to claim 1, further comprising at least partly invaginating an elongated support, protruding from the movement restriction device, in the portion of the fundus before attaching the fundus to the esophagus.
7. The method according to claim 6, wherein the support is shaped as a lever, wherein the method further comprises orienting the support along the esophagus.
8. The method according to claim 1, further comprising arranging an electrode arrangement between the movement restriction device and the portion of the fundus and/or the serosa, wherein the electrode arrangement is configured to electrically stimulate muscle tissue of the portion of the fundus and/or the serosa to improve the conditions for long term implantation of the movement restriction device.

9. The method according to claim 8, wherein the electrode arrangement comprises a plurality of electrode elements, each of which being configured to engage and electrically stimulate the muscle tissue.

10. The method according to claim 8, wherein the electrode arrangement comprises a bare electrode portion configured to form a metal-tissue interface with the muscle tissue, thereby allowing faradaic charge transfer to the be predominant charge transfer mechanism over said interface.

11. The method according to claim 8, wherein the electrode arrangement comprises an electrode portion at least partly covered by a dielectric material configured to form a dielectric-tissue interface with the muscle tissue, thereby allowing for a faradaic portion of the charge transfer mechanism over said interface to be reduced.

12. The method according to claim 8, wherein the electrode arrangement is further configured to be arranged to electrically stimulate the cardiac sphincter to cause the cardiac sphincter to contract.

13. The method according to claim 12, wherein the electrode arrangement comprises at least two electrode elements, wherein the method further comprises arranging said electrode elements on opposing sides of the cardiac sphincter.

14. The method according to claim 8, further comprising implanting an implantable energy source configured to provide the electrode with electrical power.

15. The method according to claim 14, wherein the implantable energy source is arranged inside the movement restriction device.

16. The method according to claim 14, wherein the implantable energy source is configured to be arranged outside the movement restriction device, and wherein the method further comprises implanting the implantable energy source in the patient's body.

17. The method according to claim 14, further comprising implanting the implantable energy source subcutaneously.

18. The method according to claim 14, further comprising implanting a controller configured to indicate a functional status of the implantable energy source.

19. The method according to claim 18, wherein the functional status indicates a charge level of the implantable energy source.

20. The method according to claim 18, wherein the functional status indicates a temperature of at least one of the implantable energy source, the muscle tissue, and the electrode arrangement.

21. The method according to claim 18, wherein the implantable energy source is configured to be charged by an external energy source arranged outside the patient's body.

22. The method according to claim 8, further comprising implanting a controller configured to be operably connected to the electrode arrangement for controlling the electrical stimulation of the muscle tissue.

23. The method according to claim 22, wherein the controller is configured to control the electrical stimulation such that the muscle tissue is stimulated by a series of electrical pulses.

24. The method according to claim 22, wherein the controller is configured to control the electrical stimulation such that a pulse of a first polarity is followed by a pulse of a second, reversed polarity.

25. The method according to any of claim 22, further comprising implanting an implantable sensor configured to sense actions potentials generated by pacemaker cells of the muscle tissue, and wherein the controller is configured to control the electrical simulation based at least partly on the sensed action potentials.

26. The method according to claim 25, wherein the controller is configured to generate electrical pulses amplifying the sensed action potentials.

* * * * *